United States Patent
Aliprantis et al.

(10) Patent No.: US 12,110,324 B2
(45) Date of Patent: Oct. 8, 2024

(54) ANTIGEN BINDING MOLECULES TARGETING THYMIC STROMAL LYMPHOPOIETIN (TSLP)

(71) Applicant: Flagship Pioneering Innovations VI, LLC, Cambridge, MA (US)

(72) Inventors: Antonios O. Aliprantis, Natick, MA (US); Zachary Kohl Costello, Cambridge, MA (US); Anthony John Coyle, Boston, MA (US); Kristen Park Hopson, Lincoln, MA (US); Ryan Terrell Phennicie, Andover, MA (US); Alexis Hiram Ramos, Wilbraham, MA (US); Adam Reid Root, Newbury, MA (US); Lana Dinic, Newton, MA (US); Karin Alma Frieda Reif, San Francisco, CA (US)

(73) Assignee: Flagship Pioneering Innovations VI, LLC, Cambridge, MA (US)

( * ) Notice: Subject to any disclaimer, the term of this patent is extended or adjusted under 35 U.S.C. 154(b) by 0 days.

(21) Appl. No.: 18/356,891

(22) Filed: Jul. 21, 2023

(65) Prior Publication Data

US 2024/0034780 A1 Feb. 1, 2024

Related U.S. Application Data

(60) Provisional application No. 63/369,202, filed on Jul. 22, 2022, provisional application No. 63/369,152, filed on Jul. 22, 2022, provisional application No. 63/369,203, filed on Jul. 22, 2022, provisional application No. 63/369,165, filed on Jul. 22, 2022, provisional application No. 63/369,175, filed on Jul. 22, 2022, provisional application No. 63/369,204, filed on Jul. 22, 2022, provisional application No. 63/369,158, filed on Jul. 22, 2022, provisional application No. 63/369,206, filed on Jul. 22, 2022.

(51) Int. Cl.
*C07K 16/24* (2006.01)
*A61P 11/06* (2006.01)

(52) U.S. Cl.
CPC ............ *C07K 16/244* (2013.01); *A61P 11/06* (2018.01); *C07K 2317/24* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 6,180,370 B1 * | 1/2001 | Queen | A61P 31/12 435/69.6 |
| 6,555,520 B2 | 4/2003 | Sims et al. | |
| 6,890,734 B2 | 5/2005 | Reche-Gallardo et al. | |
| 7,083,784 B2 | 8/2006 | Dall'Acqua et al. | |
| 7,304,144 B2 | 12/2007 | Sims et al. | |
| 7,405,058 B2 | 7/2008 | Sims et al. | |
| 7,670,600 B2 | 3/2010 | Dall'Acqua et al. | |
| 7,704,497 B2 | 4/2010 | Dall'Acqua et al. | |
| 7,709,217 B2 | 5/2010 | Lyman et al. | |
| 7,786,271 B2 | 8/2010 | Sims et al. | |
| 7,964,713 B2 | 6/2011 | Saris et al. | |
| 7,973,151 B2 | 7/2011 | Lyman et al. | |
| 7,982,016 B2 | 7/2011 | Comeau et al. | |
| 8,012,476 B2 | 9/2011 | Dall'Acqua et al. | |
| 8,088,376 B2 | 1/2012 | Chamberlain et al. | |
| 8,097,705 B2 | 1/2012 | Dong et al. | |
| 8,163,284 B2 | 4/2012 | Comeau et al. | |
| 8,232,372 B2 | 7/2012 | Presta et al. | |
| 8,323,962 B2 | 12/2012 | Dall'Acqua et al. | |
| 8,344,110 B2 | 1/2013 | Saris et al. | |
| 8,444,979 B2 | 5/2013 | Sims et al. | |
| 8,475,792 B2 | 7/2013 | Dall'Acqua et al. | |
| 8,475,793 B2 | 7/2013 | De Waal Malefyt et al. | |
| 8,512,705 B2 * | 8/2013 | Presta | A61P 37/08 424/152.1 |
| 8,598,318 B2 | 12/2013 | Lyman et al. | |
| 8,795,661 B2 | 8/2014 | Dall'Acqua et al. | |

(Continued)

FOREIGN PATENT DOCUMENTS

| AU | 2014277673 A1 | 1/2015 |
|---|---|---|
| EP | 1793856 A2 | 6/2007 |

(Continued)

OTHER PUBLICATIONS

Noti, Mario et al. "Thymic stromal lymphopoietin-elicited basophil responses promote eosinophilic esophagitis." Nature medicine vol. 19,8 (2013): 1005-13. doi:10.1038/nm.3281 (Year: 2013).*

Pavord, Ian D., et al. "Tezepelumab reduces exacerbations across all seasons in patients with severe, uncontrolled asthma (Navigator)." Annals of Allergy, Asthma & Immunology 131.5 (2023): 587-597)). (Year: 2023).*

(Continued)

*Primary Examiner* — Michael Szperka
*Assistant Examiner* — Lia E Taylor
(74) *Attorney, Agent, or Firm* — Hamilton, Brook, Smith & Reynolds, P.C.

(57) ABSTRACT

The disclosure provides, in various embodiments, polypeptides (e.g., antibodies and antigen binding fragments thereof) that specifically bind to a thymic stromal lymphopoietin (TSLP) (e.g., a full-length human TSLP). The disclosure also provides, in various embodiments, fusion proteins comprising one or more of the polypeptides, polynucleotides encoding the polypeptides, vectors and host cells suitable for expressing the polypeptides, and methods for treating a TSLP-associated disease or condition.

23 Claims, 27 Drawing Sheets

Figure 4A:
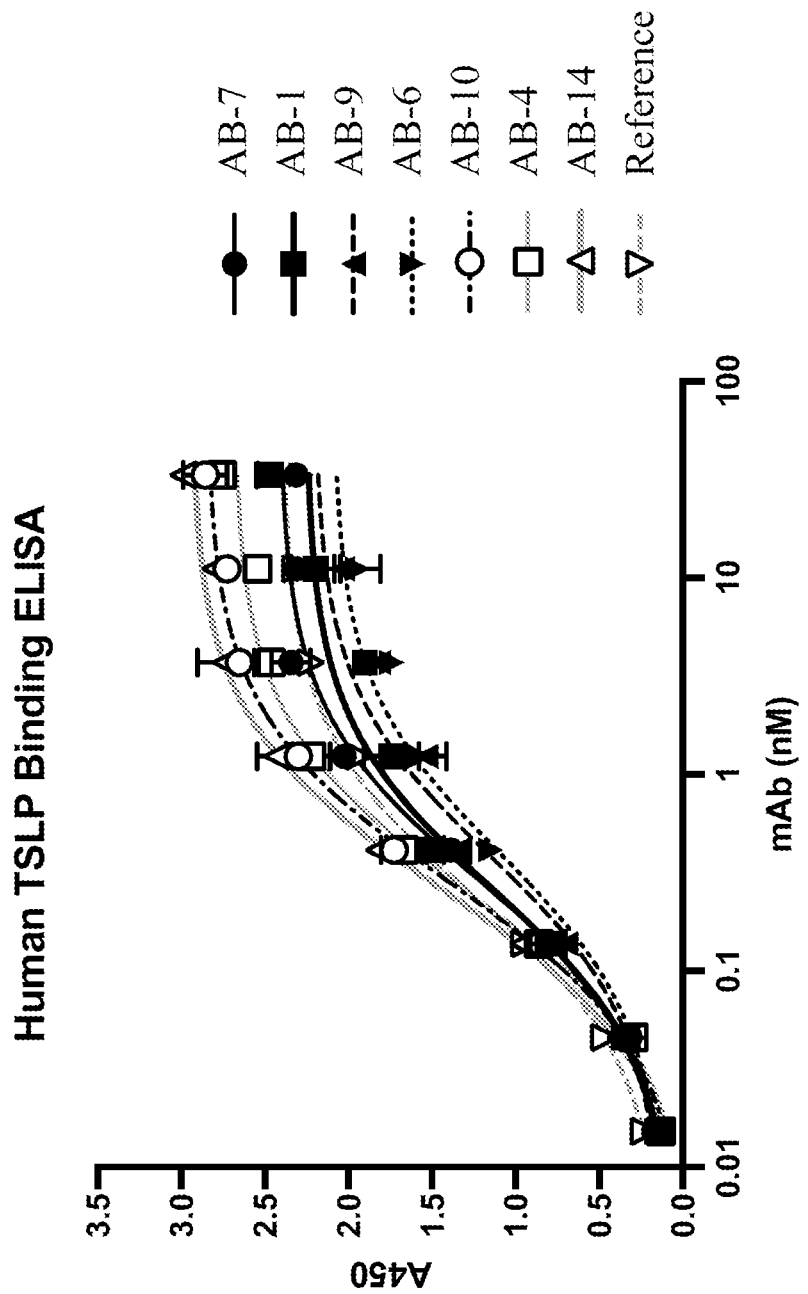

Specification includes a Sequence Listing.

(56) References Cited

U.S. PATENT DOCUMENTS

| | | |
|---|---|---|
| 8,911,730 B2 | 12/2014 | Saris et al. |
| 9,045,558 B2 | 6/2015 | Lyman et al. |
| 9,284,372 B2 | 3/2016 | Comeau et al. |
| 9,328,171 B2 | 5/2016 | Sato et al. |
| 9,346,870 B2 | 5/2016 | Sims et al. |
| 9,562,100 B2 | 2/2017 | Dall'Acqua et al. |
| 9,803,023 B2 | 10/2017 | Chamberlain et al. |
| 10,000,561 B2 | 6/2018 | Edwards et al. |
| 10,287,348 B2 | 5/2019 | Comeau et al. |
| 10,336,818 B2 | 7/2019 | Chamberlain et al. |
| 10,722,655 B2 | 7/2020 | Folk et al. |
| 10,745,473 B2 | 8/2020 | Edwards et al. |
| 10,828,365 B2 | 11/2020 | Parnes et al. |
| 10,994,011 B2 | 5/2021 | Ikeda et al. |
| 11,059,908 B2 | 7/2021 | Huh et al. |
| 11,385,238 B2 | 7/2022 | Ren et al. |
| 11,712,472 B2 | 8/2023 | Ikeda et al. |
| 11,827,699 B2 | 11/2023 | Igawa et al. |
| 2006/0039910 A1 | 2/2006 | Comeau et al. |
| 2006/0171943 A1 | 8/2006 | Comeau et al. |
| 2010/0266601 A1 | 10/2010 | Sims et al. |
| 2011/0117053 A1 | 5/2011 | Comeau et al. |
| 2011/0230637 A1 | 9/2011 | Lyman et al. |
| 2013/0225490 A1 | 8/2013 | Sims et al. |
| 2015/0050296 A1 | 2/2015 | Igawa et al. |
| 2015/0252089 A1 | 9/2015 | Lyman et al. |
| 2016/0377630 A1 | 12/2016 | Lyman et al. |
| 2017/0022270 A1 | 1/2017 | Igawa et al. |
| 2017/0081668 A1 | 3/2017 | Comeau et al. |
| 2018/0193562 A1 | 7/2018 | Gibson et al. |
| 2018/0303753 A1 | 10/2018 | Ung et al. |
| 2019/0203209 A1 | 7/2019 | Comeau et al. |
| 2020/0048367 A1 | 2/2020 | Agrawal et al. |
| 2020/0071393 A1 | 3/2020 | Comeau et al. |
| 2020/0240993 A1 | 7/2020 | Wu |
| 2020/0316303 A1 | 10/2020 | Folk et al. |
| 2020/0352857 A1 | 11/2020 | Gu et al. |
| 2020/0355582 A1 | 11/2020 | Wu |
| 2021/0041453 A1 | 2/2021 | Benchaar et al. |
| 2021/0052726 A1 | 2/2021 | Parnes et al. |
| 2021/0069416 A1 | 3/2021 | Gibson et al. |
| 2021/0121406 A1 | 4/2021 | Huntington et al. |
| 2021/0148910 A1 | 5/2021 | Howell |
| 2021/0214431 A1 | 7/2021 | Rommelaere et al. |
| 2021/0255075 A1 | 8/2021 | Ren et al. |
| 2022/0137061 A1 | 5/2022 | Wu et al. |
| 2022/0146413 A1 | 5/2022 | Duff et al. |
| 2022/0288324 A1 | 9/2022 | Davis et al. |
| 2022/0288326 A1 | 9/2022 | Eilertsen et al. |
| 2022/0404370 A1 | 12/2022 | Ren et al. |
| 2023/0029835 A1 | 2/2023 | Wang et al. |
| 2023/0073888 A1 | 3/2023 | Parnes et al. |
| 2023/0078678 A1 | 3/2023 | Lueras et al. |
| 2023/0081261 A1 | 3/2023 | Roschen et al. |
| 2023/0201120 A1 | 6/2023 | Huntington et al. |
| 2023/0398213 A1 | 12/2023 | Ikeda et al. |

FOREIGN PATENT DOCUMENTS

| | | |
|---|---|---|
| EP | 1294879 B1 | 12/2008 |
| EP | 1355919 B1 | 11/2010 |
| EP | 1843789 B1 | 3/2011 |
| EP | 2357187 A1 | 8/2011 |
| EP | 2077279 B1 | 9/2012 |
| EP | 1417231 B1 | 6/2013 |
| EP | 2703414 A1 | 3/2014 |
| EP | 2205635 B1 | 5/2016 |
| EP | 3031913 A1 | 6/2016 |
| EP | 1129190 B2 | 1/2017 |
| EP | 2354149 B1 | 8/2017 |
| EP | 3346987 A1 | 7/2018 |
| EP | 3391904 A1 | 10/2018 |
| EP | 2341060 B1 | 2/2019 |
| EP | 3524622 A1 | 8/2019 |
| EP | 3569610 A2 | 11/2019 |
| EP | 3609917 A1 | 2/2020 |
| EP | 3615065 A1 | 3/2020 |
| EP | 3615069 A1 | 3/2020 |
| EP | 3662287 A1 | 6/2020 |
| EP | 3662288 A1 | 6/2020 |
| EP | 3669004 A1 | 6/2020 |
| EP | 3765856 A1 | 1/2021 |
| EP | 3765857 A1 | 1/2021 |
| EP | 3139977 B1 | 2/2021 |
| EP | 3347377 B1 | 2/2021 |
| EP | 3785749 A1 | 3/2021 |
| EP | 2762493 B1 | 6/2021 |
| EP | 3842457 A1 | 6/2021 |
| EP | 3894839 A1 | 10/2021 |
| EP | 3261690 B1 | 12/2021 |
| EP | 3924083 A1 | 12/2021 |
| EP | 3939996 A1 | 1/2022 |
| EP | 3981450 A1 | 4/2022 |
| EP | 4051708 A1 | 9/2022 |
| EP | 4103235 A1 | 12/2022 |
| EP | 4103605 A1 | 12/2022 |
| EP | 4106811 A1 | 12/2022 |
| EP | 4257604 A1 | 10/2023 |
| WO | 2000/029581 A1 | 5/2000 |
| WO | 2002/000724 A2 | 1/2002 |
| WO | 2002/060919 A2 | 8/2002 |
| WO | 2006/023791 A2 | 3/2006 |
| WO | 2006/053301 A2 | 5/2006 |
| WO | 2006/083947 A2 | 8/2006 |
| WO | 2009/035577 A1 | 3/2009 |
| WO | 2009/086320 A1 | 7/2009 |
| WO | 2013/047748 A1 | 4/2013 |
| WO | 2015/171777 A1 | 11/2015 |
| WO | 2016/138434 A1 | 9/2016 |
| WO | 2016/142426 A1 | 9/2016 |
| WO | 2017/042696 A1 | 3/2017 |
| WO | 2017/042701 A1 | 3/2017 |
| WO | 2017/104778 A1 | 6/2017 |
| WO | 2018/191479 A1 | 10/2018 |
| WO | 2018/200533 A1 | 11/2018 |
| WO | 2018/201064 A1 | 11/2018 |
| WO | 2019/028187 A1 | 2/2019 |
| WO | 2019/028191 A1 | 2/2019 |
| WO | 2019/035005 A1 | 2/2019 |
| WO | 2019/178151 A1 | 2/2019 |
| WO | 2019/178280 A1 | 9/2019 |
| WO | 2020/043221 A1 | 3/2020 |
| WO | 2020/124008 A1 | 6/2020 |
| WO | 2020/168156 A1 | 8/2020 |
| WO | 2020/244544 A1 | 12/2020 |
| WO | 2021/007533 A1 | 1/2021 |
| WO | 2021/083908 A1 | 5/2021 |
| WO | 2021/104053 A9 | 6/2021 |
| WO | 2021/115240 A1 | 6/2021 |
| WO | 2021/163504 A1 | 8/2021 |
| WO | 2021/163588 A1 | 8/2021 |
| WO | 2021/168100 A1 | 8/2021 |
| WO | 2022/098595 A1 | 5/2022 |
| WO | 2022/104212 A1 | 5/2022 |
| WO | 2022/116858 A1 | 6/2022 |
| WO | 2022/184074 A1 | 9/2022 |
| WO | 2022/192310 A1 | 9/2022 |
| WO | 2022/192311 A1 | 9/2022 |
| WO | 2022/203830 A1 | 9/2022 |
| WO | 2022/223514 A1 | 10/2022 |
| WO | 2022/226339 A1 | 10/2022 |
| WO | 2022/226342 A2 | 10/2022 |
| WO | 2024/020590 A2 | 1/2024 |
| WO | 2024/020591 A2 | 1/2024 |

OTHER PUBLICATIONS

Sterba, Patricia M., Allen Myers, and Sarbjit S. Saini. "Expression of TSLP and TSLP-R in chronic idiopathic urticaria." Journal of Allergy and Clinical Immunology 133.2 (2014): AB166. (Year: 2014).*

Ying, Sun, et al. "Expression and cellular provenance of thymic stromal lymphopoietin and chemokines in patients with severe

(56) References Cited

OTHER PUBLICATIONS asthma and chronic obstructive pulmonary disease." The Journal of Immunology 181.4 (2008): 2790-2798 (Year: 2008).*
Matsuda, Akira et al. "Functional role of thymic stromal lymphopoietin in chronic allergic keratoconjunctivitis." Investigative ophthalmology & visual science vol. 51,1 (2010): 151-5. doi:10.1167/iovs.09-4183 (Year: 2010).*
Ebina-Shibuya, Risa, and Warren J. Leonard. "Role of thymic stromal lymphopoietin in allergy and beyond." Nature Reviews Immunology 23.1 (2023): 24-37. (Year: 2023).*
Laidlaw, Tanya M., and Kathleen M. Buchheit. "Biologics in chronic rhinosinusitis with nasal polyposis." Annals of Allergy, Asthma & Immunology 124.4 (2020): 326-332. (Year: 2020).*
Tsuji, Gaku, et al. "Novel Therapeutic Targets for the Treatment of Atopic Dermatitis." Biomedicines 11.5 (2023): 1303. (Year: 2023).*
Chu, Derek K., et al. "IL-33, but not thymic stromal lymphopoietin or IL-25, is central to mite and peanut allergic sensitization." Journal of Allergy and Clinical Immunology 131.1 (2013): 187-200. (Year: 2013).*
Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
Bleck B, Kazeros A, Bakal K, et al. Coexpression of type 2 immune targets in sputum-derived epithelial and dendritic cells from asthmatic subjects. Journal of Allergy and Clinical Immunology. 2015;136(3). doi:10.1016/j.jaci.2014.12.1950.
Center for Drug Evaluation and Research (CDER) NDA/BLA Multi-disciplinary Review and Evaluation (BLA 761224) for Tezspire/Tezepelumab. Dated: Oct. 12, 2018. Accessed: Jul. 24, 2023. Available online: https://www.accessdata.fda.gov/drugsatfda_docs/nda/2022/761224Orig1s000MultidisciplineR.pdf.
Corren J, Parnes JR, Wang L, et al. Tezepelumab in Adults with Uncontrolled Asthma [published correction appears in N Engl J Med. May 23, 2019;380(21):2082]. N Engl J Med. 2017;377(10):936-946. doi:10.1056/NEJMoa1704064.
Corren J, Pham TH, Garcia Gil E, et al. Baseline type 2 biomarker levels and response to tezepelumab in severe asthma. Allergy. 2022;77(6):1786-1796. doi:10.1111/all. 15197.
Corren J, Ziegler SF. TSLP: From allergy to cancer. Nature Immunology. 2019;20(12):1603-1609. doi:10.1038/s41590-019-0524-9.
Dall'Acqua WF, Woods RM, Ward ES, et al. Increasing the affinity of a human IgG1 for the neonatal Fc receptor: biological consequences. J Immunol. 2002;169(9):5171-5180. doi:10.4049/jimmunol. 169.9.5171.
Deng R, Iyer S, Theil FP, et al. Projecting human pharmacokinetics of therapeutic antibodies from nonclinical data: what have we learned?. MAbs. 2011;3(1):61-66. doi:10.4161/mabs.3.1.13799.
Dorey-Stein ZL and Shenoy KV. Tezepelumab as an Emerging Therapeutic Option for the Treatment of Severe Asthma: Evidence to Date. Drug Des Devel Ther. 2021;15:331-338. Published Jan. 27, 2021. doi: 10.2147/DDDT.S250825.
Dragonieri S and Carpagnano GE. Biological therapy for severe asthma. Asthma Res Pract. 2021;7(1):12. Published Aug. 13, 2021. doi:10.1186/s40733-021-00078-w.
FDA Guidance for Industry: Estimating the Maximum Safe Starting Dose in Initial Clinical Trials for Therapeutics in Adult Healthy Volunteers (Jul. 2005).
Gauvreau GM, O'Byrne PM, Boulet LP, et al. Effects of an anti-TSLP antibody on allergen-induced asthmatic responses. N Engl J Med. 2014;370(22):2102-2110. doi:10.1056/NEJMoa1402895.
Gelhorn HL, Balantac Z, Ambrose CS, et al. Patient and physician preferences for attributes of biologic medications for severe asthma. Patient Prefer Adherence. 2019;13:1253-1268. Published Jul. 25, 2019. doi:10.2147/PPA.S198953.
Gina Global Strategy for Asthma Management and Prevention, 2023.
Haraya K, Tachibana T. Translational Approach for Predicting Human Pharmacokinetics of Engineered Therapeutic Monoclonal Antibodies with Increased FcRn-Binding Mutations. BioDrugs. Jan. 2023;37(1):99-108. doi:10.1007/s40259-022-00566-2. Epub Nov. 30, 2022. PMID: 36449140; PMCID: PMC9709760.
Kapitanov GI, Chabot JR, Narula J, et al. A Mechanistic Site-Of-Action Model: A Tool for Informing Right Target, Right Compound, And Right Dose for Therapeutic Antagonistic Antibody Programs. Front Bioinform. 2021;1:731340. Published Sep. 3, 2021. doi: 10.3389/fbinf.2021.731340.
Kenakin T. The mass action equation in pharmacology. Br J Clin Pharmacol. 2016;81(1):41-51. doi:10.1111/bcp.12810.
Menzies-Gow A, Corren J, Bourdin A, et al. Tezepelumab in Adults and Adolescents with Severe, Uncontrolled Asthma. N Engl J Med. 2021;384(19):1800-1809. doi:10.1056/NEJMoa2034975.
Murrison LB, Ren X, Preusse K, et al. TSLP disease-associated genetic variants combined with airway TSLP expression influence asthma risk. Journal of Allergy and Clinical Immunology. 2022;149(1):79-88. doi:10.1016/j.jaci.2021.05.033.
Pham TH, Kearley J, Pames J, et al. Development of a highly sensitive assay to quantitate circulating thymic stromal lymphopoietin (TSLP) levels in blood. Journal of Allergy and Clinical Immunology. 2020; 145(2): Supplement AB30. doi:https://doi.org/10.1016/j.jaci.2019.12.820.
Robbie GJ, Criste R, Dall'acqua WF, et al. A novel investigational Fc-modified humanized monoclonal antibody, motavizumab-YTE, has an extended half-life in healthy adults. Antimicrob Agents Chemother. 2013;57(12):6147-6153. doi:10.1128/AAC.01285-13.
Rochman and Leonard WJ. The role of thymic stromal lymphopoietin in CD8+ T cell homeostasis. J Immunol. 2008;181(11):7699-7705. doi:10.4049/jimmunol.181.11.7699.
Shikotra A, Choy DF, Ohri CM, et al. Increased expression of immunoreactive thymic stromal lymphopoietin in patients with severe asthma. Journal of Allergy and Clinical Immunology. 2012;129(1). doi:10.1016/j.jaci.2011.08.031.
Singh D, Fuhr R, Bird NP, et al. A Phase 1 study of the long-acting anti-IL-5 monoclonal antibody GSK3511294 in patients with asthma. Br J Clin Pharmacol. Feb. 2022; 88(2): 702-712. Published online Aug. 24, 2021. doi: 10.1111/bcp.15002.
Song HJ, Blake KV, Wilson DL, Winterstein AG, Park H. Medical Costs and Productivity Loss Due to Mild, Moderate, and Severe Asthma in the United States. J Asthma Allergy.Oct. 29, 2020;13:545-555. doi: 10.2147/JAA.S272681. PMID: 33149626; PMCID:PMC7605920.
Van Gerven J and Bonelli M. Commentary on the EMA Guideline on strategies to identify and mitigate risks for first-in-human and early clinical trials with investigational medicinal products. Br J Clin Pharmacol. 2018;84(7):1401-1409. doi:10.1111/bcp.13550.
Corren J, Parnes JR, Wang L, et al. Supplementary Appendix to: Tezepelumab in Adults with Uncontrolled Asthma [published correction appears in N Engl J Med. May 23, 2019;380(21):2082]. N Engl J Med. 2017;377(10):936-946. doi:10.1056/NEJMoa1704064.
Dedrick RL. Animal scale-up. J Pharmacokinet Biopharm. 1973;1(5):435-461. doi:10.1007/BF01059667.
EMA Guideline. Guideline on strategies to identify and mitigate risks for first-in-human and early clinical trials with investigational medicinal products (Jul. 2017).
Markovic et al., Modulation of Signaling Mediated by TSLP and IL-7 in Inflammation, Autoimmune Diseases, and Cancer Front Immunol. Jul. 21, 2020; 11:1557. doi: 10.3389/fimmu.2020.01557. PMID: 32849527; PMCID: PMC7396566.
Berger, "Evaluation and management of severe refractory atopicdermatitis (eczema) in adults" UpToDate 2022.
Bhatt et al., "Dupilumab for COPD with Type 2 Inflammation Indicated by Eosinophil Counts" N Engl J Med 2023; 389:205-214.
AstraZeneca Clinical Study Protocol 5.0 Tezepelumab—D5180C00007 A Multicentre, Randomized, Double-Blind, Placebo Controlled, Parallel Group, Phase 3 Study to Evaluate the Efficacy and Safety of Tezepelumab in Adults and Adolescents with Severe Uncontrolled Asthma (Navigator): May 14, 2020.
Cohen et al., "Treatment of rheumatoid arthritis in adults resistant toinitial conventional synthetic (nonbiologic) DMARDtherapy" UpToDate 2022.
The GlaxoSmithKline group of companies Protocol Amendment "A randomised double-blind (sponsor open), placebo controlled, single

(56) References Cited

OTHER PUBLICATIONS ascending dose, First Time in Human study in participants with mild to moderate asthma to assess safety, tolerability, immunogenicity, pharmacokinetics and pharmacodynamics of GSK3511294 administered subcutaneously." Jan. 7, 2019.
Han et al., "Chronic obstructive pulmonary disease: Definition, clinical manifestations, diagnosis, and staging" UpToDate 2023.
Prescribing Information Tezspire® (tezepelumab-ekko) injection, for subcutaneous use 2023.
Howe, "Treatment of atopic dermatitis (eczema)" UpToDate 2022.
Khoury et al., "Clinical and Biological Markers in Hypereosinophilic Syndromes" Front. Med. 4:240. Dec. 2017 doi: 10.3389/fmed.2017.00240.
Kolkhir et al., "Type 2 chronic inflammatory diseases: targets, therapies and unmet needs" Nature Reviews Drug Discovery vol. Sep. 22, 2023 p. 743-767.
Martin "Investigational agents for asthma" UpToDate 2022.
Matucci et al., "The use of intravenous versus subcutaneous monoclonal antibodies in the treatment of severe asthma: a review" Respiratory Research (2018) 19:154.
Menzies-Gow A, Corren J, Bourdin A, et al. Supplementary Appendix to: Tezepelumab in Adults and Adolescents with Severe, Uncontrolled Asthma. N Engl J Med. 2021;384(19):1800-1809. doi:10.1056/NEJMoa2034975.
Miyano et al., "A mathematical model to identify optimal combinations of drug targets for dupilumab poor responders in atopic dermatitis" medRxiv 2021.02.08.21251317; doi: https://doi.org/10.1101/2021.02.08.21251317.
Parnes et al., "Pharmacokinetics, Safety, and Tolerability of Tezepelumab (AMG 157) in Healthy and Atopic Dermatitis Adult Subjects" Clin Pharmacol Ther. Aug. 2019;106(2):441-449. doi: 10.1002/cpt.1401. Epub Mar. 23, 2019. PMID: 30779339; PMCID: PMC6766783.
AstraZeneca Statistical Analysis Plan Study Code D5180C00007 "A Multicentre, Randomised, Double-Blind, Placebo-Controlled, Parallel Group, Phase 3 Study to Evaluate the Efficacy and Safety of Tezepelumab in Adults and Adolescents with Severe Uncontrolled Asthma (Navigator)" Oct. 22, 2020.
Venkataramani et al., "Design and characterization of Zweimab and Doppelmab, high affinity dual antagonistic anti-TSLP/IL13 bispecific antibodies" Biochemical and Biophysical Research Communications 504 (2018) 19-24.
Wenzel "Treatment of severe asthma in adolescents and adults" UpToDate 2022.
Zheng et al., "Tezepelumab Pharmacokinetics, Safety, and Tolerability After Administration via Vial-and-syringe, Accessorized Prefilled Syringe, or Autoinjector: A Randomized Trial in Healthy Volunteers" Clin Ther. Jan. 2021;43(1):142-155.e5. doi: 10.1016/j.clinthera.2020.11.014. Epub Dec. 27, 2020. PMID: 33380362.
Pieris Pharmaceuticals PRS-060: First-In-Class Inhaled IL4RA Antagonist for Asthma 2020.
Zervas et al., "An algorithmic approach for the treatment of severe uncontrolled asthma" ERJ Open Res. Mar. 6, 2018;4(1):00125-2017. doi: 10.1183/23120541.00125-2017. PMID: 29531957; PMCID: PMC5838355.
Database, PDB: 5J13_C, PDB: 5J13_B [Online], "Structural basis for TSLP antagonism by the therapeutic antibody Tezepelumab (MEDI9929 / AMG-157)" PDB DOI: https://doi.org/10.2210/pdb5J13/pdb, 5 pages (2017).
Database, GenBank: AAK67490.1 [Online], "Sthymic stromal lymphopoietin [Homo sapiens]" https://www.ncbi.nlm.nih.gov/protein/AAK67490.1, 1 page (2001).
Database, GenBank: EHH54440.1 [Online], "hypothetical protein EGM_15282 [Macaca fascicularis]" https://www.ncbi.nlm.nih.gov/protein/EHH54440.1, 2 pages (2015).
Diver, S. et al., "Effect of tezepelumab on airway inflammatory cells, remodelling, and hyperresponsiveness in patients with moderate-to-severe uncontrolled asthma (Cascade): a double-blind, randomised, placebo-controlled, phase 2 trial," The Lancet Respir. Med., vol. 9; 1299-1312 (2021).
Dumet et al. "Insights into the IgG heavy chain engineering patent landscape as applied to IgG4 antibody development" MAbs. 11(8):1341-50 (2019).
Gauvreau et al. "Thymic stromal lymphopoietin: its role and potential as a therapeutic target in asthma" Expert Opin Ther Targets. Aug. 2020;24(8):777-792. doi: 10.1080/14728222.2020.1783242. Epub Jun. 27, 2020. PMID: 32567399.
Gorska, K. et al., "Comparison of Thymic Stromal Lymphopoietin Concentration in Various Human Biospecimens from Asthma and COPD Patients Measured with Two Different ELISA Kits," Advs. Exp. Medicine, Biology, DOI 10.1007/5584_2016_162; 9 pages (2016).
Hoy, S.M., "Tezepelumab: First Approval," Drugs, vol. 82; 461-468 (2022).
Li, Y. et al., "Elevated Expression of IL-33 and TSLP in the Airways of Human Asthmatics In Vivo: A Potential Biomarker of Severe Refractory Disease," The Journal of Immunology, vol. 200; No. 7; 2253-2262 (2018).
Ly, N. et al., "Pharmacokinetic and Pharmacodynamic Modeling of Tezepelumab to Guide Phase 3 Dose Selection for Patients With Severe Asthma," The Journal of Clinical Pharmacology, vol. 61; No. 7; 901-912 (2021).
Numazaki, M. et al., "ASP7266, a Novel Antibody against Human Thymic Stromal Lymphopoietin Receptor for the Treatment of Allergic Diseases," The Journal of Pharmacology and Experimental Therapeutics, vol. 380; 26-33 (2022).
Sanofi, "Late Breaking Abstract—Early improvement in asthmasmall airway dysfunction after one dose of SAR443765, a novel bispecific anti-thymic stromal lymphopoietin/anti-IL-13 nanobody molecule," European Respiratory Journal; 62: Suppl. 67, OA4296; 2 pages (2023).
Soumelis, V. et al., "Human epithelial cells trigger dendritic cell-mediated allergic inflammation by producing TSLP," Nature Immunology, vol. 3; No. 7; 673-680 (2002).
Venkataramani, S. et al., "Design and characterization of Zweimab and Doppelmab, high affinity dual antagonistic anti-TSLP/IL13 bispecific antibodies," Biochemical and Biophysical Research Communications, vol. 504; 19-24 (2018).
Verstraete et al. "Structure and antagonism of the receptor complex mediated by human TSLP in allergy and asthma" Nat Commun. 8:14937 (2017).
Verstraete, K. et al., "Structural basis of the proinflammatory signaling complex mediated by TSLP," Nature Structural & Molecular Biology, vol. 21; No. 4; 375-382 (2014).
Wechsler, M.E. et al., "Evaluation of the oral corticosteroid-sparing effect of tezepelumab in adults with oral corticosteroid-dependent asthma (Source): a randomised, placebo-controlled, phase 3 study," The Lancet; vol. 10; 650-660 (2022).
Ying, S. et al., "Expression and Cellular Provenance of Thymic Stromal Lymphopoietin and Chemokines in Patients with Severe Asthma and Chronic Obstructive Pulmonary Disease," The Journal of Immunology, vol. 181; No. 4; 2790-2798 (2008).
Ziegler et al. "The biology of thymic stromal lymphopoietin (TSLP)" Adv Pharmacol. 66:129-55 (2013).
Flynn, T. et al., "Amgen Inc. (Amgen): Framing expectations for upcoming Tezepelumab Ph3 asthma data," Goldman Sachs: Equity Research, 11 pages (2020).
"AstraZeneca/Amgen's Phase III tezepelumab potential to expand to noneosinopilic asthma patients backed by early data and MOA but caution remains, experts say," GlobalData, Insight Details, 4 pages (2020).
Gordon, J.D. et al., "Previewing approaching teze Phase III data, $3bn potential under our base-case, with a $5bn peak under our bull scenario," J.P. Morgan Cazenove, Europe Equity Research, AstraZeneca, 32 pages (2020).
EMA Assessment report Tezspire International non-proprietary name: tezepelumab Procedure No. EMEA/H/C/005588/0000 Jul. 21, 2022 EMA/682391/2022 Committee for Medicinal Products for Human Use (CHMP).
Menzies-Gow et al., "Unmet need in severe, uncontrolled asthma: can anti-TSLP therapy with tezepelumab provide a valuable new treatment option?" Respir Res. Oct. 15, 2020;21(1):268. doi: 10.1186/s12931-020-01505-x. PMID: 33059715; PMCID: PMC7560289.

(56) References Cited

OTHER PUBLICATIONS

International Search Report and Written Opinion received for PCT Patent Application No. PCT/US23/70789, mailed on Jan. 29, 2024, 23 pages.
International Search Report and Written Opinion received for PCT Patent Application No. PCT/US23/70790, mailed on Jan. 29, 2024, 25 pages.
Invitation to Pay Additional Fee received for PCT Patent Application No. PCT/US23/70789, mailed on Mar. 7, 2024, 20 pages.
Invitation to Pay Additional Fee received for PCT Patent Application No. PCT/US23/70790, mailed on Mar. 7, 2024, 20 pages.
Notification of Transmittal of the International Search Report and the Written Opinion for International Application No. PCT/US2023/070789, mailed Apr. 29, 2024.
Notification of Transmittal of the International Search Report and the Written Opinion for International Application No. PCT/US2023/070790, mailed Apr. 29, 2024.

* cited by examiner

```
                    **********  **
MFPFALLYVLSVSFRKIFILQLVGLVLTYDFTNCDFEKIKAAYLSTISKDLITYMSGTKSTEFNNTVSCSNRPHCLTE
                                                      ** *
IQSLTFNPTAGCASLAKEMFAMKTKAALAIWCPGYSETQINATQAMKKRRKRKVTTNKCLEQVSQLQGLWRRFNRPLL

KQQ(SEQ ID NO:1)
```

FIG. 1

|  | HCDR1 | HCDR2 |
|---|---|---|
|  | \*\*\* \*\*\* | \* |
| Reference | QMQLVESGGGVVQPGRSLRLSCAASGFTFRTYGMHWVRQAPGKGLEWVAVIWYDGSNKHYADSVKGR |
| AB-1 | QMQLVESGGGVVQPGRSLRLSCAASGFTFRTYGMHWVRQAPGKGLEWVAVVWYSGSYTHYADSVKGR |
| AB-2 | QMQLVESGGGVVQPGRSLRLSCAASGFTFRTYGMHWVRQAPGKGLEWVAVIWYDGTYTHYADSVKGR |
| AB-3 | QMQLVESGGGVVQPGRSLRLSCAASGFTFRTYGMHWVRQAPGKGLEWVAVIWYSGSDTHYADSVKGR |
| AB-4 | QMQLVESGGGVVQPGRSLRLSCAASGFTFRTYGMHWVRQAPGKGLEWVAVVWYDGYDTHYADSVKGR |
| AB-5 | QMQLVESGGGVVQPGRSLRLSCAASGFTFRTYGMHWVRQAPGKGLEWVAVVWYDGSDIHYADSVKGR |
| AB-6 | QMQLVESGGGVVQPGRSLRLSCAASGFTFRTYGMHWVRQAPGKGLEWVAVIWYSGAYIHYADSVKGR |
| AB-7 | QMQLVESGGGVVQPGRSLRLSCAASGFTFRTYGMHWVRQAPGKGLEWVAVIWYDGSYTHYADSVKGR |
| AB-8 | QMQLVESGGGVVQPGRSLRLSCAASGFTFRTYGMHWVRQAPGKGLEWVAVIWYDGSYTHYADSVKGR |
| AB-9 | QMQLVESGGGVVQPGRSLRLSCAASGFTFRTYGMHWVRQAPGKGLEWVAVIWYSGTTTHYADSVKGR |
| AB-10 | QMQLVESGGGVVQPGRSLRLSCAASGFTFRTYGMHWVRQAPGKGLEWVAVISYSGSYIHYADSVKGR |
| AB-11 | QMQLVESGGGVVQPGRSLRLSCAASGFTFRTYGMHWVRQAPGKGLEWVAVVWYDGSNTHYADSVKGR |
| AB-12 | QMQLVESGGGVVQPGRSLRLSCAASGFTFRTYGMHWVRQAPGKGLEWVAVISYDGSTKHYADSVKGR |
| AB-13 | QMQLVESGGGVVQPGRSLRLSCAASGFTFRTYGMHWVRQAPGKGLEWVAVISYDGSNTHYADSVKGR |
| AB-14 | QMQLVESGGGVVQPGRSLRLSCAASGFTFRTYGMHWVRQAPGKGLEWVAVIWYDGSTKHYADSVKGR |

FIG. 2A

| | HCDR3 | |
|---|---|---|
| | `* **** * *****  *` | |
| Reference | FTITRDNSKNTLNLQMNSLRAEDTAVYYCARAPQWELVHEAFDIWGQGTMVTVSS | (SEQ ID NO:3) |
| AB-1 | FTITRDNSKNTLNLQMNSLRAEDTAVYYCSRSPQWEDIFEAMDIWGQGTMVTVSS | (SEQ ID NO:4) |
| AB-2 | FTITRDNSKNTLNLQMNSLRAEDTAVYYCARSPQWEEIFEAMDIWGQGTMVTVSS | (SEQ ID NO:5) |
| AB-3 | FTITRDNSKNTLNLQMNSLRAEDTAVYYCARSPQWESIFEAFDIWGQGTMVTVSS | (SEQ ID NO:6) |
| AB-4 | FTITRDNSKNTLNLQMNSLRAEDTAVYYCARSPQWEDIFESMDVWGQGTMVTVSS | (SEQ ID NO:7) |
| AB-5 | FTITRDNSKNTLNLQMNSLRAEDTAVYYCARSPQWEDIFESMDIWGQGTMVTVSS | (SEQ ID NO:8) |
| AB-6 | FTITRDNSKNTLNLQMNSLRAEDTAVYYCSRSPQWEDIFESMDIWGQGTMVTVSS | (SEQ ID NO:9) |
| AB-7 | FTITRDNSKNTLNLQMNSLRAEDTAVYYCSRSPQWEDIFEAMDIWGQGTMVTVSS | (SEQ ID NO:10) |
| AB-8 | FTITRDNSKNTLNLQMNSLRAEDTAVYYCARSPQWEDIFEAFDIWGQGTMVTVSS | (SEQ ID NO:11) |
| AB-9 | FTITRDNSKNTLNLQMNSLRAEDTAVYYCARSPQWESIFEAFDIWGQGTMVTVSS | (SEQ ID NO:12) |
| AB-10 | FTITRDNSKNTLNLQMNSLRAEDTAVYYCSRSPQWEDIFESMDIWGQGTMVTVSS | (SEQ ID NO:13) |
| AB-11 | FTITRDNSKNTLNLQMNSLRAEDTAVYYCTRSPQWEEVYEALDIWGQGTMVTVSS | (SEQ ID NO:14) |
| AB-12 | FTITRDNSKNTLNLQMNSLRAEDTAVYYCARAPQWESVHEAFDIWGQGTMVTVSS | (SEQ ID NO:15) |
| AB-13 | FTITRDNSKNTLNLQMNSLRAEDTAVYYCARAPQWESVYEAFDIWGQGTMVTVSS | (SEQ ID NO:16) |
| AB-14 | FTITRDNSKNTLNLQMNSLRAEDTAVYYCARAPQWELVHEAFDIWGQGTMVTVSS | (SEQ ID NO:17) |

FIG. 2B

| | LCDR1 | LCDR2 |
|---|---|---|
| Reference | SYVLTQPPSVSVAPGQTARITCGGNNLGSKSVHWYQQKPGQAPVLVVYDDSDRPSWIPER | |
| AB-1,3,8,9 | SYVLTQPPSVSVAPGQTARITCGGNNIGSKSVHWYQQKPGQAPVLVVYDDSDRPSWIPER | |
| AB-2 | SYVLTQPPSVSVAPGQTARITCGGNNIGSKSVHWYQQKPGQAPVLVVYDDSDRPSWIPER | |
| AB-4 | SYVLTQPPSVSVAPGQTARITCGGNNYIGSFSVHWYQQKPGQAPVLVVYDDSDRPSWIPER | |
| AB-5 | SYVLTQPPSVSVAPGQTARITCGGNNLGSKSVHWYQQKPGQAPVLVVYDDSDRPSWIPER | |
| AB-6 | SYVLTQPPSVSVAPGQTARITCGGNNIGSKSVHWYQQKPGQAPVLVVYDDSDRPSWIPER | |
| AB-7 | SYVLTQPPSVSVAPGQTARITCGGNNLGSYSVHWYQQKPGQAPVLVVYDDSDRPSWIPER | |
| AB-10 | SYVLTQPPSVSVAPGQTARITCGGNNIGSKNVHWYQQKPGQAPVLVVYDDSDRPSWIPER | |
| AB-11 | SYVLTQPPSVSVAPGQTARITCGGNNIGSFSVHWYQQKPGQAPVLVVYDDSDRPSWIPER | |
| AB-12 | SYVLTQPPSVSVAPGQTARITCGGNNIGRFSVHWYQQKPGQAPVLVVYDDSDRPSWIPER | |
| AB-13 | SYVLTQPPSVSVAPGQTARITCGGNNLGSFSVHWYQQKPGQAPVLVVYDDSDRPSWIPER | |
| AB-14 | SYVLTQPPSVSVAPGQTARITCGGNNIGSKNVHWYQQKPGQAPVLVVYDDSDRPSWIPER | |

FIG. 3A

LCDR3

| | |
|---|---|
| Reference | FSGSNSGNTATLTISRGEAGDEADYYCQVWDSSSDHVVFGGGTKLTVL (SEQ ID NO:19) |
| AB-1,3,8,9 | FSGSNSGNTATLTISRGEAGDEADYYCQVWDSSSSLVVFGGGTKLTVL (SEQ ID NO:20) |
| AB-2 | FSGSNSGNTATLTISRGEAGDEADYYCQIWDSSSLVVFGGGTKLTVL (SEQ ID NO:21) |
| AB-4 | FSGSNSGNTATLTISRGEAGDEADYYCQIYVSASRLVVFGGGTKLTVL (SEQ ID NO:22) |
| AB-5 | FSGSNSGNTATLTISRGEAGDEADYYCQVWDMSSDLVVFGGGTKLTVL (SEQ ID NO:23) |
| AB-6 | FSGSNSGNTATLTISRGEAGDEADYYCQVWDSSSDHVVFGGGTKLTVL (SEQ ID NO:24) |
| AB-7 | FSGSNSGNTATLTISRGEAGDEADYYCQIWDSSSDHVVFGGGTKLTVL (SEQ ID NO:25) |
| AB-10 | FSGSNSGNTATLTISRGEAGDEADYYCQVWDMSSSLVVFGGGTKLTVL (SEQ ID NO:26) |
| AB-11 | FSGSNSGNTATLTISRGEAGDEADYYCQVWDSSDFLVVFGGGTKLTVL (SEQ ID NO:27) |
| AB-12 | FSGSNSGNTATLTISRGEAGDEADYYCQVWSSTSRHVVFGGGTKLTVL (SEQ ID NO:28) |
| AB-13 | FSGSNSGNTATLTISRGEAGDEADYYCQVWVSTSDKVVFGGGTKLTVL (SEQ ID NO:29) |
| AB-14 | FSGSNSGNTATLTISRGEAGDEADYYCQVWDSSEDLVVFGGGTKLTVL (SEQ ID NO:29) |
| AB-14 | FSGSNSGNTATLTISRGEAGDEADYYCQVWDESSDEVVFGGGTKLTVL (SEQ ID NO:30) |

FIG. 3B

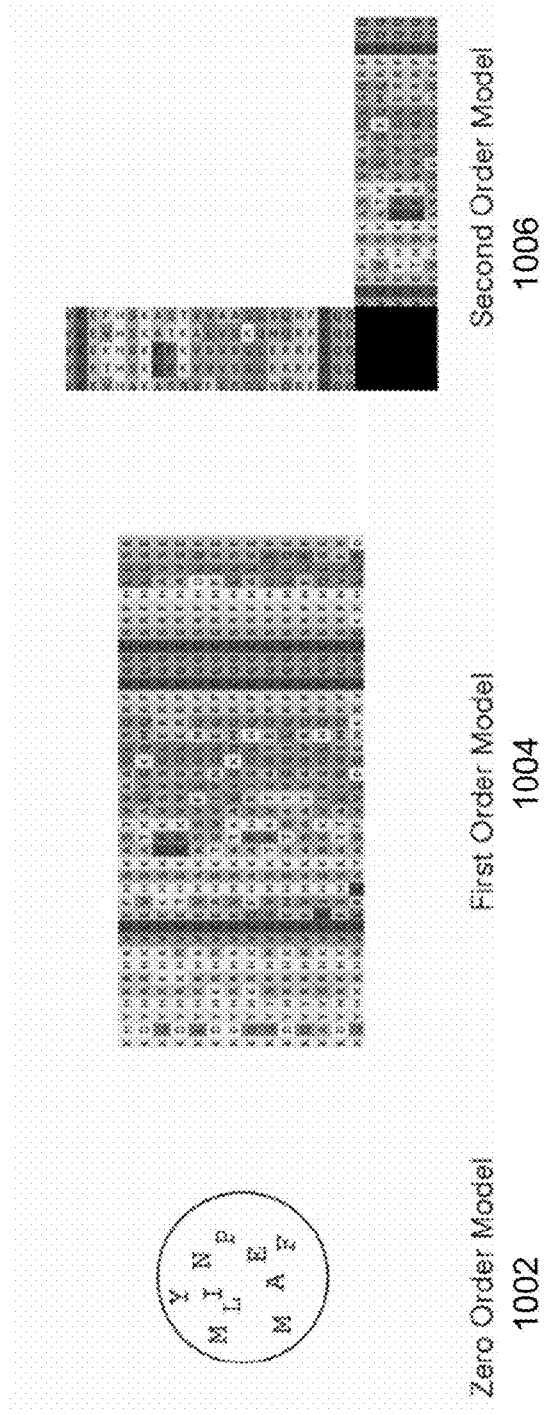

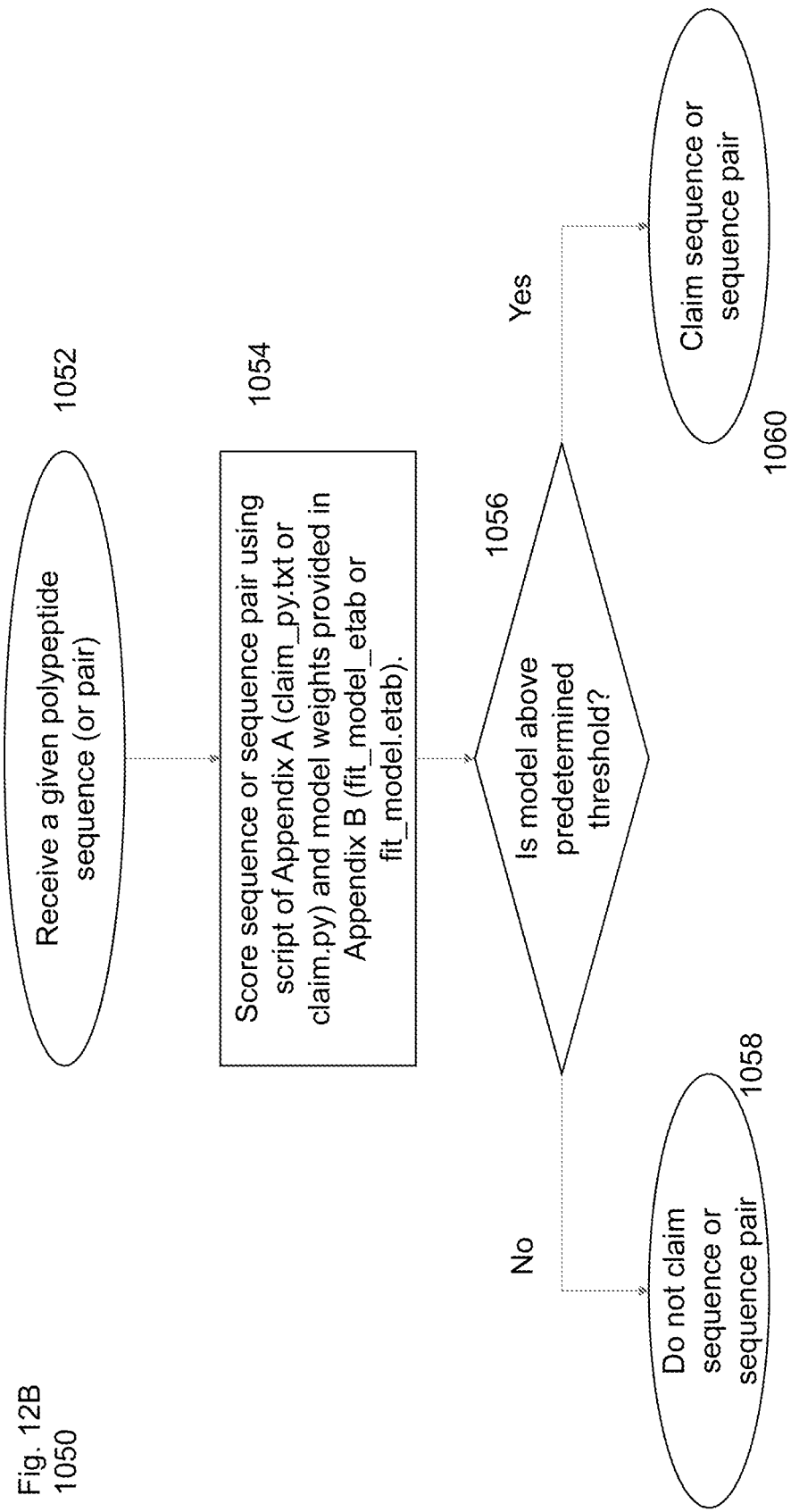

ANTIGEN BINDING MOLECULES TARGETING THYMIC STROMAL LYMPHOPOIETIN (TSLP)

RELATED APPLICATION(S)

This application claims the benefit of U.S. Provisional Application No. 63/369,152, filed on Jul. 22, 2022; U.S. Provisional Application No. 63/369,158, filed on Jul. 22, 2022; U.S. Provisional Application No. 63/369,165, filed on Jul. 22, 2022; U.S. Provisional Application No. 63/369,175, filed on Jul. 22, 2022; U.S. Provisional Application No. 63/369,202, filed on Jul. 22, 2022; U.S. Provisional Application No. 63/369,203, filed on Jul. 22, 2022; U.S. Provisional Application No. 63/369,204, filed on Jul. 22, 2022; and U.S. Provisional Application No. 63/369,206, filed on Jul. 22, 2022. The entire teachings of the above applications are incorporated herein by reference.

INCORPORATION BY REFERENCE OF MATERIAL IN XML

This application incorporates by reference the Sequence Listing contained in the following eXtensible Markup Language (XML) file being submitted concurrently herewith:
  a) File name: 57081061003_Sequence_Listing.xml; created Jul. 21, 2023, 212,457 Bytes in size.

INCORPORATION BY REFERENCE OF MATERIAL IN AN ASCII FILE

This application incorporates by reference the Computer Program Listing contained in the following ASCII file being submitted concurrently herewith:
  a) File name: claim.txt; created Jul. 20, 2023, 4,774 Bytes in size.
  b) File name: fit_model.txt; created Jul. 20, 2023, 2,888,059 Bytes in size.

BACKGROUND

Thymic stromal lymphopoietin (TSLP) is a cytokine that has been implicated in the pathogenesis of a variety of inflammatory conditions. Released upon epithelial exposure to "insults" such as allergens, TSLP initiates a cascade of downstream inflammation. TSLP receptors (TSLPRs) are expressed in a wide range of cell types, including airway smooth muscle cells (ASMCs), basophils, dendritic cells, eosinophils, group 2 innate lymphoid cells (ILC2s), hematopoietic progenitor cells, lymphocytes, macrophages, mast cells and monocytes (Gauvreau et al., *Thymic stromal lymphopoietin: its role and potential as a therapeutic target in asthma*, Expert Opin Ther Targets 24(8):777-92 (2020)). There is compelling evidence that dysregulated TSLP expression can lead to allergic disease through the development of type 2 inflammatory responses (Ziegler et al., *The biology of thymic stromal lymphopoietin (TSLP)*, Adv Pharmacol. 66:129-55 (2013)).

SUMMARY

There is a critical need for therapeutic agents for modulating (e.g., reducing or neutralizing) thymic stromal lymphopoietin (TSLP) binding and/or activity. The disclosure provides such agents.

The disclosure provided herein is based, in part, on the discovery that polypeptides disclosed herein specifically bind to TSLP and demonstrate various additional beneficial properties. Accordingly, the disclosure generally relates to polypeptides (e.g., antibodies), compositions (e.g., pharmaceutical compositions) and methods that are useful for modulating (e.g., reducing or neutralizing) TSLP function and/or activity (e.g., in vivo).

Provided herein, among other things, are polypeptides (e.g., antibodies and antigen binding fragments thereof) that specifically bind TSLP (e.g., a full-length human TSLP) or a variant thereof. In some embodiments, a polypeptide disclosed herein binds TSLP at an AB-loop region and C-terminal region of helix D.

In some embodiments, a polypeptide modulates (e.g., reduces, such as inhibits) binding between TSLP and TSLPR (e.g., alone or in a heterodimeric complex with interleukin 7 receptor alpha (IL-7Rα)). In some embodiments, a polypeptide modulates (e.g., reduces, such as inhibits) TSLP-mediated signaling in vitro and/or in vivo.

The disclosure provides, among other things, a polypeptide (e.g., an antibody or an antigen binding fragment thereof) that specifically binds a TSLP, wherein the polypeptide has one or more properties selected from:
  a binding affinity for a TSLP characterized by a $K_D$ of 10 pM or less (e.g., as measured by KinExA);
  a binding specificity for the AB-loop region and the C-terminal region of helix D of a TSLP;
  a neutralizing activity against a TSLP (e.g., a full-length human TSLP); or
  an inhibitory activity against TSLP-mediated signaling, or a combination of the foregoing.

The disclosure also provides, among other things, a polypeptide (e.g., an antibody or an antigen binding fragment thereof) that comprises a paratope that is substantially similar to the paratope of an antibody comprising an immunoglobulin heavy chain variable domain ($V_H$)/an immunoglobulin light chain variable domain ($V_L$) combination selected from:
  SEQ ID NO:4 and SEQ ID NO:20 (AB-1);
  SEQ ID NO:5 and SEQ ID NO: 21 (AB-2);
  SEQ ID NO:6 and SEQ ID NO:20 (AB-3);
  SEQ ID NO:7 and SEQ ID NO:22 (AB-4);
  SEQ ID NO:8 and SEQ ID NO:23 (AB-5);
  SEQ ID NO:9 and SEQ ID NO:24 (AB-6);
  SEQ ID NO:10 and SEQ ID NO:25 (AB-7);
  SEQ ID NO:11 and SEQ ID NO:20 (AB-8);
  SEQ ID NO:12 and SEQ ID NO:20 (AB-9);
  SEQ ID NO:13 and SEQ ID NO:26 (AB-10);
  SEQ ID NO:14 and SEQ ID NO:27 (AB-11);
  SEQ ID NO:15 and SEQ ID NO:28 (AB-12);
  SEQ ID NO:16 and SEQ ID NO:29 (AB-13); or
  SEQ ID NO:17 and SEQ ID NO:30 (AB-14), or
  a combination of the foregoing,
  wherein the polypeptide does not comprise a heavy chain comprising SEQ ID NO:81 and a light chain comprising SEQ ID NO:82.

In some embodiments, a polypeptide comprises a paratope that is substantially similar to a paratope of an antibody comprising a $V_H$/$V_L$ combination selected from:
  SEQ ID NO:4 and SEQ ID NO:20 (AB-1);
  SEQ ID NO:5 and SEQ ID NO:21 (AB-2);
  SEQ ID NO:6 and SEQ ID NO:20 (AB-3); or
  SEQ ID NO:7 and SEQ ID NO:22 (AB-4), or
  a combination of the foregoing,
  wherein the polypeptide does not comprise a heavy chain comprising SEQ ID NO:81 and a light chain comprising SEQ ID NO:82.

The disclosure also provides, among other things, a polypeptide (e.g., an antibody or an antigen binding fragment thereof) comprising:
- a $V_H$ amino acid sequence comprising a heavy chain complementarity determining region 1 (HCDR1), a heavy chain complementarity determining region 2 (HCDR2) and a heavy chain complementarity determining region 3 (HCDR3) that are substantially similar to a HCDR1, a HCDR2 and a HCDR3, respectively, of the amino acid sequence of any one of SEQ ID NOs: 4-17; and
- a $V_L$ amino acid sequence comprising a light chain complementarity determining region 1 (LCDR1), a light chain complementarity determining region 2 (LCDR2) and a light chain complementarity determining region 3 (LCDR3) that are substantially similar to a LCDR1, a LCDR2 and a LCDR3, respectively, of the amino acid sequence of any one of SEQ ID NOs:20-30, wherein the polypeptide does not comprise a heavy chain comprising SEQ ID NO:81 and a light chain comprising SEQ ID NO:82.

In some embodiments, a polypeptide comprises:
- a $V_H$ amino acid sequence comprising a HCDR1, a HCDR2 and a HCDR3 that are substantially similar to a HCDR1, a HCDR2 and a HCDR3, respectively, of the amino acid sequence of any one of SEQ ID NOs:4-7; and
- a $V_L$ amino acid sequence comprising a LCDR1, a LCDR2 and a LCDR3 that are substantially similar to a LCDR1, a LCDR2 and a LCDR3, respectively, of the amino acid sequence of any one of SEQ ID NOs:20-22.

In some embodiments, a polypeptide comprises a HCDR1, a HCDR2 and a HCDR3, and a LCDR1, a LCDR2 and a LCDR3, of an antibody comprising a $V_H/V_L$ combination selected from:
- SEQ ID NO:4 and SEQ ID NO:20 (AB-1);
- SEQ ID NO:5 and SEQ ID NO: 21 (AB-2);
- SEQ ID NO:6 and SEQ ID NO:20 (AB-3);
- SEQ ID NO:7 and SEQ ID NO:22 (AB-4);
- SEQ ID NO:8 and SEQ ID NO:23 (AB-5);
- SEQ ID NO:9 and SEQ ID NO:24 (AB-6);
- SEQ ID NO:10 and SEQ ID NO:25 (AB-7);
- SEQ ID NO:11 and SEQ ID NO:20 (AB-8);
- SEQ ID NO:12 and SEQ ID NO:20 (AB-9);
- SEQ ID NO:13 and SEQ ID NO:26 (AB-10);
- SEQ ID NO:14 and SEQ ID NO:27 (AB-11);
- SEQ ID NO:15 and SEQ ID NO:28 (AB-12);
- SEQ ID NO:16 and SEQ ID NO:29 (AB-13); or
- SEQ ID NO:17 and SEQ ID NO:30 (AB-14).

In some embodiments, a polypeptide further comprises a paratope that has 100% sequence identity to a paratope of an antibody comprising a $V_H/V_L$ combination selected from:
- SEQ ID NO:4 and SEQ ID NO:20 (AB-1);
- SEQ ID NO:5 and SEQ ID NO: 21 (AB-2);
- SEQ ID NO:6 and SEQ ID NO:20 (AB-3);
- SEQ ID NO:7 and SEQ ID NO:22 (AB-4);
- SEQ ID NO:8 and SEQ ID NO:23 (AB-5);
- SEQ ID NO:9 and SEQ ID NO:24 (AB-6);
- SEQ ID NO:10 and SEQ ID NO:25 (AB-7);
- SEQ ID NO:11 and SEQ ID NO:20 (AB-8);
- SEQ ID NO:12 and SEQ ID NO:20 (AB-9);
- SEQ ID NO:13 and SEQ ID NO:26 (AB-10);
- SEQ ID NO:14 and SEQ ID NO:27 (AB-11);
- SEQ ID NO:15 and SEQ ID NO:28 (AB-12);
- SEQ ID NO:16 and SEQ ID NO:29 (AB-13); or
- SEQ ID NO:17 and SEQ ID NO:30 (AB-14).

In some embodiments, a polypeptide comprises a HCDR1, a HCDR2 and a HCDR3, and a LCDR1, a LCDR2 and a LCDR3, of an antibody comprising a $V_H/V_L$ combination selected from:
- SEQ ID NO:4 and SEQ ID NO:20 (AB-1);
- SEQ ID NO:5 and SEQ ID NO:21 (AB-2);
- SEQ ID NO:6 and SEQ ID NO:20 (AB-3); or
- SEQ ID NO:7 and SEQ ID NO:22 (AB-4).

In some embodiments, a polypeptide comprises a paratope that has 100% sequence identity to a paratope of an antibody comprising a $V_H/V_L$ combination selected from:
- SEQ ID NO:4 and SEQ ID NO:20 (AB-1);
- SEQ ID NO:5 and SEQ ID NO:21 (AB-2);
- SEQ ID NO:6 and SEQ ID NO:20 (AB-3); or
- SEQ ID NO:7 and SEQ ID NO:22 (AB-4).

The disclosure also provides, among other things, a polypeptide (e.g., an antibody or an antigen binding fragment thereof) that comprises a $V_H$ comprising SEQ ID NO:2, wherein:
- $X_1$ is not I;
- $X_2$ is not W;
- $X_3$ is not D;
- $X_4$ is not S;
- $X_5$ is not N;
- $X_6$ is not K;
- $X_7$ is not A;
- $X_8$ is not A;
- $X_9$ is not L;
- $X_{10}$ is not V;
- $X_{11}$ is not H,
- $X_{12}$ is not A;
- $X_{13}$ is not F;
- $X_{14}$ is not I, or any combination of the foregoing.

In some embodiments, a polypeptide comprises a $V_L$ comprising SEQ ID NO:18, wherein:
- $X_{15}$ is not N;
- $X_{16}$ is not L;
- $X_{17}$ is not S;
- $X_{18}$ is not K;
- $X_{19}$ is not S;
- $X_{20}$ is not V;
- $X_{21}$ is not W;
- $X_{22}$ is not D;
- $X_{23}$ is not S;
- $X_{24}$ is not S;
- $X_{25}$ is not S;
- $X_{26}$ is not D;
- $X_{27}$ is not H, or any combination of the foregoing.

The disclosure also provides, among other things, a polypeptide (e.g., an antibody or an antigen binding fragment thereof) comprising a $V_H$ sequence that has at least 70% sequence identity to SEQ ID NO:3, a $V_L$ sequence that has at least 70% sequence identity to SEQ ID NO:19, or both, wherein the $V_H$ sequence does not comprise SEQ ID NO:3, the $V_L$ sequence does not comprise SEQ ID NO:19, or both.

The disclosure also provides, among other things, a polypeptide comprising:
a) a HCDR1 comprising the amino acid sequence of SEQ ID NO:31, a HCDR2 comprising the amino acid sequence of SEQ ID NO:35, and a HCDR3 comprising the amino acid sequence of SEQ ID NO:50; and
b) a LCDR 1 comprising the amino acid sequence of SEQ ID NO:60, a LCDR2 comprising the amino acid sequence DDS, and a LCDR3 comprising the amino acid sequence of SEQ ID NO:71, wherein the polypeptide is an antibody or an antigen-binding fragment thereof.

The disclosure also provides, among other things, a polypeptide comprising:
a) a HCDR1 consisting of the amino acid sequence of SEQ ID NO:31, a HCDR2 consisting of the amino acid sequence of SEQ ID NO:35, and a HCDR3 consisting of the amino acid sequence of SEQ ID NO:50; and
b) a LCDR 1 consisting of the amino acid sequence of SEQ ID NO:60, a LCDR2 consisting of the amino acid sequence DDS, and a LCDR3 consisting of the amino acid sequence of SEQ ID NO:71, wherein the polypeptide is an antibody or an antigen-binding fragment thereof.

In some embodiments, a polypeptide comprises:
a) a $V_H$ that is humanized, contains human framework regions, or a combination thereof;
b) a $V_L$ that is humanized, contains human framework regions, or a combination thereof, or
both a) and b).

In some embodiments, a polypeptide comprises:
a) a $V_H$ comprising the amino acid sequence of SEQ ID NO:5;
b) a $V_L$ comprising the amino acid sequence of SEQ ID NO:21, or
both a) and b).

In some embodiments, an antigen-binding fragment comprises a single-chain fragment variable (scFv), a variable heavy domain of heavy chain ($V_{HH}$), a fragment antigen-binding (Fab), a Fab' or a F(ab')$_2$.

In some embodiments, a polypeptide comprises:
a) an antibody heavy chain constant domain;
b) an antibody light chain constant domain,
or both a) and b).

In some embodiments, an antibody heavy chain constant domain is an IgG1, IgG2, IgG3 or IgG4 constant domain.

In some embodiments, an antibody heavy chain constant domain is an IgG1 or IgG2 constant domain.

In some embodiments, an antibody heavy chain constant domain comprises one or more mutations which increase serum half-life of the antibody or antigen-binding fragment thereof in humans. In some embodiments, an antibody heavy chain constant domain comprises, relative to a wild-type human IgG constant domain, amino acid substitutions with tyrosine, threonine and glutamic acid at amino acid residues 252, 254 and 256, respectively, wherein the amino acid residues are numbered according to the EU index as in Kabat.

In some embodiments, a polypeptide comprises:
a) an antibody heavy chain (HC) comprising the amino acid sequence of SEQ ID NO:92;
b) an antibody light chain (LC) comprising the amino acid sequence of SEQ ID NO:120, or
both a) and b).

In some embodiments, a polypeptide comprises:
a) an antibody heavy chain (HC) comprising the amino acid sequence of SEQ ID NO:106;
b) an antibody light chain (LC) comprising the amino acid sequence of SEQ ID NO:120, or
both a) and b).

In some embodiments, a polypeptide specifically binds TSLP.

In some embodiments, a polypeptide is a fusion protein.

In some embodiments, the disclosure provides a polynucleotide encoding a polypeptide disclosed herein, a vector comprising such a polynucleotide, and/or a host cell comprising such a polynucleotide and/or vector.

In some embodiments, the disclosure provides a composition (e.g., a pharmaceutical composition) comprising a polypeptide disclosed herein. In some embodiments, a composition further comprises one or more pharmaceutical excipients, diluents, or carriers. In some embodiments, a composition further comprises one or more additional therapeutic agents (e.g., an anti-inflammatory agent). In some embodiment, a polypeptide is conjugated (directly or by a linker) to one or more additional therapeutic agents (e.g., an anti-inflammatory agent). In some embodiments, one or more additional therapeutic agents comprise a corticosteroid, a beta-agonist, a muscarinic antagonist, an anti-inflammatory agent, an IL-4 and/or IL-13 antagonist (e.g., an antibody or antigen-binding fragment thereof targeting IL-13, IL-4 or IL-4R), or a combination thereof.

The disclosure also provides, among other things, a method of treating a subject in need thereof (e.g., a subject having a TSLP-associated disease or condition), comprising administering to the subject an effective amount of a polypeptide disclosed herein and/or a composition (e.g., pharmaceutical composition) comprising one or more polypeptides disclosed herein.

The disclosure also provides, among other things, a method of modulating (e.g., reducing) a TSLP-mediated signaling in a cell (e.g., a cell in a subject), comprising contacting the cell with a polypeptide disclosed herein and/or a composition (e.g., pharmaceutical composition) comprising one or more polypeptides disclosed herein.

In some embodiments, a subject has asthma, atopic dermatitis (AD), allergic conjunctivitis, chronic obstructive pulmonary disease (COPD), chronic spontaneous urticaria (CSU), rheumatoid arthritis (RA), rhinosinusitis (RS), eosinophilic esophagitis (EE), or a food-hypersensitivity reaction. In some embodiments, a subject has moderate asthma. In some embodiments, a subject has severe asthma. In some embodiments, a subject has COPD. In some embodiments, a subject has COPD and/or either moderate asthma or severe asthma.

The disclosure also provides, among other things, a method of reducing binding of TSLP to a TSLP receptor (TSLPR) on a cell in a subject, comprising contacting the cell with an effective amount of a composition (e.g., pharmaceutical composition) comprising one or more polypeptides disclosed herein.

The disclosure also provides, among other things, a method of making a polypeptide disclosed herein, comprising culturing a host cell comprising a nucleotide sequence encoding the polypeptide under conditions where the polypeptide is expressed in the host cell.

The disclosure also provides, among other things, a computer-implemented method that comprises scoring a polypeptide comprising an amino acid sequence with a computationally binding optimized (CBO) model. The CBO model, for each amino acid position of the amino acid sequence of the polypeptide, calculates multiple energy scores, the multiple energy scores based on having substituted the amino acid at a given position in the amino acid sequence with each of a plurality of different amino acids. The CBO model further adds each energy score calculated to an array. The CBO model further generates a normalized sum of the energy scores for each position. The CBO model further calculates a logarithm of each energy score calculated. The CBO model further generates a score of the polypeptide by summing the logarithms of each energy score calculated, the score representing a functional property of the polypeptide.

The disclosure also provides, among other things, a system that includes a processor and a memory with computer code instructions stored thereon. The processor and the memory, with the computer code instructions, are configured to cause the system to score a polypeptide sequence with a CBO model. The CBO model, for each amino acid position of the amino acid sequence of the polypeptide, calculates multiple energy scores, the multiple energy scores based on having substituted the amino acid at a given position in the amino acid sequence with each of a plurality of different amino acids. The CBO model further adds each energy score calculated to an array. The CBO model further generates a normalized sum of the energy scores for each position. The CBO model further calculates a logarithm of each energy score calculated. The CBO model further generates a score of the polypeptide by summing the logarithms of each energy score calculated, the score representing a functional property of the polypeptide.

Figure 13:
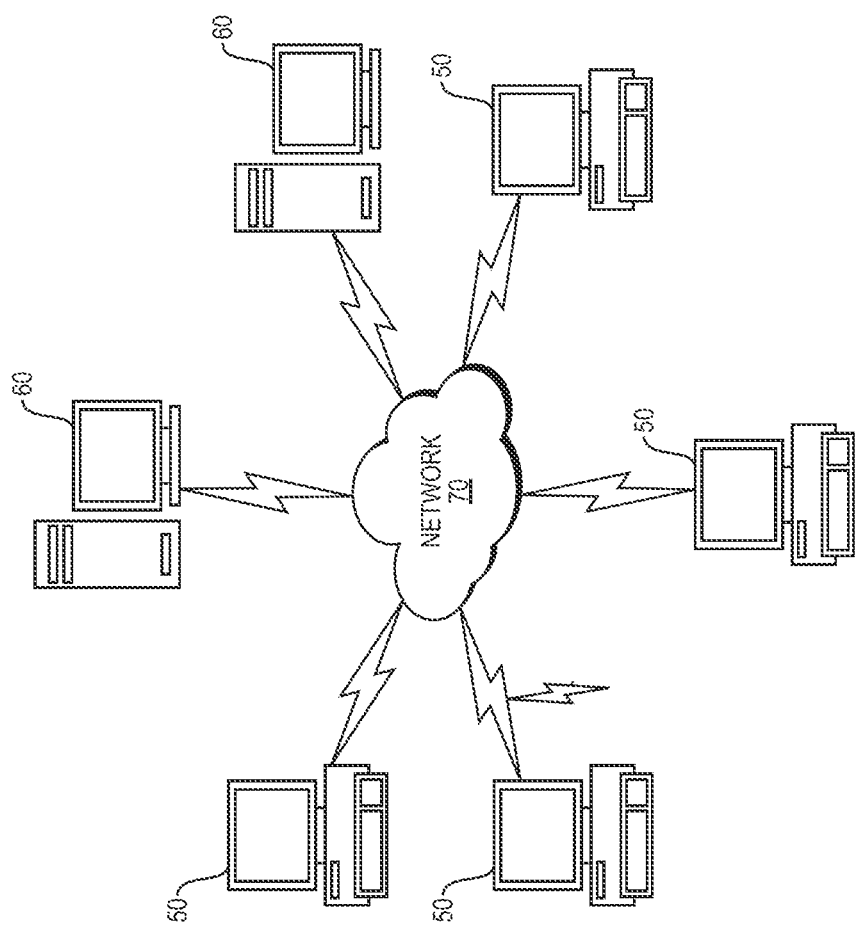

Also provide herein, among other things, is a polypeptide that specifically binds a thymic stromal lymphopoietin (TSLP) and comprises an amino acid sequence that is assigned a score above a predetermined threshold by a computationally binding optimized (CBO) model upon scoring the amino acid sequence of the polypeptide.

The disclosure also provides, among other things, a polypeptide that binds human thymic stromal lymphopoietin (TSLP) and which is designed by a method comprising generating a polypeptide sequence with a CBO model. In some embodiments, the polypeptide is further designed by verifying the generated polypeptide sequence using the CBO model by, for each amino acid position of the polypeptide sequence, calculating a plurality of energy scores. The energy scores can be based on having substituted the amino acid at a given position in the polypeptide sequence with each of a plurality of different amino acids. In some embodiments, the polypeptide is further verified by adding each energy score calculated to an array. In some embodiments, the polypeptide is further verified by generating a normalized sum of the energy scores for each position. In some embodiments, the polypeptide is further verified by calculating a logarithm of each energy score calculated. In some embodiments, the polypeptide is further verified by generating a score of the polypeptide sequence by summing the logarithms of each energy score calculated. The score represents a functional property of the polypeptide's ability to bind to human TSLP. In some embodiments, the polypeptide sequence is verified if the polypeptide scores above a particular threshold.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

In the drawings, "Reference" refers to the Reference Antibody.

FIG. 1 depicts the amino acid sequence of human thymic stromal lymphopoietin (TSLP) (SEQ ID NO:1). The epitope residues bound by the Reference Antibody disclosed herein are indicated by asterisks.

FIGS. 2A-2B depict an alignment of heavy chain variable domain ($V_H$) amino acid sequences of the Reference Antibody and example antibodies AB-1 to AB-14. The heavy chain complementarity determining region (HCDR) amino acid sequences as determined by ImMunoGeneTics (IMGT) numbering are indicated using underlining. The bold letters indicate variable residues (designated throughout this disclosure by "$X_n$") in the Reference Antibody and AB-1 to AB-14. "*" indicates paratope residues. See also $V_H$ consensus sequence (SEQ ID NO:2) in Table 1. Paratope residues were defined as antibody residues in the Reference Antibody that, when bound to human TSLP, are within 5 angstroms of the antigen.

FIGS. 3A-3B depict an alignment of light chain variable domain ($V_L$) amino acid sequences of the Reference Antibody and example antibodies AB-1 to AB-14. The heavy chain complementarity determining region (LCDR) amino acid sequences as determined by ImMunoGeneTics (IMGT) numbering are indicated using underlining. The bold letters indicate variable residues (designated throughout this disclosure by "$X_n$") in the Reference Antibody and AB-1 to AB-14. See also $V_L$ consensus sequence (SEQ ID NO:18) in Table 2.

FIGS. 4A-4B show binding profiles of non-limiting examples of anti-TSLP antibodies to human TSLP (hTSLP), generated using a direct enzyme-linked immunosorbent assay (ELISA).

FIGS. 5A-5B show binding profiles of non-limiting examples of anti-TSLP antibodies to cynomolgus monkey TSLP (cynoTSLP), generated using a direct ELISA.

FIGS. 6A-6B show binding profiles of non-limiting examples of anti-TSLP antibodies to hTSLP, generated using a blocking ELISA.

FIGS. 7A-7B show binding profiles of non-limiting examples of anti-TSLP antibodies to cynoTSLP, generated using a blocking ELISA.

FIGS. 8A-8C show that non-limiting examples of anti-TSLP antibodies neutralizing binding of hTSLP to TSLP receptor (TSLPR). Ba/F3-STAT5-Luc cells, STAT5 reporter cells that express hTSLPR and hIL-7Rα, were used to assess binding between hTSLP and TSLPR based on hTSLP-induced STAT5 activity. FIG. 8A shows TSLP-mediated STAT5 signaling as a function of hTSLP concentration. FIGS. 8B-8C show effects of the anti-TSLP antibodies on TSLP-mediated STAT5 signaling.

FIGS. 9A-9B are graphs showing that example anti-TSLP antibodies block TSLP binding to human myeloid dendritic cells (mDCs) from peripheral blood. The curves show effects of the anti-TSLP antibodies on TSLP-induced CCL17 expression by mDCs from one representative donor.

FIGS. 10A-10D are graphs showing binding profiles of AB-2a, AB-2b, the Reference Antibody, IgG1 isotype control, and IgG2 isotype control, generated using a direct ELISA. FIG. 10A shows binding profiles to hTSLP. FIG. 10B shows binding profiles to cynoTSLP. FIG. 10C shows binding profiles to mouse TSLP. FIG. 10D shows binding profiles to human IL-7.

FIGS. 11A-11B are graphs showing Ba/F3 assay results for AB-2a, AB-2b, the Reference Antibody, IgG1 isotype control, and IgG2 isotype control. FIG. 11A shows human TSLPR/IL-7Rα Ba/F3 assay results. FIG. 11B shows cyno TSLPR/IL-7Rα Ba/F3 assay results.

FIG. 12A is a diagram illustrating zero-order (1002), first-order (1004), and second-order (1006) models.

FIG. 12B is a flow diagram illustrating an example of the process used by embodiments of this disclosure to determine claimed sequences.

FIG. 13 illustrates a computer network or similar digital processing environment in which embodiments of the present invention may be implemented.

Figure 14:
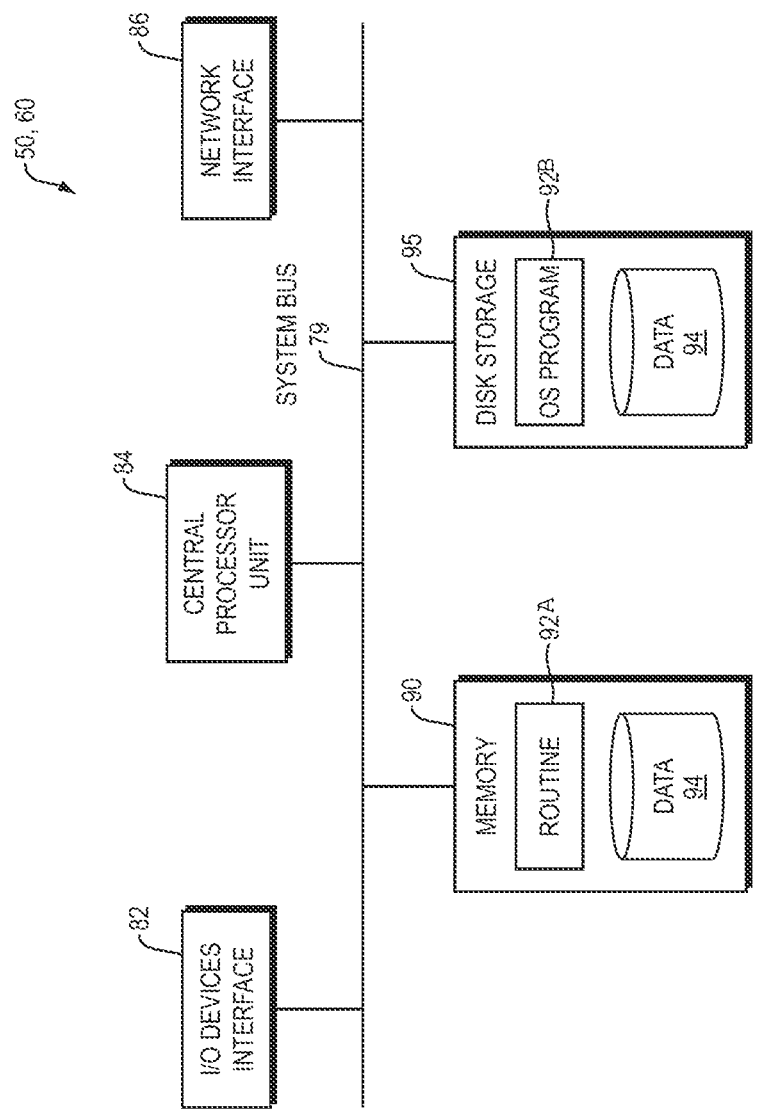

FIG. 14 is a diagram of an example internal structure of a computer (e.g., client processor/device or server computers) in the computer system of FIG. 13.

DETAILED DESCRIPTION

A description of example embodiments follows.

Several aspects of the disclosure are described below, with reference to examples for illustrative purposes only. It should be understood that numerous specific details, relationships, and methods are set forth to provide a full understanding of the disclosure. One having ordinary skill in the relevant art, however, will readily recognize that the disclosure can be practiced without one or more of the specific details or practiced with other methods, protocols, reagents, cell lines and animals. The disclosure is not limited by the illustrated ordering of acts or events, as some acts may occur in different orders and/or concurrently with other acts or events. Furthermore, not all illustrated acts, steps or events are required to implement a methodology in accordance with the disclosure. Many of the techniques and procedures described, or referenced herein, are well understood and commonly employed using conventional methodology by those skilled in the art.

Definitions

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly-used dictionaries, should be interpreted as having a meaning that is consistent with their meaning in the context of the relevant art and/or as otherwise defined herein.

The terminology used herein is for the purpose of describing particular embodiments only and is not intended to be limiting.

When introducing elements disclosed herein, the articles "a," "an," "the," and "said" are intended to mean that there are one or more of the elements. Further, the one or more elements may be the same or different. For example, unless the context clearly indicates otherwise, "a polypeptide" includes a single polypeptide, and two or more polypeptides.

Throughout this specification and the claims which follow, unless the context requires otherwise, the term "comprise," and variations such as "comprises" and "comprising", will be understood to imply the inclusion of, e.g., a stated integer or step or group of integers or steps, but not the exclusion of any other integer or step or group of integer or step. When used herein, the term "comprising" can be substituted with the term "containing" or "including."

As used herein, the term "consisting of" excludes any element, step, or ingredient not specified in the claim element. When used herein, the term "consisting essentially of" does not exclude materials or steps that do not materially affect the basic and novel characteristics of the claim.

Also provided herein are corresponding embodiments for each and every embodiment featuring the term "comprising," "containing," "including," or "having," wherein those terms are replaced by the term "consisting of" and/or "consisting essentially of".

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and, therefore, satisfy the requirement of the term "and/or" as used herein. Concurrent applicability of more than one of the options is also understood to fall within the meaning, and, therefore, satisfy the requirement of the term "and/or."

It should be understood that for all numerical bounds describing some parameter in this application, such as "about," "at least," "less than," "fewer than," and "more than," the description also necessarily encompasses any range bounded by the recited values. Accordingly, for example, the description "at least 1, 2, 3, 4, or 5" also describes, inter alia, the ranges 1-2, 1-3, 1-4, 1-5, 2-3, 2-4, 2-5, 3-4, 3-5, and 4-5, et cetera.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

As used herein, the term "about" means within an acceptable error range for a particular value, as determined by one of ordinary skill in the art. Typically, an acceptable error range for a particular value depends, at least in part, on how the value is measured or determined, e.g., the limitations of the measurement system. For example, "about" can mean within an acceptable standard deviation, per the practice in the art. Alternatively, "about" can mean a range of ±20%, e.g., ±10%, ±5% or ±1% of a given value. It is to be understood that the term "about" can precede any particular value specified herein, except for particular values used in the Exemplification. When "about" precedes a range, as in "90-99.9%," the term "about" should be read as applying to both given values of the range, such that "about 90-99.9%" means about 90% repeats to about 99.9%.

As used herein, the term "polypeptide" refers to a polymer of at least two amino acids covalently linked by an amide bond, regardless of length or post-translational modification (e.g., glycosylation or phosphorylation). A polypeptide can comprise any suitable L- and/or D-amino acid, for example, common α-amino acids (e.g., alanine, glycine, valine), non-α-amino acids (e.g., β-alanine, 4-aminobutyric acid, 6-aminocaproic acid, sarcosine, statine), and unusual amino acids (e.g., citrulline, homocitruline, homoserine, norleucine, norvaline, ornithine). The amino, carboxyl, and/or other functional groups on a polypeptide can be free (e.g., unmodified) or protected with a suitable protecting group. Suitable protecting groups for amino and carboxyl groups, and methods for adding or removing protecting groups are known in the art and are disclosed in, for example, Green and Wuts, "*Protecting Groups in Organic Synthesis*," John Wiley and Sons, 1991. The functional groups of a polypeptide can also be derivatized (e.g., alkylated) or labeled (e.g., with a detectable label, such as a fluorogen or a hapten) using methods known in the art. A polypeptide can comprise one or more modifications (e.g., amino acid linkers, acylation, acetylation, amidation, methylation, terminal modifiers (e.g., cyclizing modifications), N-methyl-α-amino group substitution), if desired. In addition, a polypeptide can be an analog of a known and/or naturally-occurring peptide, for example, a peptide analog having conservative amino acid residue substitution(s).

As used herein, a "polynucleotide" is defined as a plurality of nucleotides and/or nucleotide analogs linked together in a single molecule. In some embodiments, a polynucleotide disclosed herein comprises deoxyribonucleotides. In some embodiments, the polynucleotide comprises ribonucleotides. Non-limiting examples of polynucleotides include single-, double- or multi-stranded DNA or RNA, DNA-RNA hybrids (e.g., each "T" position may be independently substituted by a "U" or vice versa), or a polymer comprising purine and pyrimidine bases, or other natural, chemically, or biochemically modified, non-natural, or derivatized nucleotide bases. The backbone of the polynucleotide can comprise sugars and phosphate groups, modified or substituted sugar or phosphate groups, a polymer of synthetic subunits such as phosphoramidates, or a combination thereof.

As used herein, the term "sequence identity" refers to the extent to which two nucleotide sequences have the same residues at the same positions when the sequences are aligned to achieve a maximal level of identity, expressed as a percentage. For sequence alignment and comparison, typically one sequence is designated as a reference sequence, to which test sequences are compared. Sequence identity between reference and test sequences is expressed as a percentage of positions across the entire length of the reference sequence where the reference and test sequences share the same nucleotide or amino acid upon alignment of the reference and test sequences to achieve a maximal level of identity. As an example, two sequences are considered to have 70% sequence identity when, upon alignment to achieve a maximal level of identity, the test sequence has the same nucleotide residue at 70% of the same positions over the entire length of the reference sequence.

Alignment of sequences for comparison to achieve maximal levels of identity can be readily performed by a person of ordinary skill in the art using an appropriate alignment method or algorithm. In some instances, alignment can include introduced gaps to provide for the maximal level of identity. Examples include the local homology algorithm of Smith & Waterman, *Adv. Appl. Math.* 2:482 (1981), the homology alignment algorithm of Needleman & Wunsch, *J. Mol. Biol.* 48:443 (1970), the search for similarity method of Pearson & Lipman, *Proc. Nat'l. Acad. Sci. USA* 85:2444 (1988), computerized implementations of these algorithms (GAP, BESTFIT, FASTA, and TFASTA in the Wisconsin Genetics Software Package, Genetics Computer Group, 575 Science Dr., Madison, Wis.), and visual inspection (see generally Ausubel et al., *Current Protocols in Molecular Biology*).

When using a sequence comparison algorithm, test and reference sequences are input into a computer, subsequent coordinates are designated, if necessary, and sequence algorithm program parameters are designated. The sequence comparison algorithm then calculates the percent sequence identity for the test sequence(s) relative to the reference sequence, based on the designated program parameters. A commonly used tool for determining percent sequence identity is Protein Basic Local Alignment Search Tool (BLASTP) available through National Center for Biotechnology Information, National Library of Medicine, of the United States National Institutes of Health. (Altschul et al., 1990).

As used herein, the term "substantially similar to" refers to a polypeptide disclosed herein that is substantially similar in amino acid sequence (e.g., has at least about 80%, at least about 90%, at least about 95%, at least about 96%, at least about 97%, at least about 98%, or at least about 99% of the amino acid residues amino acid sequence identity) and substantially preserves one or more functional properties of a specified polypeptide disclosed herein (e.g., AB-1). In some embodiments, the one or more functional properties are selected from, without limitation, a substantially similar binding affinity, a substantially similar binding specificity, a substantially similar inhibitory activity, a substantially similar neutralization activity, and a substantially similar self-association property.

As used herein, a "complementarity determining region (CDR)" encompasses any CDR defined by an art-recognized method for identifying the CDR residues on an antibody. See, e.g., Kabat, E. A., et al., (1991) Sequences of Proteins of Immunological Interest, Fifth Edition, U.S. Department of Health and Human Services, NIH Publication No. 91-3242, Chothia et al., (1989) Nature 342:877; Chothia, C. et al., (1987) J. Mol. Biol. 196:901-917; Al-lazikani et al., (1997) J. Molec. Biol. 273:927-948; and Almagro, J. Mol. Recognit. 17:132-143 (2004). See also hgmp.mrc.ac.uk and bioinf.org.uk/abs. Two antibodies are determined to have the same CDR as one another with respect to a HCDR1, HCDR2, HCDR3, LCDR1, LCDR2 and/or LCDR3, when the identity of that CDR is determined for both antibodies using the same method.

The extent of the framework region and the CDRs of an antibody can be identified using one of several suitable methodologies that are well known in the art, for example, by the Kabat definition, the Chothia definition, the AbM definition, and/or the contact definition. Publicly and/or commercially available tools for identifying framework and/or CDR regions include, IgBlast (accessible at www.ncbi.nlm.nih.gov/igblast/), Scaligner (available from drugdesigntech at www.scaligner.com/), IMGT rules and/or tools (see, for example, www.imgt.org/IMGTScientific-Chart/Nomenclature/IMGT-FRCDRdefinition.html, also accessible at www.imgt.org/), Chothia Canonical Assignment (accessible at www.bioinforg.uk/abs/chothia.html), Antigen receptor Numbering And Receptor CalssificatiIon (ANARCI, accessible at opig.stats.ox.ac.uk/webapps/news-abdab/sabpred/anarci/), or the Paratome web server (accessible at www.ofranlab.org/paratome/, or the Paratome web server (accessible at www.ofranlab.org/paratome/see Vered Kunik, et al, Nucleic Acids Research, Volume 40, Issue W1, 1 Jul. 2012, Pages W521-W524).

For example, for AB-2, the HCDR1, HCDR2, HCDR3, LCDR1, LCDR2 and LCDR3 amino acid sequences: (1) comprise SEQ ID NO:31, SEQ ID NO:35, SEQ ID NO:50, SEQ ID NO:60, DDS, and SEQ ID NO:71, respectively, as determined by IMGT numbering; (2) comprise SEQ ID NO:130, SEQ ID NO:131, SEQ ID NO:132, SEQ ID NO:133, SEQ ID NO:134, and SEQ ID NO:71, respectively, as determined by Kabat numbering; and (3) comprise SEQ ID NO: 135, SEQ ID NO:136, SEQ ID NO: 132, SEQ ID NO: 133, SEQ ID NO:134, and SEQ ID NO:71, respectively, as determined by Chothia numbering.

As used herein, the term "paratope" refers to a set of amino acid residues in an antibody or an antigen-binding fragment thereof that contribute to a binding interaction with an epitope of a target protein. The binding interaction can be a hydrogen bond, a salt bridge, a van der Waal interaction, an ionic bond or a combination thereof. A binding interaction may be direct, or indirect, e.g., via a coordinated intermediate molecule, such as an ion or water. The residues of a paratope, in some embodiments, comprise only residues that are part of a defined CDR. In other embodiments, the residues of a paratope further comprise one or more residues that are not part of a defined CDR.

As used herein, the term "antibody mimetic" refers to polypeptides capable of mimicking an antibody's ability to bind an antigen, but structurally differ from native antibody structures. Examples of antibody mimetics include, but not limited to, Adnectins, Affibodies, Affilins, Affimers, Affitins, Alphabodies, Anticalins, Avimers, DARPins, Fynomers, Kunitz domain peptides, monobodies, nanobodies, nanoCLAMPs, and Versabodies.

As used herein the term "$K_D$," also referred to as "binding constant," "equilibrium dissociation constant" or "affinity constant," is a measure of the extent of a reversible association between two molecular species (e.g., antibody and target protein) and includes both the actual binding affinity as well as the apparent binding affinity. Binding affinity can be determined using methods known in the art including, for example, by measurement of surface plasmon resonance, e.g., using a Biolayer interferometry (Octet, ForteBio) or a surface plasmon resonance (Biacore) system and assay. A reference that compares various surface technologies for measuring binding affinity and kinetics is Yang, D., Singh, A., Wu, H., & Kroe-Barrett, R., *Comparison of biosensor platforms in the evaluation of high affinity antibody-antigen binding kinetics*, Analytical Biochemistry 508: 78-96 (2016), the contents of which are incorporated by reference herein in their entirety.

The term "subject" or "patient" refers to an animal (e.g., a mammal such as a human), diagnosed with or suspected of having a TSLP-associated disease or condition (e.g., a disease or condition associated with dysregulated TSLP expression such as, asthma or atopic dermatitis (AD)), or one at risk of developing such conditions. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

The phrase "pharmaceutically acceptable" means that the substance or composition the phrase modifies is, within the scope of sound medical judgment, suitable for use in contact with the tissues of humans and lower animals without undue toxicity, irritation, allergic response, and the like, and are commensurate with a reasonable benefit/risk ratio.

As used herein, the term "pharmaceutically acceptable salt" refers to those salts which are, within the scope of sound medical judgment, suitable for use in contact with the tissues of mammals without undue toxicity, irritation, allergic response, and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the agents/compounds described herein include salts derived from suitable inorganic and organic acids, and suitable inorganic and organic bases.

Examples of salts derived from suitable acids include salts of an amino group formed with inorganic acids such as hydrochloric acid, hydrobromic acid, phosphoric acid, sulfuric acid and perchloric acid, or with organic acids such as acetic acid, oxalic acid, maleic acid, tartaric acid, citric acid, succinic acid or malonic acid or by using other methods used in the art, such as ion exchange. Other pharmaceutically acceptable salts derived from suitable acids include adipate, alginate, ascorbate, aspartate, benzenesulfonate, benzoate, bisulfate, borate, butyrate, camphorate, camphorsulfonate, cinnamate, citrate, cyclopentanepropionate, digluconate, dodecylsulfate, ethanesulfonate, formate, fumarate, glucoheptonate, glycerophosphate, gluconate, glutarate, glycolate, hemisulfate, heptanoate, hexanoate, hydroiodide, hydroxybenzoate, 2-hydroxy-ethanesulfonate, hydroxymaleate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 2-phenoxybenzoate, phenylacetate, 3-phenylpropionate, phosphate, pivalate, propionate, pyruvate, salicylate, stearate, succinate, sulfate, tartrate, thiocyanate, p-toluenesulfonate, undecanoate, valerate salts, and the like.

Either the mono-, di- or tri-acid salts can be formed, and such salts can exist in either a hydrated, solvated or substantially anhydrous form.

Salts derived from appropriate bases include salts derived from inorganic bases, such as alkali metal, alkaline earth metal, and ammonium bases, and salts derived from aliphatic, alicyclic or aromatic organic amines, such as methylamine, trimethylamine and picoline, or $N^+((C_1-C_4)alkyl)_4$ salts. Representative alkali or alkaline earth metal salts include sodium, lithium, potassium, calcium, magnesium, barium and the like. Further pharmaceutically acceptable salts include, when appropriate, nontoxic ammonium, quaternary ammonium, and amine cations formed using counterions such as halide, hydroxide, carboxyl, sulfate, phosphate, nitrate, lower alkyl sulfonate and aryl sulfonate.

"Pharmaceutically acceptable carrier" refers to a nontoxic carrier or excipient that does not destroy the pharmacological activity of the agent with which it is formulated and is nontoxic when administered in doses sufficient to deliver a therapeutic amount of the agent. Pharmaceutically acceptable carriers that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

"Treating" or "treatment," as used herein, refers to taking steps to deliver a therapy to a subject, such as a mammal, in need thereof (e.g., as by administering to a mammal one or more therapeutic agents). "Treating" or "treatment" includes inhibiting the disease or condition (e.g., as by slowing or stopping its progression or causing regression of the disease or condition) and relieving the symptoms resulting from the disease or condition.

The term "treating," or "treatment" refers to the medical management of a subject with the intent to improve, ameliorate, stabilize (i.e., not worsen), prevent, or cure a disease, pathological condition, or disorder-such as the particular indications exemplified herein. This term includes active treatment (treatment directed to improve the disease, pathological condition, or disorder), causal treatment (treatment directed to the cause of the associated disease, pathological condition, or disorder), palliative treatment (treatment designed for the relief of symptoms), preventative treatment (treatment directed to minimizing or partially or completely inhibiting the development of the associated disease, pathological condition, or disorder); and supportive treatment (treatment employed to supplement another therapy). Treatment also includes diminishment of the extent of the disease or condition; preventing spread of the disease or condition; delay or slowing the progress of the disease or condition; amelioration or palliation of the disease or condition; and remission (whether partial or total), whether detectable or undetectable. "Ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment. "Treatment" can also mean prolonging survival as compared to expected survival if not receiving treatment. Those in need of treatment include those already with the condition or disorder, as well as those prone to have the condition or disorder or those in which the condition or disorder is to be prevented.

A "pharmaceutical composition" refers to a formulation of one or more therapeutic agents and a medium generally accepted in the art for delivery of a biologically active agent to subjects, e.g., humans. In some embodiments, a pharmaceutical composition may include one or more pharmaceutically acceptable excipients, diluents, or carriers. In some embodiments, a pharmaceutical composition suitable for use in methods disclosed herein further comprises one or more pharmaceutically acceptable carriers.

"Pharmaceutically acceptable carrier, diluent, or excipient" includes any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative. In some embodiments, the carrier may be a diluent, adjuvant, excipient, or vehicle with which the agent (e.g., polynucleotide) is administered. Such vehicles may be liquids, such as water and oils, including those of petroleum, animal, vegetable or synthetic origin, such as peanut oil, soybean oil, mineral oil, sesame oil, and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating, and coloring agents, etc. The concentration of the agent in such pharmaceutical formulation may vary widely, i.e., from less than about 0.5%, to at least about 1%, or to as much as 15% or 20%, 25%, 30%, 35%, 40%, 45% or 50% by weight. The concentration will be selected primarily based on required dose, fluid volumes, viscosities, etc., according to the mode of administration. Suitable vehicles and formulations, inclusive of other human proteins, e.g., human serum albumin, are described, for example, in Remington: The Science and Practice of Pharmacy, 21$^{st}$ Edition, Troy, D. B. ed., Lipincott Williams and Wilkins, Philadelphia, PA 2006, Part 5, Pharmaceutical Manufacturing: 691-1092 (e.g., pages 958-89).

Non-limiting examples of pharmaceutically acceptable carriers are solvents, dispersion media, coatings, antibacterial and antifungal agents, isotonic and absorption delaying agents, and the like that are physiologically compatible, such as salts, buffers, antioxidants, saccharides, aqueous or non-aqueous carriers, preservatives, wetting agents, surfactants or emulsifying agents, or combinations thereof.

Non-limiting examples of buffers are acetic acid, citric acid, formic acid, succinic acid, phosphoric acid, carbonic acid, malic acid, aspartic acid, histidine, boric acid, Tris buffers, HEPPSO, and HEPES.

Non-limiting examples of antioxidants are ascorbic acid, methionine, cysteine hydrochloride, sodium bisulfate, sodium metabisulfite, sodium sulfite, lecithin, citric acid, ethylenediamine tetraacetic acid (EDTA), sorbitol, and tartaric acid.

Non-limiting examples of amino acids are histidine, isoleucine, methionine, glycine, arginine, lysine, L-leucine, tri-leucine, alanine, glutamic acid, L-threonine, and 2-phenylamine.

Non-limiting examples of surfactants are polysorbates (e.g., polysorbate-20 or polysorbate-80); polyoxamers (e.g., poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N.J.), polyethyl glycol, polypropyl glycol, and copolymers of ethylene and propylene glycol (e.g., PLURONICS™, PF68, etc.).

Non-limiting examples of preservatives are phenol, m-cresol, p-cresol, o-cresol, chlorocresol, benzyl alcohol, phenylmercuric nitrite, phenoxyethanol, formaldehyde, chlorobutanol, magnesium chloride, alkylparaben (methyl, ethyl, propyl, butyl, and the like), benzalkonium chloride, benzethonium chloride, sodium dehydroacetate, and thimerosal, or mixtures thereof.

Non-limiting examples of saccharides are monosaccharides, disaccharides, trisaccharides, polysaccharides, sugar alcohols, reducing sugars, nonreducing sugars such as glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, or iso-maltulose.

Non-limiting examples of salts are acid addition salts and base addition salts. Acid addition salts include those derived from nontoxic inorganic acids, such as hydrochloric, nitric, phosphoric, sulfuric, hydrobromic, hydroiodic, phosphorous, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids, and the like. Base addition salts include those derived from alkaline earth metals, such as sodium, potassium, magnesium, calcium, and the like, as well as from nontoxic organic amines, such as N,N'-dibenzylethylenediamine, N-methylglucamine, chloroprocaine, choline, diethanolamine, ethylenediamine, procaine, and the like. In some embodiments, the salt is sodium chloride (NaCl).

Agents (e.g., polynucleotides) described herein may be prepared in accordance with standard procedures and are administered at dosages that are selected to reduce, prevent, or eliminate, or to slow or halt progression of, a condition being treated (see, e.g., Remington's Pharmaceutical Sciences, Mack Publishing Company, Easton, PA, and Goodman and Gilman's The Pharmaceutical Basis of Therapeutics, McGraw-Hill, New York, N.Y., the contents of which are incorporated herein by reference, for a general description of methods for administering various agents for human therapy).

"Administering" or "administration," as used herein, refers to providing a compound, composition, or pharmaceutically acceptable salt thereof described herein to a subject in need of treatment or prevention. Administering can be performed, for example, once, a plurality of times, and/or over one or more extended periods. Administration includes both direct administration (including self-administration), and indirect administration (including an act of prescribing a drug or directing a subject to consume an agent). For example, as used herein, one (e.g., a physician) who instructs a subject (e.g., a human patient) to self-administer an agent (e.g., a drug), or to have an agent administered by another and/or who provides a patient with a prescription for a drug is administering an agent to a subject.

"A therapeutically effective amount," "an effective amount" or "an effective dosage" refers to an amount effective, at dosages and for periods of time necessary, to achieve a desired therapeutic result (e.g., treatment, healing, inhibition or amelioration of physiological response or condition, etc.). A full therapeutic effect does not necessarily occur by administration of one dose and may occur only after administration of a series of doses. Thus, a therapeutically effective amount may be administered in one or more administrations. A therapeutically effective amount may vary according to factors such as the disease state, age, sex, and weight of a mammal (e.g., a human patient), mode of administration, and the ability of a therapeutic or a combination of therapeutics to elicit a desired response.

An effective amount of an agent to be administered can be determined by a clinician of ordinary skill using the guidance provided herein and other methods known in the art. Relevant factors include the given agent, the pharmaceutical formulation, the route of administration, the type of disease or disorder, the identity of the subject (e.g., age, sex, weight) or host being treated, and the like. For example, suitable dosages can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Determining the dosage for a particular agent, subject and disease is well within the abilities of one of skill in the art. Preferably, the dosage does not cause or produces minimal adverse side effects.

Desired response or desired results include effects at the cellular level, tissue level, or clinical results. As such, "a therapeutically effective amount" or synonym thereto depends upon the context in which it is being applied. For example, in some embodiments it is an amount of the composition sufficient to achieve a treatment response as compared to the response obtained without administration of the composition. In other embodiments, it is an amount that results in a beneficial or desired result in a subject as compared to a control. As defined herein, a therapeutically effective amount of a composition (e.g., a pharmaceutical composition) disclosed herein may be readily determined by one of ordinary skill by routine methods known in the art.

Dosage regimen and route of administration may be adjusted to provide the optimum therapeutic response.

Thymic Stromal Lymphopoietin (TSLP)

As used herein, TSLP includes wild-type TSLP proteins (e.g., wild-type human TSLP proteins or homologs thereof) and truncated forms thereof, mutant, and engineered versions of full-length and truncated TSLP proteins, and modified forms (e.g., post-translationally modified forms) of full-length and truncated TSLP proteins.

A non-limiting example of human TSLP sequences is GenBank: AAK67490.1 (SEQ ID NO:1).

```
                                              (SEQ ID NO: 1)
MFPFALLYVLSVSFRKIFILQLVGLVLTYDFTNCDFEKIKAAYLST

ISKDLITYMSGTKSTEFNNTVSCSNRPHCLTEIQSLTFNPTAGCAS

LAKEMFAMKTKAALAIWCPGYSETQINATQAMKKRRKRKVTTNKCL

EQVSQLQGLWRRFNRPLLKQQ.
```

A non-limiting example of cyno monkey TSLP sequences is GenBank: EHH54440.1 (SEQ ID NO:83).

```
                                             (SEQ ID NO: 83)
MKSLGQSKKEEVSFRKFFIFQLVGLVLTYDFTNCDFQKIEADYLRT

ISKDLITYMSGTKSTDFNNTVSCSNRPHCLTEIQSLTFNPTPRCAS

LAKEMFARKTKATLALWCPGYSETQINATQAMKKRRKRKVTTNKCL

EQVSQLLGLWRRFIRTLLKKQ.
```

In some embodiments, a polypeptide binds to a wild-type TSLP protein (e.g., a TSLP protein having the amino acid sequence of SEQ ID NO:1, SEQ ID NO:83, or both). In some embodiments, a polypeptide binds to a TSLP protein comprising the amino acid sequence of SEQ ID NO:1. In some embodiments, a polypeptide binds to a TSLP protein comprising the amino acid sequence of SEQ ID NO:1 and a TSLP protein comprising the amino acid sequence of SEQ ID NO:83.

In some embodiments, a polypeptide binds to a mutant or engineered TSLP protein. In some embodiments, a mutant or engineered TSLP protein comprises an amino acid sequence that has at least about 90% sequence identity to a wildtype TSLP protein, for example, at least about: 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence identity to a wildtype TSLP protein (e.g., SEQ ID NO:1 or SEQ ID NO:83). In some embodiments, a mutant or engineered TSLP protein comprises an amino acid sequence that has about 90-99.9%, 90-99.8%, 92-99.8%, 92-99.6%, 94-99.6%, 94-99.5%, 95-99.5%, 95-99.4%, 96-99.4%, 96-99.2%, 97-99.2% or 97-99% sequence identity to a wildtype TSLP protein.

In some embodiments, a polypeptide binds to a modified TSLP protein.

In some embodiments, a polypeptide is capable of binding to one or more epitope residues in a TSLP protein (e.g., a full-length human TSLP), for example, 1, 2, 3, 4, 5, 6, 7, 8, 9, 10, 11, 12, 13, 14, or 15 epitope residues of a TSLP protein. In some embodiments, a polypeptide is capable of binding to one or more epitope residues (e.g., 1, 2, 3, 4, 5, 6, 7, 8, 9, 10, 11, 12, 13, 14, or all 15 residues) selected from N64, N65, T66, V67, S68, C69, S70, N71, R72, H74, C75, E78, R150, F151 and R153 of SEQ ID NO:1.

In some embodiments, a polypeptide binds to one or more epitope residues of a TSLP protein (e.g., one or more epitope residues in SEQ ID NO:1). In some embodiments, a polypeptide binds to one or more epitope residues (e.g., 1, 2, 3, 4, 5, 6, 7, 8, 9, 10, 11, 12, 13, 14, or all 15 residues) selected from N64, N65, T66, V67, S68, C69, S70, N71, R72, H74, C75, E78, R150, F151 and R153 of SEQ ID NO:1.

Comparator Polypeptides

As used herein, the term "comparator" or "comparator polypeptide" refers to a polypeptide (e.g., immunoglobulin molecule) that specifically binds to a TSLP protein and is not a polypeptide disclosed herein. The sequence of a comparator polypeptide and a polypeptide disclosed herein may be compared to illustrate structural differences between them (e.g., differences at one or more amino acid positions, such as amino acid substitutions). Polypeptides disclosed herein have more than insubstantial differences (e.g., one or more substantial differences) in comparison to a comparator polypeptide, such that, polypeptides disclosed herein will, under controlled conditions, exhibit one or more (i.e., one, two, or all three) of: a different function, in a different way, to achieve a different result, in comparison to a comparator polypeptide. A comparator polypeptide may vary from a polypeptide disclosed herein by one or more amino acids, e.g., in some embodiments, by 1, 2, 3, 4, 5, 6, 7, 8, 9, 10, 11, 12, 13, 14, 15, 16, 17, 18, 19, 20 or more amino acids. In some embodiments, a comparator polypeptide diverges from a polypeptide disclosed herein by at least about: 0.4%, 0.8%, 1%, 2%, 3%, 4%, 5%, 6%, 7% 8%, 9% 10%, 15%, 20%, 25%, 30%, 35%, 40%, 45%, 50%, 55%, or more amino acid percent identity.

In some embodiments, a comparator polypeptide is an antibody comprising:
  a) a heavy chain complementarity determining region 1 (HCDR1), a heavy chain complementarity determining region 2 (HCDR2) and a heavy chain complementarity determining region 3 (HCDR3) sequences of SEQ ID NO:31, SEQ ID NO:33 and SEQ ID NO:48, respectively;
  b) a light chain complementarity determining region 1 (LCDR1), a light chain complementarity determining region 2 (LCDR2) and a light chain complementarity determining region 3 (LCDR3) sequences of SEQ ID NO:59, DDS and SEQ ID NO:69, respectively, or both a) and b).

In some embodiments, a comparator polypeptide is an antibody comprising:
  a) a HCDR1, a HCDR2 and a HCDR3 sequences of SEQ ID NO:31, SEQ ID NO:33 and SEQ ID NO:48, respectively; and
  a LCDR1, a LCDR2 and a LCDR3 sequences of SEQ ID NO:59, DDS and SEQ ID NO:69, respectively.

See Table 3 and FIG. 2 for SEQ ID NOs:31, 33 and 48. See Table 3 and FIG. 3 for SEQ ID NOs:59, 67 and 69.

In some embodiments, a comparator polypeptide is an antibody comprising:
  a) an immunoglobulin heavy chain variable region ($V_H$) domain comprising the amino acid sequence of SEQ ID NO:3;
  b) an immunoglobulin light chain variable region ($V_L$) domain comprising the amino acid sequence of SEQ ID NO:19, or
  both a) and b).

In some embodiments, a comparator polypeptide is an antibody comprising:
  a) an immunoglobulin heavy chain variable region ($V_H$) domain comprising the amino acid sequence of SEQ ID NO:3; and
  b) an immunoglobulin light chain variable region ($V_L$) domain comprising the amino acid sequence of SEQ ID NO:19.

See Table 1 and FIG. 2 for SEQ ID NO:3. See Table 2 and FIG. 3 for SEQ ID NO:19.

In some embodiments, a comparator polypeptide is an antibody referred to herein as the "Reference Antibody." The Reference Antibody comprises:
  a) a heavy chain comprising the amino acid sequence of SEQ ID NO: 81; and
  b) a light chain comprising the amino acid sequence of SEQ ID NO: 82.

See Table 4 for SEQ ID NO:81. See Table 5 for SEQ ID NO:82.

The Reference Antibody binds and neutralizes TSLP.

Polypeptides

In some embodiments, a polypeptide specifically binds a TSLP.

In some embodiments, a polypeptide is an antibody or antigen-binding fragment thereof.

Variable Domains

In some embodiments, a polypeptide (e.g., an antibody or antigen-binding fragment thereof) comprises an immunoglobulin heavy chain variable region ($V_H$), an immunoglobulin light chain variable region ($V_L$), or both. In some embodiments, a polypeptide comprises a $V_H$ having less than 100% sequence identity to the amino acid sequence of SEQ ID NO:3, a $V_L$ having less than 100% sequence identity to the amino acid sequence of SEQ ID NO:19, or both.

In some embodiments, a polypeptide comprises a $V_H$ (e.g., a mammalian $V_H$ such as a rodent (e.g., mouse) $V_H$, a primate (e.g., a human) $V_H$). In some embodiments, a polypeptide comprises a $V_H$ that is humanized (e.g., at least about: 10%, 20%, 30%, 40%, 50%, 60%, 70%, 80%, 90%, 95%, 98% or 99% humanized), contains human framework regions, or both.

In some embodiments, a polypeptide comprises a $V_H$ that has less than 100% sequence identity to the amino acid sequence of SEQ ID NO:3.

In some embodiments, a polypeptide comprises a $V_H$ that has at least about 70% sequence identity to the amino acid sequence of SEQ ID NO:3. In some embodiments, a polypeptide comprises a $V_H$ that has at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:3. In some embodiments, a polypeptide comprises a $V_H$ that has at least about 85% sequence identity to the amino acid sequence of SEQ ID NO:3. In some embodiments, a polypeptide comprises a $V_H$ that has at least about 90% sequence identity to the amino acid sequence of SEQ ID NO:3.

In some embodiments, a polypeptide comprises a $V_H$ that comprises at least one amino acid substitution (e.g., at least one conservative substitution such as highly conservative substitution) relative to the amino acid sequence of SEQ ID NO:3. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises a $V_H$ that comprises about 1-10 amino acid substitutions, relative to the amino acid sequence of SEQ ID NO:3. In some embodiments, the at least one amino acid substitution replaces only a heavy chain complementarity determining region 1 (HCDR1), a heavy chain complementarity determining region 2 (HCDR2), and/or a heavy chain complementarity determining region 3 (HCDR3) residue, of SEQ ID NO:3. In some embodiments, the at least one amino acid substitution replaces only a non-CDR residue (e.g., within a framework region), of SEQ ID NO:3.

In some embodiments, an amino acid substitution is a conservative substitution. The term "a conservative amino acid substitution" or "a conservative substitution" refers to an amino acid substitution having a value of 0 or greater in BLOSUM62.

In some embodiments, an amino acid substitution is a highly conservative substitution. The term "a highly conservative amino acid substitution" or "a highly conservative substitution" refers to an amino acid substitution having a value of at least 1 (e.g., at least 2) in BLOSUM62.

In some embodiments, a polypeptide comprises a $V_H$ that has 100% sequence identity to the amino acid sequence of SEQ ID NO:3. In some embodiments, a polypeptide comprises a $V_H$ that comprises the amino acid sequence of SEQ ID NO:3.

In some embodiments, a polypeptide comprises a $V_H$ that has at least about 70% sequence identity to the amino acid sequence of any one or more of SEQ ID NOs:4-17. The sequences identified as SEQ ID NOs:4-17 are shown in Table 1, which correspond to human $V_H$ domains. In some embodiments, a polypeptide comprises a $V_H$ that has at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of any one or more of SEQ ID NOs:4-17. In some embodiments, a polypeptide comprises a $V_H$ that has at least about 85% sequence identity to the amino acid sequence of any one or more of SEQ ID NOs:4-17. In some embodiments, a polypeptide comprises a $V_H$ that has at least about 90% sequence identity to the amino acid sequence of any one or more of SEQ ID NOs:4-17.

In some embodiments, a polypeptide comprises a $V_H$ that comprises at least one amino acid substitution relative to the amino acid sequence of any one or more of SEQ ID NOs:4-17. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises a $V_H$ that comprises about 1-10 amino acid substitutions, relative to the amino acid sequence of any one or more of SEQ ID NOs:4-17.

In some embodiments, a polypeptide comprises a $V_H$ that has 100% sequence identity to the amino acid sequence of any one of SEQ ID NOs:4-17. In some embodiments, a polypeptide comprises a $V_H$ that comprises the amino acid sequence of any one of SEQ ID NOs:4-17.

In some embodiments, a polypeptide comprises a $V_H$ that has at least about 70% sequence identity to the amino acid sequence of any one or more of SEQ ID NOs:4-7. In some embodiments, a polypeptide comprises a $V_H$ that has at least about: 71%, 72%, 73%, 74%, 75%, 76%, 77%7, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of any one or more of SEQ ID NOs:4-7. In some embodiments, a polypeptide comprises a $V_H$ that has at least about 85% sequence identity to the amino acid sequence of any one or more of SEQ ID NOs:4-7. In some embodiments, a polypeptide comprises a $V_H$ that has at least about 90% sequence identity to the amino acid sequence of any one or more of SEQ ID NOs:4-7.

In some embodiments, a polypeptide comprises a $V_H$ that comprises at least one amino acid substitution relative to the amino acid sequence of any one or more of SEQ ID NOs:4-7. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises a $V_H$ that comprises about 1-10 amino acid substitutions, relative to the amino acid sequence of any one or more of SEQ ID NOs:4-7.

In some embodiments, a polypeptide comprises a $V_H$ that has 100% sequence identity to the amino acid sequence of any one of SEQ ID NOs:4-7. In some embodiments, a polypeptide comprises a $V_H$ that comprises the amino acid sequence of any one of SEQ ID NOs:4-7.

In some embodiments, a polypeptide comprises a $V_L$ (e.g., a mammalian $V_L$ such as a rodent (e.g., mouse) $V_L$, a primate (e.g., a human) $V_L$). In some embodiments, a polypeptide comprises a $V_L$ that is humanized (e.g., at least about: 10%, 20%, 30%, 40%, 50%, 60%, 70%, 80%, 90%, 95%, 98% or 99% humanized), contains human framework regions, or both.

In some embodiments, a polypeptide comprises a $V_L$ that has less than 100% sequence identity to the amino acid sequence of SEQ ID NO:19.

In some embodiments, a polypeptide comprises a $V_L$ that has at least about 70% sequence identity to the amino acid sequence of SEQ ID NO:19. In some embodiments, a polypeptide comprises a $V_L$ that has at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:19. In some embodiments, a polypeptide comprises a $V_L$ that has at least about 85% sequence identity to the amino acid sequence of SEQ ID NO:19. In some embodiments, a polypeptide comprises a $V_L$ that has at least about 90% sequence identity to the amino acid sequence of SEQ ID NO:19.

In some embodiments, a polypeptide comprises a $V_L$ that comprises at least one amino acid substitution (e.g., at least one conservative substitution such as highly conservative substitution) relative to the amino acid sequence of SEQ ID NO:19. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises a $V_L$ that comprises about 1-10 amino acid substitutions, relative to the amino acid sequence of SEQ ID NO:19. In some embodiments, the at least one amino acid substitution replaces only a light chain complementarity determining region 1 (LCDR1), a light chain complementarity determining region 2 (LCDR2), and/or a light chain complementarity determining region 3 (LCDR3) residue, of SEQ ID NO:19. In some embodiments, the at least one amino acid substitution replaces only a non-CDR residue (e.g., within a framework region), of SEQ ID NO:19.

In some embodiments, an amino acid substitution is a conservative substitution.

In some embodiments, an amino acid substitution is a highly conservative substitution.

In some embodiments, a polypeptide comprises a $V_L$ that has 100% sequence identity to the amino acid sequence of SEQ ID NO:19. In some embodiments, a polypeptide comprises a $V_L$ that comprises the amino acid sequence of SEQ ID NO:19.

In some embodiments, a polypeptide comprises a $V_L$ that has at least about 70% sequence identity to the amino acid sequence of any one or more of SEQ ID NOs:20-30. The sequences identified as SEQ ID NOs:20-30 are shown in Table 2, which correspond to human $V_L$ domains. In some embodiments, a polypeptide comprises a $V_L$ that has at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of any one or more of SEQ ID NOs:20-30. In some embodiments, a polypeptide comprises a $V_L$ that has at least about 85% sequence identity to the amino acid sequence of any one or more of SEQ ID NOs:20-30. In some embodiments, a polypeptide comprises a $V_L$ that has at least about 90% sequence identity to the amino acid sequence of any one or more of SEQ ID NOs:20-30.

In some embodiments, a polypeptide comprises a $V_L$ that comprises at least one amino acid substitution relative to the amino acid sequence of any one or more of SEQ ID NOs:20-30. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises a $V_L$ that comprises about 1-10 amino acid substitutions, relative to the amino acid sequence of any one or more of SEQ ID NOs:20-30.

In some embodiments, a polypeptide comprises a $V_L$ that has 100% sequence identity to the amino acid sequence of any one of SEQ ID NOs:20-30. In some embodiments, a polypeptide comprises a $V_L$ that comprises the amino acid sequence of any one of SEQ ID NOs:20-30.

In some embodiments, a polypeptide comprises a $V_L$ that has at least about 70% sequence identity to the amino acid sequence of any one or more of SEQ ID NOs:20-22. In some embodiments, a polypeptide comprises a $V_L$ that has at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of any one or more of SEQ ID NOs:20-22. In some embodiments, a polypeptide comprises a $V_L$ that has at least about 85% sequence identity to the amino acid sequence of any one or more of SEQ ID NOs:20-22. In some embodiments, a polypeptide comprises a $V_L$ that has at least about 90% sequence identity to the amino acid sequence of any one or more of SEQ ID NOs:20-22.

In some embodiments, a polypeptide comprises a $V_L$ that comprises at least one amino acid substitution relative to the amino acid sequence of any one or more of SEQ ID NOs:20-22. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises a $V_L$ that comprises about 1-10 amino acid substitutions, relative to the amino acid sequence of any one or more of SEQ ID NOs:20-22.

In some embodiments, a polypeptide comprises a $V_L$ that has 100% sequence identity to the amino acid sequence of any one of SEQ ID NOs:20-22. In some embodiments, a polypeptide comprises a $V_L$ that comprises the amino acid sequence of any one of SEQ ID NOs:20-22.

In some embodiments, a polypeptide comprises a $V_H$ (e.g., a mammalian $V_H$ such as a rodent (e.g., mouse) $V_H$, a primate (e.g., a human) $V_H$) and a $V_L$ (e.g., a mammalian $V_L$ such as a rodent (e.g., mouse) $V_L$, a primate (e.g., a human) $V_L$). In some embodiments, a polypeptide comprises a $V_H$ and $V_L$ that are humanized (e.g., at least about: 10%, 20%, 30%, 40%, 50%, 60%, 70%, 80%, 90%, 95%, 98% or 99% humanized), contain human framework regions, or both.

In some embodiments, a polypeptide comprises:
a) a $V_H$ that has less than 100% sequence identity to the amino acid sequence of SEQ ID NO:3;
b) a $V_L$ that has less than 100% sequence identity to the amino acid sequence of SEQ ID NO:19, or
both a) and b).

In some embodiments, a polypeptide comprises:
a) a $V_H$ that has less than 100% sequence identity to the amino acid sequence of SEQ ID NO:3; and
b) a $V_L$ that has less than 100% sequence identity to the amino acid sequence of SEQ ID NO:19.

In some embodiments, a polypeptide comprises:
a) a $V_H$ that has at least about 55% (e.g., at least about: 60, 65, 70, 75, 80, 85, 90, 95, 98, or 99%) sequence identity to the amino acid sequence of SEQ ID NO:3;
b) a $V_L$ that has at least about 55% (e.g., at least about: 60, 65, 70, 75, 80, 85, 90, 95, 98, or 99%) sequence identity to the amino acid sequence of SEQ ID NO:19, or
both a) and b),
wherein the polypeptide does not comprise all 6 CDRs of an antibody comprising a $V_H$ amino acid sequence of SEQ ID NO:3 and a $V_L$ amino acid sequence of SEQ ID NO:19.

In some embodiments, a polypeptide comprises:
a) a $V_H$ that has at least about 55% (e.g., at least about: 60, 65, 70, 75, 80, 85, 90, 95, 98, or 99%) sequence identity to the amino acid sequence of SEQ ID NO:3; and
b) a $V_L$ that has at least about 55% (e.g., at least about: 60, 65, 70, 75, 80, 85, 90, 95, 98, or 99%) sequence identity to the amino acid sequence of SEQ ID NO:19,
wherein the polypeptide does not comprise all 6 CDRs of an antibody comprising a $V_H$ amino acid sequence of SEQ ID NO:3 and a $V_L$ amino acid sequence of SEQ ID NO:19.

In some embodiments, a polypeptide comprises:
a) a $V_H$ that comprises at least one amino acid substitution (e.g., at least one conservative substitution such as highly conservative substitution) relative to the amino acid sequence of SEQ ID NO:3;
b) a $V_L$ that comprises at least one amino acid substitution (e.g., at least one conservative substitution such as highly conservative substitution) relative to the amino acid sequence of SEQ ID NO:19, or
both a) and b).

In some embodiments, a polypeptide comprises:
a) a $V_H$ that comprises at least one amino acid substitution (e.g., at least one conservative substitution such as highly conservative amino acid substitution) relative to the amino acid sequence of SEQ ID NO:3; and
b) a $V_L$ that comprises at least one amino acid substitution (e.g., at least one conservative substitution such as highly conservative amino acid substitution) relative to the amino acid sequence of SEQ ID NO:19.

In some embodiments, a polypeptide comprises:
a) a $V_H$ that comprises at least one amino acid substitution (e.g., at least one conservative substitution such as highly conservative amino acid substitution) of a HCDR1, a HCDR2 and/or a HCDR3 residue, of SEQ ID NO:3;
b) a $V_L$ that comprises at least one amino acid substitution (e.g., at least one conservative substitution such as highly conservative amino acid substitution) of a LCDR1, a LCDR2 and/or a LCDR3 residue, of SEQ ID NO:19, or both a) and b).

In some embodiments, a polypeptide comprises:
a) a $V_H$ that comprises at least one amino acid substitution (e.g., at least one conservative substitution such as highly conservative amino acid substitution) of a HCDR1, a HCDR2 and/or a HCDR3 residue, of SEQ ID NO:3; and
b) a $V_L$ that comprises at least one amino acid substitution (e.g., at least one conservative substitution such as highly conservative amino acid substitution) of a LCDR1, a LCDR2 and/or a LCDR3 residue, of SEQ ID NO:19.

In some embodiments, a polypeptide comprises:
a) a $V_H$ that comprises at least one amino acid substitution (e.g., at least one conservative substitution such as highly conservative amino acid substitution) of a non-CDR residue (e.g., within a framework region), of SEQ ID NO:3;
b) a $V_L$ that comprises at least one amino acid substitution (e.g., at least one conservative substitution such as highly conservative amino acid substitution) of a non-CDR residue (e.g., within a framework region), of SEQ ID NO:19, or both a) and b).

In some embodiments, a polypeptide comprises:
a) a $V_H$ that comprises at least one amino acid substitution (e.g., at least one conservative substitution such as highly conservative amino acid substitution) of a non-CDR residue (e.g., within a framework region), of SEQ ID NO:3; and
b) a $V_L$ that comprises at least one amino acid substitution (e.g., at least one conservative substitution such as highly conservative amino acid substitution) of a non-CDR residue (e.g., within a framework region), of SEQ ID NO:19.

In some embodiments, a polypeptide comprises:
a) a $V_H$ that has at least about 70% (e.g., at least about: 75, 80, 85, 90, 95, 98, or 99%) sequence identity to the amino acid sequence of any one or more of SEQ ID NOs:4-17;
b) a $V_L$ that has at least about 70% (e.g., at least about: 75, 80, 85, 90, 95, 98, or 99%) sequence identity to the amino acid sequence of any one or more of SEQ ID NOs:20-30, or both a) and b).

In some embodiments, a polypeptide comprises:
a) a $V_H$ that has at least about 70% (e.g., at least about: 75, 80, 85, 90, 95, 98, or 99%) sequence identity to the amino acid sequence of any one or more of SEQ ID NOs:4-17; and
b) a $V_L$ that has at least about 70% (e.g., at least about: 75, 80, 85, 90, 95, 98, or 99%) sequence identity to the amino acid sequence of any one or more of SEQ ID NOs:20-30.

In some embodiments, a polypeptide comprises:
a) a $V_H$ that comprises at least one amino acid substitution (e.g., at least one conservative substitution such as highly conservative amino acid substitution) relative to the amino acid sequence of any one or more of SEQ ID NOs:4-17;
b) a $V_L$ that comprises at least one amino acid substitution (e.g., at least one conservative substitution such as highly conservative amino acid substitution) relative to the amino acid sequence of any one or more of SEQ ID NOs:20-30, or both a) and b).

In some embodiments, a polypeptide comprises:
a) a $V_H$ that comprises at least one amino acid substitution (e.g., at least one conservative substitution such as highly conservative amino acid substitution) relative to the amino acid sequence of any one or more of SEQ ID NOs:4-17; and
b) a $V_L$ that comprises at least one amino acid substitution (e.g., at least one conservative substitution such as highly conservative amino acid substitution) relative to the amino acid sequence of any one or more of SEQ ID NOs:20-30.

In some embodiments, a polypeptide comprises:
a) a $V_H$ that comprises at least one amino acid substitution (e.g., at least one conservative substitution such as highly conservative amino acid substitution) of a HCDR1, a HCDR2 and/or a HCDR3 residue, of any one or more of SEQ ID NOs:4-17;
b) a $V_L$ that comprises at least one amino acid substitution (e.g., at least one conservative substitution such as highly conservative amino acid substitution) of a LCDR1, a LCDR2 and/or a LCDR3 residue, of any one or more of SEQ ID NOs:20-30, or both a) and b).

In some embodiments, a polypeptide comprises:
a) a $V_H$ that comprises at least one amino acid substitution (e.g., at least one conservative substitution such as highly conservative amino acid substitution) of a HCDR1, a HCDR2 and/or a HCDR3 residue, of any one or more of SEQ ID NOs:4-17; and
b) a $V_L$ that comprises at least one amino acid substitution (e.g., at least one conservative substitution such as highly conservative amino acid substitution) of a LCDR1, a LCDR2 and/or a LCDR3 residue, of any one or more of SEQ ID NOs:20-30.

In some embodiments, a polypeptide comprises:
a) a $V_H$ that comprises at least one amino acid substitution (e.g., at least one conservative substitution such as highly conservative amino acid substitution) of a non-CDR residue (e.g., within a framework region), of any one or more of SEQ ID NOs:4-17;
b) a $V_L$ that comprises at least one amino acid substitution (e.g., at least one conservative substitution such as highly conservative amino acid substitution) of a non-CDR residue (e.g., within a framework region), of any one or more of SEQ ID NOs:20-30, or both a) and b).

In some embodiments, a polypeptide comprises:
a) a $V_H$ that comprises at least one amino acid substitution (e.g., at least one conservative substitution such as highly conservative amino acid substitution) of a non-CDR residue (e.g., within a framework region), of any one or more of SEQ ID NOs:4-17; and
b) a $V_L$ that comprises at least one amino acid substitution (e.g., at least one conservative substitution such as highly conservative amino acid substitution) of a non-CDR residue (e.g., within a framework region), of any one or more of SEQ ID NOs:20-30.

In some embodiments, a polypeptide disclosed herein comprises:
a) a $V_H$ comprising the amino acid sequence of any one of SEQ ID NOs:4-17; and
b) a $V_L$ comprising the amino acid sequence of any one of SEQ ID NOs:20-30.

In some embodiments, a polypeptide comprises:
a) a $V_H$ comprising the amino acid sequence of any one of SEQ ID NOs:4-17; and
b) a $V_L$ comprising the amino acid sequence of SEQ ID NO:19.

In some embodiments, a polypeptide comprises:
a) a $V_H$ comprising the amino acid sequence of SEQ ID NO:3; and
b) a $V_L$ comprising the amino acid sequence of any one of SEQ ID NOs:20-30.

In some embodiments, a polypeptide comprises:
a) a $V_H$ that has at least about 70% (e.g., at least about: 75, 80, 85, 90, 95, 98, or 99%) sequence identity to the amino acid sequence of any one or more of SEQ ID NOs:4-7;
b) a $V_L$ that has at least about 70% (e.g., at least about: 75, 80, 85, 90, 95, 98, or 99%) sequence identity to the amino acid sequence of any one or more of SEQ ID NOs:20-22, or
both a) and b).

In some embodiments, a polypeptide comprises:
a) a $V_H$ that has at least about 70% (e.g., at least about: 75, 80, 85, 90, 95, 98, or 99%) sequence identity to the amino acid sequence of any one or more of SEQ ID NOs:4-7; and
b) a $V_L$ that has at least about 70% (e.g., at least about: 75, 80, 85, 90, 95, 98, or 99%) sequence identity to the amino acid sequence of any one or more of SEQ ID NOs:20-22.

In some embodiments, a polypeptide comprises:
a) a $V_H$ that comprises at least one amino acid substitution (e.g., at least one conservative substitution such as highly conservative amino acid substitution) relative to the amino acid sequence of any one or more of SEQ ID NOs:4-7;
b) a $V_L$ that comprises at least one amino acid substitution (e.g., at least one conservative substitution such as highly conservative amino acid substitution) relative to the amino acid sequence of any one or more of SEQ ID NOs:20-22, or
both a) and b).

In some embodiments, a polypeptide comprises:
a) a $V_H$ that comprises at least one amino acid substitution (e.g., at least one conservative substitution such as highly conservative amino acid substitution) relative to the amino acid sequence of any one or more of SEQ ID NOs:4-7; and
b) a $V_L$ that comprises at least one amino acid substitution (e.g., at least one conservative substitution such as highly conservative amino acid substitution) relative to the amino acid sequence of any one or more of SEQ ID NOs:20-22.

In some embodiments, a polypeptide comprises:
a) a $V_H$ that comprises at least one amino acid substitution (e.g., at least one conservative substitution such as highly conservative amino acid substitution) of a HCDR1, a HCDR2 and/or a HCDR3 residue, of any one or more of SEQ ID NOs:4-7;
b) a $V_L$ that comprises at least one amino acid substitution (e.g., at least one conservative substitution such as highly conservative amino acid substitution) of a LCDR1, a LCDR2 and/or a LCDR3 residue, of any one or more of SEQ ID NOs:20-22, or
both a) and b).

In some embodiments, a polypeptide comprises:
a) a $V_H$ that comprises at least one amino acid substitution (e.g., at least one conservative substitution such as highly conservative amino acid substitution) of a HCDR1, a HCDR2 and/or a HCDR3 residue, of any one or more of SEQ ID NOs:4-7; and
b) a $V_L$ that comprises at least one amino acid substitution (e.g., at least one conservative substitution such as highly conservative amino acid substitution) of a LCDR1, a LCDR2 and/or a LCDR3 residue, of any one or more of SEQ ID NOs:20-22.

In some embodiments, a polypeptide comprises:
a) a $V_H$ that comprises at least one amino acid substitution (e.g., at least one conservative substitution such as highly conservative amino acid substitution) of a non-CDR residue (e.g., within a framework region), of any one or more of SEQ ID NOs:4-7;
b) a $V_L$ that comprises at least one amino acid substitution (e.g., at least one conservative substitution such as highly conservative amino acid substitution) of a non-CDR residue (e.g., within a framework region), of any one or more of SEQ ID NOs:20-22, or
both a) and b).

In some embodiments, a polypeptide comprises:
a) a $V_H$ that comprises at least one amino acid substitution (e.g., at least one conservative substitution such as highly conservative amino acid substitution) of a non-CDR residue (e.g., within a framework region), of any one or more of SEQ ID NOs:4-7; and
b) a $V_L$ that comprises at least one amino acid substitution (e.g., at least one conservative substitution such as highly conservative amino acid substitution) of a non-CDR residue (e.g., within a framework region), of any one or more of SEQ ID NOs:20-22.

In some embodiments, a polypeptide disclosed herein comprises:
a) a $V_H$ comprising the amino acid sequence of any one of SEQ ID NOs:4-7; and
b) a $V_L$ comprising the amino acid sequence of any one of SEQ ID NOs:20-22.

In some embodiments, a polypeptide comprises:
a) a $V_H$ comprising the amino acid sequence of any one of SEQ ID NOs:4-7; and
b) a $V_L$ comprising the amino acid sequence of SEQ ID NO:19.

In some embodiments, a polypeptide comprises:
a) a $V_H$ comprising the amino acid sequence of SEQ ID NO:3; and
b) a $V_L$ comprising the amino acid sequence of any one of SEQ ID NOs:20-22.

In some embodiments, a polypeptide comprises:
a) a $V_H$ that has at least about 70% (e.g., at least about: 75, 80, 85, 90, 95, 98, or 99%) sequence identity to the amino acid sequence of SEQ ID NO:5;
b) a $V_L$ that has at least about 70% (e.g., at least about: 75, 80, 85, 90, 95, 98, or 99%) sequence identity to the amino acid sequence of SEQ ID NO:21, or
both a) and b).

In some embodiments, a polypeptide comprises:
a) a $V_H$ that has at least about 70% (e.g., at least about: 75, 80, 85, 90, 95, 98, or 99%) sequence identity to the amino acid sequence of SEQ ID NO:5; and
b) a $V_L$ that has at least about 70% (e.g., at least about: 75, 80, 85, 90, 95, 98, or 99%) sequence identity to the amino acid sequence of SEQ ID NO:21.

In some embodiments, a polypeptide comprises:
a) a $V_H$ that comprises at least one amino acid substitution (e.g., at least one conservative substitution such as highly conservative amino acid substitution) relative to the amino acid sequence of SEQ ID NO:5;

b) a $V_L$ that comprises at least one amino acid substitution (e.g., at least one conservative substitution such as highly conservative amino acid substitution) relative to the amino acid sequence of SEQ ID NO:21, or both a) and b).

In some embodiments, a polypeptide comprises:
a) a $V_H$ that comprises at least one amino acid substitution (e.g., at least one conservative substitution such as highly conservative amino acid substitution) relative to the amino acid sequence of SEQ ID NO:5; and
b) a $V_L$ that comprises at least one amino acid substitution (e.g., at least one conservative substitution such as highly conservative amino acid substitution) relative to the amino acid sequence of SEQ ID NO:21.

In some embodiments, a polypeptide comprises:
a) a $V_H$ that comprises at least one amino acid substitution (e.g., at least one conservative substitution such as highly conservative amino acid substitution) of a HCDR1, a HCDR2 and/or a HCDR3 residue, of SEQ ID NO:5;
b) a $V_L$ that comprises at least one amino acid substitution (e.g., at least one conservative substitution such as highly conservative amino acid substitution) of a LCDR1, a LCDR2 and/or a LCDR3 residue, of SEQ ID NO:21, or both a) and b).

In some embodiments, a polypeptide comprises:
a) a $V_H$ that comprises at least one amino acid substitution (e.g., at least one conservative substitution such as highly conservative amino acid substitution) of a HCDR1, a HCDR2 and/or a HCDR3 residue, of SEQ ID NO:5; and
b) a $V_L$ that comprises at least one amino acid substitution (e.g., at least one conservative substitution such as highly conservative amino acid substitution) of a LCDR1, a LCDR2 and/or a LCDR3 residue, of SEQ ID NO:21.

In some embodiments, a polypeptide comprises:
a) a $V_H$ that comprises at least one amino acid substitution (e.g., at least one conservative substitution such as highly conservative amino acid substitution) of a non-CDR residue (e.g., within a framework region), of SEQ ID NO:5;
b) a $V_L$ that comprises at least one amino acid substitution (e.g., at least one conservative substitution such as highly conservative amino acid substitution) of a non-CDR residue (e.g., within a framework region), of SEQ ID NO:21, or both a) and b).

In some embodiments, a polypeptide comprises:
a) a $V_H$ that comprises at least one amino acid substitution (e.g., at least one conservative substitution such as highly conservative amino acid substitution) of a non-CDR residue (e.g., within a framework region), of SEQ ID NO:5; and
b) a $V_L$ that comprises at least one amino acid substitution (e.g., at least one conservative substitution such as highly conservative amino acid substitution) of a non-CDR residue (e.g., within a framework region), of SEQ ID NO:21.

In some embodiments, a polypeptide disclosed herein comprises:
a) a $V_H$ comprising the amino acid sequence of SEQ ID NO:4, and
b) a $V_L$ comprising the amino acid sequence of SEQ ID NO:20 (AB-1).

In some embodiments, a polypeptide disclosed herein comprises:
a) a $V_H$ comprising the amino acid sequence of SEQ ID NO:5, and
b) a $V_L$ comprising the amino acid sequence of SEQ ID NO:21 (AB-2).

In some embodiments, a polypeptide disclosed herein comprises:
a) a $V_H$ comprising the amino acid sequence of SEQ ID NO:6, and
b) a $V_L$ comprising the amino acid sequence of SEQ ID NO:20 (AB-3).

In some embodiments, a polypeptide disclosed herein comprises:
a) a $V_H$ comprising the amino acid sequence of SEQ ID NO:7, and
b) a $V_L$ comprising the amino acid sequence of SEQ ID NO:22 (AB-4).

In some embodiments, a polypeptide disclosed herein comprises:
a) a $V_H$ comprising the amino acid sequence of SEQ ID NO:8, and
b) a $V_L$ comprising the amino acid sequence of SEQ ID NO:23 (AB-5).

In some embodiments, a polypeptide disclosed herein comprises:
a) a $V_H$ comprising the amino acid sequence of SEQ ID NO:9, and
b) a $V_L$ comprising the amino acid sequence of SEQ ID NO:24 (AB-6).

In some embodiments, a polypeptide disclosed herein comprises:
a) a $V_H$ comprising the amino acid sequence of SEQ ID NO:10, and
b) a $V_L$ comprising the amino acid sequence of SEQ ID NO:25 (AB-7).

In some embodiments, a polypeptide disclosed herein comprises:
a) a $V_H$ comprising the amino acid sequence of SEQ ID NO:11, and
b) a $V_L$ comprising the amino acid sequence of SEQ ID NO:20 (AB-8).

In some embodiments, a polypeptide disclosed herein comprises:
a) a $V_H$ comprising the amino acid sequence of SEQ ID NO:12, and
b) a $V_L$ comprising the amino acid sequence of SEQ ID NO:20 (AB-9).

In some embodiments, a polypeptide disclosed herein comprises:
a) a $V_H$ comprising the amino acid sequence of SEQ ID NO:13, and
b) a $V_L$ comprising the amino acid sequence of SEQ ID NO:26 (AB-10).

In some embodiments, a polypeptide disclosed herein comprises:
a) a $V_H$ comprising the amino acid sequence of SEQ ID NO:14, and
b) a $V_L$ comprising the amino acid sequence of SEQ ID NO:27 (AB-11).

In some embodiments, a polypeptide disclosed herein comprises:
a) a $V_H$ comprising the amino acid sequence of SEQ ID NO:15, and
b) a $V_L$ comprising the amino acid sequence of SEQ ID NO:28 (AB-12).

In some embodiments, a polypeptide disclosed herein comprises:
a) a $V_H$ comprising the amino acid sequence of SEQ ID NO:16, and
b) a $V_L$ comprising the amino acid sequence of SEQ ID NO:29 (AB-13).

In some embodiments, a polypeptide disclosed herein comprises:
a) a $V_H$ comprising the amino acid sequence of SEQ ID NO:17, and
b) a $V_L$ comprising the amino acid sequence of SEQ ID NO:30 (AB-14).

Complementarity Determining Regions (CDRs)

A CDR (e.g., HCDR1, HCDR2, HCDR3, LCDR1, LCDR2 and/or LCDR3) can be a CDR defined by any art-recognized method for identifying CDR residues of an antibody, as described further herein (e.g., a CDR as defined by Kabat, a CDR as defined by Chothia, or a CDR as defined by IMGT).

In some embodiments, a polypeptide (e.g., an antibody or antigen-binding fragment thereof) does not comprise all six CDRs of an antibody that comprises a $V_H$ amino acid sequence of SEQ ID NO:3 and a $V_L$ amino acid sequence of SEQ ID NO:19. In some embodiments, a polypeptide does not comprise all six sequences of SEQ ID NO:31, SEQ ID NO:33, SEQ ID NO:48, SEQ ID NO:59, DDS and SEQ ID NO:69. See Table 3 for SEQ ID NO:31, SEQ ID NO:33, SEQ ID NO:48, SEQ ID NO:59, DDS and SEQ ID NO:69. In some embodiments, a polypeptide does not comprise all four sequences of SEQ ID NO:33, SEQ ID NO:48, SEQ ID NO:59, and SEQ ID NO:69.

In some embodiments, a polypeptide comprises fewer than six (e.g., 1, 2, 3, 4 or 5) CDRs of an antibody that comprises a $V_H$ amino acid sequence of SEQ ID NO:3 and a $V_L$ amino acid sequence of SEQ ID NO:19. In some embodiments, a polypeptide comprises 1, 2, 3, 4 or 5 sequences, but not all 6 sequences, selected from SEQ ID NO:31, SEQ ID NO:33, SEQ ID NO:48, SEQ ID NO:59, DDS and SEQ ID NO:69. In some embodiments, a polypeptide comprises 1, 2, or 3 sequences, but not all 4 sequences, selected from SEQ ID NO:33, SEQ ID NO:48, SEQ ID NO:59, and SEQ ID NO:69.

In some embodiments, a polypeptide comprises all six CDRs of a specific polypeptide disclosed herein. In some embodiments, a polypeptide comprises fewer than six (e.g., 1, 2, 3, 4 or 5) of CDRs of a specific polypeptide disclosed herein.

In some embodiments, a polypeptide comprises:
a) a $V_H$ amino acid sequence comprising a HCDR1, a HCDR2, and a HCDR3 that are substantially similar (e.g., having at least about 90% sequence identity) in amino acid sequence to a HCDR1, a HCDR2 and a HCDR3, respectively, of a $V_H$ amino acid sequence of any one or more of SEQ ID NOs:4-17;
b) a $V_L$ amino acid sequence comprising a LCDR1, a LCDR2 and a LCDR3 that are substantially similar (e.g., having at least about 90% sequence identity) in amino acid sequence to a LCDR1, a LCDR2 and a LCDR3, respectively, of a $V_L$ amino acid sequence of any one or more of SEQ ID NOs:20-30, or
both a) and b).

In some embodiments, a polypeptide comprises:
a) a $V_H$ amino acid sequence comprising a HCDR1, a HCDR2, and a HCDR3 that are substantially similar (e.g., having at least about 90% sequence identity) in amino acid sequence to a HCDR1, a HCDR2 and a HCDR3, respectively, of a $V_H$ amino acid sequence of any one or more of SEQ ID NOs:4-17; and
b) a $V_L$ amino acid sequence comprising a LCDR1, a LCDR2 and a LCDR3 that are substantially similar (e.g., having at least about 90% sequence identity) in amino acid sequence to a LCDR1, a LCDR2 and a LCDR3, respectively, of a $V_L$ amino acid sequence of any one or more of SEQ ID NOs:20-30.

See Tables 2-3 and FIGS. 2A-3B for SEQ ID NOs:4-17 and 20-30, and non-limiting examples of corresponding HCDR1, HCDR2, HCDR3, LCDR1, LCDR2, and LCDR3 sequences.

In some embodiments, a polypeptide comprises:
a) a $V_H$ amino acid sequence comprising a HCDR1, a HCDR2, and a HCDR3 that substantially preserve one or more functional properties of a HCDR1, a HCDR2 and a HCDR3, respectively, of a $V_H$ amino acid sequence of any one or more of SEQ ID NOs:4-17; or
b) a $V_L$ amino acid sequence comprising a LCDR1, a LCDR2, and a LCDR3 that substantially preserve one or more functional properties of a LCDR1, a LCDR2 and a LCDR3, respectively, of a $V_L$ amino acid sequence of any one or more of SEQ ID NOs:20-30, or
both a) and b).

In some embodiments, a polypeptide comprises:
a) a $V_H$ amino acid sequence comprising a HCDR1, a HCDR2, and a HCDR3 that substantially preserve one or more functional properties of a HCDR1, a HCDR2 and a HCDR3, respectively, of a $V_H$ amino acid sequence of any one or more of SEQ ID NOs:4-17; and
b) a $V_L$ amino acid sequence comprising a LCDR1, a LCDR2, and a LCDR3 that substantially preserve one or more functional properties of a LCDR1, a LCDR2 and a LCDR3, respectively, of a $V_L$ amino acid sequence of any one or more of SEQ ID NOs:20-30.

In some embodiments, a polypeptide comprises:
a) a $V_H$ amino acid sequence that comprises a HCDR1, a HCDR2, and a HCDR3 comprising only one or more conservative substitutions (e.g., only one or more highly conservative substitutions), relative to a HCDR1, a HCDR2 and a HCDR3, respectively, of a $V_H$ amino acid sequence of any one or more of SEQ ID NOs:4-17; or
b) a $V_L$ amino acid sequence that comprises a LCDR1, a LCDR2, and a LCDR3 comprising only one or more conservative substitutions (e.g., only one or more highly conservative substitutions), relative to a LCDR1, a LCDR2 and a LCDR3, respectively, of a $V_L$ amino acid sequence of any one or more of SEQ ID NOs:20-30, or
both a) and b).

In some embodiments, a polypeptide comprises:
a) a $V_H$ amino acid sequence that comprises a HCDR1, a HCDR2, and a HCDR3 comprising only one or more conservative substitutions (e.g., only one or more highly conservative substitutions), relative to a HCDR1, a HCDR2 and a HCDR3, respectively, of a $V_H$ amino acid sequence of any one or more of SEQ ID NOs:4-17; and
b) a $V_L$ amino acid sequence that comprises a LCDR1, a LCDR2, and a LCDR3 comprising only one or more conservative substitutions (e.g., only one or more highly conservative substitutions), relative to a LCDR1, a LCDR2 and a LCDR3, respectively, of a $V_L$ amino acid sequence of any one or more of SEQ ID NOs:20-30.

In some embodiments, a polypeptide comprises:
a) a $V_H$ amino acid sequence that comprises a HCDR1, a HCDR2, and a HCDR3 comprising up to 1, 2, or 3 conservative substitutions (e.g., up to 1, 2, or 3 highly conservative substitutions), relative to a HCDR1, a HCDR2 and a HCDR3, respectively, of a $V_H$ amino acid sequence of any one or more of SEQ ID NOs:4-17; or
b) a $V_L$ amino acid sequence that comprises a LCDR1, a LCDR2, and a LCDR3 comprising up to 1, 2, or 3 conservative substitutions (e.g., up to 1, 2, or 3 highly conservative substitutions), relative to a LCDR1, a LCDR2 and a LCDR3, respectively, of a $V_L$ amino acid sequence of any one or more of SEQ ID NOs:20-30, or both a) and b).

In some embodiments, a polypeptide comprises:
a) a $V_H$ amino acid sequence that comprises a HCDR1, a HCDR2, and a HCDR3 comprising up to 1, 2, or 3 conservative substitutions (e.g., up to 1, 2, or 3 highly conservative substitutions), relative to a HCDR1, a HCDR2 and a HCDR3, respectively, of a $V_H$ amino acid sequence of any one or more of SEQ ID NOs:4-17; and
b) a $V_L$ amino acid sequence that comprises a LCDR1, a LCDR2, and a LCDR3 comprising up to 1, 2, or 3 conservative substitutions (e.g., up to 1, 2, or 3 highly conservative substitutions), relative to a LCDR1, a LCDR2 and a LCDR3, respectively, of a $V_L$ amino acid sequence of any one or more of SEQ ID NOs:20-30.

In some embodiments, a polypeptide comprises:
a) a $V_H$ amino acid sequence that comprises a HCDR1, a HCDR2, and a HCDR3 having 100% sequence identity to a HCDR1, a HCDR2 and a HCDR3, respectively, of a $V_H$ amino acid sequence of any one or more of SEQ ID NOs:4-17; or
b) a $V_L$ amino acid sequence that comprises a LCDR1, a LCDR2, and a LCDR3 having 100% sequence identity to a LCDR1, a LCDR2 and a LCDR3, respectively, of a $V_L$ amino acid sequence of any one or more of SEQ ID NOs:20-30, or both a) and b).

In some embodiments, a polypeptide comprises:
a) a $V_H$ amino acid sequence that comprises a HCDR1, a HCDR2, and a HCDR3 having 100% sequence identity to a HCDR1, a HCDR2 and a HCDR3, respectively, of a $V_H$ amino acid sequence of any one or more of SEQ ID NOs:4-17; and
b) a $V_L$ amino acid sequence that comprises a LCDR1, a LCDR2, and a LCDR3 having 100% sequence identity to a LCDR1, a LCDR2 and a LCDR3, respectively, of a $V_L$ amino acid sequence of any one or more of SEQ ID NOs:20-30.

In some embodiments, a polypeptide comprises a HCDR1, a HCDR2, a HCDR3, a LCDR1, a LCDR2 and a LCDR3, of an antibody comprising a $V_H/V_L$ combination selected from:
SEQ ID NO:4 and SEQ ID NO:20 (AB-1);
SEQ ID NO:5 and SEQ ID NO: 21 (AB-2);
SEQ ID NO:6 and SEQ ID NO:20 (AB-3);
SEQ ID NO:7 and SEQ ID NO:22 (AB-4);
SEQ ID NO:8 and SEQ ID NO:23 (AB-5);
SEQ ID NO:9 and SEQ ID NO:24 (AB-6);
SEQ ID NO:10 and SEQ ID NO:25 (AB-7);
SEQ ID NO:11 and SEQ ID NO:20 (AB-8);
SEQ ID NO:12 and SEQ ID NO:20 (AB-9);
SEQ ID NO:13 and SEQ ID NO:26 (AB-10);
SEQ ID NO:14 and SEQ ID NO:27 (AB-11);
SEQ ID NO:15 and SEQ ID NO:28 (AB-12);
SEQ ID NO:16 and SEQ ID NO:29 (AB-13); or
SEQ ID NO:17 and SEQ ID NO:30 (AB-14).

In some embodiments, a polypeptide comprises:
a) a HCDR1 comprising the amino acid sequence set forth in SEQ ID NO:31;
b) a HCDR2 comprising at least one amino acid substitution relative to at least one amino acid sequence set forth in SEQ ID NOs:33-46 (e.g., at least one amino acid sequence set forth in SEQ ID NOs:34-46);
c) a HCDR3 comprising at least one amino acid substitution relative to at least one amino acid sequence set forth in SEQ ID NOs:48-57 (e.g., at least one amino acid sequence set forth in SEQ ID NOs:49-57);
d) a LCDR1 comprising at least one amino acid substitution relative to at least one amino acid sequence set forth in SEQ ID NOs:59-66 (e.g., at least one amino acid sequence set forth in SEQ ID NOs:60-66);
e) a LCDR2 comprising the amino acid sequence DDS;
f) a LCDR3 comprising at least one amino acid substitution relative to at least one amino acid sequence set forth in SEQ ID NOs:69-80 (e.g., at least one amino acid sequence set forth in SEQ ID NOs:70-80);
or any combination of the foregoing.

In some embodiments, a polypeptide comprises:
a) a $V_H$ amino acid sequence comprising a HCDR1, a HCDR2, and a HCDR3 that are substantially similar (e.g., having at least about 90% sequence identity) in amino acid sequence to a HCDR1, a HCDR2 and a HCDR3, respectively, of a $V_H$ amino acid sequence set forth in any one of SEQ ID NOs:4-7;
b) a $V_L$ amino acid sequence comprising a LCDR1, a LCDR2 and a LCDR3 that are substantially similar (e.g., having at least about 90% sequence identity) in amino acid sequence to a LCDR1, a LCDR2 and a LCDR3, respectively, of a $V_L$ amino acid sequence set forth in any one of SEQ ID NOs:20-22, or
both a) and b).

In some embodiments, a polypeptide comprises:
a) a $V_H$ amino acid sequence comprising a HCDR1, a HCDR2, and a HCDR3 that are substantially similar (e.g., having at least about 90% sequence identity) in amino acid sequence to a HCDR1, a HCDR2 and a HCDR3, respectively, of a $V_H$ amino acid sequence of any one or more of SEQ ID NOs:4-7;
b) a $V_L$ amino acid sequence comprising a LCDR1, a LCDR2 and a LCDR3 that are substantially similar (e.g., having at least about 90% sequence identity) in amino acid sequence to a LCDR1, a LCDR2 and a LCDR3, respectively, of a $V_L$ amino acid sequence of any one or more of SEQ ID NOs:20-22, or
both a) and b).

In some embodiments, a polypeptide comprises:
a) a $V_H$ amino acid sequence comprising a HCDR1, a HCDR2, and a HCDR3 that are substantially similar (e.g., having at least about 90% sequence identity) in amino acid sequence to a HCDR1, a HCDR2 and a HCDR3, respectively, of a $V_H$ amino acid sequence of any one or more of SEQ ID NOs:4-7; and
b) a $V_L$ amino acid sequence comprising a LCDR1, a LCDR2 and a LCDR3 that are substantially similar (e.g., having at least about 90% sequence identity) in amino acid sequence to a LCDR1, a LCDR2 and a LCDR3, respectively, of a $V_L$ amino acid sequence of any one or more of SEQ ID NOs:20-22.

In some embodiments, a polypeptide comprises:
a) a $V_H$ amino acid sequence comprising a HCDR1, a HCDR2, and a HCDR3 that substantially preserve one or more functional properties of a HCDR1, a HCDR2 and a HCDR3, respectively, of a $V_H$ amino acid sequence of any one or more of SEQ ID NOs:4-7; or b) a $V_L$ amino acid sequence comprising a LCDR1, a LCDR2, and a LCDR3 that substantially preserve one or more functional properties of a LCDR1, a LCDR2 and a LCDR3, respectively, of a $V_L$ amino acid sequence of any one or more of SEQ ID NOs:20-22, or both a) and b).

In some embodiments, a polypeptide comprises:
a) a $V_H$ amino acid sequence comprising a HCDR1, a HCDR2, and a HCDR3 that substantially preserve one or more functional properties of a HCDR1, a HCDR2 and a HCDR3, respectively, of a $V_H$ amino acid sequence of any one or more of SEQ ID NOs:4-7; and b) a $V_L$ amino acid sequence comprising a LCDR1, a LCDR2, and a LCDR3 that substantially preserve one or more functional properties of a LCDR1, a LCDR2 and a LCDR3, respectively, of a $V_L$ amino acid sequence of any one or more of SEQ ID NOs:20-22.

In some embodiments, a polypeptide comprises:
a) a $V_H$ amino acid sequence that comprises a HCDR1, a HCDR2, and a HCDR3 comprising only one or more conservative substitutions (e.g., only one or more highly conservative substitutions), relative to a HCDR1, a HCDR2 and a HCDR3, respectively, of a $V_H$ amino acid sequence of any one or more of SEQ ID NOs:4-7; or b) a $V_L$ amino acid sequence that comprises a LCDR1, a LCDR2, and a LCDR3 comprising only one or more conservative substitutions (e.g., only one or more highly conservative substitutions), relative to a LCDR1, a LCDR2 and a LCDR3, respectively, of a $V_L$ amino acid sequence of any one or more of SEQ ID NOs:20-22, or both a) and b).

In some embodiments, a polypeptide comprises:
a) a $V_H$ amino acid sequence that comprises a HCDR1, a HCDR2, and a HCDR3 comprising only one or more conservative substitutions (e.g., only one or more highly conservative substitutions), relative to a HCDR1, a HCDR2 and a HCDR3, respectively, of a $V_H$ amino acid sequence of any one or more of SEQ ID NOs:4-7; and b) a $V_L$ amino acid sequence that comprises a LCDR1, a LCDR2, and a LCDR3 comprising only one or more conservative substitutions (e.g., only one or more highly conservative substitutions), relative to a LCDR1, a LCDR2 and a LCDR3, respectively, of a $V_L$ amino acid sequence of any one or more of SEQ ID NOs:20-22.

In some embodiments, a polypeptide comprises:
a) a $V_H$ amino acid sequence that comprises a HCDR1, a HCDR2, and a HCDR3 comprising up to 1, 2, or 3 conservative substitutions (e.g., up to 1, 2, or 3 highly conservative substitutions), relative to a HCDR1, a HCDR2 and a HCDR3, respectively, of a $V_H$ amino acid sequence of any one or more of SEQ ID NOs:4-7; or b) a $V_L$ amino acid sequence that comprises a LCDR1, a LCDR2, and a LCDR3 comprising up to 1, 2, or 3 conservative substitutions (e.g., up to 1, 2, or 3 highly conservative substitutions), relative to a LCDR1, a LCDR2 and a LCDR3, respectively, of a $V_L$ amino acid sequence of any one or more of SEQ ID NOs:20-22, or both a) and b).

In some embodiments, a polypeptide comprises:
a) a $V_H$ amino acid sequence that comprises a HCDR1, a HCDR2, and a HCDR3 comprising up to 1, 2, or 3 conservative substitutions (e.g., up to 1, 2, or 3 highly conservative substitutions), relative to a HCDR1, a HCDR2 and a HCDR3, respectively, of a $V_H$ amino acid sequence of any one or more of SEQ ID NOs:4-7; and b) a $V_L$ amino acid sequence that comprises a LCDR1, a LCDR2, and a LCDR3 comprising up to 1, 2, or 3 conservative substitutions (e.g., up to 1, 2, or 3 highly conservative substitutions), relative to a LCDR1, a LCDR2 and a LCDR3, respectively, of a $V_L$ amino acid sequence of any one or more of SEQ ID NOs:20-22.

In some embodiments, a polypeptide comprises:
a) a $V_H$ amino acid sequence that comprises a HCDR1, a HCDR2, and a HCDR3 having 100% sequence identity to a HCDR1, a HCDR2 and a HCDR3, respectively, of a $V_H$ amino acid sequence of any one or more of SEQ ID NOs:4-7; or b) a $V_L$ amino acid sequence that comprises a LCDR1, a LCDR2, and a LCDR3 having 100% sequence identity to a LCDR1, a LCDR2 and a LCDR3, respectively, of a $V_L$ amino acid sequence of any one or more of SEQ ID NOs:20-22, or both a) and b).

In some embodiments, a polypeptide comprises:
a) a $V_H$ amino acid sequence that comprises a HCDR1, a HCDR2, and a HCDR3 having 100% sequence identity to a HCDR1, a HCDR2 and a HCDR3, respectively, of a $V_H$ amino acid sequence of any one or more of SEQ ID NOs:4-7; and b) a $V_L$ amino acid sequence that comprises a LCDR1, a LCDR2, and a LCDR3 having 100% sequence identity to a LCDR1, a LCDR2 and a LCDR3, respectively, of a $V_L$ amino acid sequence of any one or more of SEQ ID NOs:20-22.

In some embodiments, a polypeptide comprises a HCDR1, a HCDR2, a HCDR3, a LCDR1, a LCDR2 and a LCDR3, of an antibody comprising a $V_H/V_L$ combination selected from:
SEQ ID NO:4 and SEQ ID NO:20 (AB-1);
SEQ ID NO:5 and SEQ ID NO:21 (AB-2);
SEQ ID NO:6 and SEQ ID NO:20 (AB-3); or
SEQ ID NO:7 and SEQ ID NO:22 (AB-4).

In some embodiments, a polypeptide comprises:
a) a HCDR1 comprising the amino acid sequence set forth in SEQ ID NO:31;
b) a HCDR2 comprising at least one amino acid substitution relative to at least one amino acid sequence set forth in SEQ ID NOs:33-37 (e.g., at least one amino acid sequence set forth in SEQ ID NOs:34-37);
c) a HCDR3 comprising at least one amino acid substitution relative to at least one amino acid sequence set forth in SEQ ID NOs:48-52 (e.g., at least one amino acid sequence set forth in SEQ ID NOs:49-52);
d) a LCDR1 comprising at least one amino acid substitution relative to at least one amino acid sequence set forth in SEQ ID NOs:59-61 (e.g., at least one amino acid sequence set forth in SEQ ID NO:60 or SEQ ID NO:61);
e) a LCDR2 comprising the amino acid sequence DDS;
f) a LCDR3 comprising at least one amino acid substitution relative to at least one amino acid sequence set forth in SEQ ID NOs:69-72 (e.g., at least one amino acid sequence set forth in SEQ ID NOs:70-72);
or any combination of the foregoing.

In some embodiments, a polypeptide comprises:
a) a $V_H$ amino acid sequence comprising a HCDR1, a HCDR2, and a HCDR3 that are substantially similar (e.g., having at least about 90% sequence identity) in amino acid sequence to a HCDR1, a HCDR2 and a HCDR3, respectively, of a $V_H$ amino acid sequence of SEQ ID NO:5;
b) a $V_L$ amino acid sequence comprising a LCDR1, a LCDR2 and a LCDR3 that are substantially similar (e.g., having at least about 90% sequence identity) in amino acid sequence to a LCDR1, a LCDR2 and a LCDR3, respectively, of a $V_L$ amino acid sequence of SEQ ID NO:21, or
both a) and b).

In some embodiments, a polypeptide comprises:
a) a $V_H$ amino acid sequence comprising a HCDR1, a HCDR2, and a HCDR3 that are substantially similar (e.g., having at least about 90% sequence identity) in amino acid sequence to a HCDR1, a HCDR2 and a HCDR3, respectively, of a $V_H$ amino acid sequence of SEQ ID NO:5; and
b) a $V_L$ amino acid sequence comprising a LCDR1, a LCDR2 and a LCDR3 that are substantially similar (e.g., having at least about 90% sequence identity) in amino acid sequence to a LCDR1, a LCDR2 and a LCDR3, respectively, of a $V_L$ amino acid sequence of SEQ ID NO:21.

In some embodiments, a polypeptide comprises:
a) a $V_H$ amino acid sequence comprising a HCDR1, a HCDR2, and a HCDR3 that substantially preserve one or more functional properties of a HCDR1, a HCDR2 and a HCDR3, respectively, of a $V_H$ amino acid sequence of SEQ ID NO:5; or
b) a $V_L$ amino acid sequence comprising a LCDR1, a LCDR2, and a LCDR3 that substantially preserve one or more functional properties of a LCDR1, a LCDR2 and a LCDR3, respectively, of a $V_L$ amino acid sequence of SEQ ID NO:21, or
both a) and b).

In some embodiments, a polypeptide comprises:
a) a $V_H$ amino acid sequence comprising a HCDR1, a HCDR2, and a HCDR3 that substantially preserve one or more functional properties of a HCDR1, a HCDR2 and a HCDR3, respectively, of a $V_H$ amino acid sequence of SEQ ID NO:5; and
b) a $V_L$ amino acid sequence comprising a LCDR1, a LCDR2, and a LCDR3 that substantially preserve one or more functional properties of a LCDR1, a LCDR2 and a LCDR3, respectively, of a $V_L$ amino acid sequence of SEQ ID NO:21.

In some embodiments, a polypeptide comprises:
a) a $V_H$ amino acid sequence that comprises a HCDR1, a HCDR2, and a HCDR3 comprising only one or more conservative substitutions (e.g., only one or more highly conservative substitutions), relative to a HCDR1, a HCDR2 and a HCDR3, respectively, of a $V_H$ amino acid sequence of SEQ ID NO:5; or
b) a $V_L$ amino acid sequence that comprises a LCDR1, a LCDR2, and a LCDR3 comprising only one or more conservative substitutions (e.g., only one or more highly conservative substitutions), relative to a LCDR1, a LCDR2 and a LCDR3, respectively, of a $V_L$ amino acid sequence of SEQ ID NO:21, or
both a) and b).

In some embodiments, a polypeptide comprises:
a) a $V_H$ amino acid sequence that comprises a HCDR1, a HCDR2, and a HCDR3 comprising only one or more conservative substitutions (e.g., only one or more highly conservative substitutions), relative to a HCDR1, a HCDR2 and a HCDR3, respectively, of a $V_H$ amino acid sequence of SEQ ID NO:5; and
b) a $V_L$ amino acid sequence that comprises a LCDR1, a LCDR2, and a LCDR3 comprising only one or more conservative substitutions (e.g., only one or more highly conservative substitutions), relative to a LCDR1, a LCDR2 and a LCDR3, respectively, of a $V_L$ amino acid sequence of SEQ ID NO:21.

In some embodiments, a polypeptide comprises:
a) a $V_H$ amino acid sequence that comprises a HCDR1, a HCDR2, and a HCDR3 comprising up to 1, 2, or 3 conservative substitutions (e.g., up to 1, 2, or 3 highly conservative substitutions), relative to a HCDR1, a HCDR2 and a HCDR3, respectively, of a $V_H$ amino acid sequence of SEQ ID NO:5; or
b) a $V_L$ amino acid sequence that comprises a LCDR1, a LCDR2, and a LCDR3 comprising up to 1, 2, or 3 conservative substitutions (e.g., up to 1, 2, or 3 highly conservative substitutions), relative to a LCDR1, a LCDR2 and a LCDR3, respectively, of a $V_L$ amino acid sequence of SEQ ID NO:21, or
both a) and b).

In some embodiments, a polypeptide comprises:
a) a $V_H$ amino acid sequence that comprises a HCDR1, a HCDR2, and a HCDR3 comprising up to 1, 2, or 3 conservative substitutions (e.g., up to 1, 2, or 3 highly conservative substitutions), relative to a HCDR1, a HCDR2 and a HCDR3, respectively, of a $V_H$ amino acid sequence of SEQ ID NO:5; and
b) a $V_L$ amino acid sequence that comprises a LCDR1, a LCDR2, and a LCDR3 comprising up to 1, 2, or 3 conservative substitutions (e.g., up to 1, 2, or 3 highly conservative substitutions), relative to a LCDR1, a LCDR2 and a LCDR3, respectively, of a $V_L$ amino acid sequence of SEQ ID NO:21.

In some embodiments, a polypeptide comprises:
a) a $V_H$ amino acid sequence that comprises a HCDR1, a HCDR2, and a HCDR3 having 100% sequence identity to a HCDR1, a HCDR2 and a HCDR3, respectively, of a $V_H$ amino acid sequence of SEQ ID NO:5; or
b) a $V_L$ amino acid sequence that comprises a LCDR1, a LCDR2, and a LCDR3 having 100% sequence identity to a LCDR1, a LCDR2 and a LCDR3, respectively, of a $V_L$ amino acid sequence of SEQ ID NO:21, or
both a) and b).

In some embodiments, a polypeptide comprises:
a) a $V_H$ amino acid sequence that comprises a HCDR1, a HCDR2, and a HCDR3 having 100% sequence identity to a HCDR1, a HCDR2 and a HCDR3, respectively, of a $V_H$ amino acid sequence of SEQ ID NO:5; and
b) a $V_L$ amino acid sequence that comprises a LCDR1, a LCDR2, and a LCDR3 having 100% sequence identity to a LCDR1, a LCDR2 and a LCDR3, respectively, of a $V_L$ amino acid sequence of SEQ ID NO:21.

In some embodiments, a polypeptide comprises:
a) a $V_H$ comprising a HCDR1, a HCDR2 and a HCDR3 amino acid sequences of SEQ ID NO:4, and
b) a $V_L$ comprising a LCDR1, a LCDR2 and a LCDR3 amino acid sequences of SEQ ID NO:20 (AB-1).

In some embodiments, a polypeptide comprises:
a) a $V_H$ comprising a HCDR1, a HCDR2 and a HCDR3 amino acid sequences of SEQ ID NO:5; and
b) a $V_L$ comprising a LCDR1, a LCDR2 and a LCDR3 amino acid sequences of SEQ ID NO:21 (AB-2).

In some embodiments, a polypeptide comprises:
a) a $V_H$ comprising a HCDR1, a HCDR2 and a HCDR3 amino acid sequences of SEQ ID NO:6; and
b) a $V_L$ comprising a LCDR1, a LCDR2 and a LCDR3 amino acid sequences of SEQ ID NO:20 (AB-3).

In some embodiments, a polypeptide comprises:
a) a $V_H$ comprising a HCDR1, a HCDR2 and a HCDR3 amino acid sequences of SEQ ID NO:7; and
b) a $V_L$ comprising a LCDR1, a LCDR2 and a LCDR3 amino acid sequences of SEQ ID NO:22 (AB-4).

In some embodiments, a polypeptide comprises:
a) a $V_H$ comprising a HCDR1, a HCDR2 and a HCDR3 amino acid sequences of SEQ ID NO:8; and
b) a $V_L$ comprising a LCDR1, a LCDR2 and a LCDR3 amino acid sequences of SEQ ID NO:23 (AB-5).

In some embodiments, a polypeptide comprises:
a) a $V_H$ comprising a HCDR1, a HCDR2 and a HCDR3 amino acid sequences of SEQ ID NO:9; and
b) a $V_L$ comprising a LCDR1, a LCDR2 and a LCDR3 amino acid sequences of SEQ ID NO:24 (AB-6).

In some embodiments, a polypeptide comprises:
a) a $V_H$ comprising a HCDR1, a HCDR2 and a HCDR3 amino acid sequences of SEQ ID NO:10; and
b) a $V_L$ comprising a LCDR1, a LCDR2 and a LCDR3 amino acid sequences of SEQ ID NO:25 (AB-7).

In some embodiments, a polypeptide comprises:
a) a $V_H$ comprising a HCDR1, a HCDR2 and a HCDR3 amino acid sequences of SEQ ID NO:11; and
b) a $V_L$ comprising a LCDR1, a LCDR2 and a LCDR3 amino acid sequences of SEQ ID NO:20 (AB-8).

In some embodiments, a polypeptide comprises:
a) a $V_H$ comprising a HCDR1, a HCDR2 and a HCDR3 amino acid sequences of SEQ ID NO:12; and
b) a $V_L$ comprising a LCDR1, a LCDR2 and a LCDR3 amino acid sequences of SEQ ID NO:20 (AB-9).

In some embodiments, a polypeptide comprises:
a) a $V_H$ comprising a HCDR1, a HCDR2 and a HCDR3 amino acid sequences of SEQ ID NO:13; and
b) a $V_L$ comprising a LCDR1, a LCDR2 and a LCDR3 amino acid sequences of SEQ ID NO:26 (AB-10).

In some embodiments, a polypeptide comprises:
a) a $V_H$ comprising a HCDR1, a HCDR2 and a HCDR3 amino acid sequences of SEQ ID NO:14; and
b) a $V_L$ comprising a LCDR1, a LCDR2 and a LCDR3 amino acid sequences of SEQ ID NO:27 (AB-11).

In some embodiments, a polypeptide comprises:
a) a $V_H$ comprising a HCDR1, a HCDR2 and a HCDR3 amino acid sequences of SEQ ID NO:15; and
b) a $V_L$ comprising a LCDR1, a LCDR2 and a LCDR3 amino acid sequences of SEQ ID NO:28 (AB-12).

In some embodiments, a polypeptide comprises:
a) a $V_H$ comprising a HCDR1, a HCDR2 and a HCDR3 amino acid sequences of SEQ ID NO:16; and
b) a $V_L$ comprising a LCDR1, a LCDR2 and a LCDR3 amino acid sequences of SEQ ID NO:29 (AB-13).

In some embodiments, a polypeptide comprises:
a) a $V_H$ comprising a HCDR1, a HCDR2 and a HCDR3 amino acid sequences of SEQ ID NO:17; and
b) a $V_L$ comprising a LCDR1, a LCDR2 and a LCDR3 amino acid sequences of SEQ ID NO:30 (AB-14).

In some embodiments, a polypeptide comprises:
a) a HCDR1 comprising the amino acid sequence of SEQ ID NO:31;
b) a HCDR2 comprising the amino acid sequence of SEQ ID NO:34;
a HCDR3 comprising the amino acid sequence of SEQ ID NO:49; c)
d) a LCDR1 comprising the amino acid sequence of SEQ ID NO:60;
e) a LCDR2 comprising the amino acid sequence DDS;
f) a LCDR3 comprising the amino acid sequence of SEQ ID NO:70, or
any combination of the foregoing.

In some embodiments, a polypeptide comprises:
a) a HCDR1 comprising the amino acid sequence of SEQ ID NO:31;
b) a HCDR2 comprising the amino acid sequence of SEQ ID NO:35;
c) a HCDR3 comprising the amino acid sequence of SEQ ID NO:50;
d) a LCDR1 comprising the amino acid sequence of SEQ ID NO:60;
e) a LCDR2 comprising the amino acid sequence DDS;
f) a LCDR3 comprising the amino acid sequence of SEQ ID NO:71, or
any combination of the foregoing.

In some embodiments, a polypeptide comprises:
a) a HCDR1 comprising the amino acid sequence of SEQ ID NO:31;
b) a HCDR2 comprising the amino acid sequence of SEQ ID NO:36;
c) a HCDR3 comprising the amino acid sequence of SEQ ID NO:51;
d) a LCDR1 comprising the amino acid sequence of SEQ ID NO:60;
e) a LCDR2 comprising the amino acid sequence DDS;
f) a LCDR3 comprising the amino acid sequence of SEQ ID NO:70, or
any combination of the foregoing.

In some embodiments, a polypeptide comprises:
a) a HCDR1 comprising the amino acid sequence of SEQ ID NO:31;
b) a HCDR2 comprising the amino acid sequence of SEQ ID NO:37;
a HCDR3 comprising the amino acid sequence of SEQ ID NO:52; c)
d) a LCDR1 comprising the amino acid sequence of SEQ ID NO:61;
e) a LCDR2 comprising the amino acid sequence DDS;
f) a LCDR3 comprising the amino acid sequence of SEQ ID NO:72, or
any combination of the foregoing.

In some embodiments, a polypeptide comprises:
a) a HCDR1 comprising the amino acid sequence of SEQ ID NO:31;
b) a HCDR2 comprising the amino acid sequence of SEQ ID NO:38;
c) a HCDR3 comprising the amino acid sequence of SEQ ID NO:53;
d) a LCDR1 comprising the amino acid sequence of SEQ ID NO:59;
e) a LCDR2 comprising the amino acid sequence DDS;
f) a LCDR3 comprising the amino acid sequence of SEQ ID NO:73, or
any combination of the foregoing.

In some embodiments, a polypeptide comprises:
a) a HCDR1 comprising the amino acid sequence of SEQ ID NO:31;
b) a HCDR2 comprising the amino acid sequence of SEQ ID NO:39;
c) a HCDR3 comprising the amino acid sequence of SEQ ID NO:53;
d) a LCDR1 comprising the amino acid sequence of SEQ ID NO:60;

e) a LCDR2 comprising the amino acid sequence DDS;
f) a LCDR3 comprising the amino acid sequence of SEQ ID NO:74, or
any combination of the foregoing.
In some embodiments, a polypeptide comprises:
a) a HCDR1 comprising the amino acid sequence of SEQ ID NO:31;
b) a HCDR2 comprising the amino acid sequence of SEQ ID NO:40;
a HCDR3 comprising the amino acid sequence of SEQ ID NO:49; c)
d) a LCDR1 comprising the amino acid sequence of SEQ ID NO:62;
e) a LCDR2 comprising the amino acid sequence DDS;
f) a LCDR3 comprising the amino acid sequence of SEQ ID NO:75, or
any combination of the foregoing.
In some embodiments, a polypeptide comprises:
a) a HCDR1 comprising the amino acid sequence of SEQ ID NO:31;
b) a HCDR2 comprising the amino acid sequence of SEQ ID NO:41;
c) a HCDR3 comprising the amino acid sequence of SEQ ID NO:54;
d) a LCDR1 comprising the amino acid sequence of SEQ ID NO:60;
e) a LCDR2 comprising the amino acid sequence DDS;
f) a LCDR3 comprising the amino acid sequence of SEQ ID NO:70, or
any combination of the foregoing.
In some embodiments, a polypeptide comprises:
a) a HCDR1 comprising the amino acid sequence of SEQ ID NO:31;
b) a HCDR2 comprising the amino acid sequence of SEQ ID NO:41;
c) a HCDR3 comprising the amino acid sequence of SEQ ID NO:51;
d) a LCDR1 comprising the amino acid sequence of SEQ ID NO:60;
e) a LCDR2 comprising the amino acid sequence DDS;
f) a LCDR3 comprising the amino acid sequence of SEQ ID NO:70, or
any combination of the foregoing.
In some embodiments, a polypeptide comprises:
a) a HCDR1 comprising the amino acid sequence of SEQ ID NO:31;
b) a HCDR2 comprising the amino acid sequence of SEQ ID NO:42;
c) a HCDR3 comprising the amino acid sequence of SEQ ID NO:53;
d) a LCDR1 comprising the amino acid sequence of SEQ ID NO:63;
e) a LCDR2 comprising the amino acid sequence DDS;
f) a LCDR3 comprising the amino acid sequence of SEQ ID NO:76, or
any combination of the foregoing.
In some embodiments, a polypeptide comprises:
a) a HCDR1 comprising the amino acid sequence of SEQ ID NO:31;
b) a HCDR2 comprising the amino acid sequence of SEQ ID NO:43;
c) a HCDR3 comprising the amino acid sequence of SEQ ID NO:55;
d) a LCDR1 comprising the amino acid sequence of SEQ ID NO:64;
e) a LCDR2 comprising the amino acid sequence DDS;
f) a LCDR3 comprising the amino acid sequence of SEQ ID NO:77, or
any combination of the foregoing.
In some embodiments, a polypeptide comprises:
a) a HCDR1 comprising the amino acid sequence of SEQ ID NO:31;
b) a HCDR2 comprising the amino acid sequence of SEQ ID NO:44;
c) a HCDR3 comprising the amino acid sequence of SEQ ID NO:56;
d) a LCDR1 comprising the amino acid sequence of SEQ ID NO:65;
e) a LCDR2 comprising the amino acid sequence DDS;
f) a LCDR3 comprising the amino acid sequence of SEQ ID NO:78, or
any combination of the foregoing.
In some embodiments, a polypeptide comprises:
a) a HCDR1 comprising the amino acid sequence of SEQ ID NO:31;
b) a HCDR2 comprising the amino acid sequence of SEQ ID NO:45;
c) a HCDR3 comprising the amino acid sequence of SEQ ID NO:57;
d) a LCDR1 comprising the amino acid sequence of SEQ ID NO:66;
e) a LCDR2 comprising the amino acid sequence DDS;
f) a LCDR3 comprising the amino acid sequence of SEQ ID NO:79, or
any combination of the foregoing.
In some embodiments, a polypeptide comprises:
a) a HCDR1 comprising the amino acid sequence of SEQ ID NO:31;
b) a HCDR2 comprising the amino acid sequence of SEQ ID NO:46;
c) a HCDR3 comprising the amino acid sequence of SEQ ID NO:48;
d) a LCDR1 comprising the amino acid sequence of SEQ ID NO:63;
e) a LCDR2 comprising the amino acid sequence DDS;
f) a LCDR3 comprising the amino acid sequence of SEQ ID NO:80, or
any combination of the foregoing.

Paratopes

Amino acid residues of a paratope contribute to an antibody's interaction with an epitope of its target protein. An interaction can be a hydrogen bond, a salt bridge, a van der Waals interaction, an electrostatic interaction, a hydrophobic interaction, pi-interaction effects, an ionic bond, and/or any combination thereof. An interaction can be direct, or indirect, e.g., via a coordinated intermediate molecule, such as an ion or water. The residues of a paratope, in some embodiments, comprise only residues that are part of a defined CDR. In some embodiments, the residues of a paratope further comprise one or more residues that are not part of a defined CDR (e.g., residues within a defined framework region).

In some embodiments, a paratope is oriented less than about 5.0 angstroms from an epitope on a target antigen when a polypeptide is bound to the target antigen, e.g., less than about: 4.5, 4.0, 3.5, 3.0, 2.5, 2.4, 2.3, 2.2, 2.1, 2.0, 1.9, 1.8, 1.7, 1.6, 1.5, 1.4, 1.3, 1.2, 1.1, 1.0 or 0.9 angstroms, or about: 0.9-5.0, 0.9-4.8, 1.0-5, 1.0-4.5, 1.0-4.0, 1.0-3.5, 1.1-3.5, 1.1-3.0, 1.2-3.0, 1.2-2.5, 1.3-2.5, 1.3-2.4, 1.4-2.4, 1.4-2.3, 1.5-2.3, 1.5-2.2, 1.6-2.2, 1.6-2.1, 1.7-2.1, 1.7-2.0 or 1.8-2.0 angstroms, from the epitope. In some embodiments, less than all of the amino acid residues constituting a paratope (e.g., about 40%, about 50%, about 60%, about 70%, about 80%, about 90%, about 95%, about 96%, about 97%, about 98%, or about 99% of the amino acid residues) in the paratope are oriented less than about 5.0 angstroms from an epitope on a target antigen when a polypeptide is bound to the target antigen.

In some embodiments, a polypeptide (e.g., an antibody or antigen-binding fragment thereof) comprising a paratope disclosed herein comprises a $V_H$ and a $V_L$. In some embodiments, paratope residues are contained within the $V_H$ and $V_L$ of a polypeptide.

In some embodiments, a polypeptide comprises a paratope that differs from a paratope of an antibody comprising a $V_H/V_L$ combination of SEQ ID NO:3/SEQ ID NO:19.

In some embodiments, a polypeptide comprises a paratope that differs from a paratope of an antibody comprising a $V_H/V_L$ combination of SEQ ID NO:3/SEQ ID NO:19, by substitution (e.g., conservative substitution such as highly conservative substitution) of from 1 to 3 (e.g., 1, 2 or 3) residues.

In some embodiments, a polypeptide comprises a paratope that is substantially similar (e.g., having at least about 90% sequence identity) to a paratope of an antibody comprising a $V_H/V_L$ combination of SEQ ID NO:3/SEQ ID NO:19. In some embodiments, a polypeptide comprises a paratope that is substantially similar (e.g., having at least about 90% sequence identity) to, and substantially preserves one or more functional properties of, a paratope of an antibody comprising a $V_H/V_L$ combination of SEQ ID NO:3/ SEQ ID NO:19.

In some embodiments, a polypeptide comprises a paratope that has 100% sequence identity to a paratope of an antibody comprising a $V_H/V_L$ combination of SEQ ID NO:3/ SEQ ID NO:19

In some embodiments, a polypeptide comprises a paratope that differs from a paratope of an antibody comprising a $V_H/V_L$ combination selected from: SEQ ID NO:4/ SEQ ID NO:20 (AB-1), SEQ ID NO:5/SEQ ID NO:21 (AB-2), SEQ ID NO:6/SEQ ID NO:20 (AB-3), SEQ ID NO:7/SEQ ID NO:22 (AB-4), SEQ ID NO:8/SEQ ID NO:23 (AB-5), SEQ ID NO:9/SEQ ID NO:24 (AB-6), SEQ ID NO:10/SEQ ID NO:25 (AB-7), SEQ ID NO:11/SEQ ID NO:20 (AB-8), SEQ ID NO:12/SEQ ID NO:20 (AB-9), SEQ ID NO:13/SEQ ID NO:26 (AB-10), SEQ ID NO:14/ SEQ ID NO:27 (AB-11), SEQ ID NO:15/SEQ ID NO:28 (AB-12), SEQ ID NO:16/SEQ ID NO:29 (AB-13) or SEQ ID NO:17/SEQ ID NO:30 (AB-14).

See Table 1 for SEQ ID NOs:4-17 and FIGS. 2A-2B for the paratope residues of antibodies comprising a $V_H$ sequence set forth in any one of SEQ ID Nos:4-17. See Table 2 for SEQ ID NOs:20-30.

In some embodiments, a polypeptide comprises a paratope that differs from a paratope of an antibody comprising a $V_H/V_L$ combination selected from: SEQ ID NO:4/ SEQ ID NO:20 (AB-1), SEQ ID NO:5/SEQ ID NO:21 (AB-2), SEQ ID NO:6/SEQ ID NO:20 (AB-3), SEQ ID NO:7/SEQ ID NO:22 (AB-4), SEQ ID NO:8/SEQ ID NO:23 (AB-5), SEQ ID NO:9/SEQ ID NO:24 (AB-6), SEQ ID NO:10/SEQ ID NO:25 (AB-7), SEQ ID NO:11/SEQ ID NO:20 (AB-8), SEQ ID NO:12/SEQ ID NO:20 (AB-9), SEQ ID NO:13/SEQ ID NO:26 (AB-10), SEQ ID NO:14/ SEQ ID NO:27 (AB-11), SEQ ID NO:15/SEQ ID NO:28 (AB-12), SEQ ID NO:16/SEQ ID NO:29 (AB-13) or SEQ ID NO:17/SEQ ID NO:30 (AB-14), by substitution (e.g., conservative substitution such as highly conservative substitution) of from 1 to 3 (e.g., 1, 2 or 3) residues.

In some embodiments, a polypeptide comprises a paratope that is substantially similar (e.g., having at least about 90% sequence identity) to a paratope of an antibody comprising a $V_H/V_L$ combination selected from:
SEQ ID NO:4 and SEQ ID NO:20 (AB-1);
SEQ ID NO:5 and SEQ ID NO: 21 (AB-2);
SEQ ID NO:6 and SEQ ID NO:20 (AB-3);
SEQ ID NO:7 and SEQ ID NO:22 (AB-4);
SEQ ID NO:8 and SEQ ID NO:23 (AB-5);
SEQ ID NO:9 and SEQ ID NO:24 (AB-6);
SEQ ID NO:10 and SEQ ID NO:25 (AB-7);
SEQ ID NO:11 and SEQ ID NO:20 (AB-8);
SEQ ID NO:12 and SEQ ID NO:20 (AB-9);
SEQ ID NO:13 and SEQ ID NO:26 (AB-10);
SEQ ID NO:14 and SEQ ID NO:27 (AB-11);
SEQ ID NO:15 and SEQ ID NO:28 (AB-12);
SEQ ID NO:16 and SEQ ID NO:29 (AB-13); or
SEQ ID NO:17 and SEQ ID NO:30 (AB-14), or
a combination thereof.

In some embodiments, a polypeptide comprises a paratope that is substantially similar (e.g., having at least about 90% sequence identity) to, and substantially preserves one or more functional properties of, a paratope of an antibody comprising a $V_H/V_L$ combination selected from:
SEQ ID NO:4 and SEQ ID NO:20 (AB-1);
SEQ ID NO:5 and SEQ ID NO: 21 (AB-2);
SEQ ID NO:6 and SEQ ID NO:20 (AB-3);
SEQ ID NO:7 and SEQ ID NO:22 (AB-4);
SEQ ID NO:8 and SEQ ID NO:23 (AB-5);
SEQ ID NO:9 and SEQ ID NO:24 (AB-6);
SEQ ID NO:10 and SEQ ID NO:25 (AB-7);
SEQ ID NO:11 and SEQ ID NO:20 (AB-8);
SEQ ID NO:12 and SEQ ID NO:20 (AB-9);
SEQ ID NO:13 and SEQ ID NO:26 (AB-10);
SEQ ID NO:14 and SEQ ID NO:27 (AB-11);
SEQ ID NO:15 and SEQ ID NO:28 (AB-12);
SEQ ID NO:16 and SEQ ID NO:29 (AB-13); or
SEQ ID NO:17 and SEQ ID NO:30 (AB-14), or
a combination thereof.

In some embodiments, a polypeptide comprises a paratope comprising only one or more conservative substitutions (e.g., only one or more highly conservative substitutions) relative a paratope of an antibody comprising a $V_H/V_L$ combination selected from:
SEQ ID NO:4 and SEQ ID NO:20 (AB-1);
SEQ ID NO:5 and SEQ ID NO: 21 (AB-2);
SEQ ID NO:6 and SEQ ID NO:20 (AB-3);
SEQ ID NO:7 and SEQ ID NO:22 (AB-4);
SEQ ID NO:8 and SEQ ID NO:23 (AB-5);
SEQ ID NO:9 and SEQ ID NO:24 (AB-6);
SEQ ID NO:10 and SEQ ID NO:25 (AB-7);
SEQ ID NO:11 and SEQ ID NO:20 (AB-8);
SEQ ID NO:12 and SEQ ID NO:20 (AB-9);
SEQ ID NO:13 and SEQ ID NO:26 (AB-10);
SEQ ID NO:14 and SEQ ID NO:27 (AB-11);
SEQ ID NO:15 and SEQ ID NO:28 (AB-12);
SEQ ID NO:16 and SEQ ID NO:29 (AB-13); or
SEQ ID NO:17 and SEQ ID NO:30 (AB-14), or
a combination thereof.

In some embodiments, a polypeptide comprises a paratope comprising up to 1, 2, 3, 4, 5, 6, 7, 8, 9, 10, 11, 12, 13, 14 or 15 conservative substitutions (e.g., up to 1, 2, 3, 4, 5, 6, 7, 8, 9, 10, 11, 12, 13, 14 or 15 highly conservative substitutions), relative a paratope of an antibody comprising a $V_H/V_L$ combination selected from:
SEQ ID NO:4 and SEQ ID NO:20 (AB-1);
SEQ ID NO:5 and SEQ ID NO: 21 (AB-2);

SEQ ID NO:6 and SEQ ID NO:20 (AB-3);
SEQ ID NO:7 and SEQ ID NO:22 (AB-4);
SEQ ID NO:8 and SEQ ID NO:23 (AB-5);
SEQ ID NO:9 and SEQ ID NO:24 (AB-6);
SEQ ID NO:10 and SEQ ID NO:25 (AB-7);
SEQ ID NO:11 and SEQ ID NO:20 (AB-8);
SEQ ID NO:12 and SEQ ID NO:20 (AB-9);
SEQ ID NO:13 and SEQ ID NO:26 (AB-10);
SEQ ID NO:14 and SEQ ID NO:27 (AB-11);
SEQ ID NO:15 and SEQ ID NO:28 (AB-12);
SEQ ID NO:16 and SEQ ID NO:29 (AB-13); or
SEQ ID NO:17 and SEQ ID NO:30 (AB-14), or
a combination thereof.

In some embodiments, a polypeptide comprises a paratope that has 100% sequence identity to a paratope of an antibody comprising a $V_H/V_L$ combination selected from:
SEQ ID NO:4 and SEQ ID NO:20 (AB-1);
SEQ ID NO:5 and SEQ ID NO: 21 (AB-2);
SEQ ID NO:6 and SEQ ID NO:20 (AB-3);
SEQ ID NO:7 and SEQ ID NO:22 (AB-4);
SEQ ID NO:8 and SEQ ID NO:23 (AB-5);
SEQ ID NO:9 and SEQ ID NO:24 (AB-6);
SEQ ID NO:10 and SEQ ID NO:25 (AB-7);
SEQ ID NO:11 and SEQ ID NO:20 (AB-8);
SEQ ID NO:12 and SEQ ID NO:20 (AB-9);
SEQ ID NO:13 and SEQ ID NO:26 (AB-10);
SEQ ID NO:14 and SEQ ID NO:27 (AB-11);
SEQ ID NO:15 and SEQ ID NO:28 (AB-12);
SEQ ID NO:16 and SEQ ID NO:29 (AB-13); or
SEQ ID NO:17 and SEQ ID NO:30 (AB-14), or
a combination thereof.

In some embodiments, a polypeptide comprises a paratope that differs from a paratope of an antibody comprising a $V_H/V_L$ combination selected from: SEQ ID NO:4/SEQ ID NO:20 (AB-1), SEQ ID NO:5/SEQ ID NO:21 (AB-2), SEQ ID NO:6/SEQ ID NO:20 (AB-3) or SEQ ID NO:7/SEQ ID NO:22 (AB-4).

In some embodiments, a polypeptide comprises a paratope that differs from a paratope of an antibody comprising a $V_H/V_L$ combination selected from: SEQ ID NO:4/SEQ ID NO:20 (AB-1), SEQ ID NO:5/SEQ ID NO:21 (AB-2), SEQ ID NO:6/SEQ ID NO:20 (AB-3) or SEQ ID NO:7/SEQ ID NO:22 (AB-4), by substitution (e.g., conservative substitution such as highly conservative substitution) of from 1 to 3 (e.g., 1, 2 or 3) residues.

In some embodiments, a polypeptide comprises a paratope that is substantially similar (e.g., having at least about 90% sequence identity) to a paratope of an antibody comprising a $V_H/V_L$ combination selected from:
SEQ ID NO:4 and SEQ ID NO:20 (AB-1);
SEQ ID NO:5 and SEQ ID NO: 21 (AB-2);
SEQ ID NO:6 and SEQ ID NO:20 (AB-3); or
SEQ ID NO:7 and SEQ ID NO:22 (AB-4), or
a combination thereof.

In some embodiments, a polypeptide comprises a paratope that is substantially similar (e.g., having at least about 90% sequence identity) to, and substantially preserves one or more functional properties of, a paratope of an antibody comprising a $V_H/V_L$ combination selected from:
SEQ ID NO:4 and SEQ ID NO:20 (AB-1);
SEQ ID NO:5 and SEQ ID NO:21 (AB-2);
SEQ ID NO:6 and SEQ ID NO:20 (AB-3); or
SEQ ID NO:7 and SEQ ID NO:22 (AB-4), or
a combination thereof.

In some embodiments, a polypeptide comprises a paratope comprising only one or more conservative substitutions (e.g., only one or more highly conservative substitutions) relative a paratope of an antibody comprising a $V_H/V_L$ combination selected from:
SEQ ID NO:4 and SEQ ID NO:20 (AB-1);
SEQ ID NO:5 and SEQ ID NO:21 (AB-2);
SEQ ID NO:6 and SEQ ID NO:20 (AB-3); or
SEQ ID NO:7 and SEQ ID NO:22 (AB-4), or
a combination thereof.

In some embodiments, a polypeptide comprises a paratope comprising up to 1, 2, 3, 4, 5, 6, 7, 8, 9, 10, 11, 12, 13, 14 or 15 conservative substitutions (e.g., up to 1, 2, 3, 4, 5, 6, 7, 8, 9, 10, 11, 12, 13, 14 or 15 highly conservative substitutions), relative a paratope of an antibody comprising a $V_H/V_L$ combination selected from:
SEQ ID NO:4 and SEQ ID NO:20 (AB-1);
SEQ ID NO:5 and SEQ ID NO: 21 (AB-2);
SEQ ID NO:6 and SEQ ID NO:20 (AB-3); or
SEQ ID NO:7 and SEQ ID NO:22 (AB-4), or
a combination thereof.

In some embodiments, a polypeptide comprises a paratope that has 100% sequence identity to a paratope of an antibody comprising a $V_H/V_L$ combination selected from:
SEQ ID NO:4 and SEQ ID NO:20 (AB-1);
SEQ ID NO:5 and SEQ ID NO:21 (AB-2);
SEQ ID NO:6 and SEQ ID NO:20 (AB-3); or
SEQ ID NO:7 and SEQ ID NO:22 (AB-4), or
a combination thereof.

In some embodiments, a polypeptide comprises a paratope comprising amino acid residues corresponding to each of M2, G26, F27, T28, R30, T31, Y32, Y53, R98, P100, Q101, W102, E103, and E107 of SEQ ID NO:2, or a subset thereof. In some embodiments, a polypeptide comprises a paratope comprising amino acid residues corresponding to each of T28, T31, Y32, Y53, R98, W102, and E107 of SEQ ID NO:2.

Consensus Sequences

In some embodiments, a polypeptide (e.g., an antibody or antigen-binding fragment thereof) comprises a $V_H$ comprising the amino acid sequence of SEQ ID NO:2, wherein:
$X_1$ is not I;
$X_2$ is not W;
$X_3$ is not D;
$X_4$ is not S;
$X_5$ is not N;
$X_6$ is not K;
$X_7$ is not A;
$X_8$ is not A;
$X_9$ is not L;
$X_{10}$ is not V;
$X_{11}$ is not H;
$X_{12}$ is not A;
$X_{13}$ is not F; or
$X_{14}$ is not I, or
any combination of the foregoing.

The sequence identified as SEQ ID NO:2 is shown in Table 1, which is a consensus $V_H$ sequence for SEQ ID Nos:3-17 herein.

In some embodiments:
$X_1$ is I or V;
$X_2$ is W or S;
$X_3$ is D or S;
$X_4$ is S, T, Y or A;
$X_5$ is N, Y, D or T;
$X_6$ is K, T or I;
$X_7$ is A, S or T;
$X_8$ is A or S;
$X_9$ is L, D, E or S;
$X_{10}$ is V or I;

$X_{11}$ is H, F or Y;
$X_{12}$ is A or S;
$X_{13}$ is F, M or L;
$X_{14}$ is I or V,
or any combination of the foregoing.

In some embodiments:
$X_1$ is V;
$X_2$ is S;
$X_3$ is S;
$X_4$ is T, Y or A;
$X_5$ is Y, D or T;
$X_6$ is T or I;
$X_7$ is S or T;
$X_8$ is S;
$X_9$ is D, E or S;
$X_{10}$ is I;
$X_{11}$ is F or Y;
$X_{12}$ is S;
$X_{13}$ is M or L;
$X_{14}$ is V,
or any combination of the foregoing.

In some embodiments, $X_1$ is not I. In some embodiments, $X_1$ is I or V. In some embodiments, $X_1$ is V. In some embodiments, $X_1$ is I.

In some embodiments, $X_2$ is not W. In some embodiments, $X_2$ is W or S. In some embodiments, $X_2$ is S. In some embodiments, $X_2$ is W.

In some embodiments, $X_3$ is not D. In some embodiments, $X_3$ is D or S. In some embodiments, $X_3$ is S. In some embodiments, $X_3$ is D.

In some embodiments, $X_4$ is not S. In some embodiments, $X_4$ is S, T, Y or A. In some embodiments, $X_4$ is T, Y or A. In some embodiments, $X_4$ is T. In some embodiments, $X_4$ is Y. In some embodiments, $X_4$ is A. In some embodiments, $X_4$ is S.

In some embodiments, $X_5$ is not N. In some embodiments, $X_5$ is N, Y, D or T. In some embodiments, $X_5$ is Y, D or T. In some embodiments, $X_5$ is Y. In some embodiments, $X_5$ is D. In some embodiments, $X_5$ is T. In some embodiments, $X_5$ is N.

In some embodiments, $X_6$ is not K. In some embodiments, $X_6$ is K, T or I. In some embodiments, $X_6$ is T or I. In some embodiments, $X_6$ is T. In some embodiments, $X_6$ is I. In some embodiments, $X_6$ is K.

In some embodiments, $X_7$ is not A. In some embodiments, $X_7$ is A, S or T. In some embodiments, $X_7$ is S or T. In some embodiments, $X_7$ is S. In some embodiments, $X_7$ is T. In some embodiments, $X_7$ is A.

In some embodiments, $X_8$ is not A. In some embodiments, $X_8$ is A or S. In some embodiments, $X_8$ is S. In some embodiments, $X_8$ is A.

In some embodiments, $X_9$ is not L. In some embodiments, $X_9$ is L, D, E or S. In some embodiments, $X_9$ is D, E or S. In some embodiments, $X_9$ is D. In some embodiments, $X_9$ is E. In some embodiments, $X_9$ is S. In some embodiments, $X_9$ is L.

In some embodiments, $X_{10}$ is not V. In some embodiments, $X_{10}$ is V or I. In some embodiments, $X_{10}$ is I. In some embodiments, $X_{10}$ is V.

In some embodiments, $X_{11}$ is not H. In some embodiments, $X_{11}$ is H, F or Y. In some embodiments, $X_{11}$ is F or Y. In some embodiments, $X_{11}$ is F. In some embodiments, $X_{11}$ is Y. In some embodiments, $X_{11}$ is H.

In some embodiments, $X_{12}$ is not A. In some embodiments, $X_{12}$ is A or S. In some embodiments, $X_{12}$ is S. In some embodiments, $X_{12}$ is A.

In some embodiments, $X_{13}$ is not F. In some embodiments, $X_{13}$ is F, M or L. In some embodiments, $X_{13}$ is M or L. In some embodiments, $X_{13}$ is M. In some embodiments, $X_{13}$ is L. In some embodiments, $X_{13}$ is F.

In some embodiments, $X_{14}$ is not I. In some embodiments, $X_{14}$ is I or V. In some embodiments, $X_{14}$ is V. In some embodiments, $X_{14}$ is I.

In some embodiments, the polypeptides comprise a $V_L$ comprising the amino acid sequence of SEQ ID NO:18, wherein:
$X_{15}$ is not N;
$X_{11}$ is not L;
$X_{17}$ is not S;
$X_{18}$ is not K;
$X_{19}$ is not S;
$X_{20}$ is not V;
$X_{21}$ is not W;
$X_{22}$ is not D;
$X_{23}$ is not S;
$X_{24}$ is not S;
$X_{25}$ is not S;
$X_{26}$ is not D; or
$X_{27}$ is not H, or
any combination of the foregoing.

The sequence identified as SEQ ID NO:18 is shown in Table 2, which is a consensus $V_L$ sequence for SEQ ID NOs:19-30 herein.

In some embodiments:
$X_{15}$ is N or Y;
$X_{16}$ is L or I;
$X_{17}$ is S or R;
$X_{18}$ is K, F or Y;
$X_{19}$ is S or N;
$X_{20}$ is V or I;
$X_{21}$ is W or Y;
$X_{22}$ is D, V or S;
$X_{23}$ is S, M or E;
$X_{24}$ is S, A or T;
$X_{25}$ is S, D or E;
$X_{26}$ is D, S, R or F;
$X_{27}$ is H, L, K or E,
or any combination of the foregoing.

In some embodiments:
$X_{15}$ is Y;
$X_{16}$ is I;
$X_{17}$ is R;
$X_{18}$ is F or Y;
$X_{19}$ is N;
$X_{20}$ is I;
$X_{21}$ is Y;
$X_{22}$ is V or S;
$X_{23}$ is M or E;
$X_{24}$ is A or T;
$X_{25}$ is D or E;
$X_{26}$ is S, R or F;
$X_{27}$ is L, K or E,
or any combination of the foregoing.

In some embodiments, $X_{15}$ is not N. In some embodiments, $X_{15}$ is N or Y. In some embodiments, $X_{15}$ is Y. In some embodiments, $X_{15}$ is N.

In some embodiments, $X_{11}$ is not L. In some embodiments, $X_{11}$ is L or I. In some embodiments, $X_{11}$ is I. In some embodiments, $X_{11}$ is L.

In some embodiments, $X_{17}$ is not S. In some embodiments, $X_{17}$ is S or R. In some embodiments, $X_{17}$ is R. In some embodiments, $X_{17}$ is S.

In some embodiments, $X_{18}$ is not K. In some embodiments, $X_{18}$ is K, F or Y. In some embodiments, $X_{18}$ is F or Y. In some embodiments, $X_{18}$ is F. In some embodiments, $X_{18}$ is Y. In some embodiments, $X_{18}$ is K.

In some embodiments, $X_{19}$ is not S. In some embodiments, $X_{19}$ is S or N. In some embodiments, $X_{19}$ is N. In some embodiments, $X_{19}$ is S.

In some embodiments, $X_{20}$ is not V. In some embodiments, $X_{20}$ is V or I. In some embodiments, $X_{20}$ is I. In some embodiments, $X_{20}$ is V.

In some embodiments, $X_{21}$ is not W. In some embodiments, $X_{21}$ is W or Y. In some embodiments, $X_{21}$ is Y. In some embodiments, $X_{21}$ is W.

In some embodiments, $X_{22}$ is not D. In some embodiments, $X_{22}$ is D, V or S. In some embodiments, $X_{22}$ is V or S. In some embodiments, $X_{22}$ is V. In some embodiments, $X_{22}$ is S. In some embodiments, $X_{22}$ is D.

In some embodiments, $X_{23}$ is not S. In some embodiments, $X_{23}$ is S, M or E. In some embodiments, $X_{23}$ is M or E. In some embodiments, $X_{23}$ is M. In some embodiments, $X_{23}$ is E. In some embodiments, $X_{23}$ is S.

In some embodiments, $X_{24}$ is not S. In some embodiments, $X_{24}$ is S, A or T. In some embodiments, $X_{24}$ is A or T. In some embodiments, $X_{24}$ is A. In some embodiments, $X_{24}$ is T. In some embodiments, $X_{24}$ is S.

In some embodiments, $X_{25}$ is not S. In some embodiments, $X_{25}$ is S, D or E. In some embodiments, $X_{25}$ is D or E. In some embodiments, $X_{25}$ is D. In some embodiments, $X_{25}$ is E. In some embodiments, $X_{25}$ is S.

In some embodiments, $X_{26}$ is not D. In some embodiments, $X_{26}$ is D, S, R or F. In some embodiments, $X_{26}$ is S, R or F. In some embodiments, $X_{26}$ is S. In some embodiments, $X_{26}$ is R. In some embodiments, $X_{26}$ is F. In some embodiments, $X_{26}$ is D.

In some embodiments, $X_{27}$ is not H. In some embodiments, $X_{27}$ is H, L, K or E. In some embodiments, $X_{27}$ is L, K or E. In some embodiments, $X_{27}$ is L. In some embodiments, $X_{27}$ is K. In some embodiments, $X_{27}$ is E. In some embodiments, $X_{27}$ is H.

In some embodiments, a) $X_1$ is V, $X_2$ is W, $X_3$ is S, $X_4$ is S, $X_5$ is Y, $X_6$ is T, $X_7$ is S, $X_8$ is S, $X_9$ is D, $X_{10}$ is I, $X_{11}$ is F, $X_{12}$ is A, $X_{13}$ is M, $X_{14}$ is I, $X_{15}$ is N, $X_{16}$ is I, $X_{17}$ is S, $X_{18}$ is K, $X_{19}$ is S, $X_{20}$ is V, $X_{21}$ is W, $X_{22}$ is D, $X_{23}$ is S, $X_{24}$ is S, $X_{25}$ is S, $X_{26}$ is S, or $X_{27}$ is L, or a combination thereof;

b) $X_1$ is V, $X_2$ is W, $X_3$ is D, $X_4$ is S, $X_5$ is Y, $X_6$ is T, $X_7$ is A, $X_8$ is S, $X_9$ is E, $X_{10}$ is I, $X_{11}$ is F, $X_{12}$ is A, $X_{13}$ is M, $X_{14}$ is I, $X_{15}$ is N, $X_{16}$ is I, $X_{17}$ is S, $X_{18}$ is K, $X_{19}$ is S, $X_{20}$ is I, $X_{21}$ is W, $X_{22}$ is D, $X_{23}$ is S, $X_{24}$ is S, $X_{25}$ is S, $X_{26}$ is S, or $X_{27}$ is L, or a combination thereof;

c) $X_1$ is I, $X_2$ is W, $X_3$ is D, $X_4$ is T, $X_5$ is Y, $X_6$ is T, $X_7$ is A, $X_8$ is S, $X_9$ is S, $X_{10}$ is I, $X_{11}$ is F, $X_{12}$ is A, $X_{13}$ is F, $X_{14}$ is I, $X_{15}$ is N, $X_{16}$ is I, $X_{17}$ is S, $X_{18}$ is K, $X_{19}$ is S, $X_{20}$ is V, $X_{21}$ is W, $X_{22}$ is D, $X_{23}$ is S, $X_{24}$ is S, $X_{25}$ is S, $X_{26}$ is S, or $X_{27}$ is L, or a combination thereof;

d) $X_1$ is I, $X_2$ is W, $X_3$ is S, $X_4$ is S, $X_5$ is D, $X_6$ is T, $X_7$ is A, $X_8$ is S, $X_9$ is D, $X_{10}$ is I, $X_{11}$ is F, $X_{12}$ is S, $X_{13}$ is M, $X_{14}$ is V, $X_{15}$ is Y, $X_{16}$ is I, $X_{17}$ is S, $X_{18}$ is F, $X_{19}$ is S, $X_{20}$ is I, $X_{21}$ is Y, $X_{22}$ is V, $X_{23}$ is S, $X_{24}$ is A, $X_{25}$ is S, $X_{26}$ is R, or $X_{27}$ is L, or a combination thereof;

e) $X_1$ is V, $X_2$ is W, $X_3$ is D, $X_4$ is Y, $X_5$ is D, $X_6$ is T, $X_7$ is S, $X_8$ is S, $X_9$ is D, $X_{10}$ is I, $X_{11}$ is F, $X_{12}$ is S, $X_{13}$ is M, $X_{14}$ is I, $X_{15}$ is N, $X_{16}$ is L, $X_{17}$ is S, $X_{18}$ is K, $X_{19}$ is S, $X_{20}$ is V, $X_{21}$ is W, $X_{22}$ is D, $X_{23}$ is M, $X_{24}$ is S, $X_{25}$ is S, $X_{26}$ is D, or $X_{27}$ is L, or a combination thereof;

f) $X_1$ is V, $X_2$ is W, $X_3$ is D, $X_4$ is S, $X_5$ is D, $X_6$ is I, $X_7$ is S, $X_8$ is S, $X_9$ is D, $X_{10}$ is I, $X_{11}$ is F, $X_{12}$ is S, $X_{13}$ is M, $X_{14}$ is I, $X_{15}$ is N, $X_{16}$ is I, $X_{17}$ is S, $X_{18}$ is K, $X_{19}$ is S, $X_{20}$ is I, $X_{21}$ is W, $X_{22}$ is D, $X_{23}$ is S, $X_{24}$ is S, $X_{25}$ is S, $X_{26}$ is D, or $X_{27}$ is H, or a combination thereof;

g) $X_1$ is I, $X_2$ is W, $X_3$ is S, $X_4$ is A, $X_5$ is Y, $X_6$ is I, $X_7$ is S, $X_8$ is S, $X_9$ is D, $X_{10}$ is I, $X_{11}$ is F, $X_{12}$ is A, $X_{13}$ is M, $X_{14}$ is I, $X_{15}$ is N, $X_{16}$ is L, $X_{17}$ is S, $X_{18}$ is Y, $X_{19}$ is S, $X_{20}$ is V, $X_{21}$ is W, $X_{22}$ is D, $X_{23}$ is M, $X_{24}$ is S, $X_{25}$ is S, $X_{26}$ is S, or $X_{27}$ is L, or a combination thereof;

h) $X_1$ is I, $X_2$ is W, $X_3$ is D, $X_4$ is S, $X_5$ is Y, $X_6$ is T, $X_7$ is A, $X_8$ is S, $X_9$ is D, $X_{10}$ is I, $X_{11}$ is F, $X_{12}$ is A, $X_{13}$ is F, $X_{14}$ is I, $X_{15}$ is N, $X_{16}$ is I, $X_{17}$ is S, $X_{18}$ is K, $X_{19}$ is S, $X_{20}$ is V, $X_{21}$ is W, $X_{22}$ is D, $X_{23}$ is S, $X_{24}$ is S, $X_{25}$ is S, $X_{26}$ is S, or $X_{27}$ is L, or a combination thereof;

i) $X_1$ is I, $X_2$ is W, $X_3$ is D, $X_4$ is S, $X_5$ is Y, $X_6$ is T, $X_7$ is A, $X_8$ is S, $X_9$ is S, $X_{10}$ is I, $X_{11}$ is F, $X_{12}$ is A, $X_{13}$ is F, $X_{14}$ is I, $X_{15}$ is N, $X_{16}$ is I, $X_{17}$ is S, $X_{18}$ is K, $X_{19}$ is S, $X_{20}$ is V, $X_{21}$ is W, $X_{22}$ is D, $X_{23}$ is S, $X_{24}$ is S, $X_{25}$ is S, $X_{26}$ is S, or $X_{27}$ is L, or a combination thereof;

j) $X_1$ is I, $X_2$ is W, $X_3$ is S, $X_4$ is T, $X_5$ is T, $X_6$ is T, $X_7$ is S, $X_8$ is S, $X_9$ is D, $X_{10}$ is I, $X_{11}$ is F, $X_{12}$ is S, $X_{13}$ is M, $X_{14}$ is I, $X_{15}$ is N, $X_{16}$ is I, $X_{17}$ is S, $X_{18}$ is K, $X_{19}$ is N, $X_{20}$ is V, $X_{21}$ is W, $X_{22}$ is D, $X_{23}$ is S, $X_{24}$ is S, $X_{25}$ is D, $X_{26}$ is F, or $X_{27}$ is L, or a combination thereof;

k) $X_1$ is I, $X_2$ is S, $X_3$ is S, $X_4$ is S, $X_5$ is Y, $X_6$ is I, $X_7$ is T, $X_8$ is S, $X_9$ is E, $X_{10}$ is V, $X_{11}$ is Y, $X_{12}$ is A, $X_{13}$ is L, $X_{14}$ is I, $X_{15}$ is N, $X_{16}$ is I, $X_{17}$ is S, $X_{18}$ is F, $X_{19}$ is S, $X_{20}$ is V, $X_{21}$ is W, $X_{22}$ is S, $X_{23}$ is S, $X_{24}$ is T, $X_{25}$ is S, $X_{26}$ is R, or $X_{27}$ is H, or a combination thereof;

l) $X_1$ is V, $X_2$ is W, $X_3$ is D, $X_4$ is S, $X_5$ is N, $X_6$ is T, $X_7$ is A, $X_8$ is A, $X_9$ is S, $X_{10}$ is V, $X_{11}$ is H, $X_{12}$ is A, $X_{13}$ is F, $X_{14}$ is I, $X_{15}$ is N, $X_{16}$ is I, $X_{17}$ is R, $X_{18}$ is F, $X_{19}$ is S, $X_{20}$ is V, $X_{21}$ is W, $X_{22}$ is V, $X_{23}$ is S, $X_{24}$ is T, $X_{25}$ is S, $X_{26}$ is D, or $X_{27}$ is K, or a combination thereof;

m) $X_1$ is I, $X_2$ is S, $X_3$ is D, $X_4$ is S, $X_5$ is T, $X_6$ is K, $X_7$ is A, $X_8$ is A, $X_9$ is S, $X_{10}$ is V, $X_{11}$ is Y, $X_{12}$ is A, $X_{13}$ is F, $X_{14}$ is I, $X_{15}$ is N, $X_{16}$ is L, $X_{17}$ is S, $X_{18}$ is F, $X_{19}$ is S, $X_{20}$ is V, $X_{21}$ is W, $X_{22}$ is D, $X_{23}$ is S, $X_{24}$ is S, $X_{25}$ is E, $X_{26}$ is D, or $X_{27}$ is L, or a combination thereof; or n) $X_1$ is I, $X_2$ is W, $X_3$ is D, $X_4$ is S, $X_5$ is T, $X_6$ is K, $X_7$ is A, $X_8$ is A, $X_9$ is L, $X_{10}$ is V, $X_{11}$ is H, $X_{12}$ is A, $X_{13}$ is F, $X_{14}$ is I, $X_{15}$ is N, $X_{16}$ is I, $X_{17}$ is S, $X_{18}$ is K, $X_{19}$ is N, $X_{20}$ is V, $X_{21}$ is W, $X_{22}$ is D, $X_{23}$ is E, $X_{24}$ is S, $X_{25}$ is S, $X_{26}$ is D, or $X_{27}$ is E, or a combination thereof.

In some embodiments:

$X_1$ is I or V;

$X_2$ is W;

$X_3$ is D or S;

$X_4$ is S or T;

$X_5$ is N, Y or D;

$X_6$ is K or T;

$X_7$ is A or S;

$X_8$ is A or S;

$X_9$ is L, D, E or S;

$X_{10}$ is V or I;

$X_{11}$ is H or F;

$X_{12}$ is A or S;

$X_{13}$ is F or M; or $X_{14}$ is I or V, or any combination of the foregoing.

In some embodiments:

$X_1$ is V;

$X_2$ is W;

$X_3$ is S;

$X_4$ is T;

$X_5$ is Y or D;

$X_6$ is T;

$X_7$ is S;

$X_8$ is S;
$X_9$ is D, E or S;
$X_{10}$ is I;
$X_{11}$ is F;
$X_{12}$ is S;
$X_{13}$ is M;
$X_{14}$ is V,
or any combination of the foregoing.

In some embodiments, $X_1$ is not I. In some embodiments, $X_1$ is I or V. In some embodiments, $X_1$ is V. In some embodiments, $X_1$ is I.

In some embodiments, $X_2$ is W.

In some embodiments, $X_3$ is not D. In some embodiments, $X_3$ is D or S. In some embodiments, $X_3$ is S. In some embodiments, $X_3$ is D.

In some embodiments, $X_4$ is not S. In some embodiments, $X_4$ is S or T. In some embodiments, $X_4$ is T. In some embodiments, $X_4$ is S.

In some embodiments, $X_5$ is not N. In some embodiments, $X_5$ is N, Y or D. In some embodiments, $X_5$ is Y or D. In some embodiments, $X_5$ is Y. In some embodiments, $X_5$ is D. In some embodiments, $X_5$ is N.

In some embodiments, $X_6$ is not K. In some embodiments, $X_6$ is K or T. In some embodiments, $X_6$ is T. In some embodiments, $X_6$ is K.

In some embodiments, $X_7$ is not A. In some embodiments, $X_7$ is A or S. In some embodiments, $X_7$ is S. In some embodiments, $X_7$ is A.

In some embodiments, $X_8$ is not A. In some embodiments, $X_8$ is A or S. In some embodiments, $X_8$ is S. In some embodiments, $X_8$ is A.

In some embodiments, $X_9$ is not L. In some embodiments, $X_9$ is L, D, E or S. In some embodiments, $X_9$ is D, E or S. In some embodiments, $X_9$ is D. In some embodiments, $X_9$ is E. In some embodiments, $X_9$ is S. In some embodiments, $X_9$ is L.

In some embodiments, $X_{10}$ is not V. In some embodiments, $X_{10}$ is V or I. In some embodiments, $X_{10}$ is I. In some embodiments, $X_{10}$ is V.

In some embodiments, $X_{11}$ is not H. In some embodiments, $X_{11}$ is H or F. In some embodiments, $X_{11}$ is F. In some embodiments, $X_{11}$ is H.

In some embodiments, $X_{12}$ is not A. In some embodiments, $X_{12}$ is A or S. In some embodiments, $X_{12}$ is S. In some embodiments, $X_{12}$ is A.

In some embodiments, $X_{13}$ is not F. In some embodiments, $X_{13}$ is F or M. In some embodiments, $X_{13}$ is M. In some embodiments, $X_{13}$ is F.

In some embodiments, $X_{14}$ is not I. In some embodiments, $X_{14}$ is I or V. In some embodiments, $X_{14}$ is V. In some embodiments, $X_{14}$ is I.

In some embodiments:
$X_{15}$ is N or Y;
$X_{16}$ is L or I;
$X_{17}$ is S;
$X_{18}$ is K or F;
$X_{19}$ is S;
$X_{20}$ is V or I;
$X_{21}$ is W or Y;
$X_{22}$ is D or V;
$X_{23}$ is S;
$X_{24}$ is S or A;
$X_{25}$ is S;
$X_{26}$ is D, S or R;
$X_{27}$ is H or L,
or any combination of the foregoing.

In some embodiments:
$X_{15}$ is Y;
$X_{16}$ is I;
$X_{17}$ is S;
$X_{18}$ is F;
$X_{19}$ is S;
$X_{20}$ is I;
$X_{21}$ is Y;
$X_{22}$ is V;
$X_{23}$ is S;
$X_{24}$ is A;
$X_{25}$ is S;
$X_{26}$ is S or R;
$X_{27}$ is L,
or any combination of the foregoing.

In some embodiments, $X_{15}$ is not N. In some embodiments, $X_{15}$ is N or Y. In some embodiments, $X_{15}$ is Y. In some embodiments, $X_{15}$ is N.

In some embodiments, $X_{16}$ is not L. In some embodiments, $X_{16}$ is L or I. In some embodiments, $X_{16}$ is I. In some embodiments, $X_{16}$ is L.

In some embodiments, $X_{17}$ is S.

In some embodiments, $X_{18}$ is not K. In some embodiments, $X_{18}$ is K or F. In some embodiments, $X_{18}$ is F. In some embodiments, $X_{18}$ is K.

In some embodiments, $X_{19}$ is S.

In some embodiments, $X_{20}$ is not V. In some embodiments, $X_{20}$ is V or I. In some embodiments, $X_{20}$ is I. In some embodiments, $X_{20}$ is V.

In some embodiments, $X_{21}$ is not W. In some embodiments, $X_{21}$ is W or Y. In some embodiments, $X_{21}$ is Y. In some embodiments, $X_{21}$ is W.

In some embodiments, $X_{22}$ is not D. In some embodiments, $X_{22}$ is D or V. In some embodiments, $X_{22}$ is V. In some embodiments, $X_{22}$ is D.

In some embodiments, $X_{23}$ is S.

In some embodiments, $X_{24}$ is not S. In some embodiments, $X_{24}$ is S or A. In some embodiments, $X_{24}$ is A. In some embodiments, $X_{24}$ is S.

In some embodiments, $X_{25}$ is S.

In some embodiments, $X_{26}$ is not D. In some embodiments, $X_{26}$ is D, S or R. In some embodiments, $X_{26}$ is S or R. In some embodiments, $X_{26}$ is S. In some embodiments, $X_{26}$ is R. In some embodiments, $X_{26}$ is D.

In some embodiments, $X_{27}$ is not H. In some embodiments, $X_{27}$ is H or L. In some embodiments, $X_{27}$ is L. In some embodiments, $X_{27}$ is H.

In some embodiments,
a) $X_1$ is V, $X_2$ is W, $X_3$ is S, $X_4$ is S, $X_5$ is Y, $X_6$ is T, $X_7$ is S, $X_8$ is S, $X_9$ is D, $X_{10}$ is I, $X_{11}$ is F, $X_{12}$ is A, $X_{13}$ is M, $X_{14}$ is I, $X_{15}$ is N, $X_{16}$ is I, $X_{17}$ is S, $X_{18}$ is K, $X_{19}$ is S, $X_{20}$ is V, $X_{21}$ is W, $X_{22}$ is D, $X_{23}$ is S, $X_{24}$ is S, $X_{25}$ is S, $X_{26}$ is S, or $X_{27}$ is L, or a combination thereof;
b) $X_1$ is V, $X_2$ is W, $X_3$ is D, $X_4$ is S, $X_5$ is Y, $X_6$ is T, $X_7$ is A, $X_8$ is S, $X_9$ is E, $X_{10}$ is I, $X_{11}$ is F, $X_{12}$ is A, $X_{13}$ is M, $X_{14}$ is I, $X_{15}$ is N, $X_{16}$ is I, $X_{17}$ is S, $X_{18}$ is K, $X_{19}$ is S, $X_{20}$ is I, $X_{21}$ is W, $X_{22}$ is D, $X_{23}$ is S, $X_{24}$ is S, $X_{25}$ is S, $X_{26}$ is S, or $X_{27}$ is L, or a combination thereof;
c) $X_1$ is I, $X_2$ is W, $X_3$ is D, $X_4$ is T, $X_5$ is Y, $X_6$ is T, $X_7$ is A, $X_8$ is S, $X_9$ is S, $X_{10}$ is I, $X_{11}$ is F, $X_{12}$ is A, $X_{13}$ is F, $X_{14}$ is I, $X_{15}$ is N, $X_{16}$ is I, $X_{17}$ is S, $X_{18}$ is K, $X_{19}$ is S, $X_{20}$ is V, $X_{21}$ is W, $X_{22}$ is D, $X_{23}$ is S, $X_{24}$ is S, $X_{25}$ is S, $X_{26}$ is S, or $X_{27}$ is L, or a combination thereof; or
d) $X_1$ is I, $X_2$ is W, $X_3$ is S, $X_4$ is S, $X_5$ is D, $X_6$ is T, $X_7$ is A, $X_8$ is S, $X_9$ is D, $X_{10}$ is I, $X_{11}$ is F, $X_{12}$ is S, $X_{13}$ is M, $X_{14}$ is V, $X_{15}$ is Y, $X_{16}$ is I, $X_{17}$ is S, $X_{18}$ is F, $X_{19}$ is S, $X_{20}$ is I, $X_{21}$ is Y, $X_{22}$ is V, $X_{23}$ is S, $X_{24}$ is A, $X_{25}$ is S, $X_{26}$ is R, or $X_{27}$ is L, or a combination thereof.

Constant Domains

In some embodiments, a polypeptide (e.g., an antibody or antigen-binding fragment thereof) comprises:
- a) an antibody heavy chain constant domain sequence;
- b) an antibody light chain constant domain sequence; or both a) and b).

In some embodiments, a polypeptide comprises an antibody heavy chain constant domain sequence. In some embodiments, an antibody heavy chain constant domain is selected from the group consisting of an IgA constant domain, an IgD constant domain, an IgE constant domain, an IgG constant domain and an IgM constant domain.

In some embodiments, an IgG constant domain is an IgG1 constant domain (e.g., any one of SEQ ID NOs:84-86), an IgG2 constant domain (e.g., SEQ ID NO:87 or SEQ ID NO:88), an IgG3 constant domain or an IgG4 constant domain. In some embodiments, the IgG2 constant domain is an IgG2a, an IgG2b constant domain or an IgG2c constant domain. In some embodiments, an IgA constant domain is an IgA1 constant domain or an IgA2 constant domain. In some embodiments, the antibody heavy chain constant domain is an IgG1 constant domain (e.g., IGHV1-5 or IGHV5-51).

(SEQ ID NO: 84)
ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNT
KVDKRVEPKSCDKTHTCPPCPAPELLGGPSVFLFPPKPKDTLMISR
TPEVTCVVVDVSHEDPEVKFNWYVDGVEVHNAKTKPREEQYNSTYR
VVSVLTVLHQDWLNGKEYKCKVSNKALPAPIEKTISKAKGQPREPQ
VYTLPPSREEMTKNQVSLTCLVKGFYPSDIAVEWESNGQPENNYKT
TPPVLDSDGSFFLYSKLTVDKSRWQQGNVFSCSVMHEALHNHYTQK
SLSLSPGK.

(SEQ ID NO: 85)
ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNT
KVDKRVEPKSCDKTHTCPPCPAPELLGGPSVFLFPPKPKDTLYITR
EPEVTCVVVDVSHEDPEVKFNWYVDGVEVHNAKTKPREEQYNSTYR
VVSVLTVLHQDWLNGKEYKCKVSNKALPAPIEKTISKAKGQPREPQ
VYTLPPSREEMTKNQVSLTCLVKGFYPSDIAVEWESNGQPENNYKT
TPPVLDSDGSFFLYSKLTVDKSRWQQGNVFSCSVMHEALHNHYTQK
SLSLSPGK.

(SEQ ID NO: 86)
ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNT
KVDKKVEPKSCDKTHTCPPCPAPELLGGPSVFLFPPKPKDTLMISR
TPEVTCVVVDVSHEDPEVKFNWYVDGVEVHNAKTKPREEQYNSTYR
VVSVLTVLHQDWLNGKEYKCKVSNKALPAPIEKTISKAKGQPREPQ
VYTLPPSRDELTKNQVSLTCLVKGFYPSDIAVEWESNGQPENNYKT
TPPVLDSDGSFFLYSKLTVDKSRWQQGNVFSCSVMHEALHNHYTQK
SLSLSPGK.

(SEQ ID NO: 87)
ASTKGPSVFPLAPCSRSTSESTAALGCLVKDYFPEPVTVSWNSGAL
TSGVHTFPAVLQSSGLYSLSSVVTVPSSNFGTQTYTCNVDHKPSNT
KVDKTVERKCCVECPPCPAPPVAGPSVFLFPPKPKDTLMISRTPEV
TCVVVDVSHEDPEVQFNWYVDGVEVHNAKTKPREEQFNSTFRVVSV
LTVVHQDWLNGKEYKCKVSNKGLPAPIEKTISKTKGQPREPQVYTL
PPSREEMTKNQVSLTCLVKGFYPSDIAVEWESNGQPENNYKTTPPM
LDSDGSFFLYSKLTVDKSRWQQGNVFSCSVMHEALHNHYTQKSLSL
SPGK.

(SEQ ID NO: 88)
ASTKGPSVFPLAPCSRSTSESTAALGCLVKDYFPEPVTVSWNSGAL
TSGVHTFPAVLQSSGLYSLSSVVTVPSSNFGTQTYTCNVDHKPSNT
KVDKTVERKCCVECPPCPAPPVAGPSVFLFPPKPKDTLMISRTPEV
TCVVVDVSHEDPEVQFNWYVDGVEVHNAKTKPREEQFNSTFRVVSV
LTVVHQDWLNGKEYKCKVSNKGLPAPIEKTISKTKGQPREPQVYTL
PPSREEMTKNQVSLTCLVKGFYPSDIAVEWESNGQPENNYKTFPPM
LDSDGSFFLYSKLTVDKSRWQQGNVFSCSVMHEALHNHYTQKSLSL
SPGK.

In some embodiments, a polypeptide comprises an antibody heavy chain constant domain sequence that has at least about 60% sequence identity to the amino acid sequence of any one of SEQ ID NOs:84-88 (e.g., any one of SEQ ID NOs:84-86). For example, a polypeptide can comprise an antibody heavy chain constant domain sequence that has at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of any one of SEQ ID NOs:84-88 (e.g., any one of SEQ ID NOs:84-86). In some embodiments, a polypeptide comprises an antibody heavy chain constant domain sequence that has at least about 70% or at least about 80% sequence identity to the amino acid sequence of any one of SEQ ID NOs:84-88 (e.g., any one of SEQ ID NOs:84-86).

In some embodiments, a polypeptide comprises an antibody heavy chain constant domain sequence that comprises at least one amino acid substitution relative to the amino acid sequence of any one of SEQ ID NOs:84-88 (e.g., any one of SEQ ID NOs:84-86). For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises an antibody heavy chain constant domain sequence that comprises about 1-10 amino acid substitutions, relative to the amino acid sequence of any one of SEQ ID NOs:84-88 (e.g., any one of SEQ ID NOs:84-86).

In some embodiments, a polypeptide comprises an antibody heavy chain constant domain sequence that has 100% sequence identity to the amino acid sequence of any one of SEQ ID Nos:84-88 (e.g., any one of SEQ ID NOs:84-86).

In some embodiments, a polypeptide comprises an antibody heavy chain constant domain sequence that has at least about 60% sequence identity to the amino acid sequence of SEQ ID NO:84. For example, a polypeptide can comprise an antibody heavy chain constant domain sequence that has at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:84. In some embodiments, a polypeptide comprises an antibody heavy chain constant domain sequence that has at least about 70% or at least about 80% sequence identity to the amino acid sequence of SEQ ID NO:84.

In some embodiments, a polypeptide comprises an antibody heavy chain constant domain sequence that comprises at least one amino acid substitution relative to the amino acid sequence of SEQ ID NO:84. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises an antibody heavy chain constant domain sequence that comprises about 1-10 amino acid substitutions, relative to the amino acid sequence of SEQ ID NO:84.

In some embodiments, a polypeptide comprises an antibody heavy chain constant domain sequence that has 100% sequence identity to the amino acid sequence of SEQ ID NO:84. Antibodies disclosed herein using a designation "AB-[ ]a" (e.g., AB-2a, see, e.g., Table 4)) comprise the heavy chain constant domain amino acid sequence of SEQ ID NO:84, i.e., comprising M135, S137, and T139.

In some embodiments, a polypeptide comprises (e.g., an antibody or antigen-binding fragment thereof) an antibody heavy chain constant domain sequence that has at least about 60% sequence identity to the amino acid sequence of SEQ ID NO:85. For example, a polypeptide can comprise an antibody heavy chain constant domain sequence that has at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:85. In some embodiments, a polypeptide comprises an antibody heavy chain constant domain sequence that has at least about 70% or at least about 80% sequence identity to the amino acid sequence of SEQ ID NO:85.

In some embodiments, a polypeptide comprises an antibody heavy chain constant domain sequence that comprises at least one amino acid substitution relative to the amino acid sequence of SEQ ID NO:85. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises an antibody heavy chain constant domain sequence that comprises about 1-10 amino acid substitutions, relative to the amino acid sequence of SEQ ID NO:85.

In some embodiments, a polypeptide comprises an antibody heavy chain constant domain sequence that has 100% sequence identity to the amino acid sequence of SEQ ID NO:85. Antibodies disclosed herein using a designation "AB-[ ]b" (e.g., AB-2b, see, e.g., Table 4)) comprise the heavy chain constant domain amino acid sequence of SEQ ID NO:85, i.e., comprising Y135, T137, and E139).

In some embodiments, a polypeptide comprises an Fc polypeptide, or Fc domain (e.g., an IgG1 domain, an IgG2 domain or an IgG4 domain). In some embodiments, an Fc domain comprises one or more mutations that, for example, decreases (e.g., inhibits, ablates) an effector function of the Fc domain, increases half-life of an antibody or antibody fragment that comprises the Fc domain, or a combination thereof. See, e.g., Dumet et al., *Insights into the IgG heavy chain engineering patent landscape as applied to IgG4 antibody development*, Mabs. 11(8):1341-50 (2019) (particularly Tables 1 and 2 therein) and WO02060919, the contents of which are incorporated by reference herein in their entirety. In some embodiments, an Fc domain comprises a LS modification (i.e., M428L/N434S substitutions with numbering determined by Kabat) or a YTE modification (i.e., M252Y/S254T/T256E substitutions as determined by Kabat numbering, corresponding to M135Y/S137T/T139E when comparing SEQ ID NO:84 with SEQ ID NO:85). In some embodiments, an Fc domain comprises a YTE modification.

In some embodiments, a polypeptide (e.g., an antibody or antigen-binding fragment thereof) comprises an antibody light chain constant domain sequence.

In some embodiments, a polypeptide comprises an antibody light chain constant domain sequence that is selected from the group consisting of a κ constant domain (e.g., SEQ ID NO:89) and a λ constant domain (e.g., SEQ ID NO:90).

```
                                            (SEQ ID NO: 89)
RTVAAPSVFIFPPSDEQLKSGTASVVCLLNNFYPREAKVQWKVDNA

LQSGNSQESVTEQDSKDSTYSLSSTLTLSKADYEKHKVYACEVTHQ

GLSSPVTKSFNRGEC.
                                            (SEQ ID NO: 90)
GQPKAAPSVTLFPPSSEELQANKATLVCLISDFYPGAVTVAWKADS

SPVKAGVETTTPSKQSNNKYAASSYLSLTPEQWKSHRSYSCQVTHE

GSTVEKTVAPTECS.
```

In some embodiments, a polypeptide comprises an antibody light chain constant domain sequence that has at least about 60% sequence identity to the amino acid sequence of SEQ ID NO:89 or SEQ ID NO:90. For example, a polypeptide can comprise an antibody light chain constant domain sequence that has at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:89 or SEQ ID NO:90. In some embodiments, a polypeptide comprises an antibody light chain constant domain sequence that has at least about 70% or at least about 80% sequence identity to SEQ ID NO:89 or SEQ ID NO:90.

In some embodiments, a polypeptide comprises an antibody light chain constant domain sequence that comprises at least one amino acid substitution relative to the amino acid sequence of SEQ ID NO:89 or SEQ ID NO:90. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises an antibody light chain constant domain sequence that comprises about 1-10 amino acid substitutions, relative to the amino acid sequence of SEQ ID NO:89 or SEQ ID NO:90. In some embodiments, the at least one amino acid substitution is a conservative substitution. In some embodiments, the at least one amino acid substitution is a highly conservative substitution.

In some embodiments, a polypeptide comprises an antibody light chain constant domain sequence that has 100% sequence identity to the amino acid sequence of SEQ ID NO:89 or SEQ ID NO:90.

In some embodiments, a polypeptide comprises an antibody light chain constant domain sequence that has at least about 60% sequence identity to the amino acid sequence of SEQ ID NO:90. For example, a polypeptide can comprise an antibody light chain constant domain sequence that has at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:90. In some embodiments, a polypeptide comprises an antibody light chain constant domain sequence that has at least about 70% or at least about 80% sequence identity to SEQ ID NO:90.

In some embodiments, a polypeptide comprises an antibody light chain constant domain sequence that comprises at least one amino acid substitution relative to the amino acid sequence of SEQ ID NO:90. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises an antibody light chain constant domain sequence that comprises about 1-10 amino acid substitutions, relative to the amino acid sequence of SEQ ID NO:90. In some embodiments, the at least one amino acid substitution is a conservative substitution. In some embodiments, the at least one amino acid substitution is a highly conservative substitution.

In some embodiments, a polypeptide comprises an antibody light chain constant domain sequence that has 100% sequence identity to the amino acid sequence of SEQ ID NO:90.

In some embodiments, a polypeptide comprises:
a) an antibody heavy chain constant domain sequence; and
b) an antibody light chain constant domain sequence.

In some embodiments, a polypeptide comprises an antibody heavy chain constant domain that is an IgG1 constant domain (e.g., SEQ ID NO:84 or SEQ ID NO:85), and an antibody light chain constant domain that is a λ constant domain (e.g., SEQ ID NO:90).

In some embodiments, a polypeptide comprises:
a) an antibody heavy chain constant domain comprising SEQ ID NO:85; or
b) an antibody light chain constant domain comprising SEQ ID NO:90,
or both a) and b).

In some embodiments, a polypeptide comprises:
a) an antibody heavy chain constant domain comprising SEQ ID NO:85; and
b) an antibody light chain constant domain comprising SEQ ID NO:90, In some embodiments, a polypeptide comprises:
a) an antibody heavy chain constant domain comprising SEQ ID NO:84; or
b) an antibody light chain constant domain comprising SEQ ID NO:90,
or both a) and b).

In some embodiments, a polypeptide comprises:
a) an antibody heavy chain constant domain comprising SEQ ID NO:84; and
b) an antibody light chain constant domain comprising SEQ ID NO:90, Antibodies and Antigen Binding Fragments In some embodiments, a polypeptide is an immunoglobulin molecule, such as an antibody (e.g., a whole antibody, an intact antibody) or an antigen-binding fragment of an antibody.

In some embodiments, a polypeptide is an antibody. As used herein, the term "antibody" refers to an immunoglobulin molecule capable of specific binding to a target, such as a carbohydrate, polynucleotide, lipid, polypeptide, etc., through at least one antigen recognition site, located in the variable domain of the immunoglobulin molecule. As used herein, the term "antibody" refers to a full-length antibody.

In some embodiments, a polypeptide is an antibody comprising two heavy (H) chains and two light (L) chains inter-connected by disulfide bonds or multimers thereof (for example, IgM). Each heavy chain comprises a $V_H$ and a heavy chain constant domain (comprising domains CH1, hinge CH2 and CH3). Each light chain comprises a $V_L$ and a light chain constant domain (CL). $V_H$ and $V_L$ regions may be further subdivided into regions of hypervariability, termed complementarity determining regions (CDRs), interspersed within framework regions (FRs). $V_H$ and $V_L$ each comprises three CDRs and four FRs, arranged from the amino-terminus to the carboxy-terminus in the following order: FR1, CDR1, FR2, CDR2, FR3, CDR3, and FR4. An antibody can be of any species, such as a murine antibody, a human antibody, or a humanized antibody.

In some embodiments, a polypeptide comprises a heavy chain amino acid sequence that has at least about 60% sequence identity to the amino acid sequence of any one or more of SEQ ID NOs:91-118. For example, a polypeptide can comprise a heavy chain amino acid sequence that has at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of any one or more of SEQ ID NOs:91-118. In some embodiments, a polypeptide comprises a heavy chain amino acid sequence that has at least about 70% or at least about 80% sequence identity to the amino acid sequence of any one or more of SEQ ID NOs:91-118.

In some embodiments, a polypeptide comprises a heavy chain amino acid sequence that comprises at least one amino acid substitution relative to the amino acid sequence of any one or more of SEQ ID NOs:91-118. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises a heavy chain amino acid sequence that comprises about 1-10 amino acid substitutions, relative to the amino acid sequence of any one or more of SEQ ID NOs:91-118.

In some embodiments, a polypeptide comprises a heavy chain amino acid sequence that has 100% sequence identity to the amino acid sequence of any one of SEQ ID NOs:91-118.

In some embodiments, a polypeptide comprises a heavy chain amino acid sequence that has at least about 60% sequence identity to the amino acid sequence of any one or more of SEQ ID NOs:91-94 and 105-108. For example, a polypeptide can comprise a heavy chain amino acid sequence that has at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of any one or more of SEQ ID NOs:91-94 and 105-108. In some embodiments, a polypeptide comprises a heavy chain amino acid sequence that has at least about 80% sequence identity to the amino acid sequence of any one or more of SEQ ID NOs:91-94 and 105-108.

In some embodiments, a polypeptide comprises a heavy chain amino acid sequence that comprises at least one amino acid substitution relative to the amino acid sequence of any one or more of SEQ ID NOs:91-94 and 105-108. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises a heavy chain amino acid sequence that comprises about 1-10 amino acid substitutions, relative to the amino acid sequence of any one or more of SEQ ID NOs:91-94 and 105-108.

In some embodiments, a polypeptide comprises a heavy chain amino acid sequence that has 100% sequence identity to the amino acid sequence of any one of SEQ ID NOs:91-94 and 105-108.

In some embodiments, a polypeptide comprises a heavy chain amino acid sequence that has at least about 60% sequence identity to the amino acid sequence of any one or more of SEQ ID NOs:91-94. For example, a polypeptide can comprise a heavy chain amino acid sequence that has at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of any one or more of SEQ ID NOs:91-94. In some embodiments, a polypeptide comprises a heavy chain amino acid sequence that has at least about 70% or at least about 80% sequence identity to the amino acid sequence of any one or more of SEQ ID NOs:91-94.

In some embodiments, a polypeptide comprises a heavy chain amino acid sequence that comprises at least one amino acid substitution relative to the amino acid sequence of any one or more of SEQ ID NOs:91-94. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises a heavy chain amino acid sequence that comprises about 1-10 amino acid substitutions, relative to the amino acid sequence of any one or more of SEQ ID NOs:91-94.

In some embodiments, a polypeptide comprises a heavy chain amino acid sequence that has 100% sequence identity to the amino acid sequence of any one of SEQ ID NOs:91-94.

In some embodiments, a polypeptide comprises a heavy chain amino acid sequence that has at least about 60% sequence identity to the amino acid sequence of SEQ ID NO:92. For example, a polypeptide can comprise a heavy chain amino acid sequence that has at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:92. In some embodiments, a polypeptide comprises a heavy chain amino acid sequence that has at least about 70% or at least about 80% sequence identity to the amino acid sequence of SEQ ID NO:92.

In some embodiments, a polypeptide comprises a heavy chain amino acid sequence that comprises at least one amino acid substitution relative to the amino acid sequence of SEQ ID NO:92. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises a heavy chain amino acid sequence that comprises about 1-10 amino acid substitutions, relative to the amino acid sequence of SEQ ID NO:92.

In some embodiments, a polypeptide comprises a heavy chain amino acid sequence that has 100% sequence identity to the amino acid sequence of SEQ ID NO:92.

In some embodiments, a polypeptide comprises a heavy chain amino acid sequence that has at least about 60% sequence identity to the amino acid sequence of any one or more of SEQ ID NOs:105-108. For example, a polypeptide can comprise a heavy chain amino acid sequence that has at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of any one or more of SEQ ID NOs:105-108. In some embodiments, a polypeptide comprises a heavy chain amino acid sequence that has at least about 70% or at least about 80% sequence identity to the amino acid sequence of any one or more of SEQ ID NOs:105-108.

In some embodiments, a polypeptide comprises a heavy chain amino acid sequence that comprises at least one amino acid substitution relative to the amino acid sequence of any one or more of SEQ ID NOs:105-108. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises a heavy chain amino acid sequence that comprises about 1-10 amino acid substitutions, relative to the amino acid sequence of any one or more of SEQ ID NOs:105-108.

In some embodiments, a polypeptide comprises a heavy chain amino acid sequence that has 100% sequence identity to the amino acid sequence of any one of SEQ ID NOs: 105-108.

In some embodiments, a polypeptide comprises a heavy chain amino acid sequence that has at least about 60% sequence identity to the amino acid sequence of SEQ ID NO:106. For example, a polypeptide can comprise a heavy chain amino acid sequence that has at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:106. In some embodiments, a polypeptide comprises a heavy chain amino acid sequence that has at least about 70% or at least about 80% sequence identity to the amino acid sequence of SEQ ID NO:106.

In some embodiments, a polypeptide comprises a heavy chain amino acid sequence that comprises at least one amino acid substitution relative to the amino acid sequence of SEQ ID NO:106. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises a heavy chain amino acid sequence that comprises about 1-10 amino acid substitutions, relative to the amino acid sequence of SEQ ID NO:106.

In some embodiments, a polypeptide comprises a heavy chain amino acid sequence that has 100% sequence identity to the amino acid sequence of SEQ ID NO:106.

In some embodiments, a polypeptide comprises a light chain amino acid sequence that has at least about 60% sequence identity to the amino acid sequence of any one or more of SEQ ID NOs:119-129. For example, a polypeptide can comprise a light chain amino acid sequence that has at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of any one or more of SEQ ID NOs:119-129. In some embodiments, a polypeptide comprises a light chain amino acid sequence that has at least about 70% or at least about 80% sequence identity to the amino acid sequence of any one or more of SEQ ID NOs:119-129.

In some embodiments, a polypeptide comprises a light chain amino acid sequence that comprises at least one amino acid substitution relative to the amino acid sequence of any one or more of SEQ ID NOs:119-129. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises a light chain amino acid sequence that comprises about 1-10 amino acid substitutions, relative to the amino acid sequence of any one or more of SEQ ID NOs:119-129.

In some embodiments, a polypeptide comprises a light chain amino acid sequence that has 100% sequence identity to the amino acid sequence of any one of SEQ ID NOs: 119-129.

In some embodiments, a polypeptide comprises a light chain amino acid sequence that has at least about 60% sequence identity to the amino acid sequence of any one or more of SEQ ID NOs:119-121. For example, a polypeptide can comprise a light chain amino acid sequence that has at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of any one or more of SEQ ID NOs:119-121. In some embodiments, a polypeptide comprises a light chain amino acid sequence that has at least about 80% sequence identity to the amino acid sequence of any one or more of SEQ ID NOs:119-121.

In some embodiments, a polypeptide comprises a light chain amino acid sequence that comprises at least one amino acid substitution relative to the amino acid sequence of any one or more of SEQ ID NOs:119-121. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises a light chain amino acid sequence that comprises about 1-10 amino acid substitutions, relative to the amino acid sequence of any one or more of SEQ ID NOs:119-121.

In some embodiments, a polypeptide comprises a light chain amino acid sequence that has 100% sequence identity to the amino acid sequence of any one of SEQ ID NOs: 119-121.

In some embodiments, a polypeptide comprises a light chain amino acid sequence that has at least about 60% sequence identity to the amino acid sequence of SEQ ID NO:120. For example, a polypeptide can comprise a light chain amino acid sequence that has at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:120. In some embodiments, a polypeptide comprises a light chain amino acid sequence that has at least about 70% or at least about 80% sequence identity to the amino acid sequence of SEQ ID NO:120.

In some embodiments, a polypeptide comprises a light chain amino acid sequence that comprises at least one amino acid substitution relative to the amino acid sequence of SEQ ID NO:120. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, a polypeptide comprises a light chain amino acid sequence that comprises about 1-10 amino acid substitutions, relative to the amino acid sequence of SEQ ID NO:120.

In some embodiments, a polypeptide comprises a light chain amino acid sequence that has 100% sequence identity to the amino acid sequence of SEQ ID NO:120.

In some embodiments, a polypeptide comprises:
a) a heavy chain amino acid sequence that has at least about 60% sequence identity to the amino acid sequence of any one or more of SEQ ID NOs:91-118; or
b) a light chain amino acid sequence that has at least about 60% sequence identity to the amino acid sequence of any one or more of SEQ ID NOs:119-129, or
both a) and b).

In some embodiments, a polypeptide comprises:
a) a heavy chain amino acid sequence that has at least about 60% sequence identity to the amino acid sequence of any one or more of SEQ ID NOs:91-118; and
b) a light chain amino acid sequence that has at least about 60% sequence identity to the amino acid sequence of any one or more of SEQ ID NOs:119-129.

In some embodiments, a polypeptide comprises:
a) a heavy chain amino acid sequence comprising at least one amino acid substitution relative to the amino acid sequence of any one or more of SEQ ID NOs:91-118; or
b) a light chain amino acid sequence comprising at least one amino acid substitution relative to the amino acid sequence of any one or more of SEQ ID NOs:119-129, or
both a) and b).

In some embodiments, a polypeptide comprises:
a) a heavy chain amino acid sequence comprising at least one amino acid substitution relative to the amino acid sequence of any one or more of SEQ ID NOs:91-118; and b) a light chain amino acid sequence comprising at least one amino acid substitution relative to the amino acid sequence of any one or more of SEQ ID NOs:119-129.

In some embodiments, a polypeptide comprises:
a) a heavy chain amino acid sequence comprising about 1-10 amino acid substitutions, relative to the amino acid sequence of any one or more of SEQ ID NOs:91-118; or
b) a light chain amino acid sequence comprising about 1-10 amino acid substitutions, relative to the amino acid sequence of any one or more of SEQ ID NOs: 119-129, or
both a) and b).

In some embodiments, a polypeptide comprises:
a) a heavy chain amino acid sequence comprising about 1-10 amino acid substitutions, relative to the amino acid sequence of any one or more of SEQ ID NOs:91-118; and
b) a light chain amino acid sequence comprising about 1-10 amino acid substitutions, relative to the amino acid sequence of any one or more of SEQ ID NOs: 119-129.

In some embodiments, a polypeptide comprises:
a) a heavy chain amino acid sequence that has 100% sequence identity to the amino acid sequence of any one of SEQ ID NOs:91-118; or
b) a light chain amino acid sequence that has 100% sequence identity to the amino acid sequence of any one of SEQ ID NOs:119-129, or
both a) and b).

In some embodiments, a polypeptide comprises:
a) a heavy chain amino acid sequence that has 100% sequence identity to the amino acid sequence of any one of SEQ ID NOs:91-118; and
b) a light chain amino acid sequence that has 100% sequence identity to the amino acid sequence of any one of SEQ ID NOs:119-129.

In some embodiments, a polypeptide comprises:
a) a heavy chain amino acid sequence that has at least about 60% sequence identity to the amino acid sequence of any one or more of SEQ ID NOs:91-94 and 105-108; or
b) a light chain amino acid sequence that has at least about 60% sequence identity to the amino acid sequence of any one or more of SEQ ID NOs:119-121, or
both a) and b).

In some embodiments, a polypeptide comprises:
a) a heavy chain amino acid sequence that has at least about 60% sequence identity to the amino acid sequence of any one or more of SEQ ID NOs:91-94 and 105-108; and
b) a light chain amino acid sequence that has at least about 60% sequence identity to the amino acid sequence of any one or more of SEQ ID NOs:119-121.

In some embodiments, a polypeptide comprises:
a) a heavy chain amino acid sequence comprising at least one amino acid substitution relative to the amino acid sequence of any one or more of SEQ ID NOs:91-94 and 105-108; or
b) a light chain amino acid sequence comprising at least one amino acid substitution relative to the amino acid sequence of any one or more of SEQ ID NOs:119-121, or
both a) and b).

In some embodiments, a polypeptide comprises:
a) a heavy chain amino acid sequence comprising at least one amino acid substitution relative to the amino acid sequence of any one or more of SEQ ID NOs:91-94 and 105-108; and
b) a light chain amino acid sequence comprising at least one amino acid substitution relative to the amino acid sequence of any one or more of SEQ ID NOs:119-121.

In some embodiments, a polypeptide comprises:
a) a heavy chain amino acid sequence comprising about 1-10 amino acid substitutions, relative to the amino acid sequence of any one or more of SEQ ID NOs:91-94 and 105-108; or
b) a light chain amino acid sequence comprising about 1-10 amino acid substitutions, relative to the amino acid sequence of any one or more of SEQ ID NOs: 119-121, or
both a) and b).

In some embodiments, a polypeptide comprises:
a) a heavy chain amino acid sequence comprising about 1-10 amino acid substitutions, relative to the amino acid sequence of any one or more of SEQ ID NOs:91-94 and 105-108; and
b) a light chain amino acid sequence comprising about 1-10 amino acid substitutions, relative to the amino acid sequence of any one or more of SEQ ID NOs: 119-121.

In some embodiments, a polypeptide comprises:
a) a heavy chain amino acid sequence that has 100% sequence identity to the amino acid sequence of any one of SEQ ID NOs:91-94 and 105-108; or
b) a light chain amino acid sequence that has 100% sequence identity to the amino acid sequence of any one of SEQ ID NOs:119-121, or
both a) and b).

In some embodiments, a polypeptide comprises:
a) a heavy chain amino acid sequence that has 100% sequence identity to the amino acid sequence of any one of SEQ ID NOs:91-94 and 105-108; and
b) a light chain amino acid sequence that has 100% sequence identity to the amino acid sequence of any one of SEQ ID NOs:119-121.

In some embodiments, a polypeptide comprises:
a) a heavy chain amino acid sequence that has at least about 60% sequence identity to the amino acid sequence of any one or more of SEQ ID NOs:105-108; or
b) a light chain amino acid sequence that has at least about 60% sequence identity to the amino acid sequence of any one or more of SEQ ID NOs:119-121, or
both a) and b).

In some embodiments, a polypeptide comprises:
a) a heavy chain amino acid sequence that has at least about 60% sequence identity to the amino acid sequence of any one or more of SEQ ID NOs:105-108; and
b) a light chain amino acid sequence that has at least about 60% sequence identity to the amino acid sequence of any one or more of SEQ ID NOs:119-121.

In some embodiments, a polypeptide comprises:
a) a heavy chain amino acid sequence comprising at least one amino acid substitution relative to the amino acid sequence of any one or more of SEQ ID NOs:105-108; or
b) a light chain amino acid sequence comprising at least one amino acid substitution relative to the amino acid sequence of any one or more of SEQ ID NOs:119-121, or both a) and b).

In some embodiments, a polypeptide comprises:
a) a heavy chain amino acid sequence comprising at least one amino acid substitution relative to the amino acid sequence of any one or more of SEQ ID NOs:105-108; and
b) a light chain amino acid sequence comprising at least one amino acid substitution relative to the amino acid sequence of any one or more of SEQ ID NOs:119-121.

In some embodiments, a polypeptide comprises:
a) a heavy chain amino acid sequence comprising about 1-10 amino acid substitutions, relative to the amino acid sequence of any one or more of SEQ ID NOs: 105-108; or
b) a light chain amino acid sequence comprising about 1-10 amino acid substitutions, relative to the amino acid sequence of any one or more of SEQ ID NOs: 119-121, or
both a) and b).

In some embodiments, a polypeptide comprises:
a) a heavy chain amino acid sequence comprising about 1-10 amino acid substitutions, relative to the amino acid sequence of any one or more of SEQ ID NOs: 105-108; and
b) a light chain amino acid sequence comprising about 1-10 amino acid substitutions, relative to the amino acid sequence of any one or more of SEQ ID NOs: 119-121.

In some embodiments, a polypeptide comprises:
a) a heavy chain amino acid sequence that has 100% sequence identity to the amino acid sequence of any one of SEQ ID NOs:105-108; or
b) a light chain amino acid sequence that has 100% sequence identity to the amino acid sequence of any one of SEQ ID NOs:119-121, or
both a) and b).

In some embodiments, a polypeptide comprises:
a) a heavy chain amino acid sequence that has 100% sequence identity to the amino acid sequence of any one of SEQ ID NOs:105-108; and
b) a light chain amino acid sequence that has 100% sequence identity to the amino acid sequence of any one of SEQ ID NOs:119-121.

In some embodiments, a polypeptide comprises:
a) a heavy chain amino acid sequence that has at least about 60% sequence identity to the amino acid sequence of SEQ ID NO:106; or
b) a light chain amino acid sequence that has at least about 60% sequence identity to the amino acid sequence of SEQ ID NO:120, or
both a) and b).

In some embodiments, a polypeptide comprises:
a) a heavy chain amino acid sequence that has at least about 60% sequence identity to the amino acid sequence of SEQ ID NO:106; and
b) a light chain amino acid sequence that has at least about 60% sequence identity to the amino acid sequence of SEQ ID NO:120.

In some embodiments, a polypeptide comprises:
a) a heavy chain amino acid sequence comprising at least one amino acid substitution relative to the amino acid sequence of SEQ ID NO:106; or
b) a light chain amino acid sequence comprising about 1-10 amino acid substitutions, relative to the amino acid sequence of SEQ ID NO:120, or
both a) and b).

In some embodiments, a polypeptide comprises:
a) a heavy chain amino acid sequence comprising at least one amino acid substitution relative to the amino acid sequence of SEQ ID NO:106; and
b) a light chain amino acid sequence comprising about 1-10 amino acid substitutions, relative to the amino acid sequence of SEQ ID NO:120.

In some embodiments, a polypeptide comprises:
a) a heavy chain comprising the amino acid sequence of SEQ ID NO:105; and
b) a light chain comprising the amino acid sequence of SEQ ID NO:119 (AB-1b).

In some embodiments, a polypeptide comprises:
a) a heavy chain comprising the amino acid sequence of SEQ ID NO:106; and
b) a light chain comprising the amino acid sequence of SEQ ID NO:120 (AB-2b).

In some embodiments, a polypeptide comprises:
a) a heavy chain comprising the amino acid sequence of SEQ ID NO:107; and
b) a light chain comprising the amino acid sequence of SEQ ID NO:119 (AB-3b).

In some embodiments, a polypeptide comprises:
a) a heavy chain comprising the amino acid sequence of SEQ ID NO:108; and
b) a light chain comprising the amino acid sequence of SEQ ID NO:121 (AB-4b).

In some embodiments, a polypeptide comprises:
a) a heavy chain comprising the amino acid sequence of SEQ ID NO:109; and
b) a light chain comprising the amino acid sequence of SEQ ID NO:122 (AB-5b).

In some embodiments, a polypeptide comprises:
a) a heavy chain comprising the amino acid sequence of SEQ ID NO:110; and
b) a light chain comprising the amino acid sequence of SEQ ID NO:123 (AB-6b).

In some embodiments, a polypeptide comprises:
a) a heavy chain comprising the amino acid sequence of SEQ ID NO:111; and
b) a light chain comprising the amino acid sequence of SEQ ID NO:124 (AB-7b).

In some embodiments, a polypeptide comprises:
a) a heavy chain comprising the amino acid sequence of SEQ ID NO:112; and
b) a light chain comprising the amino acid sequence of SEQ ID NO:119 (AB-8b).

In some embodiments, a polypeptide comprises:
a) a heavy chain comprising the amino acid sequence of SEQ ID NO:113; and
b) a light chain comprising the amino acid sequence of SEQ ID NO:119 (AB-9b).

In some embodiments, a polypeptide comprises:
a) a heavy chain comprising the amino acid sequence of SEQ ID NO:114; and
b) a light chain comprising the amino acid sequence of SEQ ID NO:125 (AB-10b).

In some embodiments, a polypeptide comprises:
a) a heavy chain comprising the amino acid sequence of SEQ ID NO:115; and
b) a light chain comprising the amino acid sequence of SEQ ID NO:126 (AB-11b).

In some embodiments, a polypeptide comprises:
a) a heavy chain comprising the amino acid sequence of SEQ ID NO:116; and
b) a light chain comprising the amino acid sequence of SEQ ID NO:127 (AB-12b).

In some embodiments, a polypeptide comprises:
a) a heavy chain comprising the amino acid sequence of SEQ ID NO:117; and
b) a light chain comprising the amino acid sequence of SEQ ID NO:128 (AB-13b).

In some embodiments, a polypeptide comprises:
a) a heavy chain comprising the amino acid sequence of SEQ ID NO:118; and
b) a light chain comprising the amino acid sequence of SEQ ID NO:129 (AB-14b).

In some embodiments, a polypeptide is a single-domain antibody or an antigen-binding fragment thereof. As used herein, the term "single-domain antibody (sdAb)" or "nanobody" refers to an immunoglobulin molecule consisting of a single monomeric variable antibody domain and capable of specific binding to a target. A single-domain antibody can be of any species, such as a murine antibody, a human antibody or a humanized single-domain antibody.

In some embodiments, a $V_H$ domain and a $V_L$ domain may be linked together via a linker (e.g., a synthetic linker) to form various types of single-chain antibody designs in which the $V_H/V_L$ domains pair intramolecularly, or intermolecularly in those cases when the $V_H$ and $V_L$ domains are expressed by separate chains, to form a monovalent antigen binding site.

In some embodiments, a polypeptide is a heavy-chain antibody comprising two or more heavy chains, but lacking light chain, or an antigen-binding fragment thereof. Non-limiting examples of heavy chain antibodies include camelid Vhh (also referred to as $V_{HH}$ or $V_{HH}$) antibodies. Camelid antibodies are antibodies from the Camelidae family of mammals that include llamas, camels, and alpacas.

In some embodiments, a polypeptide is an antibody mimetic. The term "antibody mimetic" refers to polypeptides capable of mimicking an antibody's ability to bind an antigen, but structurally differ from native antibody structures. Non-limiting examples of antibody mimetics include Adnectins, Affibodies, Affilins, Affimers, Affitins, Alphabodies, Anticalins, Avimers, DARPins, Fynomers, Kunitz domain peptides, monobodies, nanobodies, nanoCLAMPs, and Versabodies.

In some embodiments, a polypeptide is an antigen-binding fragment of an antibody. The term "antigen-binding fragment" refers to a portion of an immunoglobulin molecule (e.g., antibody) that retains the antigen binding properties of the full-length Reference Antibody. Non-limiting examples of antigen-binding fragments include a $V_H$ region, a $V_L$ region, an Fab fragment, an F(ab')$_2$ fragment, an Fd fragment, an Fv fragment, and a domain antibody (dAb) consisting of one $V_H$ domain or one $V_L$ domain, etc. $V_H$ and $V_L$ domains may be linked together via a synthetic linker to form various types of single-chain antibody designs in which the $V_H/V_L$ domains pair intramolecularly, or intermolecularly in those cases when the $V_H$ and $V_L$ domains are expressed by separate chains, to form a monovalent antigen binding site, such as single chain Fv (scFv) or diabody. In some embodiments, a polypeptide disclosed herein is an antigen binding fragment selected from Fab, F(ab')2, Fab', scFv, or Fv. In some embodiments, a polypeptide is a scFv.

In some embodiments, a polypeptide is an isolated polypeptide.

In some embodiments, a polypeptide (e.g., an isolated polypeptide) is recombinantly produced. In some embodiments, a polypeptide (e.g., an isolated polypeptide) is synthetically produced.

In some embodiments, a polypeptide is linked to a second polypeptide. The term "linked" means attached, via a covalent or noncovalent interaction. Conjugation can employ a suitable linking agent. Non-limiting examples include peptide linkers, compound linkers, and chemical cross-linking agents. In some embodiments, the linker is a disulfide bond.

In some embodiments, a polypeptide is conjugated to a heterologous moiety. The term "conjugated" refers to attached, via a covalent or noncovalent interaction. Conjugation can employ any one or more of suitable linking agents. Non-limiting examples include peptide linkers, compound linkers, and chemical cross-linking agents.

In some embodiments, a heterologous moiety comprises a therapeutic agent, a diagnostic agent, or both. In some embodiments, a heterologous moiety is selected from polyethylene glycol (PEG), hexadecanoic acid, hydrogels, nanoparticles, multimerization domains and carrier peptides.

In some embodiments, a nanoparticle is a lipid nanoparticle. In some embodiments, a nanoparticle is a polymer nanoparticle. In some embodiments, a polymer is an amphiphilic polymer. In some embodiments, a polymer is a hydrophobic or hydrophilic polymer. Non-limiting examples of polymers include poly(lactic acid)-poly(ethylene glycol), poly(lactic-co-glycolic acid)-poly(ethylene glycol), poly(lactic-co-glycolic) acid (PLGA), poly(lactic-co-glycolic acid)-d-α-tocopheryl polyethylene glycol succinate, poly(lactic-co-glycolic acid)-ethylene oxide fumarate, poly(glycolic acid)-poly(ethylene glycol), poly-caprolactone-poly(ethylene glycol), or any salts thereof. In some embodiments, a polymer nanoparticle comprises poly (lactic-co-glycolic) acid (PLGA).

In some embodiments, a carrier polypeptide is albumin or an Fc polypeptide.

In some embodiments, a polypeptide:
a) binds to a TSLP protein with a $K_D$ of 10 pM or less (e.g., as measured by KinExA);
b) binds to AB-loop region and C-terminal region of helix D of a TSLP protein;
c) binds to an epitope in a TSLP protein (e.g., a full-length human TSLP);
d) competes with the Reference Antibody for binding to a TSLP protein;
e) reduces binding of a TSLP protein to a TSLPR;
f) modulates (e.g., reduces, inhibits, neutralizes) against a TSLP-mediated biological activity, or
a combination of the foregoing.

In some embodiments, a polypeptide binds to a TSLP (e.g., human) with a $K_D$ of 10 pM or less (e.g., as measured by KinExA).

In some embodiments, a polypeptide binds (e.g., has a binding affinity for, has a binding specificity for) an AB-loop region and a C-terminal region of helix D of a TSLP.

In some embodiments, a polypeptide has neutralizing activity against a TSLP (e.g., a full-length human TSLP). In some embodiments, the polypeptides have inhibitory activity against TSLP-mediated signaling.

In some embodiments, a polypeptide binds to a TSLP protein (e.g., SEQ ID NO:1) with a $K_D$ of about: 10 pM, 8 pM, 5 pM, 4 pM, 3 pM, 2 pM, 1.8 pM, 1.5 pM, 1.2 pM, 1.0 pM, 0.9 pM, 0.8 pM, 0.7 pM, 0.6 pM, 0.5 pM, 0.4 pM, 0.3 pM, 0.2 pM or 0.1 pM, or less; or about: 0.1-10 pM, 0.2-10 pM, 0.2-8 pM, 0.3-8 pM, 0.3-5 pM, 0.4-5 pM, 0.4-4 pM, 0.5-4 pM, 0.5-3 pM, 0.6-3 pM, 0.6-2 pM, 0.7-2 pM, 0.7-1.8 pM, 0.8-1.8 pM, 0.8-1.5 pM, 1.0-1.5 pM or 1.2-1.5 pM. In some embodiments, a polypeptide binds to a TSLP protein (e.g., SEQ ID NO:1) with a $K_D$ of 2 pM or less.

In some embodiments, a polypeptide binds to a TSLP protein (e.g., SEQ ID NO:1) with a $K_D$ of about: 2.0 pM, 1.9 pM, 1.8 pM, 1.7 pM, 1.6 pM, 1.5 pM, 1.4 pM, 1.3 pM, 1.2 pM, 1.1 pM, 1.0 pM, 0.9 pM, 0.8 pM, 0.7 pM, 0.6 pM, 0.5 pM, 0.4 pM, 0.3 pM, 0.2 pM or 0.1 pM, or less; or about: 0.1-2.0 pM, 0.2-2.0 pM, 0.2-1.9 pM, 0.3-1.9 pM, 0.3-1.8 pM, 0.4-1.8 pM, 0.4-1.7 pM, 0.5-1.7 pM, 0.5-1.6 pM, 0.6-1.6 pM, 0.6-1.5 pM, 0.7-1.5 pM, 0.7-1.4 pM, 0.8-1.4 pM, 0.8-1.3 pM, 0.9-1.3 pM, 1.0-1.3 pM, 1.0-1.2 pM or 1.1-1.2 pM. In some embodiments, a polypeptide binds TSLP with a $K_D$ of about 1 pM or less.

In some embodiments, a polypeptide binds to AB-loop region and C-terminal region of helix D of a TSLP protein.

In some embodiments, a polypeptide binds to an epitope in a TSLP protein (e.g., a full-length human TSLP).

In some embodiments, a polypeptide competes with the Reference Antibody for binding to a TSLP protein (e.g., SEQ ID NO:1). Techniques and assays for assessing competition between antibodies are known in the art.

In some embodiments, a polypeptide reduces binding of a TSLP protein (e.g., a full-length TSLP protein such as SEQ ID NO:1) to its receptor TSLPR (alone or in a heterodimeric complex with the IL-7Rα). In some embodiments, a polypeptide reduces binding of a TSLP protein to a TSLPR with an $IC_{50}$ of about 500 pM or less, e.g., about: 450 pM, 400 pM, 350 pM, 300 pM, 250 pM, 200 pM, 150 pM, 100 pM, 50 pM, 20 pM, 10 pM, 5 pM, 2 pM, 1 pM, 0.5 pM, 0.2 pM or 0.1 pM or less; or about: 0.1-500 pM, 0.1-450 pM, 0.2-450 pM, 0.2-400 pM, 0.5-400 pM, 0.5-350 pM, 1-350 pM, 1-300 pM, 2-300 pM, 2-250 pM, 5-250 pM, 5-200 pM, 10-200 pM, 10-150 pM, 20-150 pM, 20-100 pM or 50-100 pM.

In some embodiments, a polypeptide reduces binding of a TSLP protein (e.g., a full-length TSLP protein such as SEQ ID NO:1) to TSLPR by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, a polypeptide reduces binding of a TSLP protein (e.g., a full-length TSLP protein such as SEQ ID NO:1) to TSLPR by at least about 30%.

In some embodiments, a polypeptide modulates (e.g., reduces, inhibits, neutralizes) against a TSLP-mediated biological activity.

Non-limiting examples of TSLP-mediated activities include TSLPR-binding, TSLP-induced signal transducer and activator of transcription 5 (STAT5) signaling, TSLP-induced STAT3 signaling, TSLP-induced nuclear factor kappa-light-chain-enhancer of activated B cells (NFκB) signaling, TSLP-induced phosphoinositide-3-kinase (PI3K) signaling, TSLP-induced mitogen-activated protein kinase (MAPK) signaling, activation of one or more genes encoding interleukin-4 (IL-4), IL-5, IL-9, IL-13 and mitogen-activated protein kinase kinase 2 (MEK2), and dendritic cell activation. In some embodiments, a TSLP-mediated activity comprises one or more innate immune mechanisms of action and/or one or more adaptive immune mechanisms of action.

TSLP-mediated activities can be determined, for example, by measuring STAT5 reporter activity, dendritic cell activation, proliferation of cells expressing TSLPR and CCL17 production (see, e.g., Verstraete et al., *Structure and antagonism of the receptor complex mediated by human TSLP in allergy and asthma*, Nat Commun. 8:14937 (2017), the contents of which are incorporated herein by reference).

In some embodiments, a polypeptide neutralizes an activity mediated by a TSLP protein (e.g., a full-length TSLP protein such as SEQ ID NO:1).

In some embodiments, a polypeptide neutralizes a TSLP-mediated activity with an $IC_{50}$ of about 500 pM or less, e.g., about: 450 pM, 400 pM, 350 pM, 300 pM, 250 pM, 200 pM, 150 pM, 100 pM, 50 pM, 20 pM, 10 pM, 5 pM, 2 pM, 1 pM, 0.5 pM, 0.2 pM or 0.1 pM, or less; or about: 0.1-500 pM, 0.1-450 pM, 0.2-450 pM, 0.2-400 pM, 0.5-400 pM, 0.5-350 pM, 1-350 pM, 1-300 pM, 2-300 pM, 2-250 pM, 5-250 pM, 5-200 pM, 10-200 pM, 10-150 pM, 20-150 pM, 20-100 pM or 50-100 pM.

In some embodiments, a polypeptide reduces a TSLP-mediated activity by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, a polypeptide reduces a TSLP-mediated activity by at least about 30%.

In some embodiments, a polypeptide reduces a T2 inflammatory response mediated by one or more innate immune mechanisms of action of TSLP.

Non-limiting examples of T2 inflammatory responses include activation of group 2 innate lymphoid cells (ILC2s); activation, migration and/or local differentiation of eosinophil progenitor cells (EoPs) (e.g., via upregulation of ICAM-1 and/or CD18, and/or via suppression of L-selectin surface expression); increase of eosinophil viability (e.g., via production of IL-6, eosinophil-derived neurotoxin, and chemokines (including C-X-C Motif Chemokine Ligand 8 (CXCL8), CXCL1 and chemokine (C-C motif) ligand 2 (CCL2)); basophil differentiation; production of T2 cytokines by mast cells; production of chemokine CXCL8 and/or CCL1 by mast cells; and macrophage differentiation (e.g., via enhancing CD80 activation marker expression).

In some embodiments, a polypeptide reduces a T2 inflammatory response mediated by one or more innate immune mechanisms of action of TSLP by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, a polypeptide reduces a T2 inflammatory response mediated by one or more innate immune mechanisms of action of TSLP by at least about 30%.

In some embodiments, a polypeptide reduces a T2 inflammatory response mediated by one or more adaptive immune mechanisms of action of TSLP.

Non-limiting examples of said T2 inflammatory responses include increased expression of major histocompatibility complex class II in dendritic cells; increased expression of one or more co-stimulatory molecules (e.g., CD40, CD86, CD54, CD90, CD83 and/or CD-LAMP) in dendritic cells; increased expression of one or more chemokines (e.g., CXCL8, CCL24, CCL17, CCL22 and CCL1) in dendritic cells; increased expression of OX40 ligand (OX40 L); naive T-cell differentiation and/or polarization (e.g., differentiation of naive $CD4^+$ T cells into TNF-$\alpha^+$IL-10$^-$ T helper (Th) 2 cells); proliferation and/or differentiation of naive $CD4^+$ T cells into Th2 cells or memory T cells; and increased expansion of $CD8^+$ T cells upon TCR stimulation.

In some embodiments, a polypeptide reduces a T2 inflammatory response mediated by an adaptive immune mechanism of action of TSLP by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, a polypeptide reduces a T2 inflammatory response mediated by an adaptive immune mechanism of action of TSLP by at least about 30%.

In some embodiments, a polypeptide has a lower polyspecificity for a non-specific target (e.g., DNA) than the Reference Antibody. A DNA polyspecificity reagent (PSR) score is a measure of antibody binding to a non-specific DNA target. A DNA PSR score is calculated by dividing an ELISA or DELFIA score by a background score of a secondary antibody alone. A lower DNA PSR score, indicative of a lower poly-specific binding activity, is preferred for a polypeptide of the invention.

In some embodiments, a polypeptide has a DNA PSR score of no more than about: 1, 2, 3 or 4. In some embodiments, a polypeptide has a DNA PSR score of about: 1, 2, 3 or 4. In some embodiments, a polypeptide has a DNA PSR score of about: 1-4, 1-3, 1-2, 2-4, 2-3 or 3-4. In some embodiments, a polypeptide has a DNA PSR score of about: 2-4, 2-3 or 3-4.

In some embodiments, a polypeptide has a DNA PSR score that is at least about 10% lower than that of the Reference Antibody, for example, by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99% lower. In some embodiments, a polypeptide has a DNA PSR score that is at least about 30% lower than that of the Reference Antibody.

In some embodiments, a polypeptide has a DNA PSR score that is less than about 90% of that of the Reference Antibody, for example, less than about: 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2% or 1% of that of the Reference Antibody.

In some embodiments, a polypeptide has a DNA PSR score that is about 1-90% relative to that of the Reference Antibody, for example, about: 2-90%, 2-85%, 3-85%, 3-80%, 4-80%, 4-75%, 5-75%, 5-70%, 6-70%, 6-65%, 7-65%, 7-60%, 8-60%, 8-55%, 9-55%, 9-50%, 10-50%, 10-45%, 15-45%, 15-40%, 20-40%, 20-35%, 25-35% or 25-30%, relative to that of the Reference Antibody.

In some embodiments, a polypeptide has a weaker self-association than the Reference Antibody, for example, as determined by an affinity-capture self-interaction nanoparticle spectroscopy (AC-SINS) value. The AC-SINS value is the change in maximum absorbance wavelength in the coated-nanoparticle absorption spectra compared to the spectra of the nanoparticle alone. Thus, the greater the change in maximum absorbance wavelength, the more self-interaction of the antibody coated on the nanopartical. Self-association is an unwanted property that correlates with poor viscosity and poor PK properties. Techniques and assays for assessing self-association of proteins are known in the art. See, e.g., Patro & Przybycien, Biotechnol Bioeng. 52(2):193-203 (1996), the contents of which are incorporated herein in their entirety.

In some embodiments, a polypeptide has an AC-SINS value of no more than about: 0, 1, 2, 3, 4, 5, 6 or 7. In some embodiments, a polypeptide has an AC-SINS value of no more than about: 0, 1, 2, 3 or 4. In some embodiments, a polypeptide has an AC-SINS value of about: 0, 1, 2, 3, 4, 5, 6 or 7. In some embodiments, a polypeptide has an AC-SINS value of about: 0, 1, 2, 3 or 4. In some embodiments, a polypeptide has an AC-SINS value of at least about: 0, 1, 2, 3, 4, 5, 6 or 7. In some embodiments, a polypeptide has an AC-SINS value of about 0-4.

In some embodiments, a polypeptide has an AC-SINS value that is at least about 10% lower than that of the Reference Antibody, for example, by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99% lower than that of the Reference Antibody. In some embodiments, a polypeptide has an AC-SINS value that is at least about 30% lower than that of the Reference Antibody.

In some embodiments, a polypeptide has an AC-SINS value that is less than about 90% of that of the Reference Antibody, for example, less than about: 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2% or 1% of that of the Reference Antibody.

In some embodiments, a polypeptide has an AC-SINS value that is about 1-90% relative to that of the Reference Antibody, for example, about: 2-90%, 2-85%, 3-85%, 3-80%, 4-80%, 4-75%, 5-75%, 5-70%, 6-70%, 6-65%, 7-65%, 7-60%, 8-60%, 8-55%, 9-55%, 9-50%, 10-50%, 10-45%, 15-45%, 15-40%, 20-40%, 20-35%, 25-35% or 25-30%, relative to that of the Reference Antibody.

Fusion Proteins

The disclosure also provides, among other things, a fusion protein comprising one or more of the polypeptides disclosed herein.

The term "fusion protein" refers to a synthetic, semi-synthetic or recombinant single protein molecule. A fusion protein can comprise all or a portion of two or more different proteins and/or polypeptides that are attached by covalent bonds (e.g., peptide bonds).

Fusion proteins of the disclosure can be produced recombinantly or synthetically, using routine methods and reagents that are well known in the art. For example, a fusion protein of the disclosure can be produced recombinantly in a suitable host cell (e.g., bacteria) according to methods known in the art. See, e.g., *Current Protocols in Molecular Biology*, Second Edition, Ausubel et al. eds., John Wiley & Sons, 1992; and *Molecular Cloning: a Laboratory Manual*, 2nd edition, Sambrook et al., 1989, Cold Spring Harbor Laboratory Press. For example, a nucleic acid molecule comprising a nucleotide sequence encoding a fusion protein described herein can be introduced and expressed in suitable host cell (e.g., *E. coli*), and the expressed fusion protein can be isolated/purified from the host cell (e.g., in inclusion bodies) using routine methods and readily available reagents. For example, DNA fragments coding for different protein sequences (e.g., a light-responsive domain, a heterologous peptide component) can be ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers that give rise to complementary overhangs between two consecutive nucleic acid fragments that can subsequently be annealed and re-amplified to generate a chimeric nucleic acid sequence (see Ausubel et al., Current Protocols in Molecular Biology, 1992).

Nucleic Acids, Vectors, Host Cells

The disclosure also provides, among other things, one or more polynucleotides (e.g., DNA, RNA, or analogs of either, e.g., optionally including one or more modified nucleotides; a polynucleotide may be linear or circular, e.g., a linear or circular RNA) encoding any one of the polypeptides or fusion proteins described herein. In some embodiments, a polypeptide or fusion protein disclosed herein is encoded by a single polynucleotide. In some embodiments, a polypeptide or fusion protein disclosed herein is encoded by multiple polynucleotides.

In some embodiments, a polynucleotide comprises a nucleotide sequence that is codon-optimized for a chosen host cell.

The disclosure also provides, among other things, a vector (e.g., an expression vector, including a viral-delivery vector) comprising any one or more of the polynucleotides disclosed herein.

The term "expression vector" refers to a replicable nucleic acid from which one or more proteins can be expressed when the expression vector is transformed into a suitable expression host cell.

In some embodiments, a vector (e.g., expression vector) further comprises an expression control polynucleotide sequence operably linked to the polynucleotide, a polynucleotide sequence encoding a selectable marker, or both. In some embodiments, an expression control polynucleotide sequence comprises a promoter sequence, an enhancer sequence, or both. In some embodiments, an expression control polynucleotide sequence comprises an inducible promoter sequence. The term "promoter" refers to a region of DNA to which RNA polymerase binds and initiates the transcription of a gene. The term "operably linked" means that the nucleic acid is positioned in the recombinant polynucleotide, e.g., vector, in such a way that enables expression of the nucleic acid under control of the element (e.g., promoter) to which it is linked. The term "selectable marker element" is an element that confers a trait suitable for artificial selection. Selectable marker elements can be negative or positive selection markers.

The disclosure also provides, among other things, an expression host cell comprising any one or more of the polynucleotides or expression vectors disclosed herein.

The term "expression host cell" refers to a cell useful for receiving, maintaining, reproducing and/or amplifying a vector. Non-limiting examples of expression host cells include mammalian cells such as hybridoma cells, Chinese hamster ovary (CHO) cells, COS cells, human embryonic kidney (HEK), yeast cells such as *Pichia pastoris* cells, or bacterial cells such as *E. coli*, including DH5α, etc.

Compositions

The disclosure also provides, among other things, a composition comprising any one of the polypeptides or fusion proteins disclosed herein. In some embodiments, a composition is a pharmaceutical composition.

In some embodiments, a composition (e.g., pharmaceutical composition) further comprises pharmaceutically acceptable carriers, excipients, stabilizers, diluents or tonifiers (Remington's Pharmaceutical Sciences 16th edition, Osol, A. Ed. (1980)). Suitable pharmaceutically acceptable carriers, excipients, or stabilizers are nontoxic to recipients at the dosages and concentrations employed. Non-limiting examples of pharmaceutically acceptable carriers, excipients, stabilizers, diluents or tonifiers include buffers (e.g., phosphate, citrate, histidine), antioxidants (e.g., ascorbic acid or methionine), preservatives, proteins (e.g., serum albumin, gelatin or immunoglobulins); hydrophilic polymers, amino acids, carbohydrates (e.g., monosaccharides, disaccharides, glucose, mannose or dextrins); chelating agents (e.g., EDTA), sugars (e.g., sucrose, mannitol, trehalose or sorbitol), salt-forming counter-ions (e.g., sodium), metal complexes (e.g., Zn-protein complexes); non-ionic surfactants (e.g., Tween), PLURONICS™ and polyethylene glycol (PEG).

In some embodiments, a composition (e.g., a pharmaceutical composition) is formulated for a suitable administration schedule and route. Non-limiting examples of administration routes include oral, rectal, mucosal, intravenous, intramuscular, subcutaneous, and topical, etc. In some embodiments, a composition (e.g., a pharmaceutical composition) is stored in the form of an aqueous solution or a dried formulation (e.g., lyophilized).

In some embodiments, a composition is formulated to be administered by infusion (e.g., intravenous infusion). In other embodiments a composition is formulated for subcutaneous administration.

In some embodiments, a composition is provided in a dosage form, e.g., in a prefilled syringe or autoinjector.

In some embodiments, a pharmaceutical composition comprises from about 50 mg to about 300 mg of a polypeptide or fusion protein disclosed herein, for example, about: 50 mg, 60 mg, 70 mg, 80 mg, 90 mg, 100 mg, 120 mg, 140 mg, 150 mg, 160 mg, 180 mg, 200 mg, 220 mg, 240 mg, 250 mg, 260 mg, 280 mg, or 300 mg. In some embodiments, a pharmaceutical composition comprises from about 60 mg to about 300 mg of a polypeptide or fusion protein disclosed herein, for example, about: 60-280 mg, 80-280 mg, 80-260 mg, 100-260 mg, 100-250 mg, 120-250 mg, 120-240 mg, 140-240 mg, 140-220 mg, 150-250 mg, 150-200 mg, 160-220 mg, 160-200 mg, or 180-200 mg.

In some embodiments, a pharmaceutical composition comprises from about 50 mg/ml to about 200 mg/ml of a polypeptide or fusion protein disclosed herein, for example, about: 50 mg/ml, 60 mg/ml, 70 mg/ml, 80 mg/ml, 90 mg/ml, 100 mg/ml, 120 mg/ml, 140 mg/ml, 150 mg/ml, 160 mg/ml, 180 mg/ml, or 200 mg/ml of a polypeptide or fusion protein disclosed herein. In some embodiments, a pharmaceutical composition comprises from about 60 mg/ml to about 200 mg/ml of a polypeptide or fusion protein disclosed herein, for example, about: 60-180 mg/ml, 80-180 mg/ml, 80-160 mg/ml, 100-160 mg/ml, 100-150 mg/ml, 120-150 mg/ml or 120-140 mg/ml.

In some embodiments, a composition is formulated to be administered with a second therapeutic agent as a combination therapy. In some embodiments, a second therapeutic agent comprises a corticosteroid, a beta-agonist (e.g., a long-acting beta-agonist), a muscarinic antagonist, an anti-inflammatory agent, an IL-4 and/or IL-13 antagonist (e.g., an antibody or antigen-binding fragment thereof targeting IL-13, IL-4 or IL-4R), or any combination thereof. In some embodiments, a second therapeutic agent comprises a corticosteroid (e.g., an inhaled corticosteroid). Non-limiting examples of inhaled corticosteroids include beclomethasone dipropionate, budesonide, ciclesonide, fluticasone furoate, fluticasone propionate, mometasone, and mometasone furoate. In some embodiments, a combination therapy comprises a beta-agonist (e.g., a long-acting beta-agonist). Non-limiting examples of long-acting beta-agonists include albuterol sulfate, formoterol fumarate, salmeterol xinafoate, arformoterol tartrate, olodaterol, and combinations thereof. In some embodiments, a combination therapy comprises a muscarinic antagonist. In some embodiments, a combination therapy comprises an IL-4 and/or IL-13 antagonist (e.g., for the treatment of allergic and/or asthmatic conditions). Non-limiting examples of IL-4 and/or IL-13 antagonists include Pitrakinra, anti-IL-13 antibodies or antigen-binding fragments thereof, anti-IL-4 antibodies or antigen-binding fragments thereof, and anti-IL-4R antibodies or antigen-binding fragments thereof. Non-limiting examples of antibodies or antigen-binding fragments thereof include anti-IL-13 antibodies or antigen-binding fragments thereof (e.g., Lebrikizumab, Tralokinumab, and Anrukinzumab), anti-IL-4 antibodies or antigen-binding fragments thereof (e.g., Pascolizumab (SB 240683)), anti-IL-4R antibodies or antigen-binding fragments thereof (e.g., Dupilumab).

In some embodiments, a composition is formulated to be administered with an inhaled corticosteroid (ICS), a long-acting β2-agonist (LABA), a long-acting muscarinic antagonist (LAMA), or any combination thereof.

In some embodiments, a composition (e.g., a pharmaceutical composition) comprises a polypeptide comprising:
 a) a $V_H$ comprising a HCDR1, a HCDR2 and a HCDR3 amino acid sequences of SEQ ID NO:5; and
 b) a $V_L$ comprising a LCDR1, a LCDR2 and a LCDR3 amino acid sequences of SEQ ID NO:21 (AB-2).

In some embodiments, a composition (e.g., a pharmaceutical composition) comprises a polypeptide comprising:
 a) a $V_H$ comprising the amino acid sequence of SEQ ID NO:5, and
 b) a $V_L$ comprising the amino acid sequence of SEQ ID NO:21 (AB-2).

In some embodiments, a composition (e.g., a pharmaceutical composition) comprises a polypeptide comprising:
 a) a heavy chain comprising the amino acid sequence of SEQ ID NO:106; and
 b) a light chain comprising the amino acid sequence of SEQ ID NO:120 (AB-2b).

In some embodiments, a composition (e.g., a pharmaceutical composition) comprises a polypeptide comprising:
 a) a heavy chain comprising the amino acid sequence of SEQ ID NO:92; and
 b) a light chain comprising the amino acid sequence of SEQ ID NO:120 (AB-2a).

Methods of Use

The disclosure also provides, among other things, a method of neutralizing a TSLP protein (e.g., a full-length TSLP protein) in a subject, comprising administering to the subject an effective amount of a pharmaceutical composition comprising a pharmaceutically acceptable carrier and, wherein as an active ingredient, any one of the polypeptides or fusion proteins disclosed herein.

In some embodiments, neutralizing a TSLP protein in a subject comprises administering to the subject an effective amount of a pharmaceutical composition comprising a pharmaceutically acceptable carrier and a polypeptide comprising:
 a) a $V_H$ comprising a HCDR1, a HCDR2 and a HCDR3 amino acid sequences of SEQ ID NO:5; and
 b) a $V_L$ comprising a LCDR1, a LCDR2 and a LCDR3 amino acid sequences of SEQ ID NO:21 (AB-2).

In some embodiments, neutralizing a TSLP protein in a subject comprises administering to the subject an effective amount of a pharmaceutical composition comprising a pharmaceutically acceptable carrier and a polypeptide comprising:
 a) a $V_H$ comprising the amino acid sequence of SEQ ID NO:5, and
 b) a $V_L$ comprising the amino acid sequence of SEQ ID NO:21 (AB-2).

In some embodiments, neutralizing a TSLP protein in a subject comprises administering to the subject an effective amount of a pharmaceutical composition comprising a pharmaceutically acceptable carrier and a polypeptide comprising:
 a) a heavy chain comprising the amino acid sequence of SEQ ID NO:106; and
 b) a light chain comprising the amino acid sequence of SEQ ID NO:120 (AB-2b).

In some embodiments, neutralizing a TSLP protein in a subject comprises administering to the subject an effective amount of a pharmaceutical composition comprising a pharmaceutically acceptable carrier and a polypeptide comprising:
 a) a heavy chain comprising the amino acid sequence of SEQ ID NO:92; and
 b) a light chain comprising the amino acid sequence of SEQ ID NO:120 (AB-2a).

In some embodiments, a subject is a mammal. In some embodiments, a subject is a mammal selected from the group consisting of a dog, a cat, a mouse, a rat, a hamster, a guinea pig, a horse, a pig, a sheep, a cow, a chimpanzee, a macaque, a cynomolgus, and a human. In some embodiments, a subject is a primate. In some embodiments, a subject is a human.

In some embodiments, a subject is 18 years of age or older, for example, about: 20, 25, 30, 35, 40, 45, 50, 55, 60, 65, 70, 75 or 80 years of age or older. In some embodiments, a subject is 65 years of age or older. In some embodiments, a subject is about: 18-80, 20-80, 20-75, 25-75, 25-70, 30-70, 30-65, 35-65, 35-60, 40-60, 40-55, 45-55 years of age. In some embodiments, a subject is about 18-65 years of age.

In some embodiments, a subject is about 18 years of age or younger. In some embodiments, a subject is about: 16, 14, 12, 10, 8, 6, 4 or 2 years of age or older. In some embodiments, a subject is two years of age or older, for example, about: 2-18, 3-18, 3-16, 4-16, 4-14, 5-14, 5-12, 6-12, 6-10 or 8-10 years of age.

In some embodiments, a subject is a pediatric patient. In some embodiments, a subject is a pediatric patient who is 12 years of age or older.

In some embodiments, a subject has a blood eosinophil count of less than 150 cells/μL. In some embodiments, a subject has a blood eosinophil count of 150 to less than 300 cells/μL. In some embodiments, a subject has a blood eosinophil count of 300 cells/μL or above.

In some embodiments, a subject has, or is suspected of having, a TSLP-associated disease or condition (e.g., a disease or condition associated with dysregulated TSLP expression such as overexpression of TSLP). In some embodiments, a subject has a TSLP-associated disease or condition. In some embodiments, a subject has been diagnosed with a TSLP-associated disease or condition. In other embodiments, a subject is at risk of developing a TSLP-associated disease or condition.

Non-limiting examples of TSLP-associated diseases and/or conditions (e.g., diseases and/or conditions associated with dysregulated TSLP expression) include asthma, AD, allergic conjunctivitis, chronic obstructive pulmonary disease (COPD), chronic spontaneous urticaria (CSU), nasal polyposis, rheumatoid arthritis (RA), rhinosinusitis (RS) (e.g., allergic rhinosinusitis, severe chronic rhinosinusitis (e.g., severe chronic rhinosinusitis with nasal polyposis)), cancer and food-hypersensitivity reactions. Non-limiting examples of TSLP-associated cancer (e.g., a cancer associated with dysregulated TSLP expression) include lymphoma, acute lymphocytic leukemia (ALL), multiple sclerosis, and solid tumors (e.g., cervical, ovarian, pancreatic, gastric cancer, or colorectal cancer (e.g., colon cancer, rectal cancer, and variants thereof)).

In some embodiments, a subject has an inflammatory disorder (e.g., an allergic inflammatory disorder). In some embodiments, a subject has a pulmonary inflammatory disease or condition. In some embodiments, a subject has asthma (e.g., severe and/or uncontrolled asthma). In some embodiments, a subject has mild, moderate, moderate-to-severe, or severe asthma. In some embodiments, a subject has uncontrolled asthma (e.g., uncontrolled moderate asthma, uncontrolled moderate-to-severe asthma, or uncontrolled severe asthma), allergic asthma (e.g., mild allergic asthma, moderate allergic asthma, or severe allergic asthma), oral corticosteroid dependent asthma, or any combination thereof.

In some embodiments, a subject has been previously treated with one or more therapeutic agents prior to being administered a composition (e.g., a polypeptide, or a pharmaceutical composition disclosed herein).

In some embodiments, a subject previously received a therapeutic or prophylactic agent. For example, a COPD patient may have received an inhaled corticosteroid (ICS), a long-acting β2-agonist (LABA), a long-acting muscarinic antagonist (LAMA), or any combination thereof.

The disclosure also provides, among other things, a method of treating a TSLP-associated disease or condition in a subject, comprising administering to the subject an effective amount of a pharmaceutical composition comprising a pharmaceutically acceptable carrier and, wherein as an active ingredient, any one of the polypeptides or fusion proteins disclosed herein.

In some embodiments, treating a TSLP-associated disease or condition in a subject comprises administering to the subject an effective amount of a pharmaceutical composition comprising a pharmaceutically acceptable carrier and a polypeptide comprising:
  a) a $V_H$ comprising a HCDR1, a HCDR2 and a HCDR3 amino acid sequences of SEQ ID NO:5; and
  b) a $V_L$ comprising a LCDR1, a LCDR2 and a LCDR3 amino acid sequences of SEQ ID NO:21 (AB-2).

In some embodiments, treating a TSLP-associated disease or condition in a subject comprises administering to the subject an effective amount of a pharmaceutical composition comprising a pharmaceutically acceptable carrier and a polypeptide comprising:
  a) a $V_H$ comprising the amino acid sequence of SEQ ID NO:5, and
  b) a $V_L$ comprising the amino acid sequence of SEQ ID NO:21 (AB-2).

In some embodiments, treating a TSLP-associated disease or condition in a subject comprises administering to the subject an effective amount of a pharmaceutical composition comprising a pharmaceutically acceptable carrier and a polypeptide comprising:
  a) a heavy chain comprising the amino acid sequence of SEQ ID NO: 106; and
  b) a light chain comprising the amino acid sequence of SEQ ID NO:120 (AB-2b).

In some embodiments, treating a TSLP-associated disease or condition in a subject comprises administering to the subject an effective amount of a pharmaceutical composition comprising a pharmaceutically acceptable carrier and a polypeptide comprising:
  a) a heavy chain comprising the amino acid sequence of SEQ ID NO:92; and
  b) a light chain comprising the amino acid sequence of SEQ ID NO:120 (AB-2a).

In some embodiments, treating a TSLP-associated disease or condition comprises treating asthma (e.g., severe and/or uncontrolled asthma). In some embodiments, treating a TSLP-associated disease or condition comprises treating moderate-to-severe asthma. In some embodiments, treating a TSLP-associated disease or condition comprises treating severe asthma. In some embodiments, treating a TSLP-associated disease or condition comprises treating uncontrolled asthma. In some embodiments, treating a TSLP-associated disease or condition comprises treating severe, uncontrolled asthma. In some embodiments, treating a TSLP-associated disease or condition comprises treating AD.

In some embodiments, treating a TSLP-associated disease or condition is a prophylactic therapy.

In some embodiments, an effective amount is sufficient to prevent the subject of developing a TSLP-associated disease or condition (e.g., a disease or condition associated with dysregulated TSLP expression).

In some embodiments, an effective amount is sufficient to reduce TSLPR occupancy in a subject. In some embodiments, an effective amount is sufficient to reduce TSLPR occupancy by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, an effective amount is sufficient to reduce TSLPR occupancy by about 10-99%, e.g., by about: 10-98%, 15-98%, 15-97%, 20-97%, 20-96%, 25-96%, 25-95%, 30-95%, 30-94%, 35-94%, 35-93%, 40-93%, 40-92%, 45-92%, 45-91%, 50-91%, 50-90%, 55-90%, 55-85%, 60-85%, 60-80%, 65-80%, 65-75%, or 70-75%.

In some embodiments, an effective amount is sufficient to reduce a TSLP receptor complex in the subject. In some embodiments, an effective amount is sufficient to reduce a TSLP receptor complex by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, an effective amount is sufficient to reduce a TSLP receptor complex by about 10-99%, e.g., by about: 10-98%, 15-98%, 15-97%, 20-97%, 20-96%, 25-96%, 25-95%, 30-95%, 30-94%, 35-94%, 35-93%, 40-93%, 40-92%, 45-92%, 45-91%, 50-91%, 50-90%, 55-90%, 55-85%, 60-85%, 60-80%, 65-80%, 65-75%, or 70-75%.

In some embodiments, an effective amount is sufficient to reduce an activity of a TSLP protein in a subject. In some embodiments, an effective amount is sufficient to reduce an activity of a TSLP protein by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, an effective amount is sufficient to reduce an activity of a TSLP protein by about 10-99%, e.g., by about: 10-98%, 15-98%, 15-97%, 20-97%, 20-96%, 25-96%, 25-95%, 30-95%, 30-94%, 35-94%, 35-93%, 40-93%, 40-92%, 45-92%, 45-91%, 50-91%, 50-90%, 55-90%, 55-85%, 60-85%, 60-80%, 65-80%, 65-75%, or 70-75%.

In some embodiments, an effective amount is sufficient to reduce airway inflammation (e.g., the number and/or density of one or more types of airway submucosal inflammatory cells) in a subject. In some embodiments, an effective amount is sufficient to reduce airway inflammation by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, an effective amount is sufficient to reduce airway inflammation by about 10-99%, e.g., by about: 10-98%, 15-98%, 15-97%, 20-97%, 20-96%, 25-96%, 25-95%, 30-95%, 30-94%, 35-94%, 35-93%, 40-93%, 40-92%, 45-92%, 45-91%, 50-91%, 50-90%, 55-90%, 55-85%, 60-85%, 60-80%, 65-80%, 65-75%, or 70-75%.

In some embodiments, an effective amount is sufficient to reduce airway remodeling (e.g., reticular basement membrane thickening, airway epithelial integrity) in a subject. In some embodiments, an effective amount is sufficient to reduce airway remodeling by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, an effective amount is sufficient to reduce airway remodeling by about 10-99%, e.g., by about: 10-98%, 15-98%, 15-97%, 20-97%, 20-96%, 25-96%, 25-95%, 30-95%, 30-94%, 35-94%, 35-93%, 40-93%, 40-92%, 45-92%, 45-91%, 50-91%, 50-90%, 55-90%, 55-85%, 60-85%, 60-80%, 65-80%, 65-75%, or 70-75%.

In some embodiments, an effective amount is sufficient to treatment nasal polyps (e.g., reducing the size and/or number of nasal polyps) in a subject. In some embodiments, an effective amount is sufficient to reduce the size of nasal polyps by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, an effective amount is sufficient to reduce the size of nasal polyps by about 10-99%, e.g., by about: 10-98%, 15-98%, 15-97%, 20-97%, 20-96%, 25-96%, 25-95%, 30-95%, 30-94%, 35-94%, 35-93%, 40-93%, 40-92%, 45-92%, 45-91%, 50-91%, 50-90%, 55-90%, 55-85%, 60-85%, 60-80%, 65-80%, 65-75%, or 70-75%. In some embodiments, an effective amount is sufficient to reduce the number of nasal polyps by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, an effective amount is sufficient to reduce the number of nasal polyps by about 10-99%, e.g., by about: 10-98%, 15-98%, 15-97%, 20-97%, 20-96%, 25-96%, 25-95%, 30-95%, 30-94%, 35-94%, 35-93%, 40-93%, 40-92%, 45-92%, 45-91%, 50-91%, 50-90%, 55-90%, 55-85%, 60-85%, 60-80%, 65-80%, 65-75%, or 70-75%.

A therapeutic agent disclosed herein can be administered via a variety of routes of administration, including, for example, topical, transdermal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the compound and the particular disease to be treated.

Administration can be local or systemic as indicated. A preferred mode of administration can vary depending on a particular compound chosen.

In some embodiments, a composition (e.g., a polypeptide or pharmaceutical composition) is administered to a subject as a monotherapy.

In some embodiments, a composition (e.g., a polypeptide or pharmaceutical composition) is administered to a subject in combination with one or more additional therapeutic agents (e.g., concurrently, or sequentially with one or more additional therapeutic agents) or prophylactic agents (e.g., concurrently, or sequentially with one or more prophylactic agents).

In some embodiments, treating a TSLP-associated disease or condition further comprises administering a therapeutically effective amount of one or more additional therapeutic agents to a subject at the same time as, or following administration of a composition (e.g., a polypeptide or pharmaceutical composition). In some embodiments, treating a TSLP-associated disease or condition further comprises administering a therapeutically effective amount of one or more prophylactic agents to a subject before, at the same time as, or following administration of a composition (e.g., a polypeptide or a pharmaceutical composition).

Administration of two or more therapeutic agents encompasses co-administration of the therapeutic agents in a substantially simultaneous manner, such as in a pharmaceutical combination. Alternatively, such administration encompasses co-administration in multiple containers, or separate containers (e.g., capsules, powders, and liquids) for each therapeutic agent. Such administration also encompasses use of each type of therapeutic agent in a sequential manner, either at approximately the same time or at different times. A composition and a second therapeutic agent can be administered via the same administration route or via different administration routes.

The disclosure also provides, among other things, a method of reducing (e.g., inhibiting) binding of TSLP to TSLPR in a cell, comprising contacting the cell an effective amount of any one or more of the polypeptides or fusion proteins disclosed herein.

In some embodiments, reducing (e.g., inhibiting) binding of TSLP to TSLPR in a cell comprises contacting the cell an effective amount of a polypeptide comprising:
  a) a $V_H$ comprising a HCDR1, a HCDR2 and a HCDR3 amino acid sequences of SEQ ID NO:5; and
  b) a $V_L$ comprising a LCDR1, a LCDR2 and a LCDR3 amino acid sequences of SEQ ID NO:21 (AB-2).

In some embodiments, reducing (e.g., inhibiting) binding of TSLP to TSLPR in a cell comprises contacting the cell an effective amount of a polypeptide comprising:
  a) a $V_H$ comprising the amino acid sequence of SEQ ID NO:5, and
  b) a $V_L$ comprising the amino acid sequence of SEQ ID NO:21 (AB-2).

In some embodiments, reducing (e.g., inhibiting) binding of TSLP to TSLPR in a cell comprises contacting the cell an effective amount of a polypeptide comprising:
  a) a heavy chain comprising the amino acid sequence of SEQ ID NO:106; and
  b) a light chain comprising the amino acid sequence of SEQ ID NO:120 (AB-2b).

In some embodiments, reducing (e.g., inhibiting) binding of TSLP to TSLPR in a cell comprises contacting the cell an effective amount of a polypeptide comprising:
  a) a heavy chain comprising the amino acid sequence of SEQ ID NO:92; and
  b) a light chain comprising the amino acid sequence of SEQ ID NO:120 (AB-2a).

The disclosure also provides, among other things, a method of inhibiting TSLP-induced signaling in a cell, comprising contacting the cell an effective amount of any one of the polypeptides or fusion proteins disclosed herein.

In some embodiments, inhibiting TSLP-induced signaling in a cell comprises contacting the cell an effective amount of a polypeptide comprising:
  a) a $V_H$ comprising a HCDR1, a HCDR2 and a HCDR3 amino acid sequences of SEQ ID NO:5; and
  b) a $V_L$ comprising a LCDR1, a LCDR2 and a LCDR3 amino acid sequences of SEQ ID NO:21 (AB-2).

In some embodiments, inhibiting TSLP-induced signaling in a cell comprises contacting the cell an effective amount of a polypeptide comprising:
  a) a $V_H$ comprising the amino acid sequence of SEQ ID NO:5, and
  b) a $V_L$ comprising the amino acid sequence of SEQ ID NO:21 (AB-2).

In some embodiments, inhibiting TSLP-induced signaling in a cell comprises contacting the cell an effective amount of a polypeptide comprising:

a) a heavy chain comprising the amino acid sequence of SEQ ID NO:106; and
b) a light chain comprising the amino acid sequence of SEQ ID NO:120 (AB-2b).

In some embodiments, inhibiting TSLP-induced signaling in a cell comprises contacting the cell an effective amount of a polypeptide comprising:
a) a heavy chain comprising the amino acid sequence of SEQ ID NO:92; and
b) a light chain comprising the amino acid sequence of SEQ ID NO:120 (AB-2a).

In some embodiments, a cell is selected from the group consisting of an airway smooth muscle cell (ASMC), a basophil, a dendritic cell, an eosinophil, a Group 2 innate lymphoid cell (ILC2), a hematopoietic progenitor cell, a lymphocyte, a macrophage, a mast cell, and a monocyte.

AB-2

The disclosure also provides, among other things, a polypeptide comprising:
a) a HCDR1 comprising the amino acid sequence of SEQ ID NO:31, a HCDR2 comprising the amino acid sequence of SEQ ID NO:35, and a HCDR3 comprising the amino acid sequence of SEQ ID NO:50; and
b) a LCDR 1 comprising the amino acid sequence of SEQ ID NO:60, a LCDR2 comprising the amino acid sequence DDS, and a LCDR3 comprising the amino acid sequence of SEQ ID NO:71,
wherein the polypeptide is an antibody or an antigen-binding fragment thereof.

The disclosure also provides, among other things, a polypeptide comprising:
a) a HCDR 1 consisting of the amino acid sequence of SEQ ID NO:31, a HCDR2 consisting of the amino acid sequence of SEQ ID NO:35, and a HCDR3 consisting of the amino acid sequence of SEQ ID NO:50; and
b) a LCDR 1 consisting of the amino acid sequence of SEQ ID NO:60, a LCDR2 consisting of the amino acid sequence DDS, and a LCDR3 consisting of the amino acid sequence of SEQ ID NO:71,
wherein the polypeptide is an antibody or an antigen-binding fragment thereof.

AB-2 CDR amino acid sequences as determined by Kabat numbering are:

```
HCDR1:
                                      (SEQ ID NO: 130)
TYGMH

HCDR2:
                                      (SEQ ID NO: 131)
VVWYDGSYTHYADSVKG

HCDR3:
                                      (SEQ ID NO: 132)
SPQWEEIFEAMDI

LCDR1:
                                      (SEQ ID NO: 133)
GGNNIGSKSVH

LCDR2:
                                      (SEQ ID NO: 134)
DDSDRPS

LCDR3:
                                      (SEQ ID NO: 71)
QIWDSSSSLVV
```

The disclosure also provides, among other things, a polypeptide comprising:
a) a HCDR 1 comprising the amino acid sequence of SEQ ID NO:130, a HCDR2 comprising the amino acid sequence of SEQ ID NO:131, and a HCDR3 comprising the amino acid sequence of SEQ ID NO:132; and
b) a LCDR 1 comprising the amino acid sequence of SEQ ID NO:133, a LCDR2 comprising the amino acid sequence of SEQ ID NO:134, and a LCDR3 comprising the amino acid sequence of SEQ ID NO:71,
wherein the polypeptide is an antibody or an antigen-binding fragment thereof.

The disclosure also provides, among other things, a polypeptide comprising:
a) a HCDR 1 consisting of the amino acid sequence of SEQ ID NO:130, a HCDR2 consisting of the amino acid sequence of SEQ ID NO:131, and a HCDR3 consisting of the amino acid sequence of SEQ ID NO:132; and
b) a LCDR 1 consisting of the amino acid sequence of SEQ ID NO:133, a LCDR2 consisting of the amino acid sequence of SEQ ID NO:134, and a LCDR3 consisting of the amino acid sequence of SEQ ID NO:71,
wherein the polypeptide is an antibody or an antigen-binding fragment thereof.

AB-2 CDR amino acid sequences as determined by Chothia numbering are:

```
HCDR1:
                                      (SEQ ID NO: 135)
GFTFRTY

HCDR2:
                                      (SEQ ID NO: 136)
WYDGSY

HCDR3:
                                      (SEQ ID NO: 132)
SPQWEEIFEAMDI

LCDR1:
                                      (SEQ ID NO: 133)
GGNNIGSKSVH

LCDR2:
                                      (SEQ ID NO: 134)
DDSDRPS

LCDR3:
                                      (SEQ ID NO: 71)
QIWDSSSSLVV
```

The disclosure also provides, among other things, a polypeptide comprising:
a) a HCDR 1 comprising the amino acid sequence of SEQ ID NO:135, a HCDR2 comprising the amino acid sequence of SEQ ID NO:136, and a HCDR3 comprising the amino acid sequence of SEQ ID NO:132; and
b) a LCDR 1 comprising the amino acid sequence of SEQ ID NO:133, a LCDR2 comprising the amino acid sequence of SEQ ID NO:134, and a LCDR3 comprising the amino acid sequence of SEQ ID NO:71,
wherein the polypeptide is an antibody or an antigen-binding fragment thereof.

The disclosure also provides, among other things, a polypeptide comprising:
a) a HCDR 1 consisting of the amino acid sequence of SEQ ID NO:135, a HCDR2 consisting of the amino acid sequence of SEQ ID NO:136, and a HCDR3 consisting of the amino acid sequence of SEQ ID NO:132; and b) a LCDR 1 consisting of the amino acid sequence of SEQ ID NO:133, a LCDR2 consisting of the amino acid sequence of SEQ ID NO:134, and a LCDR3 consisting of the amino acid sequence of SEQ ID NO:71, wherein the polypeptide is an antibody or an antigen-binding fragment thereof.

In some embodiments, a polypeptide comprises:
a) a $V_H$ that is humanized, contains human framework regions, or a combination thereof;
b) a $V_L$ that is humanized, contains human framework regions, or a combination thereof,
or both a) and b).

In some embodiments, a polypeptide comprises:
a) a $V_H$ comprising the amino acid sequence of SEQ ID NO:5;
b) a $V_L$ comprising the amino acid sequence of SEQ ID NO:21,
or both a) and b).

In some embodiments, an antigen-binding fragment comprises a single-chain fragment variable (scFv), a variable heavy domain of heavy chain ($V_{HH}$), a fragment antigen-binding (Fab), a Fab' or a F(ab')2.

In some embodiments, a polypeptide comprises:
a) an antibody heavy chain constant domain;
b) an antibody light chain constant domain,
or both a) and b).

In some embodiments, an antibody heavy chain constant domain is an IgG1, IgG2, IgG3 or IgG4 constant domain. In some embodiments, an antibody heavy chain constant domain is an IgG1 or IgG2 constant domain. In some embodiments, an antibody heavy chain constant domain comprises one or more mutations which increase serum half-life of the antibody or antigen-binding fragment thereof in humans. In some embodiments, an antibody heavy chain constant domain comprises, relative to a wild-type human IgG constant domain, amino acid substitutions with tyrosine, threonine and glutamic acid at amino acid residues 252, 254 and 256, respectively, wherein the amino acid residues are numbered according to the EU index as in Kabat.

In some embodiments, a polypeptide comprises:
a) an antibody heavy chain (HC) comprising the amino acid sequence of SEQ ID NO:92;
b) an antibody light chain (LC) comprising the amino acid sequence of SEQ ID NO:120,
or both a) and b).

In some embodiments, a polypeptide comprises:
a) an antibody heavy chain (HC) comprising the amino acid sequence of SEQ ID NO:106;
b) an antibody light chain (LC) comprising the amino acid sequence of SEQ ID NO:120,
or both a) and b).

In some embodiments, a polypeptide specifically binds a TSLP.

The disclosure also provides, among other things, a composition comprising one or more polypeptides disclosed in the section entitled "AB-2", and one or more pharmaceutical excipients, diluents, or carriers.

In some embodiments, a composition further comprises one or more additional therapeutic agents. In some embodiments, one or more additional therapeutic agents comprise a corticosteroid, a beta-agonist, a muscarinic antagonist, an anti-inflammatory agent, an IL-4 and/or IL-13 antagonist (e.g., an antibody or antigen-binding fragment thereof targeting IL-13, IL-4 or IL-4R), or a combination thereof.

The disclosure also provides, among other things, a method of treating a subject in need thereof, comprising administering an effective amount of a composition disclosed in the section entitled "AB-2".

In some embodiments, a subject has asthma, atopic dermatitis (AD), allergic conjunctivitis, chronic obstructive pulmonary disease (COPD), chronic spontaneous urticaria (CSU), rheumatoid arthritis (RA), rhinosinusitis (RS), eosinophilic esophagitis (EE), or a food-hypersensitivity reaction. In some embodiments, a subject has moderate asthma. In some embodiments, a subject has severe asthma. In some embodiments, a subject has COPD. In some embodiments, a subject has COPD and/or either moderate asthma or severe asthma.

In some embodiments, a method further comprises administering to the subject an effective amount of a corticosteroid, a beta-agonist, a muscarinic antagonist, an anti-inflammatory agent, an IL-4 and/or IL-13 antagonist (e.g., an antibody or antigen-binding fragment thereof targeting IL-13, IL-4 or IL-4R), or a combination thereof.

The disclosure also provides, among other things, a method of reducing binding of TSLP to a TSLPR on a cell in a subject, comprising contacting the cell with an effective amount of the composition disclosed in the section entitled "AB-2".

The disclosure also provides, among other things, a fusion protein comprising a polypeptide disclosed in the section entitled "AB-2".

The disclosure also provides, among other things, a polynucleotide comprising a nucleotide sequence encoding a polypeptide disclosed in the section entitled "AB-2".

The disclosure also provides, among other things, a host cell comprising a polynucleotide disclosed in the section entitled "AB-2".

The disclosure also provides, among other things, a method of making a polypeptide disclosed in the section entitled "AB-2", comprising culturing a host cell comprising a nucleotide sequence encoding the polypeptide under conditions where the polypeptide is expressed in the host cell.

Computational Definition and Verification of Sequences

Applicant, through computational design and experimental validation, has facilitated an understanding of structure and function interrelation of anti-TSLP antibodies and herein provides the skilled artisan the means to use such understanding. For example, the application provides Computer Program Listing Appendices (also referred to herein as Appendix A and Appendix B, respectively) that can be used to both evaluate (score) a given sequence or generate a sequence having a score that, when evaluated, is above a given threshold. These appendices include a Potts model (generalized Ising model) of polypeptides provided by the invention. In some embodiments, an implementation of a Potts model supposes that amino acids interact with their nearest neighbor but is able to determine relationship with distant (e.g., more than one position away, therefore representing features of secondary and tertiary structure) amino acids as well.

The Potts model is a second order sequence model. In some embodiments, the Potts model is energy based. The model is designed to output an energy for a particular configuration. Given a sequence provided to an energy-based model, the model can be trained to produce a quantification of any measure. The Potts model is represented by a table of model weights. The table includes first- and second-order weights. In the first-order weights, the table includes position of a residue, the residue (e.g., amino acid), and a score associated with the residue at that position. In the second-order weights, the table includes two positions, two residues, and one score for the two residues at the respective positions. The scores are self-energies or energy scores.

The Computer Program Listing Appendices are referred to as Appendix A (claim.txt) and Appendix B (fit_model.txt), which are incorporated by reference into this application. A person having ordinary skill in the art can recognize that Appendix A can be renamed "claim.py" to be executed in a python environment, compiler, or other equivalent environment that can run python scripts, and that Appendix B can be renamed "fit_model.etab" and can be loaded by the script of Appendix A. A person having ordinary skill in the art can recognize that, in some embodiments, a python environment may also run or compile the script of Appendix A without renaming. When running the claim.py file, two sequences (or one combined sequence) can be inputted. In embodiments, the below description further describes the source code and model of Appendices A and B.

FIG. 12A is a diagram 1000 illustrating zero-, first-, and second-order models. A zero-order model 1002 is a set of unordered amino acids. As the model is zero-order, there is no order or structure to the amino acids. In a physical metaphor, it can be thought of as a "bag" of amino acids because the amino acids placed in the bag would jumble around and have no order. Next, a first order model 1004 is a matrix which is represented as a quantification (e.g., a peptide mass fingerprinting (PMF) of amino acids) at each residue of a protein sequence. Each row of the matrix is an amino acid sequence, and each column is configured to have a sum of the quantification of each residue in that column be 1. These first order energies can be referred to as an h-tensor, represented below as the "first hash table." A first order term in the model is said to be at a given position, and the model can assign a number of points for each particular position. With pair terms, the model can compare the scores given any two positions. The model can output an "energy," which is a number, and the lower the number the better, in embodiments.

A second-order sequence model 1006, or Potts model, represents energy for two residues being found together and energies associated with the first-order effects. The second-order energies of the two residues being found together are considered the j-tensor, while the energies associated with the first-order effects are referred to as the h-tensor. The second order energies, in other words, compare the energies between two positions of the amino acid sequence. The second order sequences can therefore compare the energies between two positions of any amino acid sequence. A person of ordinary skill in the art can recognize that this can be repeated for multiple sequences, thereby rating many similar sequences all residue pairs of similar sequences.

FIG. 12B is a flow diagram 1050 illustrating an example of the process used by embodiments of this disclosure to determine claimed sequences. First, the process receives a given polypeptide sequence or pair of sequences (1052). The sequence pair, in different embodiments, can be separate polypeptide chains or, in some embodiments, a single polypeptide chain, e.g., an scFV. A person of ordinary skill in the art can further recognize that model of Appendix B, in embodiments, can be used to generate polypeptide sequences or pairs of sequences to test using the script of Appendix A. The script of Appendix A scores the sequence using model weights provided in Appendix B (1054). The script then determines whether the score is above a predetermined threshold (although, a person of ordinary skill in the art can recognize that with different scoring regimes, the score may be below the threshold) (1056). If not, the polypeptide sequence or pair of sequences is not verified (1058). If it is, the polypeptide sequence or pair of sequences is verified (1060).

The Potts Model disclosed herein was generated from experimental validation of approximately 100 sequences to identify sequences with advantageous functions. The model coefficients are stored in the plain text file [fit_model.etab]. These sequences when assayed had acceptable polyspecific reactivity, self-aggregation propensity, and expression. Additionally, they all possessed biological function as determined by a SEAP reporter assay. The resulting model was verified to only claim sequences not reported in existing literature.

In some embodiments, a script is employed to determine whether a sequence pair (e.g., $V_H$ and $V_L$—although, for clarity, the sequence pair, in different embodiments, can be separate polypeptide chains or, in some embodiments, a single polypeptide chain, e.g., an scFV) is claimed under the model, when scored, is above a threshold. The script is referred to as a computationally binding optimizing (CBO) script. Two hash tables are loaded from an existing file, and the script extracts first- and second-order index/position values, residue values, and corresponding scores for each. For the first-order table, the script extracts one position, one residue, and one score associated with the residue at the position. For the second-order table, the script extracts a first position, a second position, a first residue, a second residue, and a score associated with the first residue at the first position and the second residue at the second position.

The two sequences, the $V_H$ sequence and $V_L$ sequence, are inputted to the script are then aligned. The alignment confirms that the $V_H$ sequence and $V_L$ sequence are the same length as reference sequence(s) and that given sections of both sequences are the same as the reference sequence(s). Once confirmed, residues from both of the inputted sequences at specified positions are extracted to form a trimmed and concatenated sequence. The positions used to extract the residues are positions where mutations were applied during training of the model. The positions used to confirm that the given sections of both sequences are the same as the reference sequence(s) are the positions where mutations were not applied during training of the model. Once trimmed to the positions used to train the model, the two input sequences are concatenated together. Then an energy score is calculated for the given concatenated sequence and the two hash tables. The following steps describe some embodiments of calculating the energy score.

First, let $\vec{\sigma}$ designate the sequence being scored with $\sigma_i$ being its i-th amino acids. Further, let h represent the self-energy matrix (e.g., first-order matrix) of the Potts model, such that $h_i(a)$ is the energy associated with amino acid a being at position i. Finally, let J represent the pair-energy matrix (e.g., second-order matrix) of the model, such that $J_{ij}(a, b)$ is the pair energy associated with amino acids a and b being at positions i and j, respectively. With this notation, the total energy of sequence $\vec{\sigma}$ under the model is:

$$E(\vec{\sigma}) = \sum_{i=1}^{N} h_i(\sigma_i) + \sum_{i=1}^{N-1} \sum_{j=i+1}^{N} J_{ij}(\sigma_i, \sigma_j)$$

where N is the length of the sequence. Further, $\vec{\sigma}_{i \to a}$ can represent a sequence resulting in replacing the i-th amino acids of sequence $\vec{\sigma}$ with amino acid a. With this notation, a pseudo-likelihood of sequence $\vec{\sigma}$ under the model can be calculated as:

$$\rho(\vec{\sigma}) = \prod_{i=1}^{N} \frac{e^{-E(\vec{\sigma})}}{\sum_{a=1}^{\mu} e^{-E(\vec{\sigma}_{i \to a})}}$$

where $\mu$ is the total number of possible amino acids. In some embodiments, $\mu$ is 20 but a person of ordinary skill in the art can recognize that the value of $\mu$ can vary. Finally, the logarithm of the pseudo-likelihood of $\vec{\sigma}$ can be expressed as:

$$\log[\rho(\vec{\sigma})] = \sum_{i=1}^{N} \log\left[\frac{e^{-E(\vec{\sigma})}}{\sum_{a=1}^{\mu} e^{-E(\vec{\sigma}_{i \to a})}}\right] = -\sum_{i=1}^{N}\left(E(\vec{\sigma}) + \log\left[\sum_{a=1}^{\mu} e^{-E(\vec{\sigma}_{i \to a})}\right]\right)$$

The score_sequence function of the script of Appendix A calculates and returns the above value. The score_sequence function return represents a logarithmic probability that the sequence would occur given the weights of the Potts model that are inputted to the script. If the score is greater than the threshold, which in this embodiment is −7.7, then the sequences can meet the required parameters (e.g., be confirmed/verified by the Potts model) and the function returns true. This score represents a logarithmic probability. Otherwise, the function returns false and the sequence pair is not confirmed the model. When the function returns true, this indicates that the sequence pair is suitable for the given purpose (e.g., a purpose related to binding to human TSLP).

A person of ordinary skill in the art can recognize that other thresholds can be employed that represent a logarithmic probability that sequences can meet the required parameters. In some embodiments, an example range of thresholds calculated by the script can include about −7.7, −7.0, −6.5, −6.0, −5.5, −5.0, −4.5, −4.0, −3.5, −3.0, 2.9, −2.8, −2.7, −2.6, −2.5, −2.4, −2.3, −2.2, −2.1, −2.0, −1.9, −1.8, −1.7, −1.6, −1.5, −1.4, −1.3, −1.2, −1.1, −1.0, 0.9, −0.8, −0.7, −0.6, −0.5, −0.4, −0.3, −0.2, and −0.1. As the thresholds increase towards zero, the sequences spaces scored within those thresholds represent smaller sequence spaces that have higher levels of confidence. In some embodiments, the constants may be modified in script or the hash table, such as by multiplying all constants by a constant. In such an event, the threshold may be adjusted, as can be determined by a person of ordinary skill in the art. The threshold can further be calculated in a non-logarithmic manner, and represented as a confidence interval, or in a non-logarithmic range, or represented as another probabilistic threshold.

In some embodiments, the script of Appendix A defines a sequence scoring function (sequence_energy). This function calculates a sequence energy for the replacement of a residue (e.g., an amino acid) with each other possible residue a group of positions in the sequence using a Potts model trained on replacing residues at those positions. As described above, the scoring checks each possible residue at each position requested. A person of ordinary skill in the art can recognize that the script can replace residues at each given position (as in the script of Appendix A). In some embodiments, a similar script could add residues into the sequence. Each score is calculated with a sequence_energy function, and is added to an array of scores. For each position examined, sum of the scores in the array are summed and normalized with a softmax function. The scores are them logarithmically summed and returned.

In some embodiments, the sequence energy function inputs a sequence and the hash tables determined from the inputted etab file (or another format). The function iterates over all first order combinations, scoring them with a first hash table, and all second order combinations, scoring them with a second hash table. The sequence_energy function considers all replacement residues and their first and second order combinations, and sums those energies together.

In some embodiments, the etab file is read with a read_etab function. Each line in the file having three items is unpacked and converted into an entry in a first hash table for first order combinations. Each line in the file having five items is unpacked and converted into an entry of a second hash table for second order combinations. The two hash tables are returned.

The above steps and functions describe a "computationally binding optimized" (CBO) sequence, amino acid sequence, or polypeptide sequence. Such a sequence is a sequence that, when inputted into the above computationally binding optimizing script, returns a value of true. A person having ordinary skill in the art can recognize that the script can be implemented in other ways or with other series of steps. A person having ordinary skill in the art can also recognize that other functionally equivalent tables and constants can be used. However, the provided Python script, tables, and constants, when executed by a processor, are configured to output whether a given polypeptide sequence is a CBO sequence. Therefore, any sequence that, when run by the script, causes a Boolean "true" output is considered a CBO sequence. Any sequence that, when run by the script, causes a Boolean "false" output is considered excluded from the group of the CBO sequences. Thereby, in some embodiments, the script of Appendix A itself does not determine CBO sequences but is a tool to confirm whether a given sequence is a CBO sequence or not. When a CBO sequence is an amino acid sequence, the corresponding molecule having the amino acid sequence is referred to as a CBO polypeptide.

In some embodiments, a similar script is able to return the calculated scores of a given or multiple sequences in addition to or separate from a Boolean value representing a threshold.

In some embodiments, a similar script can return one or more generated sequences from the Potts model. To generate sequences, markov chain monte carlo [MCMC] sampling can be performed on the model. Then, the resulting samples can be reintegrated into the constant template. In some embodiments, a brute force method can be applied using the scoring functions.

In view of the above, Table 10 illustrates the trimmed sequences (vlt, vht) for proteins AB-1 through AB-14, the concatenated/combined sequences (vhvlt), and the resulting Potts model scores when the above script was applied to them. The sequences for AB-1 through AB-14 are illustrated in Tables 1 and 2. All of the proteins AB-1 through AB-14 were or would be verified by the script because their Potts model scores were above −7.7.

In view of Table 10, a person of ordinary skill in the art can recognize that equivalent Potts model scores, such as scores having a different scale or being multiplied by negative one, may result in scores being at or above or below a different threshold.

FIG. 13 illustrates a computer network or similar digital processing environment in which embodiments of the present invention may be implemented.

Client computer(s)/devices 50 and server computer(s) 60 provide processing, storage, and input/output devices executing application programs and the like. The client computer(s)/devices 50 can also be linked through communications network 70 to other computing devices, including other client devices/processes 50 and server computer(s) 60. The communications network 70 can be part of a remote access network, a global network (e.g., the Internet), a worldwide collection of computers, local area or wide area networks, and gateways that currently use respective protocols (TCP/IP, Bluetooth®, etc.) to communicate with one another. Other electronic device/computer network architectures are suitable.

FIG. 14 is a diagram of an example internal structure of a computer (e.g., client processor/device 50 or server computers 60) in the computer system of FIG. 13. Each computer 50, 60 contains a system bus 79, where a bus is a set of hardware lines used for data transfer among the components of a computer or processing system. The system bus 79 is essentially a shared conduit that connects different elements of a computer system (e.g., processor, disk storage, memory, input/output ports, network ports, etc.) that enables the transfer of information between the elements. Attached to the system bus 79 is an I/O device interface 82 for connecting various input and output devices (e.g., keyboard, mouse, displays, printers, speakers, etc.) to the computer 50, 60. A network interface 86 allows the computer to connect to various other devices attached to a network (e.g., network 70 of FIG. 13). Memory 90 provides volatile storage for computer software instructions 92 and data 94 used to implement some embodiments of the present invention (e.g., CBO determination script, Potts model, model weights code detailed above and in Appendices A and B). Disk storage 95 provides non-volatile storage for computer software instructions 92 and data 94 used to implement some embodiments of the present invention. A central processor unit 84 is also attached to the system bus 79 and provides for the execution of computer instructions.

In one embodiment, the processor routines 92 and data 94 are a computer program product (generally referenced 92), including a non-transitory computer-readable medium (e.g., a removable storage medium such as one or more DVD-ROM's, CD-ROM's, diskettes, tapes, etc.) that provides at least a portion of the software instructions for the invention system. The computer program product 92 can be installed by any suitable software installation procedure, as is well known in the art. In another embodiment, at least a portion of the software instructions may also be downloaded over a cable communication and/or wireless connection. In some embodiments, the invention programs are a computer program propagated signal product embodied on a propagated signal on a propagation medium (e.g., a radio wave, an infrared wave, a laser wave, a sound wave, or an electrical wave propagated over a global network such as the Internet, or other network(s)). Such carrier medium or signals may be employed to provide at least a portion of the software instructions for the present invention routines/program 92.

In another aspect, the disclosure provides a polypeptide that specifically binds a TSLP (e.g., a hTSLP): wherein a CBO model outputs a score that is above a predetermined threshold upon scoring an amino acid sequence of the polypeptide.

In another aspect, the disclosure provides a CBO polypeptide that specifically binds a TSLP (e.g., a hTSLP): wherein a CBO model outputs a score that is above a predetermined threshold upon scoring an amino acid sequence representing the CBO polypeptide.

In another aspect, the disclosure provides a polypeptide that specifically binds a TSLP (e.g., a hTSLP) and receives a score above a predetermined threshold from a CBO model upon scoring an amino acid sequence representing the polypeptide.

In another aspect, the disclosure provides a polypeptide that specifically binds a TSLP (e.g., a hTSLP): wherein the polypeptide receives a score above a predetermined threshold from a CBO model upon scoring an amino acid sequence representing the polypeptide.

In another aspect, the disclosure provides a computationally binding optimized (CBO) polypeptide, determined by a computationally binding optimized (CBO) model that specifically binds a TSLP (e.g., a hTSLP).

In some embodiments, a CBO polypeptide comprises a paratope that is substantially similar to the paratope of an antibody comprising an amino acid sequence selected from:
SEQ ID NO:4 and SEQ ID NO:20 (AB-1);
SEQ ID NO:5 and SEQ ID NO: 21 (AB-2);
SEQ ID NO:6 and SEQ ID NO:20 (AB-3);
SEQ ID NO:7 and SEQ ID NO:22 (AB-4);
SEQ ID NO:8 and SEQ ID NO:23 (AB-5);
SEQ ID NO:9 and SEQ ID NO:24 (AB-6);
SEQ ID NO:10 and SEQ ID NO:25 (AB-7);
SEQ ID NO:11 and SEQ ID NO:20 (AB-8);
SEQ ID NO:12 and SEQ ID NO:20 (AB-9);
SEQ ID NO:13 and SEQ ID NO:26 (AB-10);
SEQ ID NO:14 and SEQ ID NO:27 (AB-11);
SEQ ID NO:15 and SEQ ID NO:28 (AB-12);
SEQ ID NO:16 and SEQ ID NO:29 (AB-13); or
SEQ ID NO:17 and SEQ ID NO:30 (AB-14), or
a combination of the foregoing.

In some embodiments, the CBO polypeptide comprises a paratope that is substantially similar (e.g., having at least about 90% sequence identity; having 100% sequence identity) to the paratope of a $V_H/V_L$ combination selected from: SEQ ID NO:4/SEQ ID NO:20 (AB-1), SEQ ID NO:5/SEQ ID NO:21 (AB-2), SEQ ID NO:6/SEQ ID NO:20 (AB-3), SEQ ID NO:7/SEQ ID NO:22 (AB-4), SEQ ID NO:8/SEQ ID NO:23 (AB-5), SEQ ID NO:9/SEQ ID NO:24 (AB-6), SEQ ID NO:10/SEQ ID NO:25 (AB-7), SEQ ID NO:11/SEQ ID NO:20 (AB-8), SEQ ID NO:12/SEQ ID NO:20 (AB-9), SEQ ID NO:13/SEQ ID NO:26 (AB-10), SEQ ID NO:14/SEQ ID NO:27 (AB-11), SEQ ID NO:15/SEQ ID NO:28 (AB-12), SEQ ID NO:16/SEQ ID NO:29 (AB-13) or SEQ ID NO:17/SEQ ID NO:30 (AB-14).

In some embodiments, the CBO polypeptide comprises a paratope that differs from the paratope of a $V_H/V_L$ combination selected from: SEQ ID NO:4/SEQ ID NO:20 (AB-1), SEQ ID NO:5/SEQ ID NO:21 (AB-2), SEQ ID NO:6/SEQ ID NO:20 (AB-3), SEQ ID NO:7/SEQ ID NO:22 (AB-4), SEQ ID NO:8/SEQ ID NO:23 (AB-5), SEQ ID NO:9/SEQ ID NO:24 (AB-6), SEQ ID NO:10/SEQ ID NO:25 (AB-7), SEQ ID NO:11/SEQ ID NO:20 (AB-8), SEQ ID NO:12/SEQ ID NO:20 (AB-9), SEQ ID NO:13/SEQ ID NO:26 (AB-10), SEQ ID NO:14/SEQ ID NO:27 (AB-11), SEQ ID NO:15/SEQ ID NO:28 (AB-12), SEQ ID NO:16/SEQ ID NO:29 (AB-13) or SEQ ID NO:17/SEQ ID NO:30 (AB-14), by substitution (e.g., conservative such as highly conservative substitution) of from 1 to 3 (e.g., 1, 2 or 3) residues.

In particular embodiments, the CBO polypeptide does not comprise a $V_H$ and $V_L$ pair selected from:
SEQ ID NO:4 and SEQ ID NO:20 (AB-1),
SEQ ID NO:5 and SEQ ID NO:21 (AB-2), SEQ ID NO:6 and SEQ ID NO:20 (AB-3),
SEQ ID NO:7 and SEQ ID NO:22 (AB-4),
SEQ ID NO:8 and SEQ ID NO:23 (AB-5),
SEQ ID NO:9 and SEQ ID NO:24 (AB-6),
SEQ ID NO:10 and SEQ ID NO:25 (AB-7),
SEQ ID NO:11 and SEQ ID NO:20 (AB-8),
SEQ ID NO:12 and SEQ ID NO:20 (AB-9),
SEQ ID NO:13 and SEQ ID NO:26 (AB-10),
SEQ ID NO:14 and SEQ ID NO:27 (AB-11),
SEQ ID NO:15 and SEQ ID NO:28 (AB-12),
SEQ ID NO:16 and SEQ ID NO:29 (AB-13),
SEQ ID NO:17 and SEQ ID NO:30 (AB-14), and
combinations thereof.

In certain embodiments, a CBO polypeptide comprises a paratope that is substantially similar to the paratope of an antibody comprising an amino acid sequence selected from:
SEQ ID NO:4 and SEQ ID NO:20 (AB-1);
SEQ ID NO:5 and SEQ ID NO:21 (AB-2);
SEQ ID NO:6 and SEQ ID NO:20 (AB-3); or
SEQ ID NO:7 and SEQ ID NO:22 (AB-4), or
a combination of the foregoing.

In some embodiments, the CBO polypeptide comprises a paratope that is substantially similar (e.g., having at least about 90% sequence identity; having 100% sequence identity) to the paratope of a $V_H/V_L$ combination selected from: SEQ ID NO:4/SEQ ID NO:20 (AB-1), SEQ ID NO:5/SEQ ID NO:21 (AB-2), SEQ ID NO:6/SEQ ID NO:20 (AB-3) or SEQ ID NO:7/SEQ ID NO:22 (AB-4), by substitution (e.g., conservative such as highly conservative substitution) of from 1 to 3 (e.g., 1, 2 or 3) residues.

In some embodiments, the CBO polypeptide comprises a paratope that differs from the paratope of a $V_H/V_L$ combination selected from: SEQ ID NO:4/SEQ ID NO:20 (AB-1), SEQ ID NO:5/SEQ ID NO:21 (AB-2), SEQ ID NO:6/SEQ ID NO:20 (AB-3) or SEQ ID NO:7/SEQ ID NO:22 (AB-4).

In particular embodiments, the CBO polypeptide does not comprise a $V_H$ and $V_L$ pair selected from:
SEQ ID NO:4 and SEQ ID NO:20 (AB-1),
SEQ ID NO:5 and SEQ ID NO:21 (AB-2),
SEQ ID NO:6 and SEQ ID NO:20 (AB-3),
SEQ ID NO:7 and SEQ ID NO:22 (AB-4), and
combinations thereof.

In some embodiments, a CBO polypeptide comprises:
a $V_H$ amino acid sequence comprising a HCDR1, a HCDR2 and a HCDR3 that are substantially similar to a HCDR1, a HCDR2 and a HCDR3, respectively, of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17; and
a $V_L$ amino acid sequence comprising a LCDR1, a LCDR2 and a LCDR3 that are substantially similar to a LCDR1, a LCDR2 and a LCDR3, respectively, of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29 or SEQ ID NO:30.

In some embodiments, the CBO polypeptide comprises a HCDR1, a HCDR2, a HCDR3, a LCDR1, a LCDR2 and a LCDR3 that substantially preserve one or more functional properties of a HCDR1, a HCDR2, a HCDR3, a LCDR1, a LCDR2 and a LCDR3 of AB-1, AB-2, AB-3, AB-4, AB-5, AB-6, AB-7, AB-8, AB-9, AB-10, AB-11, AB-12, AB-13 or AB-14.

In some embodiments, the CBO polypeptide comprises a HCDR1, a HCDR2, a HCDR3, a LCDR1, a LCDR2 and a LCDR3 comprising only one or more conservative substitutions (e.g., only one or more highly conservative substitutions), relative a HCDR1, a HCDR2, a HCDR3, a LCDR1, a LCDR2 and a LCDR3 of AB-1, AB-2, AB-3, AB-4, AB-5, AB-6, AB-7, AB-8, AB-9, AB-10, AB-11, AB-12, AB-13 or AB-14.

In certain embodiments, the CBO polypeptide comprises a HCDR1, a HCDR2, a HCDR3, a LCDR1, a LCDR2 and a LCDR3 comprising up to 1, 2, or 3 conservative substitutions (e.g., up to 1, 2, or 3 highly conservative substitutions), relative a HCDR1, a HCDR2, a HCDR3, a LCDR1, a LCDR2 and a LCDR3 of AB-1, AB-2, AB-3, AB-4, AB-5, AB-6, AB-7, AB-8, AB-9, AB-10, AB-11, AB-12, AB-13 or AB-14.

In particular embodiments, the CBO polypeptide comprises a HCDR1, a HCDR2, a HCDR3, a LCDR1, a LCDR2 and a LCDR3 having 100% sequence identity to a HCDR1, a HCDR2, a HCDR3, a LCDR1, a LCDR2 and a LCDR3 of AB-1, AB-2, AB-3, AB-4, AB-5, AB-6, AB-7, AB-8, AB-9, AB-10, AB-11, AB-12, AB-13 or AB-14.

In some embodiments, the CBO polypeptide comprises:
a) a HCDR1 comprising at least 1 amino acid substitution relative to the amino acid sequence of SEQ ID NO:31;
b) a HCDR2 comprising at least 1 amino acid substitution relative to at least one amino acid sequence set forth in SEQ ID NOs:33-46 (e.g., at least one amino acid sequence set forth in SEQ ID NOs:34-46);
c) a HCDR3 comprising at least 1 amino acid substitution relative to at least one amino acid sequence set forth in SEQ ID NOs:48-57 (e.g., at least one amino acid sequence set forth in SEQ ID NOs:49-57);
d) a LCDR1 comprising at least 1 amino acid substitution relative to the amino acid sequence set forth in SEQ ID NOs:59-66 (e.g., at least one amino acid sequence set forth in SEQ ID NOs:60-66);
e) a LCDR2 comprising at least 1 amino acid substitution relative to the amino acid sequence DDS;
f) a LCDR3 comprising at least 1 amino acid substitution relative to at least one amino acid sequence set forth in SEQ ID NOs:69-80 (e.g., at least one amino acid sequence set forth in SEQ ID NOs:70-80);
or a combination of the foregoing.

In some embodiments, the CBO polypeptide comprises:
a) a HCDR2 comprising at least 1 amino acid substitution relative to at least one amino acid sequence set forth in SEQ ID NOs:33-46 (e.g., at least one amino acid sequence set forth in SEQ ID NOs:34-46);
b) a HCDR3 comprising at least 1 amino acid substitution relative to at least one amino acid sequence set forth in SEQ ID NOs:48-57 (e.g., at least one amino acid sequence set forth in SEQ ID NOs:49-57);
c) a LCDR1 comprising at least 1 amino acid substitution relative to the amino acid sequence set forth in SEQ ID NOs:59-66 (e.g., at least one amino acid sequence set forth in SEQ ID NOs:60-66);
d) a LCDR3 comprising at least 1 amino acid substitution relative to at least one amino acid sequence set forth in SEQ ID NOs:69-80 (e.g., at least one amino acid sequence set forth in SEQ ID NOs:70-80);
or a combination of the foregoing.

In particular embodiments, the CBO polypeptide does not comprise a $V_H$ and $V_L$ pair selected from:
SEQ ID NO:4 and SEQ ID NO:20 (AB-1),
SEQ ID NO:5 and SEQ ID NO:21 (AB-2),
SEQ ID NO:6 and SEQ ID NO:20 (AB-3),
SEQ ID NO:7 and SEQ ID NO:22 (AB-4),
SEQ ID NO:8 and SEQ ID NO:23 (AB-5), SEQ ID NO:9 and SEQ ID NO:24 (AB-6),
SEQ ID NO:10 and SEQ ID NO:25 (AB-7),
SEQ ID NO:11 and SEQ ID NO:20 (AB-8),
SEQ ID NO:12 and SEQ ID NO:20 (AB-9),
SEQ ID NO:13 and SEQ ID NO:26 (AB-10),
SEQ ID NO:14 and SEQ ID NO:27 (AB-11),
SEQ ID NO:15 and SEQ ID NO:28 (AB-12),
SEQ ID NO:16 and SEQ ID NO:29 (AB-13),
SEQ ID NO:17 and SEQ ID NO:30 (AB-14), and
combinations thereof.

In certain embodiments, a CBO polypeptide comprises:
a $V_H$ amino acid sequence comprising a HCDR1, a HCDR2 and a HCDR3 that are substantially similar to a HCDR1, a HCDR2 and a HCDR3, respectively, of SEQ ID NO:4, SEQ ID NO:5, SEQ ID NO:6 or SEQ ID NO:7; and
a $V_L$ amino acid sequence comprising a LCDR1, a LCDR2 and a LCDR3 that are substantially similar to a LCDR1, a LCDR2 and a LCDR3, respectively, of SEQ ID NO:20, SEQ ID NO:21 or SEQ ID NO:22.

In some embodiments, the CBO polypeptide comprises a HCDR1, a HCDR2, a HCDR3, a LCDR1, a LCDR2 and a LCDR3 that substantially preserve one or more functional properties of a HCDR1, a HCDR2, a HCDR3, a LCDR1, a LCDR2 and a LCDR3 of AB-1, AB-2, AB-3 or AB-4.

In some embodiments, the CBO polypeptide comprises a HCDR1, a HCDR2, a HCDR3, a LCDR1, a LCDR2 and a LCDR3 comprising only one or more conservative substitutions (e.g., only one or more highly conservative substitutions), relative a HCDR1, a HCDR2, a HCDR3, a LCDR1, a LCDR2 and a LCDR3 of AB-1, AB-2, AB-3 or AB-4.

In certain embodiments, the CBO polypeptide comprises a HCDR1, a HCDR2, a HCDR3, a LCDR1, a LCDR2 and a LCDR3 comprising up to 1, 2, or 3 conservative substitutions (e.g., up to 1, 2, or 3 highly conservative substitutions), relative a HCDR1, a HCDR2, a HCDR3, a LCDR1, a LCDR2 and a LCDR3 of AB-1, AB-2, AB-3 or AB-4.

In particular embodiments, the CBO polypeptide comprises a HCDR1, a HCDR2, a HCDR3, a LCDR1, a LCDR2 and a LCDR3 having 100% sequence identity to a HCDR1, a HCDR2, a HCDR3, a LCDR1, a LCDR2 and a LCDR3 of AB-1, AB-2, AB-3 or AB-4.

In some embodiments, the CBO polypeptide comprises:
a) a HCDR1 comprising at least 1 amino acid substitution relative to the amino acid sequence of SEQ ID NO:31;
b) a HCDR2 comprising at least 1 amino acid substitution relative to at least one amino acid sequence set forth in SEQ ID NOs:33-37 (e.g., at least one amino acid sequence set forth in SEQ ID NOs:34-37);
c) a HCDR3 comprising at least 1 amino acid substitution relative to at least one amino acid sequence set forth in SEQ ID NOs:48-52 (e.g., at least one amino acid sequence set forth in SEQ ID NOs:49-52);
d) a LCDR1 comprising at least 1 amino acid substitution relative to the amino acid sequence set forth in SEQ ID NOs:59-61 (e.g., at least one amino acid sequence set forth in SEQ ID NOs:60-61);
e) a LCDR2 comprising at least 1 amino acid substitution relative to the amino acid sequence DDS;
f) a LCDR3 comprising at least 1 amino acid substitution relative to at least one amino acid sequence set forth in SEQ ID NOs:69-72 (e.g., at least one amino acid sequence set forth in SEQ ID NOs:70-72);
or a combination of the foregoing.

In some embodiments, the CBO polypeptide comprises:
a) a HCDR2 comprising at least 1 amino acid substitution relative to at least one amino acid sequence set forth in SEQ ID NOs:33-37 (e.g., at least one amino acid sequence set forth in SEQ ID NOs:34-37);
b) a HCDR3 comprising at least 1 amino acid substitution relative to at least one amino acid sequence set forth in SEQ ID NOs:48-52 (e.g., at least one amino acid sequence set forth in SEQ ID NOs:49-52);
c) a LCDR1 comprising at least 1 amino acid substitution relative to the amino acid sequence set forth in SEQ ID NOs:59-61 (e.g., at least one amino acid sequence set forth in SEQ ID NOs:60-61);
d) a LCDR3 comprising at least 1 amino acid substitution relative to at least one amino acid sequence set forth in SEQ ID NOs:69-72 (e.g., at least one amino acid sequence set forth in SEQ ID NOs:70-72);
or a combination of the foregoing.

In particular embodiments, the CBO polypeptide does not comprise a $V_H$ and $V_L$ pair selected from:
SEQ ID NO:4 and SEQ ID NO:20 (AB-1),
SEQ ID NO:5 and SEQ ID NO:21 (AB-2),
SEQ ID NO:6 and SEQ ID NO:20 (AB-3),
SEQ ID NO:7 and SEQ ID NO:22 (AB-4), and
combinations thereof.

In some embodiments, a CBO polypeptide comprises:
a) a $V_H$ comprising an amino acid sequence that has at least 55% (e.g., at least 60, 65, 70, 75, 80, 85, 90, 95, 98, or 99%) sequence identity to SEQ ID NO:3;
b) a $V_L$ comprising an amino acid sequence that has at least 55% (e.g., at least 60, 65, 70, 75, 80, 85, 90, 95, 98, or 99%) sequence identity to SEQ ID NO:19; or
both a) and b),
wherein the CBO polypeptide does not comprise all 6 CDRs of an antibody comprising a $V_H$ amino acid sequence of SEQ ID NO:3 and a $V_L$ amino acid sequence of SEQ ID NO:19.

In some embodiments, the CBO polypeptide comprises a $V_H$ that has at least about 70% sequence identity to the amino acid sequence of SEQ ID NO:3. For example, the $V_H$ can have at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:3. In some embodiments, the $V_H$ has at least about 85% or at least about 90% sequence identity to the amino acid sequence of SEQ ID NO:3.

In some embodiments, the CBO polypeptide comprises a $V_H$ that comprises at least 1 amino acid substitution relative to the amino acid sequence of SEQ ID NO:3. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the $V_H$ comprises about 1-10 amino acid substitutions, relative to the amino acid sequence of SEQ ID NO:3. In certain embodiments, the at least 1 amino acid substitution replaces only a HCDR1, a HCDR2 and/or a HCDR3 residue, of SEQ ID NO:3. In particular embodiments, the at least 1 amino acid substitution replaces only a non-CDR residue (e.g., within a framework region), of SEQ ID NO:3.

In some embodiments, the CBO polypeptide comprises a $V_L$ that has at least about 70% sequence identity to the amino acid sequence of SEQ ID NO:19. For example, the $V_L$ can be at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:19. In some embodiments, the $V_L$ has at least about 85% or at least about 90% sequence identity to the amino acid sequence of SEQ ID NO:19.

In some embodiments, the CBO polypeptide comprises a $V_L$ that comprises at least 1 amino acid substitution relative to the amino acid sequence of SEQ ID NO:19. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the $V_L$ comprises about 1-10 amino acid substitutions, relative to the amino acid sequence of SEQ ID NO:19. In certain embodiments, the at least 1 amino acid substitution replaces only a LCDR1, a LCDR2 and/or a LCDR3 residue, of SEQ ID NO:19. In particular embodiments, the at least 1 amino acid substitution replaces only a non-CDR residue (e.g., within a framework region), of SEQ ID NO:19.

In some embodiments, the CBO polypeptide comprises a $V_H$ that has at least about 70% sequence identity to the amino acid sequence of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17, or a combination of the foregoing. For example, the $V_H$ can have at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16 or SEQ ID NO:17, or a combination of the foregoing. In some embodiments, the $V_H$ has at least about 85% or at least about 90% sequence identity to the amino acid sequence of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17, or a combination of the foregoing.

In some embodiments, the CBO polypeptide comprises a $V_H$ that comprises at least 1 amino acid substitution relative to the amino acid sequence of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17, or a combination of the foregoing. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the $V_H$ comprises about 1-10 amino acid substitutions, relative to the amino acid sequence of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17, or a combination of the foregoing. In certain embodiments, the at least 1 amino acid substitution replaces only a HCDR1, a HCDR2 and/or a HCDR3 residue, of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17, or a combination of the foregoing. In particular embodiments, the at least 1 amino acid substitution replaces only a non-CDR residue (e.g., within a framework region), of SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16 or SEQ ID NO:17, or a combination of the foregoing.

In some embodiments, the CBO polypeptide comprises a $V_L$ that has at least about 70% sequence identity to the amino acid sequence of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29 or SEQ ID NO:30, or a combination of the foregoing. For example, the $V_L$ can be at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29 or SEQ ID NO:30, or a combination of the foregoing. In some embodiments, the $V_L$ has at least about 85% or at least about 90% sequence identity to the amino acid sequence of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29 or SEQ ID NO:30, or a combination of the foregoing.

In some embodiments, the CBO polypeptide comprises a $V_L$ that comprises at least 1 amino acid substitution relative to the amino acid sequence of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29 or SEQ ID NO:30, or a combination of the foregoing. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the $V_L$ comprises about 1-10 amino acid substitutions, relative to the amino acid sequence of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29 or SEQ ID NO:30, or a combination of the foregoing. In certain embodiments, the at least 1 amino acid substitution replaces only a LCDR1, a LCDR2 and/or a LCDR3 residue, of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29 or SEQ ID NO:30, or a combination of the foregoing. In particular embodiments, the at least 1 amino acid substitution replaces only a non-CDR residue (e.g., within a framework region), of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29 or SEQ ID NO:30, or a combination of the foregoing.

In particular embodiments, the CBO polypeptide does not comprise a $V_H$ and $V_L$ pair selected from:
SEQ ID NO:4 and SEQ ID NO:20 (AB-1),
SEQ ID NO:5 and SEQ ID NO:21 (AB-2),
SEQ ID NO:6 and SEQ ID NO:20 (AB-3),
SEQ ID NO:7 and SEQ ID NO:22 (AB-4),
SEQ ID NO:8 and SEQ ID NO:23 (AB-5),
SEQ ID NO:9 and SEQ ID NO:24 (AB-6),
SEQ ID NO:10 and SEQ ID NO:25 (AB-7),
SEQ ID NO:11 and SEQ ID NO:20 (AB-8),
SEQ ID NO:12 and SEQ ID NO:20 (AB-9),
SEQ ID NO:13 and SEQ ID NO:26 (AB-10),
SEQ ID NO:14 and SEQ ID NO:27 (AB-11),
SEQ ID NO:15 and SEQ ID NO:28 (AB-12), SEQ ID NO:16 and SEQ ID NO:29 (AB-13),
SEQ ID NO:17 and SEQ ID NO:30 (AB-14), and
combinations thereof.

In some embodiments, a CBO polypeptide comprises a $V_H$ that has at least about 70% sequence identity to the amino acid sequence of SEQ ID NO:4, SEQ ID NO:5, SEQ ID NO:6 or SEQ ID NO:7, or a combination of the foregoing. For example, the $V_H$ can have at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:4, SEQ ID NO:5, SEQ ID NO:6 or SEQ ID NO:7, or a combination of the foregoing. In some embodiments, the $V_H$ has at least about 85% or at least about 90% sequence identity to the amino acid sequence of SEQ ID NO:4, SEQ ID NO:5, SEQ ID NO:6 or SEQ ID NO:7, or a combination of the foregoing.

In some embodiments, the CBO polypeptide comprises a $V_H$ that comprises at least 1 amino acid substitution relative to the amino acid sequence of SEQ ID NO:4, SEQ ID NO:5, SEQ ID NO:6 or SEQ ID NO:7, or a combination of the foregoing. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the $V_H$ comprises about 1-10 amino acid substitutions, relative to the amino acid sequence of SEQ ID NO:4, SEQ ID NO:5, SEQ ID NO:6 or SEQ ID NO:7, or a combination of the foregoing. In certain embodiments, the at least 1 amino acid substitution replaces only a HCDR1, a HCDR2 and/or a HCDR3 residue, of SEQ ID NO:4, SEQ ID NO:5, SEQ ID NO:6 or SEQ ID NO:7, or a combination of the foregoing. In particular embodiments, the at least 1 amino acid substitution replaces only a non-CDR residue (e.g., within a framework region), of SEQ ID NO:4, SEQ ID NO:5, SEQ ID NO:6 or SEQ ID NO:7, or a combination of the foregoing.

In some embodiments, the CBO polypeptide comprises a $V_L$ that has at least about 70% sequence identity to the amino acid sequence of SEQ ID NO:20, SEQ ID NO:21 or SEQ ID NO:22, or a combination of the foregoing. For example, the $V_L$ can be at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to the amino acid sequence of SEQ ID NO:20, SEQ ID NO:21 or SEQ ID NO:22, or a combination of the foregoing. In some embodiments, the $V_L$ has at least about 85% or at least about 90% sequence identity to the amino acid sequence of SEQ ID NO:20, SEQ ID NO:21 or SEQ ID NO:22, or a combination of the foregoing.

In some embodiments, the CBO polypeptide comprises a $V_L$ that comprises at least 1 amino acid substitution relative to the amino acid sequence of SEQ ID NO:20, SEQ ID NO:21 or SEQ ID NO:22, or a combination of the foregoing. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the $V_L$ comprises about 1-10 amino acid substitutions, relative to the amino acid sequence of SEQ ID NO:20, SEQ ID NO:21 or SEQ ID NO:22, or a combination of the foregoing. In certain embodiments, the at least 1 amino acid substitution replaces only a LCDR1, a LCDR2 and/or a LCDR3 residue, of SEQ ID NO:20, SEQ ID NO:21 or SEQ ID NO:22, or a combination of the foregoing. In particular embodiments, the at least 1 amino acid substitution replaces only a non-CDR residue (e.g., within a framework region), of SEQ ID NO:20, SEQ ID NO:21 or SEQ ID NO:22, or a combination of the foregoing.

In particular embodiments, the CBO polypeptide does not comprise a $V_H$ and $V_L$ pair selected from:
SEQ ID NO:4 and SEQ ID NO:20 (AB-1),
SEQ ID NO:5 and SEQ ID NO:21 (AB-2),
SEQ ID NO:6 and SEQ ID NO:20 (AB-3),
SEQ ID NO:7 and SEQ ID NO:22 (AB-4), and
combinations thereof.

In some embodiments, a CBO polypeptide comprises a $V_H$ comprising SEQ ID NO:2, wherein:
$X_1$ is not I;
$X_2$ is not W;
$X_3$ is not D;
$X_4$ is not S;
$X_5$ is not N;
$X_6$ is not K;
$X_7$ is not A;
$X_8$ is not A;
$X_9$ is not L;
$X_{10}$ is not V;
$X_{11}$ is not H,
$X_{12}$ is not A;
$X_{13}$ is not F;
$X_{14}$ is not I,
or any combination of the foregoing.
In some embodiments:
$X_1$ is I or V;
$X_2$ is W or S;
$X_3$ is D or S;
$X_4$ is S, T, Y or A;
$X_5$ is N, Y, D or T;
$X_6$ is K, T or I;
$X_7$ is A, S or T;
$X_8$ is A or S;
$X_9$ is L, D, E or S;
$X_{10}$ is V or I;
$X_{11}$ is H, F or Y;
$X_{12}$ is A or S;
$X_{13}$ is F, M or L;
$X_{14}$ is I or V,
or any combination of the foregoing.
In some embodiments:
$X_1$ is V;
$X_2$ is S;
$X_3$ is S;
$X_4$ is T, Y or A;
$X_5$ is Y, D or T;
$X_6$ is T or I;
$X_7$ is S or T;
$X_8$ is S;
$X_9$ is D, E or S;
$X_{10}$ is I;
$X_{11}$ is F or Y;
$X_{12}$ is S;
$X_{13}$ is M or L;
$X_{14}$ is V,
or any combination of the foregoing.
In some embodiments, the CBO polypeptide further comprises a $V_L$ comprising SEQ ID NO:18, wherein:
$X_{15}$ is not N;
$X_{16}$ is not L;
$X_{17}$ is not S;
$X_{18}$ is not K;

$X_{19}$ is not S;
$X_{20}$ is not V;
$X_{21}$ is not W;
$X_{22}$ is not D;
$X_{23}$ is not S;
$X_{24}$ is not S;
$X_{25}$ is not S;
$X_{26}$ is not D;
$X_{27}$ is not H,
or any combination of the foregoing.
In some embodiments:
$X_{15}$ is N or Y;
$X_{16}$ is L or I;
$X_{17}$ is S or R;
$X_{18}$ is K, F or Y;
$X_{19}$ is S or N;
$X_{20}$ is V or I;
$X_{21}$ is W or Y;
$X_{22}$ is D, V or S;
$X_{23}$ is S, M or E;
$X_{24}$ is S, A or T;
$X_{25}$ is S, D or E;
$X_{26}$ is D, S, R or F;
$X_{27}$ is H, L, K or E,
or any combination of the foregoing.
In some embodiments:
$X_{15}$ is Y;
$X_{16}$ is I;
$X_{17}$ is R;
$X_{18}$ is F or Y;
$X_{19}$ is N;
$X_{20}$ is I;
$X_{21}$ is Y;
$X_{22}$ is V or S;
$X_{23}$ is M or E;
$X_{24}$ is A or T;
$X_{25}$ is D or E;
$X_{26}$ is S, R or F;
$X_{27}$ is L, K or E,
or any combination of the foregoing.
In particular embodiments, the CBO polypeptide does not comprise a $V_H$ and $V_L$ pair selected from:
  SEQ ID NO:4 and SEQ ID NO:20 (AB-1),
  SEQ ID NO:5 and SEQ ID NO:21 (AB-2),
  SEQ ID NO:6 and SEQ ID NO:20 (AB-3),
  SEQ ID NO:7 and SEQ ID NO:22 (AB-4),
  SEQ ID NO:8 and SEQ ID NO:23 (AB-5),
  SEQ ID NO:9 and SEQ ID NO:24 (AB-6),
  SEQ ID NO:10 and SEQ ID NO:25 (AB-7),
  SEQ ID NO:11 and SEQ ID NO:20 (AB-8),
  SEQ ID NO:12 and SEQ ID NO:20 (AB-9),
  SEQ ID NO:13 and SEQ ID NO:26 (AB-10),
  SEQ ID NO:14 and SEQ ID NO:27 (AB-11),
  SEQ ID NO:15 and SEQ ID NO:28 (AB-12),
  SEQ ID NO:16 and SEQ ID NO:29 (AB-13),
  SEQ ID NO:17 and SEQ ID NO:30 (AB-14), and
  combinations thereof.
In some embodiments:
$X_1$ is I or V;
$X_2$ is W;
$X_3$ is D or S;
$X_4$ is S or T;
$X_5$ is N, Y or D;
$X_6$ is K or T;
$X_7$ is A or S;
$X_8$ is A or S;
$X_9$ is L, D, E or S;
$X_{10}$ is V or I;
$X_{11}$ is H or F;
$X_{12}$ is A or S;
$X_{13}$ is F or M;
$X_{14}$ is I or V,
or any combination of the foregoing.
In some embodiments:
$X_1$ is V;
$X_2$ is W;
$X_3$ is S;
$X_4$ is T;
$X_5$ is Y or D;
$X_6$ is T;
$X_7$ is S;
$X_8$ is S;
$X_9$ is D, E or S;
$X_{10}$ is I;
$X_{11}$ is F;
$X_{12}$ is S;
$X_{13}$ is M;
$X_{14}$ is V,
or any combination of the foregoing.
In some embodiments:
$X_{15}$ is N or Y;
$X_{16}$ is L or I;
$X_{17}$ is S;
$X_{18}$ is K or F;
$X_{19}$ is S;
$X_{20}$ is V or I;
$X_{21}$ is W or Y;
$X_{22}$ is D or V;
$X_{23}$ is S or M;
$X_{24}$ is S or A;
$X_{25}$ is S;
$X_{26}$ is D, S or R;
$X_{27}$ is H or L,
or any combination of the foregoing.
In some embodiments:
$X_{15}$ is Y;
$X_{11}$ is I;
$X_{17}$ is S;
$X_{18}$ is F;
$X_{19}$ is S;
$X_{20}$ is I;
$X_{21}$ is Y;
$X_{22}$ is V;
$X_{23}$ is M;
$X_{24}$ is A;
$X_{25}$ is S;
$X_{26}$ is S or R;
$X_{27}$ is L,
or any combination of the foregoing.
In particular embodiments, the CBO polypeptide does not comprise a $V_H$ and $V_L$ pair selected from:
  SEQ ID NO:4 and SEQ ID NO:20 (AB-1),
  SEQ ID NO:5 and SEQ ID NO:21 (AB-2),
  SEQ ID NO:6 and SEQ ID NO:20 (AB-3),
  SEQ ID NO:7 and SEQ ID NO:22 (AB-4), and
  combinations thereof.
In some embodiments, a computer-implemented method includes scoring a polypeptide comprising an amino acid sequence with a computationally binding optimized (CBO) model for a functional property relating to modulating the activity of a target molecule. The CBO model, for each amino acid position of the amino acid sequence of the polypeptide, calculates multiple energy scores, the multiple energy scores based on the amino acid at a given position in the amino acid sequence. The CBO model further adds each energy score calculated to an array. The CBO model further generates a normalized sum of the energy scores for each position. The CBO model further generates a score of the polypeptide by summing each energy score calculated, the score representing a functional property of the polypeptide, the functional property relating to the polypeptide modulating the activity of the target molecule.

In some embodiments, the computer-implemented method includes calculating a logarithm of each energy score calculated.

In some embodiments, summing each energy score calculated is performed by summing the logarithms of each energy score calculated.

In some embodiments, the energy scores are further calculated based on having substituted the amino acid at the given position in the amino acid sequence with each of a plurality of different amino acids.

In some embodiments, the target molecule is a target polypeptide.

In some embodiments, the scoring the polypeptide using the CBO model is implemented by the script of Appendix A.

In some embodiments, the CBO model is substantially similar to the table of Appendix B. A substantially similar table to the Computer Programming Listing Appendix B is a table that scores polypeptides in line with the Computer Programming Listing Appendix B. In some embodiments, such a substantially similar table scores polypeptides so as to maintain their relative rank order. In certain embodiments, a substantially similar table returns scores within about: 30, 25, 20, 15, 10, 9, 8, 7, 6, 5, 4, 3, 2, or 1% of the score provided by the Computer Programming Listing Appendix B. In some embodiments, table substantially similar to the Computer Programming Listing Appendix B comprises substantially the same dimensions (rows and columns, e.g., within about: 1, 2, 3, 4, 5, 6, 7, 8, 9, 10, 12, 13, 14, 15%, or in some embodiments, the identical dimensions), wherein each entry in the table is substantially similar to a corresponding value in the Computer Programming Listing Appendix B, e.g., within about: 30, 25, 20, 15, 10, 9, 8, 7, 6, 5, 4, 3, 2, 1%, or identical.

In some embodiments, scoring the polypeptide can further include extracting positions from the amino acid sequence, the extracted positions being positions where mutations were applied during training of the CBO model. Scoring the polypeptide can further include calculating the multiple energy scores is performed on the extracted positions.

In some embodiments, scoring the polypeptide further includes scoring a pair of amino acid sequences. Scoring the polypeptide can further include aligning a first amino acid sequence and second amino acid sequence of the pair of amino acid sequences such that (a) the first amino acid sequence and second amino acid sequence are the same length and that (b) given sections of the first amino acid sequence and second amino acid sequence are the same.

In some embodiments, the multiple energy scores include a first-order energy score associated with each amino acid being at its position. The multiple energy scores further include, for each pair of amino acid positions of the amino acid sequence, a second-order energy score associated with the pair of amino acid positions. The first-order energy score and second-order energy score can be calculated based on corresponding entries of a trained first- and second-order energy score table of outputted weights of a model trained by a plurality of known amino acid sequences and corresponding properties of the known amino acid sequences.

In some embodiments, the computer-implemented method includes returning, based on the score, a flag indicating whether the sequence has the functional property associated with the polypeptide.

In some embodiments, the functional property is one or more of:
a) a binding affinity for a thymic stromal lymphopoietin (TSLP) polypeptide characterized by a $K_D$ of 10 pM or less (optionally, as measured by KinExA);
b) a binding specificity for the AB-loop region and the C-terminal region of helix D of the TSLP;
c) a neutralizing activity against the TSLP (optionally, a full-length human TSLP); or
d) an inhibitory activity against TSLP-mediated signaling,
e) or a combination of the foregoing.

In some embodiments, a system includes a processor and a memory with computer code instructions stored thereon. The processor and the memory, with the computer code instructions, are configured to cause the system to score a polypeptide comprising an amino acid sequence with a CBO model for a functional property relating to modulating the activity of a target molecule. The CBO model, for each amino acid position of the amino acid sequence of the polypeptide, calculates multiple energy scores, the multiple energy scores based on the amino acid at a given position in the amino acid sequence. The CBO model further adds each energy score calculated to an array. The CBO model further generates a normalized sum of the energy scores for each position. The CBO model further generates a score of the polypeptide by summing each energy score calculated, the score representing a functional property of the polypeptide.

In some embodiments, the instructions are further configured to cause the system to calculate a logarithm of each energy score calculated.

In some embodiments, summing each energy score calculated is performed by summing the logarithms of each energy score calculated.

In some embodiments, the energy scores are further calculated based on having substituted the amino acid at the given position in the amino acid sequence with each of a plurality of different amino acids.

In some embodiments, the target molecule is a target polypeptide.

In some embodiments, the scoring the polypeptide using the CBO model is implemented by the script of Appendix A.

In some embodiments, the CBO model is substantially similar to the table of Appendix B. A substantially similar table to the Computer Programming Listing Appendix B is a table that scores polypeptides in line with the Computer Programming Listing Appendix B. In some embodiments, such a substantially similar table scores polypeptides so as to maintain their relative rank order. In certain embodiments, a substantially similar table returns scores within about: 30, 25, 20, 15, 10, 9, 8, 7, 6, 5, 4, 3, 2, 1% of the score provided by the Computer Programming Listing Appendix B. In some embodiments, table substantially similar to the Computer Programming Listing Appendix B comprises substantially the same dimensions (rows and columns, e.g., within about: 1, 2, 3, 4, 5, 6, 7, 8, 9, 10, 12, 13, 14, 15%, in some embodiments, the identical dimensions), wherein each entry in the table is substantially similar to a corresponding value in the Computer Programming Listing Appendix B, e.g., within about: 30, 25, 20, 15, 10, 9, 8, 7, 6, 5, 4, 3, 2, 1%.

In some embodiments, scoring the polypeptide further includes extracting positions from the amino acid sequence. The extracted positions can be positions where mutations were applied during training of the CBO model. Scoring the polypeptide further includes calculating the multiple energy scores is performed on the extracted positions.

In some embodiments, scoring the polypeptide further includes scoring a pair of amino acid sequences. Scoring the polypeptide further includes aligning a first amino acid sequence and second amino acid sequence of the pair of amino acid sequences such that (a) the first amino acid sequence and second amino acid sequence are the same length and that (b) given sections of the first amino acid sequence and second amino acid sequence are the same.

In some embodiments, the multiple energy scores include a first-order energy score associated with each amino acid being at its position. The multiple energy scores further include, for each pair of amino acid positions of the amino acid sequence, a second-order energy score associated with the pair of amino acid positions. The first-order energy score and second-order energy score are calculated by respective entries from a trained first- and second-order energy score table of outputted weights of a model trained by a plurality of known amino acid sequences and corresponding properties of the known amino acid sequences.

In some embodiments, the processor further is configured to cause the system to return, based on the score, a flag indicating whether the sequence has the functional property associated with the polypeptide.

In some embodiments, the functional property is at least one of:
  a) a binding affinity for the TSLP characterized by a $K_D$ of 10 pM or less (e.g., as measured by KinExA);
  b) a binding specificity for the AB-loop region and the C-terminal region of helix D of the TSLP;
  c) a neutralizing activity against the TSLP (e.g., a full-length human TSLP); or
d) an inhibitory activity against TSLP-mediated signaling,
e) or a combination of the foregoing.

In some embodiments, the score being above the particular threshold represents that the functional property is met for the given polypeptide.

In some embodiments, a polypeptide that specifically binds a thymic stromal lymphopoietin (TSLP) comprises an amino acid sequence that is assigned a score above a predetermined threshold by a computationally binding optimized (CBO) model upon scoring the amino acid sequence of the polypeptide.

In some embodiments, the polypeptide is assigned the score by the CBO model that is calculated by a table substantially similar to that of Computer Program Listing Appendix B.

In some embodiments, the polypeptide is assigned the score that is calculated using the Computer Program Listing Appendix B.

In some embodiments, the polypeptide is assigned the score by a script substantially similar to Computer Program Listing Appendix A, the script employing the CBO model substantially similar to the table of Computer Program Listing Appendix B. In some embodiments, the polypeptide has a logarithmic score above or equivalent to being above at least one of −7.7, −7.0, −6.5, −6.0, −5.5, −5.0, −4.5, −4.0, −3.5, −3.0, 2.9, −2.8, −2.7, −2.6, −2.5, −2.4, −2.3, −2.2, −2.1, −2.0, −1.9, −1.8, −1.7, −1.6, −1.5, −1.4, −1.3, −1.2, −1.1, −1.0, 0.9, −0.8, −0.7, −0.6, −0.5, −0.4, −0.3, −0.2, and −0.1.

In some embodiments, the polypeptide is scorable by the script of Computer Program Listing Appendix A.

In some embodiments, the predetermined threshold is the logarithmic probability that the sequence inputted to the script would occur given the weights of the Potts model.

In some embodiments, a CBO script assigning the score to the polypeptide includes receiving a trained first- and second-order energy score table of outputted weights of a model trained by a plurality of known amino acid sequences and corresponding properties of the known amino acid sequences.

In some embodiments, the polypeptide comprises an immunoglobulin heavy chain variable domain ($V_H$) and an immunoglobulin light chain variable domain ($V_L$).

In some embodiments, the polypeptide has one or more properties selected from:

a) a binding affinity for the TSLP characterized by a $K_D$ of 10 pM or less (e.g., as measured by KinExA);
b) a binding specificity for the AB-loop region and the C-terminal region of helix D of the TSLP;
c) a neutralizing activity against the TSLP (e.g., a full-length human TSLP); or
d) an inhibitory activity against TSLP-mediated signaling,
e) or a combination of the foregoing.

In some embodiments, the score being above the particular threshold represents that the functional property is met for the given polypeptide.

In some embodiments, the CBO model outputs a score that is equal to or above a score from the CBO model of one or more of a reference polypeptide that comprises a $V_H$ and $V_L$ pair selected from:

a) SEQ ID NO:4 and SEQ ID NO:20 (AB-1);
b) SEQ ID NO:5 and SEQ ID NO: 21 (AB-2);
c) SEQ ID NO:6 and SEQ ID NO:20 (AB-3);
d) SEQ ID NO:7 and SEQ ID NO:22 (AB-4);
e) SEQ ID NO:8 and SEQ ID NO:23 (AB-5);
f) SEQ ID NO:9 and SEQ ID NO:24 (AB-6);
g) SEQ ID NO:10 and SEQ ID NO:25 (AB-7);
h) SEQ ID NO:11 and SEQ ID NO:20 (AB-8);
i) SEQ ID NO:12 and SEQ ID NO:20 (AB-9);
j) SEQ ID NO:13 and SEQ ID NO:26 (AB-10);
k) SEQ ID NO:14 and SEQ ID NO:27 (AB-11);
l) SEQ ID NO:15 and SEQ ID NO:28 (AB-12);
m) SEQ ID NO:16 and SEQ ID NO:29 (AB-13); or
n) SEQ ID NO:17 and SEQ ID NO:30 (AB-14).

In some embodiments, the polypeptide comprises a $V_H$ and $V_L$ pair selected from:

a) SEQ ID NO:4 and SEQ ID NO:20 (AB-1);
b) SEQ ID NO:5 and SEQ ID NO: 21 (AB-2);
c) SEQ ID NO:6 and SEQ ID NO:20 (AB-3);
d) SEQ ID NO:7 and SEQ ID NO:22 (AB-4);
e) SEQ ID NO:8 and SEQ ID NO:23 (AB-5);
f) SEQ ID NO:9 and SEQ ID NO:24 (AB-6);
g) SEQ ID NO:10 and SEQ ID NO:25 (AB-7);
h) SEQ ID NO:11 and SEQ ID NO:20 (AB-8);
i) SEQ ID NO:12 and SEQ ID NO:20 (AB-9);
j) SEQ ID NO:13 and SEQ ID NO:26 (AB-10);
k) SEQ ID NO:14 and SEQ ID NO:27 (AB-11);
l) SEQ ID NO:15 and SEQ ID NO:28 (AB-12);
m) SEQ ID NO:16 and SEQ ID NO:29 (AB-13); or
n) SEQ ID NO:17 and SEQ ID NO:30 (AB-14).

In some embodiments, the polypeptide does not comprise a $V_H$ and $V_L$ pair selected from:

a) SEQ ID NO:4 and SEQ ID NO:20 (AB-1);
b) SEQ ID NO:5 and SEQ ID NO:21 (AB-2);
c) SEQ ID NO:6 and SEQ ID NO:20 (AB-3);
d) SEQ ID NO:7 and SEQ ID NO:22 (AB-4);
e) SEQ ID NO:8 and SEQ ID NO:23 (AB-5);
f) SEQ ID NO:9 and SEQ ID NO:24 (AB-6);
g) SEQ ID NO:10 and SEQ ID NO:25 (AB-7);
h) SEQ ID NO:11 and SEQ ID NO:20 (AB-8);
i) SEQ ID NO:12 and SEQ ID NO:20 (AB-9);

j) SEQ ID NO:13 and SEQ ID NO:26 (AB-10);
k) SEQ ID NO:14 and SEQ ID NO:27 (AB-11);
l) SEQ ID NO:15 and SEQ ID NO:28 (AB-12);
m) SEQ ID NO:16 and SEQ ID NO:29 (AB-13); or
n) SEQ ID NO:17 and SEQ ID NO:30 (AB-14).

In some embodiments, the polypeptide does not comprise a heavy chain comprising SEQ ID NO:81 and a light chain comprising SEQ ID NO:82.

In some embodiments, the polypeptide is an antibody or an antigen-binding fragment thereof.

In some embodiments, a polypeptide comprises an amino acid sequence that is assigned a score above a predetermined threshold by a computationally binding optimized (CBO) model upon scoring the amino acid sequence of the polypeptide.

In some embodiments, a polypeptide that binds human thymic stromal lymphopoietin (TSLP) is designed by a method comprising generating a polypeptide sequence with a CBO model. The polypeptide is further designed by verifying the generated polypeptide sequence using the CBO model by, for each amino acid position of the polypeptide sequence, calculating a plurality of energy scores. The energy scores can be based on having substituted the amino acid at a given position in the polypeptide sequence with each of a plurality of different amino acids. The polypeptide is further verified by adding each energy score calculated to an array. The polypeptide is further verified by generating a normalized sum of the energy scores for each position. The polypeptide is further verified by calculating a logarithm of each energy score calculated. The polypeptide is further verified by generating a score of the polypeptide sequence by summing the logarithms of each energy score calculated. The score represents a functional property of the polypeptide's ability to bind to human TSLP. In some embodiments, the polypeptide sequence is verified if the polypeptide scores above a particular threshold.

In some embodiments, the polypeptide is scored at least a score of one of more of −7.7, −7.0, −6.5, −6.0, −5.5, −5.0, −4.5, −4.0, −3.5, −3.0, 2.9, −2.8, −2.7, −2.6, −2.5, −2.4, −2.3, −2.2, −2.1, −2.0, −1.9, −1.8, −1.7, −1.6, −1.5, −1.4, −1.3, −1.2, −1.1, −1.0, 0.9, −0.8, −0.7, −0.6, −0.5, −0.4, −0.3, −0.2, and −0.1 (e.g., to be verified). In some embodiments, the polypeptide is an antibody or an antigen-binding fragment thereof.

In some embodiments, the polypeptide comprises a $V_H$ and $V_L$ pair comprising an amino acid sequence at least about: 60, 65, 70, 75, 80, 85, 86, 87, 88, 89, 90, 91, 92, 93, 94, 95, 96, 97, 98, or 99 identical to a $V_H$ and $V_L$ pair selected from:

a) SEQ ID NO:4 and SEQ ID NO:20 (AB-1);
b) SEQ ID NO:5 and SEQ ID NO: 21 (AB-2);
c) SEQ ID NO:6 and SEQ ID NO:20 (AB-3);
d) SEQ ID NO:7 and SEQ ID NO:22 (AB-4);
e) SEQ ID NO:8 and SEQ ID NO:23 (AB-5);
f) SEQ ID NO:9 and SEQ ID NO:24 (AB-6);
g) SEQ ID NO:10 and SEQ ID NO:25 (AB-7);
h) SEQ ID NO:11 and SEQ ID NO:20 (AB-8);
i) SEQ ID NO:12 and SEQ ID NO:20 (AB-9);
j) SEQ ID NO:13 and SEQ ID NO:26 (AB-10);
k) SEQ ID NO:14 and SEQ ID NO:27 (AB-11);
l) SEQ ID NO:15 and SEQ ID NO:28 (AB-12);
m) SEQ ID NO:16 and SEQ ID NO:29 (AB-13); or
n) SEQ ID NO:17 and SEQ ID NO:30 (AB-14).

In some embodiments, the polypeptide comprises a $V_H$ and $V_L$ pair does not comprise an amino acid sequence 100% identical to a $V_H$ and $V_L$ pair selected from:

a) SEQ ID NO:4 and SEQ ID NO:20 (AB-1);
b) SEQ ID NO:5 and SEQ ID NO: 21 (AB-2);
c) SEQ ID NO:6 and SEQ ID NO:20 (AB-3);
d) SEQ ID NO:7 and SEQ ID NO:22 (AB-4);
e) SEQ ID NO:8 and SEQ ID NO:23 (AB-5);
f) SEQ ID NO:9 and SEQ ID NO:24 (AB-6);
g) SEQ ID NO:10 and SEQ ID NO:25 (AB-7);
h) SEQ ID NO:11 and SEQ ID NO:20 (AB-8);
i) SEQ ID NO:12 and SEQ ID NO:20 (AB-9);
j) SEQ ID NO:13 and SEQ ID NO:26 (AB-10);
k) SEQ ID NO:14 and SEQ ID NO:27 (AB-11);
l) SEQ ID NO:15 and SEQ ID NO:28 (AB-12);
m) SEQ ID NO:16 and SEQ ID NO:29 (AB-13); or
n) SEQ ID NO:17 and SEQ ID NO:30 (AB-14).

EMBODIMENTS OF THE DISCLOSURE

1. A polypeptide that specifically binds a thymic stromal lymphopoietin (TSLP), wherein the polypeptide has one or more properties selected from:
   a binding affinity for the TSLP characterized by a $K_D$ of 10 pM or less (e.g., as measured by KinExA);
   a binding specificity for the AB-loop region and the C-terminal region of helix D of the TSLP;
   a neutralizing activity against the TSLP (e.g., a full-length human TSLP); or
   an inhibitory activity against TSLP-mediated signaling, or a combination of the foregoing.
2. A polypeptide that specifically binds a thymic stromal lymphopoietin (TSLP), comprising a paratope that is substantially similar to the paratope of an antibody comprising an amino acid sequence selected from:
   SEQ ID NO:4 and SEQ ID NO:20 (AB-1);
   SEQ ID NO:5 and SEQ ID NO: 21 (AB-2);
   SEQ ID NO:6 and SEQ ID NO:20 (AB-3);
   SEQ ID NO:7 and SEQ ID NO:22 (AB-4);
   SEQ ID NO:8 and SEQ ID NO:23 (AB-5);
   SEQ ID NO:9 and SEQ ID NO:24 (AB-6);
   SEQ ID NO:10 and SEQ ID NO:25 (AB-7);
   SEQ ID NO:11 and SEQ ID NO:20 (AB-8);
   SEQ ID NO:12 and SEQ ID NO:20 (AB-9);
   SEQ ID NO:13 and SEQ ID NO:26 (AB-10);
   SEQ ID NO:14 and SEQ ID NO:27 (AB-11);
   SEQ ID NO:15 and SEQ ID NO:28 (AB-12);
   SEQ ID NO:16 and SEQ ID NO:29 (AB-13); or
   SEQ ID NO:17 and SEQ ID NO:30 (AB-14), or
   a combination of the foregoing.
3. The polypeptide of Embodiment 1 or 2, comprising an immunoglobulin heavy chain variable domain ($V_H$) and an immunoglobulin light chain variable domain ($V_L$).
4. A polypeptide that specifically binds a thymic stromal lymphopoietin (TSLP), comprising:
   a) an immunoglobulin heavy chain variable domain ($V_H$) amino acid sequence comprising a heavy chain complementarity determining region 1 (HCDR1), a heavy chain complementarity determining region 2 (HCDR2) and a heavy chain complementarity determining region 3 (HCDR3) that are substantially similar to a HCDR1, HCDR2 and HCDR3, respectively, of the amino acid sequence of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17; and
   b) an immunoglobulin light chain variable domain ($V_L$) amino acid sequence comprising a light chain complementarity determining region 1 (LCDR1), a light chain complementarity determining region 2 (LCDR2) and a light chain complementarity determining region 3 (LCDR3) that are substantially similar to a LCDR1, LCDR2 and LCDR3, respectively, of the amino acid sequence of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29 or SEQ ID NO:30.

5. The polypeptide of any one of Embodiments 1-4, comprising the HCDR1, HCDR2 and HCDR3, and LCDR1, LCDR2 and LCDR3, of an antibody comprising an amino acid sequence selected from:
SEQ ID NO:4 and SEQ ID NO:20 (AB-1);
SEQ ID NO:5 and SEQ ID NO: 21 (AB-2);
SEQ ID NO:6 and SEQ ID NO:20 (AB-3);
SEQ ID NO:7 and SEQ ID NO:22 (AB-4);
SEQ ID NO:8 and SEQ ID NO:23 (AB-5);
SEQ ID NO:9 and SEQ ID NO:24 (AB-6);
SEQ ID NO:10 and SEQ ID NO:25 (AB-7);
SEQ ID NO:11 and SEQ ID NO:20 (AB-8);
SEQ ID NO:12 and SEQ ID NO:20 (AB-9);
SEQ ID NO:13 and SEQ ID NO:26 (AB-10);
SEQ ID NO:14 and SEQ ID NO:27 (AB-11);
SEQ ID NO:15 and SEQ ID NO:28 (AB-12);
SEQ ID NO:16 and SEQ ID NO:29 (AB-13); or
SEQ ID NO:17 and SEQ ID NO:30 (AB-14).

6. The polypeptide of Embodiment 4 or 5, further comprising a paratope that is identical to the paratope of an antibody comprising an amino acid sequence selected from:
SEQ ID NO:4 and SEQ ID NO:20 (AB-1);
SEQ ID NO:5 and SEQ ID NO: 21 (AB-2);
SEQ ID NO:6 and SEQ ID NO:20 (AB-3);
SEQ ID NO:7 and SEQ ID NO:22 (AB-4);
SEQ ID NO:8 and SEQ ID NO:23 (AB-5);
SEQ ID NO:9 and SEQ ID NO:24 (AB-6);
SEQ ID NO:10 and SEQ ID NO:25 (AB-7);
SEQ ID NO:11 and SEQ ID NO:20 (AB-8);
SEQ ID NO:12 and SEQ ID NO:20 (AB-9);
SEQ ID NO:13 and SEQ ID NO:26 (AB-10);
SEQ ID NO:14 and SEQ ID NO:27 (AB-11);
SEQ ID NO:15 and SEQ ID NO:28 (AB-12);
SEQ ID NO:16 and SEQ ID NO:29 (AB-13); or
SEQ ID NO:17 and SEQ ID NO:30 (AB-14).

7. A polypeptide that specifically binds a thymic stromal lymphopoietin (TSLP), comprising an immunoglobulin heavy chain variable domain ($V_H$) comprising the amino acid sequence of SEQ ID NO:2, wherein:
$X_1$ is not I;
$X_2$ is not W;
$X_3$ is not D;
$X_4$ is not S;
$X_5$ is not N;
$X_6$ is not K;
$X_7$ is not A;
$X_8$ is not A;
$X_9$ is not L;
$X_{10}$ is not V;
$X_{11}$ is not H;
$X_{12}$ is not A;
$X_{13}$ is not F;
$X_{14}$ is not I,
or any combination of the foregoing.

8. The polypeptide of Embodiment 7, further comprising an immunoglobulin light chain variable domain ($V_L$) comprising the amino acid sequence of SEQ ID NO:18, wherein:
$X_{15}$ is not N;
$X_{16}$ is not L;
$X_{17}$ is not S;
$X_{18}$ is not K;
$X_{19}$ is not S;
$X_{20}$ is not V;
$X_{21}$ is not W;
$X_{22}$ is not D;
$X_{23}$ is not S;
$X_{24}$ is not S;
$X_{25}$ is not S;
$X_{26}$ is not D;
$X_{27}$ is not H,
or any combination of the foregoing.

9. A polypeptide that specifically binds a thymic stromal lymphopoietin (TSLP), comprising an immunoglobulin heavy chain variable domain ($V_H$) comprising the amino acid sequence of SEQ ID NO:2, wherein:
$X_1$ is I or V;
$X_2$ is W or S;
$X_3$ is D or S;
$X_4$ is S, T, Y or A;
$X_5$ is N, Y, D or T;
$X_6$ is K, T or I;
$X_7$ is A, S or T;
$X_8$ is A or S;
$X_9$ is L, D, E or S;
$X_{10}$ is V or I;
$X_{11}$ is H, F or Y;
$X_{12}$ is A or S;
$X_{13}$ is F, M or L;
$X_{14}$ is I or V,
or any combination of the foregoing.

10. A polypeptide that specifically binds a thymic stromal lymphopoietin (TSLP), comprising an immunoglobulin heavy chain variable domain ($V_H$) comprising the amino acid sequence of SEQ ID NO:2, wherein:
$X_1$ is V;
$X_2$ is S;
$X_3$ is S;
$X_4$ is T, Y or A;
$X_5$ is Y, D or T;
$X_6$ is T or I;
$X_7$ is S or T;
$X_8$ is S;
$X_9$ is D, E or S;
$X_{10}$ is I;
$X_{11}$ is F or Y;
$X_{12}$ is S;
$X_{13}$ is M or L;
$X_{14}$ is V,
or any combination of the foregoing.

11. The polypeptide of Embodiment 9 or 10, further comprising an immunoglobulin light chain variable domain ($V_L$) comprising the amino acid sequence of SEQ ID NO:18, wherein:
$X_{15}$ is N or Y;
$X_{16}$ is L or I;
$X_{17}$ is S or R;
$X_{18}$ is K, F or Y;
$X_{19}$ is S or N;
$X_{20}$ is V or I;
$X_{21}$ is W or Y;

$X_{22}$ is D, V or S;
$X_{23}$ is S, M or E;
$X_{24}$ is S, A or T;
$X_{25}$ is S, D or E;
$X_{26}$ is D, S, R or F;
$X_{27}$ is H, L, K or E,
or any combination of the foregoing.

12. The polypeptide of Embodiment 11, wherein:
$X_{15}$ is Y;
$X_{16}$ is I;
$X_{17}$ is R;
$X_{18}$ is F or Y;
$X_{19}$ is N;
$X_{20}$ is I;
$X_{21}$ is Y;
$X_{22}$ is V or S;
$X_{23}$ is M or E;
$X_{24}$ is A or T;
$X_{25}$ is D or E;
$X_{26}$ is S, R or F;
$X_{27}$ is L, K or E,
or any combination of the foregoing.

13. The polypeptide of any one of Embodiments 1-4 and 6-12, wherein the $V_H$ comprises a heavy chain complementarity determining region 1 (HCDR1), a heavy chain complementarity determining region 2 (HCDR2) and a heavy chain complementarity determining region 3 (HCDR3) that are identical in amino acid sequence to the HCDR1, HCDR2 and HCDR3, respectively, of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17.

14. The polypeptide of any one of Embodiments 1-4 and 6-13, wherein the $V_L$ comprises a light chain complementarity determining region 1 (LCDR1), light chain complementarity determining region 2 (LCDR2) and light chain complementarity determining region 3 (LCDR3) that are identical in amino acid sequence to the LCDR1, LCDR2 and LCDR3, respectively, of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29 or SEQ ID NO:30.

15. The polypeptide of any one of Embodiments 1-5 and 7-14, wherein the polypeptide comprises a paratope that is identical to the paratope of a $V_H/V_L$ combination selected from the amino acid sequence of: SEQ ID NO:4/SEQ ID NO:20 (AB-1), SEQ ID NO:5/SEQ ID NO:21 (AB-2), SEQ ID NO:6/SEQ ID NO:20 (AB-3), SEQ ID NO:7/SEQ ID NO:22 (AB-4), SEQ ID NO:8/SEQ ID NO:23 (AB-5), SEQ ID NO:9/SEQ ID NO:24 (AB-6), SEQ ID NO:10/SEQ ID NO:25 (AB-7), SEQ ID NO:11/SEQ ID NO:20 (AB-8), SEQ ID NO:12/SEQ ID NO:20 (AB-9), SEQ ID NO:13/SEQ ID NO:26 (AB-10), SEQ ID NO:14/SEQ ID NO:27 (AB-11), SEQ ID NO:15/SEQ ID NO:28 (AB-12), SEQ ID NO:16/SEQ ID NO:29 (AB-13) or SEQ ID NO:17/SEQ ID NO:30 (AB-14).

16. The polypeptide of any one of Embodiments 1-15, wherein the $V_H$ has at least 85% sequence identity to the amino acid sequence of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17, or a combination of the foregoing.

17. The polypeptide of any one of Embodiments 1-16, wherein the $V_H$ comprises about 1-10 amino acid substitutions, relative to the amino acid sequence of SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16 or SEQ ID NO:17, or a combination of the foregoing.

18. The polypeptide of any one of Embodiments 1-17, wherein the $V_L$ has at least 85% sequence identity to the amino acid sequence of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29 or SEQ ID NO:30, or a combination of the foregoing.

19. The polypeptide of any one of Embodiments 1-18, wherein the $V_L$ comprises about 1-10 amino acid substitutions, relative to the amino acid sequence of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29 or SEQ ID NO:30, or a combination of the foregoing.

20. The polypeptide of Embodiment 17 or 19, wherein the amino acid substitutions are conservative substitutions.

21. The polypeptide of Embodiment 20, wherein the amino acid substitutions are highly conservative substitutions.

22. The polypeptide of any one of Embodiments 1-21, wherein:
a) the $V_H$ comprises the amino acid sequence of SEQ ID NO:4; and
b) the $V_L$ comprises the amino acid sequence of SEQ ID NO:20.

23. The polypeptide of any one of Embodiments 1-21, wherein:
a) the $V_H$ comprises the amino acid sequence of SEQ ID NO:5; and
b) the $V_L$ comprises the amino acid sequence of SEQ ID NO:21.

24. The polypeptide of any one of Embodiments 1-21, wherein:
a) the $V_H$ comprises the amino acid sequence of SEQ ID NO:6; and
b) the $V_L$ comprises the amino acid sequence of SEQ ID NO:20.

25. The polypeptide of any one of Embodiments 1-21, wherein:
a) the $V_H$ comprises the amino acid sequence of SEQ ID NO:7; and
b) the $V_L$ comprises the amino acid sequence of SEQ ID NO:22.

26. The polypeptide of any one of Embodiments 1-21, wherein:
a) the $V_H$ comprises the amino acid sequence of SEQ ID NO:8; and
b) the $V_L$ comprises the amino acid sequence of SEQ ID NO:23.

27. The polypeptide of any one of Embodiments 1-21, wherein:
a) the $V_H$ comprises the amino acid sequence of SEQ ID NO:9; and
b) the $V_L$ comprises the amino acid sequence of SEQ ID NO:24.

28. The polypeptide of any one of Embodiments 1-21, wherein:
   a) the $V_H$ comprises the amino acid sequence of SEQ ID NO:10; and
   b) the $V_L$ comprises the amino acid sequence of SEQ ID NO:25.
29. The polypeptide of any one of Embodiments 1-21, wherein:
   a) the $V_H$ comprises the amino acid sequence of SEQ ID NO:11; and
   b) the $V_L$ comprises the amino acid sequence of SEQ ID NO:20.
30. The polypeptide of any one of Embodiments 1-21, wherein:
   a) the $V_H$ comprises the amino acid sequence of SEQ ID NO:12; and
   b) the $V_L$ comprises the amino acid sequence of SEQ ID NO:20.
31. The polypeptide of any one of Embodiments 1-21, wherein:
   a) the $V_H$ comprises the amino acid sequence of SEQ ID NO:13; and
   b) the $V_L$ comprises the amino acid sequence of SEQ ID NO:26.
32. The polypeptide of any one of Embodiments 1-21, wherein:
   a) the $V_H$ comprises the amino acid sequence of SEQ ID NO:14; and
   b) the $V_L$ comprises the amino acid sequence of SEQ ID NO:27.
33. The polypeptide of any one of Embodiments 1-21, wherein:
   a) the $V_H$ comprises the amino acid sequence of SEQ ID NO:15; and
   b) the $V_L$ comprises the amino acid sequence of SEQ ID NO:28.
34. The polypeptide of any one of Embodiments 1-21, wherein:
   a) the $V_H$ comprises the amino acid sequence of SEQ ID NO:16; and
   b) the $V_L$ comprises the amino acid sequence of SEQ ID NO:29.
35. The polypeptide of any one of Embodiments 1-21, wherein:
   a) the $V_H$ comprises the amino acid sequence of SEQ ID NO:17; and
   b) the $V_L$ comprises the amino acid sequence of SEQ ID NO:30.
36. The polypeptide of any one of Embodiments 1-35, wherein the $V_H$ and $V_L$ are humanized, contain human framework regions, or a combination thereof.
37. The polypeptide of any one of Embodiments 1-36, wherein the polypeptide is an antibody or an antigen-binding fragment thereof, optionally comprising an Fc domain, in particular embodiments wherein the Fc domain comprises an effector function mutation (see, e.g., Dumet et al. MABS 2019 (particularly Tables 1 and 2 therein), WO02060919), in more particular embodiments wherein the Fc domain comprises LS (M428L/N434S by Kabat) or YTE (M252Y/S254T/T256E by Kabat numbering).
38. The polypeptide of Embodiment 37, wherein the antigen binding fragment is selected from Fab, F(ab')2, Fab', scFv, or Fv.
39. The polypeptide of Embodiment 37, further comprising an antibody heavy chain constant domain sequence, an antibody light chain constant domain sequence, or both an antibody heavy chain constant domain sequence and an antibody light chain constant domain sequence.
40. The polypeptide of Embodiment 39, wherein the antibody heavy chain constant domain is selected from the group consisting of an IgA constant domain, an IgD constant domain, an IgE constant domain, an IgG constant domain and an IgM constant domain.
41. The polypeptide of Embodiment 40, wherein the antibody heavy chain constant domain is an IgG2 heavy chain constant domain.
42. The polypeptide of any one of Embodiments 39-41, further comprising an antibody light chain constant domain selected from the group consisting of a κ constant domain or a λ constant domain.
43. The polypeptide of Embodiment 42, wherein the antibody light chain constant domain is a λ light chain constant domain.
44. The polypeptide of any one of Embodiments 1-43, wherein the polypeptide is conjugated to a heterologous moiety.
45. The polypeptide of Embodiment 44, wherein the heterologous moiety is a therapeutic agent, a diagnostic agent or a combination thereof
46. The polypeptide of Embodiment 44, wherein the heterologous moiety is selected from the group consisting of polyethylene glycol (PEG), hexadecanoic acid, a hydrogel, a lipid nanoparticle, a polymer nanoparticle, and a heterologous polypeptide sequence, or a combination thereof.
47. The polypeptide of Embodiment 46, wherein the polymer nanoparticle comprises poly(lactic-co-glycolic) acid (PLGA).
48. The polypeptide of Embodiment 44, wherein the heterologous polypeptide sequence comprises a carrier polypeptide.
49. The polypeptide of Embodiment 48, wherein the carrier polypeptide is albumin or an Fc polypeptide.
50. The polypeptide of any one of Embodiments 1-49, wherein the polypeptide:
   a) is capable of binding to an epitope in a TSLP protein (e.g., a full-length human TSLP);
   b) binds a TSLP protein with a $K_D$ of 1 pM or less;
   c) neutralizes an activity of a TSLP protein;
   d) reduces a TSLP-induced signal in a human cell,
   or any combination of the foregoing.
51. The polypeptide of Embodiment 50, wherein the polypeptide binds TSLP with a $K_D$ of about 2 pM or less as measured by KinExA.
52. The polypeptide of Embodiment 50, wherein the polypeptide neutralizes an activity of TSLP with an $IC_{50}$ of about 500 pM or less.
53. The polypeptide of Embodiment 50, wherein the polypeptide reduces a TSLP-induced signal in a human cell by at least about 30%.
54. A fusion protein comprising the polypeptide of any one of Embodiments 1-53.
55. A polynucleotide (e.g., DNA or RNA; linear or circular; optionally containing one or more modified nucleotides) comprising a sequence encoding the polypeptide of any one of Embodiments 1-53 or the fusion protein of Embodiment 54.
56. A vector (e.g., an expression vector, including a viral-delivery vector) comprising the polynucleotide of Embodiment 55.
57. A host cell comprising the polynucleotide of Embodiment 55 or the vector of Embodiment 56.

58. A composition comprising the polypeptide of any one of Embodiments 1-53 or the fusion protein of Embodiment 54 or the polynucleotide of Embodiment 55.
59. The composition of Embodiment 58, further comprising one or more pharmaceutical excipients, diluents, or carriers.
60. A method of treating a subject in need thereof, comprising administering an effective amount of the composition of Embodiment 58 or 59 to the subject.
61. A method of reducing binding of TSLP to TSLPR on a cell in a subject, comprising contacting the cell with an effective amount of the composition of Embodiment 58 or 59.
62. The method of Embodiment 60 or 61, wherein the subject has, or is suspected of having, a TSLP-associated disease or condition.
63. The method of Embodiment 60 or 61, wherein the subject is at risk of developing a TSLP-associated disease or condition.
64. The method of any one of Embodiments 60-63, wherein the subject is a human.
65. The method of any one of Embodiments 62 or 63, wherein the TSLP-associated disease or condition is selected from the group consisting of asthma, atopic dermatitis (AD), chronic obstructive pulmonary disease (COPD), chronic spontaneous urticaria (CSU), rheumatoid arthritis (RA), rhinosinusitis (RS), cancer, a food-hypersensitivity reaction, and combinations thereof.
66. The method of any one of Embodiments 60-65, wherein the subject is 18 years or older.
67. The method of any one of Embodiments 60-66, further comprising administering a therapeutically effective amount of an additional therapeutic or prophylactic agent to the subject.
68. The method of any one of Embodiments 60-67, wherein the subject has asthma.
69. The method of any one of Embodiments 60-67, wherein the subject has AD.
70. A polypeptide that specifically binds human thymic stromal lymphopoietin (TSLP):
    wherein a computationally binding optimized (CBO) model outputs a score that is above a predetermined threshold upon scoring an amino acid sequence of the polypeptide.
71. A computationally binding optimized (CBO) polypeptide that specifically binds a thymic stromal lymphopoietin (TSLP):
    wherein a computationally binding optimized (CBO) model outputs a score that is above a predetermined threshold upon scoring an amino acid sequence representing the CBO polypeptide.
72. A polypeptide that specifically binds a thymic stromal lymphopoietin (TSLP) and receives a score above a predetermined threshold from a CBO model upon scoring an amino acid sequence representing the polypeptide.
73. A polypeptide that specifically binds a thymic stromal lymphopoietin (TSLP):
    wherein the polypeptide being assigned a score above a predetermined threshold from a CBO model upon scoring an amino acid sequence representing the polypeptide.
74. A computationally binding optimized (CBO) polypeptide, determined by a computationally binding optimized (CBO) model that specifically binds a human thymic stromal lymphopoietin (TSLP).
75. The CBO polypeptide of any of Embodiments 70-74, wherein the CBO model is calculated by a table substantially similar to that of Computer Program Listing Appendix B.
76. The CBO polypeptide of any of Embodiments 70-75, wherein the CBO polypeptide is calculated using the Computer Program Listing Appendix B.
77. The CBO polypeptide of any of Embodiments 70-76, wherein the CBO polypeptide is scored by a script substantially similar to Computer Program Listing Appendix A, the script employing the CBO model substantially similar to the table of Computer Program Listing Appendix B, wherein the CBO polypeptide has a logarithmic score above −7.7.
78. The CBO polypeptide of any of Embodiments 70-77, wherein the CBO polypeptide is scorable by the script of Computer Program Listing Appendix A.
79. The polypeptide of any of Embodiments 70-78, wherein the predetermined threshold is the logarithmic probability that the sequence inputted to the script would occur given the weights of the Potts model.
80. The polypeptide of any of Embodiments 70-79, wherein a CBO script scoring the polypeptide receives a trained first- and second-order energy score table of outputted weights of a model trained by a plurality of known amino acid sequences and corresponding properties of the known amino acid sequences.
81. The polypeptide of any of Embodiments 70-80, wherein the polypeptide comprises an immunoglobulin heavy chain variable domain ($V_H$) and an immunoglobulin light chain variable domain ($V_L$).
82. The polypeptide of any of Embodiments 70-81, wherein the polypeptide has one or more properties selected from:
    a binding affinity for the TSLP characterized by a $K_D$ of 10 pM or less (e.g., as measured by KinExA);
    a binding specificity for the AB-loop region and the C-terminal region of helix D of the TSLP;
    a neutralizing activity against the TSLP (e.g., a full-length human TSLP); or
    an inhibitory activity against TSLP-mediated signaling, or a combination of the foregoing.
83. The polypeptide of any of Embodiments 70-82, wherein the polypeptide comprises a $V_H$ and $V_L$ pair selected from:
    SEQ ID NO:4 and SEQ ID NO:20 (AB-1);
    SEQ ID NO:5 and SEQ ID NO: 21 (AB-2);
    SEQ ID NO:6 and SEQ ID NO:20 (AB-3);
    SEQ ID NO:7 and SEQ ID NO:22 (AB-4);
    SEQ ID NO:8 and SEQ ID NO:23 (AB-5);
    SEQ ID NO:9 and SEQ ID NO:24 (AB-6);
    SEQ ID NO:10 and SEQ ID NO:25 (AB-7);
    SEQ ID NO:11 and SEQ ID NO:20 (AB-8);
    SEQ ID NO:12 and SEQ ID NO:20 (AB-9);
    SEQ ID NO:13 and SEQ ID NO:26 (AB-10);
    SEQ ID NO:14 and SEQ ID NO:27 (AB-11);
    SEQ ID NO:15 and SEQ ID NO:28 (AB-12);
    SEQ ID NO:16 and SEQ ID NO:29 (AB-13); or
    SEQ ID NO:17 and SEQ ID NO:30 (AB-14).
84. The polypeptide of any of Embodiments 70-83, wherein the polypeptide does not comprise a $V_H$ and $V_L$ pair selected from:
    SEQ ID NO:4 and SEQ ID NO:20 (AB-1);
    SEQ ID NO:5 and SEQ ID NO: 21 (AB-2);
    SEQ ID NO:6 and SEQ ID NO:20 (AB-3);
    SEQ ID NO:7 and SEQ ID NO:22 (AB-4);
    SEQ ID NO:8 and SEQ ID NO:23 (AB-5);

SEQ ID NO:9 and SEQ ID NO:24 (AB-6);
SEQ ID NO:10 and SEQ ID NO:25 (AB-7);
SEQ ID NO:11 and SEQ ID NO:20 (AB-8);
SEQ ID NO:12 and SEQ ID NO:20 (AB-9);
SEQ ID NO:13 and SEQ ID NO:26 (AB-10);
SEQ ID NO:14 and SEQ ID NO:27 (AB-11);
SEQ ID NO:15 and SEQ ID NO:28 (AB-12);
SEQ ID NO:16 and SEQ ID NO:29 (AB-13); or
SEQ ID NO:17 and SEQ ID NO:30 (AB-14).

85. A computer-implemented method comprising:
scoring a polypeptide sequence with a computationally binding optimized (CBO) model, the CBO model:
for each amino acid position of the polypeptide sequence, calculating a plurality of energy scores, the energy scores based on having substituted the amino acid at a given position in the polypeptide sequence with each of a plurality of different amino acids,
adding each energy score calculated to an array,
generating a normalized sum of the energy scores for each position,
calculating a logarithm of each energy score calculated, and
generating a score of the polypeptide sequence by summing the logarithms of each energy score calculated, the score representing a functional property of the polypeptide.

86. A system comprising:
a processor; and
a memory with computer code instructions stored thereon, the processor and the memory, with the computer code instructions, being configured to cause the system to: score a polypeptide sequence with a CBO model, the CBO model:
for each amino acid position of the polypeptide sequence, calculating a plurality of energy scores, the energy scores based on having substituted the amino acid at a given position in the polypeptide sequence with each of a plurality of different amino acids,
adding each energy score calculated to an array,
generating a normalized sum of the energy scores for each position,
calculating a logarithm of each energy score calculated, and
generating a score of the polypeptide sequence by summing the logarithms of each energy score calculated, the score representing a functional property of the polypeptide.

87. A computer-implemented method comprising:
scoring a polypeptide comprising an amino acid sequence with a computationally binding optimized (CBO) model for a functional property relating to modulating the activity of a target molecule, the CBO model:
for each amino acid position of the amino acid sequence of the polypeptide, calculating a plurality of energy scores, the energy scores based on the amino acid at a given position in the amino acid sequence,
adding each energy score calculated to an array,
generating a normalized sum of the energy scores for each position, and
generating a score of the polypeptide by summing each energy score calculated, the score representing the functional property of the polypeptide, the functional property relating to the polypeptide modulating the activity of the target molecule.

88. The computer-implemented method of Embodiment 87, further comprising:
calculating a logarithm of each energy score calculated.

89. The computer-implemented method of Embodiment 87 or 88, wherein summing each energy score calculated is performed by summing the logarithms of each energy score calculated.

90. The computer-implemented method of any of Embodiments 87-89, wherein the energy scores are further calculated based on having substituted the amino acid at the given position in the amino acid sequence with each of a plurality of different amino acids.

91. The computer-implemented method of any of Embodiments 87-90, wherein the target molecule is a target polypeptide.

92. The computer-implemented method of any of Embodiments 87-91, wherein scoring the polypeptide using the CBO model is implementable by the script of Appendix A.

93. The computer-implemented method of any of Embodiments 87-92, wherein the CBO model is substantially similar to the table of Appendix B.

94. The computer-implemented method of any of Embodiments 87-93, wherein scoring the polypeptide further includes:
extracting a plurality of positions from the amino acid sequence, the plurality of positions being positions where mutations were applied during training of the CBO model;
wherein calculating the plurality of energy scores is performed on the extracted plurality of positions.

95. The computer-implemented method of any of Embodiments 87-94, wherein scoring the polypeptide further includes scoring a pair of amino acid sequences, and scoring the polypeptide further comprises:
aligning a first amino acid sequence and second amino acid sequence of the pair of amino acid sequences such that the first amino acid sequence and second amino acid sequence are the same length and that given sections of the first amino acid sequence and second amino acid sequence are the same.

96. The computer-implemented method of any of Embodiments 87-95, wherein the plurality of energy scores includes a first-order energy score associated with each amino acid being at its position and, for each pair of amino acid positions of the amino acid sequence, a second-order energy score associated with the pair of amino acid positions, the first-order energy score and second-order energy score calculated based on corresponding entries of a trained first- and second-order energy score table of outputted weights of a model trained by a plurality of known amino acid sequences and corresponding properties of the known amino acid sequences.

97. The computer-implemented method of any of Embodiments 87-96, further comprising:
returning, based on the score, a flag indicating whether the sequence has the functional property associated with the polypeptide.

98. The computer-implemented method of any of Embodiment 87-97, wherein the functional property is at least one of:

a binding affinity for a thymic stromal lymphopoietin (TSLP) polypeptide characterized by a $K_D$ of 10 pM or less; (optionally, as measured by KinExA);

a binding specificity for the AB-loop region and the C-terminal region of helix D of the TSLP polypeptide;

a neutralizing activity against the TSLP polypeptide (optionally, a full-length human TSLP); or an inhibitory activity against TSLP-mediated signaling, or a combination of the foregoing.

99. A system comprising:
a processor; and
a memory with computer code instructions stored thereon, the processor and the memory, with the computer code instructions, being configured to cause the system to:
score a polypeptide comprising an amino acid sequence with a CBO model for a functional property relating to modulating the activity of a target molecule, the CBO model:
for each amino acid position of the amino acid sequence of the polypeptide, calculating a plurality of energy scores, the energy scores based on the amino acid at a given position in the amino acid sequence,
add each energy score calculated to an array,
generate a normalized sum of the energy scores for each position, and
generate a score of the amino acid sequence by summing each energy score calculated, the score representing a functional property of the polypeptide, the functional property relating to the polypeptide modulating the activity of the target molecules.

100. The system of Embodiment 99, wherein the instructions are further configured to cause the system to calculate a logarithm of each energy score calculated.

101. The system of Embodiment 99 or 100, wherein summing each energy score calculated is performed by summing the logarithms of each energy score calculated.

102. The system of any of Embodiments 99-101, wherein the energy scores are further calculated based on having substituted the amino acid at the given position in the amino acid sequence with each of a plurality of different amino acids.

103. The system of any of Embodiments 99-102, wherein the target molecule is a target polypeptide.

104. The system of any of Embodiment 99-103, wherein scoring the polypeptide using the CBO model is implemented by the script of Appendix A.

105. The system of any of Embodiments 99-104, wherein the CBO model is substantially similar to the table of Appendix B.

106. The system of any of Embodiments 99-105, wherein scoring the polypeptide further includes:
extracting a plurality of positions from the amino acid sequence, the plurality of positions being positions where mutations were applied during training of the CBO model;
wherein calculating the plurality of energy scores is performed on the extracted plurality of positions.

107. The system of any of Embodiments 99-106, wherein scoring the polypeptide further includes scoring a pair of amino acid sequences, and scoring the polypeptide further comprises:
aligning a first amino acid sequence and second amino acid sequence of the pair of amino acid sequences such that the first amino acid sequence and second amino acid sequence are the same length and that given sections of the first amino acid sequence and second amino acid sequence are the same.

108. The system of any of Embodiments 99-107, wherein the plurality of energy scores includes a first-order energy score associated with each amino acid being at its position and, for each pair of amino acid positions of the amino acid sequence, a second-order energy score associated with the pair of amino acid positions, the first-order energy score and second-order energy score being calculated by respective entries from a trained first- and second-order energy score table of outputted weights of a model trained by a plurality of known amino acid sequences and corresponding properties of the known amino acid sequences.

109. The system of any of Embodiments 99-108, further comprising:
returning, based on the score, a flag indicating whether the sequence has the functional property associated with the polypeptide.

110. The system of any of Embodiments 99-109, wherein the functional property is at least one of:
a binding affinity for a thymic stromal lymphopoietin (TSLP) polypeptide characterized by a $K_D$ of 10 pM or less; (optionally, as measured by KinExA);
a binding specificity for the AB-loop region and the C-terminal region of helix D of the TSLP polypeptide;
a neutralizing activity against the TSLP polypeptide (optionally, a full-length human TSLP); or
an inhibitory activity against TSLP-mediated signaling, or a combination of the foregoing.

111. A polypeptide that specifically binds a thymic stromal lymphopoietin (TSLP):
wherein the polypeptide comprises an amino acid sequence that is assigned a score above a predetermined threshold by a computationally binding optimized (CBO) model upon scoring the amino acid sequence of the polypeptide.

112. The polypeptide of Embodiment 111, wherein the CBO model is calculated by a table substantially similar to that of Computer Program Listing Appendix B.

113. The polypeptide of Embodiments 111-112, wherein the polypeptide is assigned the score that is calculated using the Computer Program Listing Appendix B.

114. The polypeptide of any of Embodiments 111-113, wherein the polypeptide is assigned the score by a script substantially similar to Computer Program Listing Appendix A, the script employing the CBO model substantially similar to the table of Computer Program Listing Appendix B, wherein the polypeptide has a logarithmic score of about: −7.7, −7.0, −6.5, −6.0, −5.5, −5.0, −4.5, −4.0, −3.5, −3.0, 2.9, −2.8, −2.7, −2.6, −2.5, −2.4, −2.3, −2.2, −2.1, −2.0, −1.9, −1.8, −1.7, −1.6, −1.5, −1.4, −1.3, −1.2, −1.1, −1.0, 0.9, −0.8, −0.7, −0.6, −0.5, −0.4, −0.3, −0.2, and −0.1.

115. The polypeptide of any of Embodiment 111-114, wherein the polypeptide is scorable by the script of Computer Program Listing Appendix A.s 116. The polypeptide of any of Embodiments 111-115, wherein the predetermined threshold is the logarithmic probability that the sequence inputted to the script would occur given the weights of the Potts model.

117. The polypeptide of any of Embodiments 111-116, wherein a CBO script assigning the score to the polypeptide includes receiving a trained first- and second-order energy score table of outputted weights of a model trained by a plurality of known amino acid sequences and corresponding properties of the known amino acid sequences.

118. The polypeptide of any of Embodiments 111-117, wherein the polypeptide comprises an immunoglobulin heavy chain variable domain ($V_H$) and an immunoglobulin light chain variable domain ($V_L$).

119. The polypeptide of any of Embodiments 111-118, wherein the polypeptide has one or more properties selected from:
  a binding affinity for a thymic stromal lymphopoietin (TSLP) polypeptide characterized by a $K_D$ of 10 pM or less; (optionally, as measured by KinExA);
  a binding specificity for the AB-loop region and the C-terminal region of helix D of the TSLP polypeptide;
  a neutralizing activity against the TSLP polypeptide (optionally, a full-length human TSLP); or
  an inhibitory activity against TSLP-mediated signaling, or a combination of the foregoing.

120. The polypeptide of any of Embodiments 111-119, wherein the CBO model outputs a score that is equal to or above a score from the CBO model of one or more of a reference polypeptide that comprises a $V_H$ and $V_L$ pair selected from:
  SEQ ID NO:4 and SEQ ID NO:20 (AB-1);
  SEQ ID NO:5 and SEQ ID NO: 21 (AB-2);
  SEQ ID NO:6 and SEQ ID NO:20 (AB-3);
  SEQ ID NO:7 and SEQ ID NO:22 (AB-4);
  SEQ ID NO:8 and SEQ ID NO:23 (AB-5);
  SEQ ID NO:9 and SEQ ID NO:24 (AB-6);
  SEQ ID NO:10 and SEQ ID NO:25 (AB-7);
  SEQ ID NO:11 and SEQ ID NO:20 (AB-8);
  SEQ ID NO:12 and SEQ ID NO:20 (AB-9);
  SEQ ID NO:13 and SEQ ID NO:26 (AB-10);
  SEQ ID NO:14 and SEQ ID NO:27 (AB-11);
  SEQ ID NO:15 and SEQ ID NO:28 (AB-12);
  SEQ ID NO:16 and SEQ ID NO:29 (AB-13); or
  SEQ ID NO:17 and SEQ ID NO:30 (AB-14).

121. The polypeptide of any of Embodiments 111-120, wherein the polypeptide comprises a $V_H$ and $V_L$ pair selected from:
  SEQ ID NO:4 and SEQ ID NO:20 (AB-1);
  SEQ ID NO:5 and SEQ ID NO: 21 (AB-2);
  SEQ ID NO:6 and SEQ ID NO:20 (AB-3);
  SEQ ID NO:7 and SEQ ID NO:22 (AB-4);
  SEQ ID NO:8 and SEQ ID NO:23 (AB-5);
  SEQ ID NO:9 and SEQ ID NO:24 (AB-6);
  SEQ ID NO:10 and SEQ ID NO:25 (AB-7);
  SEQ ID NO:11 and SEQ ID NO:20 (AB-8);
  SEQ ID NO:12 and SEQ ID NO:20 (AB-9);
  SEQ ID NO:13 and SEQ ID NO:26 (AB-10);
  SEQ ID NO:14 and SEQ ID NO:27 (AB-11);
  SEQ ID NO:15 and SEQ ID NO:28 (AB-12);
  SEQ ID NO:16 and SEQ ID NO:29 (AB-13); or
  SEQ ID NO:17 and SEQ ID NO:30 (AB-14).

122. The polypeptide of any of Embodiments 111-121, wherein the polypeptide does not comprise a $V_H$ and $V_L$ pair selected from:
  SEQ ID NO:4 and SEQ ID NO:20 (AB-1);
  SEQ ID NO:5 and SEQ ID NO: 21 (AB-2);
  SEQ ID NO:6 and SEQ ID NO:20 (AB-3);
  SEQ ID NO:7 and SEQ ID NO:22 (AB-4);
  SEQ ID NO:8 and SEQ ID NO:23 (AB-5);
  SEQ ID NO:9 and SEQ ID NO:24 (AB-6);
  SEQ ID NO:10 and SEQ ID NO:25 (AB-7);
  SEQ ID NO:11 and SEQ ID NO:20 (AB-8);
  SEQ ID NO:12 and SEQ ID NO:20 (AB-9);
  SEQ ID NO:13 and SEQ ID NO:26 (AB-10);
  SEQ ID NO:14 and SEQ ID NO:27 (AB-11);
  SEQ ID NO:15 and SEQ ID NO:28 (AB-12);
  SEQ ID NO:16 and SEQ ID NO:29 (AB-13); or
  SEQ ID NO:17 and SEQ ID NO:30 (AB-14).

123. The polypeptide of any of Embodiments 111-122, wherein the polypeptide does not comprise a heavy chain comprising SEQ ID NO:81 and a light chain comprising SEQ ID NO:82.

124. A polypeptide:
  wherein the polypeptide comprises an amino acid sequence that is assigned a score above a predetermined threshold by a computationally binding optimized (CBO) model upon scoring the amino acid sequence of the polypeptide.

125. A polypeptide that binds human thymic stromal lymphopoietin (TSLP), wherein the polypeptide is designed by a method comprising:
  generating a polypeptide sequence with a CBO model;
  verifying the generated polypeptide sequence using the CBO model by:
    for each amino acid position of the polypeptide sequence, calculating a plurality of energy scores, the energy scores based on having substituted the amino acid at a given position in the polypeptide sequence with each of a plurality of different amino acids,
    adding each energy score calculated to an array,
    generating a normalized sum of the energy scores for each position,
    calculating a logarithm of each energy score calculated, and
    generating a score of the polypeptide sequence by summing the logarithms of each energy score calculated, the score representing a functional property of the polypeptide's ability to bind to human TSLP.

126. The polypeptide of Embodiment 125, wherein the polypeptide is scored at least a score of about: −7.7, −7.0, −6.5, −6.0, −5.5, −5.0, −4.5, −4.0, −3.5, −3.0, 2.9, −2.8, −2.7, −2.6, −2.5, −2.4, −2.3, −2.2, −2.1, −2.0, −1.9, −1.8, −1.7, −1.6, −1.5, −1.4, −1.3, −1.2, −1.1, −1.0, 0.9, −0.8, −0.7, −0.6, −0.5, −0.4, −0.3, −0.2, and −0.1.

127. A polypeptide that specifically binds human thymic stromal lymphopoietin (TSLP):
  wherein a computationally binding optimized (CBO) model outputs a score that is equal to or above a score from the CBO model of one or more of a reference polypeptide that comprises a $V_H$ and $V_L$ pair selected from:
  SEQ ID NO:4 and SEQ ID NO:20 (AB-1);
  SEQ ID NO:5 and SEQ ID NO: 21 (AB-2);
  SEQ ID NO:6 and SEQ ID NO:20 (AB-3);
  SEQ ID NO:7 and SEQ ID NO:22 (AB-4);
  SEQ ID NO:8 and SEQ ID NO:23 (AB-5);
  SEQ ID NO:9 and SEQ ID NO:24 (AB-6);
  SEQ ID NO:10 and SEQ ID NO:25 (AB-7);
  SEQ ID NO:11 and SEQ ID NO:20 (AB-8);
  SEQ ID NO:12 and SEQ ID NO:20 (AB-9);
  SEQ ID NO:13 and SEQ ID NO:26 (AB-10);
  SEQ ID NO:14 and SEQ ID NO:27 (AB-11);
  SEQ ID NO:15 and SEQ ID NO:28 (AB-12);
  SEQ ID NO:16 and SEQ ID NO:29 (AB-13); or
  SEQ ID NO:17 and SEQ ID NO:30 (AB-14).

128. The polypeptide of any of Embodiments 111-127, wherein the polypeptide is an antibody or an antigen-binding fragment thereof.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g., elements, including numerical ranges and exemplary embodiments) of particular embodiments and aspects of the invention, including the working examples. For example, particular experimental parameters exemplified in the working examples can be adapted for use in the claimed invention piecemeal without departing from the invention. For example, for materials that are disclosed, while specific reference of each of the various individual and collective combinations and permutations of these compounds may not be explicitly disclosed, each is specifically contemplated and described herein. Thus, if a class of elements A, B, and C are disclosed as well as a class of elements D, E, and F and an example of a combination of elements A-D is disclosed, then, even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-groups of A-E, B-F, and C-E are specifically contemplated and should be considered disclosed from disclosure of A, B, and C; D, E, and F; and the example combination A-D. This concept applies to all aspects of this application, including elements of a composition of matter and steps of method of making or using the compositions.

The forgoing aspects of the invention, as recognized by the person having ordinary skill in the art following the teachings of the specification, can be claimed in any combination or permutation to the extent that they are novel and non-obvious over the prior art-thus, to the extent an element is described in one or more references known to the person having ordinary skill in the art, they may be excluded from the claimed invention by, inter alia, a negative proviso or disclaimer of the feature or combination of features.

EXEMPLIFICATION

Example 1. Production of Full-Length IgG Molecules

Variable heavy ($V_H$) chain and variable light ($V_L$) chain sequences were synthesized and cloned into mammalian expression vectors containing nucleotide sequences encoding corresponding constant regions using conventional methods to be expressed as full-length human immunoglobulin 1 (IgG1) antibodies. The antibodies were generated using one expression plasmid per chain, containing a CMV promoter to drive expression and a signal peptide to promote secretion of the fully folded IgG into the supernatant. Mammalian expression host systems (such as the Chinese hamster ovary—CHO S cell line) were employed for protein expression using cationic lipid-based transient transfection methodologies with fed-batch production procedures. The expressed, soluble full-length IgG molecules were purified using an affinity capture-based purification method using Protein A-affinity resin (such as the MabSelect SuRe™ resin, Cytiva, Marlborough, MA) and aqueous buffers. Elution was performed under acidic conditions with low pH (such as pH 3.5) and then neutralized to pH 7.5 using 2M Tris base. The purified antibodies were further stabilized in aqueous buffers (such as Histidine-based buffers containing NaCl) for long-term storage/freezing.

Example 2. Polyspecific Reactivity of Candidate TSLP Binders

Non-specific interaction, or poly-specific reactivity (PSR), measures the potential for an antibody to bind non-specifically to things other than its desired target, in this case, TSLP. PSR was measured with using a low-stringency ELISA-based method (Tiller et al., J Immunol Methods. 329:112-24 (2008)). Briefly, a 384-well assay plate was coated with 10 pg/mL salmon sperm DNA (Rockland Immunochemicals, Inc., Gilbertsville, PA) and incubated overnight at 4° C. All antigens were diluted in Tris-buffered saline (TBS). The assay plate was washed 3 times with 100 pL TBS-Tween-20 (TBS-T) on an automated plate washer and blocked with 100 pL of TBS-T with 5% bovine serum albumin (BSA) for one hour at 37° C. The assay plate was washed 3 times as before. The purified full-length IgG molecules described in Example 1 were normalized to 100 nM in TBS-T and distributed in duplicate. The plate was incubated for 1 hour at 37° C. and again washed 3 times as before. DELFIA© (dissociation-enhanced lanthanide fluorescence immunoassay) Eu-N1 anti-human IgG secondary (PerkinElmer Inc., Waltham, MA) was diluted to 100 ng/mL in TBS-T plus 5% BSA, and 25 pL was distributed into each well. The plate was incubated for 1 hour at 37° C. then washed 3 time as before. 25 pL of DELFIA© Enhancement Solution (PerkinElmer Inc.) was added to each well and incubated in the dark for 15 minutes. Time Resolved Fluorescence (TRF) was measured for each well. Polyspecific binding to DNA was quantified by dividing the raw signal over signal from buffer-only wells. Representative data are shown in Table 6.

Example 3. Self-Association of Candidate TSLP Binders

Self-interaction properties of the antibody candidates were measured by Affinity Capture Self-Interaction Nanoparticle Spectroscopy (AC-SINS) (Liu et. al., mAbs. 6:483-92 (2014)). AC-SINS leverages the ability of gold nanoparticles to absorb light at signature wavelengths and generate surface plasmons. There is an observable shift in the nanoparticle absorption spectra when inter-nanoparticle distance changes. This shift occurs when gold nanoparticles pre-coated with anti-human Fc antibodies are incubated with antibody candidates that self-interact. More self-interaction between the antibody candidates causes an increased maximum absorbance wavelength in the nanoparticle absorption spectra, compared to spectra of nanoparticles alone ($\Delta\lambda_{MAX}$). Polyclonal goat anti-human IgG Fcγ antibodies (Jackson ImmunoResearch Laboratories, Inc., West Grove, PA, #109-005-098) and non-specific goat antibodies (Jackson ImmunoResearch Laboratories, Inc., Catalog #005-000-003) were used to pre-coat the gold nanoparticle (Ted Pella Inc., Redding, CA, Catalog #15705). Coating solution was prepared at a 4:1 (v/v) ratio between capture and non-capture antibodies (0.4 mg/mL total antibodies). A 9:1 (v/v) ratio solution with gold nanoparticles and coating solution was prepared before incubation at RT and blocking of the empty gold nanoparticle sites with 0.1 pM thiolated PEG (Sigma-Aldrich, St. Louis, MO, Catalog #729140-1G). This was then filtered through 0.22 µm PVDF membrane (Millex-GV Syringe Filter Unit, 13 mm, MilliporeSigma, Burlington, MA). The particles retained on top were eluted with 1×PBS. This coating solution was incubated with the antibody candidates at RT for 2 hours in a polypropylene plate before being transferred on to a polystyrene UV transparent plate. Absorption spectra is measured at this point from 510 to 570 nm at in increment of 2 nm. These data were analyzed to determine the wavelength shifts that are indicative of self-interaction in the antibody candidates. Representative AC-SINS data is shown in Table 6.

Example 4. TSLP Binding Enzyme-Linked Immunosorbent Assay (ELISA)

Human TSLP (hTSLP) Binding ELISA

Binding affinity of anti-TSLP monoclonal antibodies (mAbs) to human TSLP was assessed using an indirect ELISA assay. A 96 well half area plate was coated with 2 µg/mL of recombinant human TSLP (BioLegend, San Diego, CA) overnight. The next day, the plate was washed three times with ELISA Wash Buffer (PBS-Tween 0.5%), blocked with 1× ELISA assay diluent (BioLegend) for one hour. Plates were then washed three times with ELISA Wash Buffer, followed by addition of the anti-TSLP antibodies at the indicated concentrations and incubation at 37° C. for one hour. The plate was washed three times with ELISA Wash Buffer, and horseradish peroxidase (HRP)-conjugated anti-human IgG Fc secondary antibody (Promega, Madison, WI) at 1:2000 dilution in 1× ELISA assay diluent was added to detect binding of the primary antibody to the antigen. The plate was incubated for 30 minutes at 37° C. with the secondary detection antibody, then the plate was washed and developed with tetramethyl benzidine (TMB) substrate solution (Thermo Fisher Scientific, Waltham, MA). The HRP enzymatic reaction was stopped after about 1 minute with acidic stop solution (Thermo Fisher Scientific), and the absorbance at 450 nm was determined using a standard plate reader. The $EC_{50}$ values were calculated by fitting a four-parameter non-linear regression line to the average of two technical replicates per concentration.

Figure 4B:
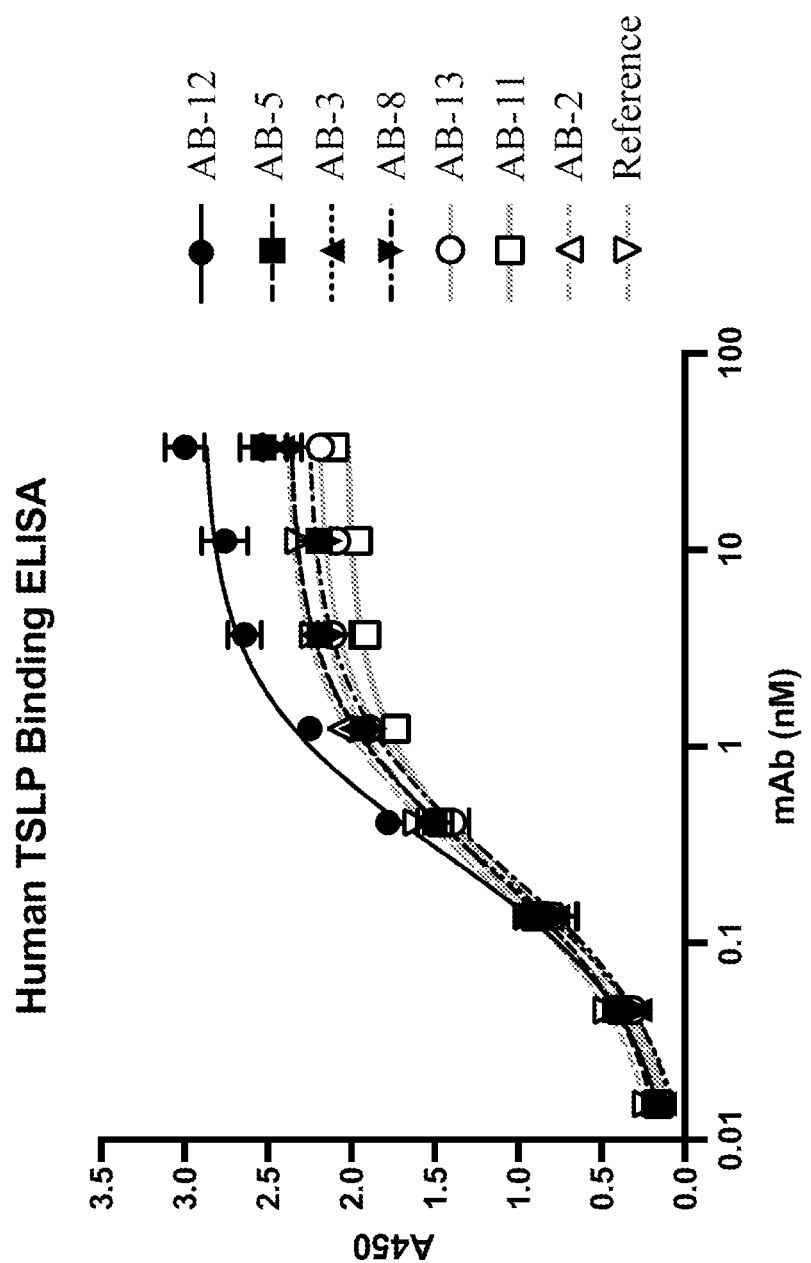

To determine the binding profile of anti-TSLP antibodies, a binding ELISA against recombinant human TSLP was completed. ELISA assay plates were coated with human TSLP cytokine, and subsequently serial dilutions of anti-TSLP antibodies were plated. After one hour of incubation, the plates were washed and the binding of anti-TSLP antibodies to hTSLP was detected with anti-human IgG Fc conjugated to HRP and developed with TMB substrate. FIGS. 4A-4B demonstrate the binding profile of anti-TSLP mAbs to hTSLP. The $EC_{50}$ values were determined by curve fitting (non-linear regression) (Table 7).

Cynomolgus Monkey TSLP Binding ELISA

The human indirect TSLP binding ELISA assay protocol as described above was used to determine species cross-reactivity of anti-TSLP antibodies to cynomolgus monkey TSLP (ACROBiosystems, Newark, DE). $EC_{50}$ values for primary antibodies binding cynomolgus monkey TSLP and human TSLP were compared.

Figure 5A:
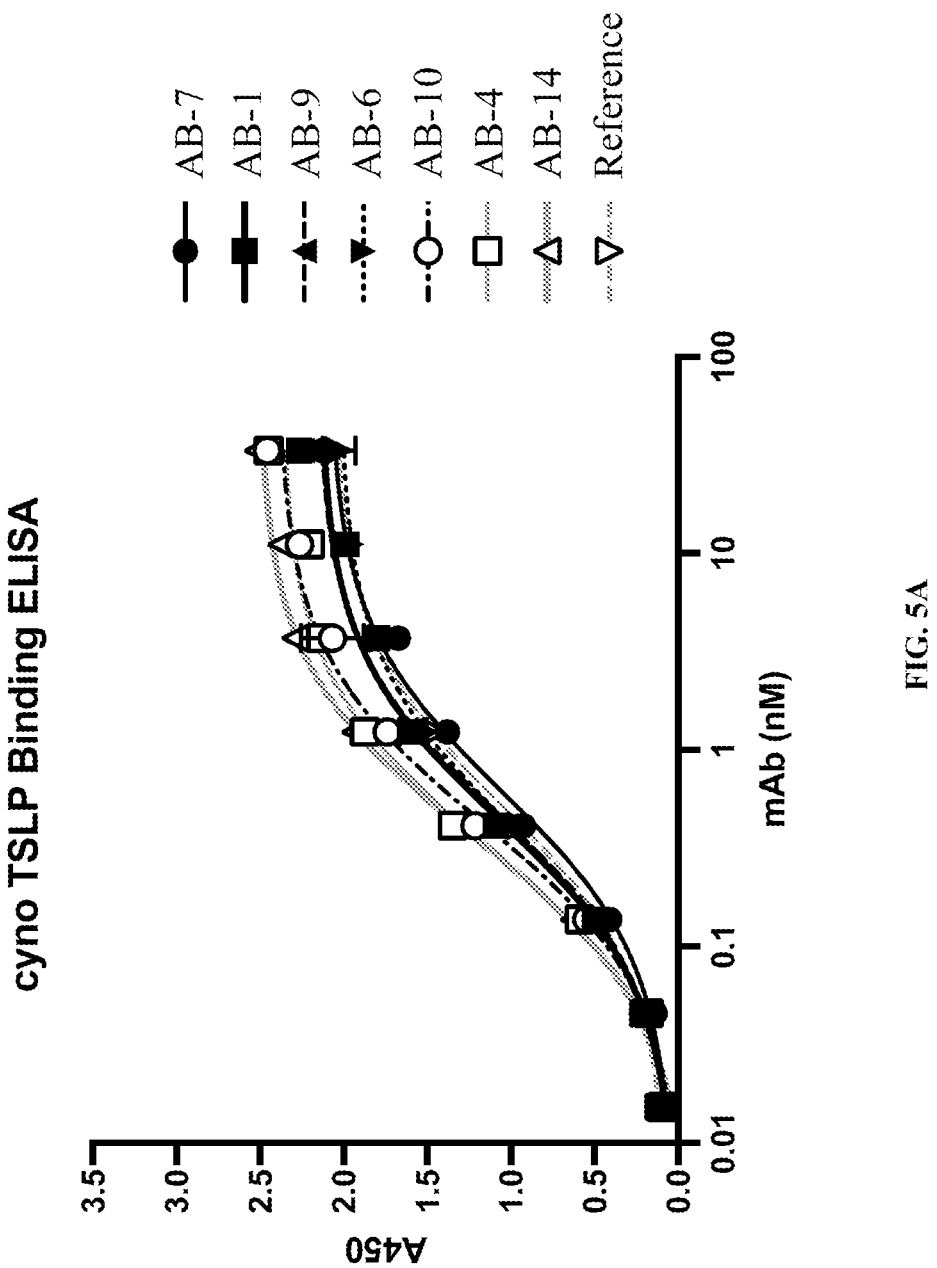
Figure 5B:
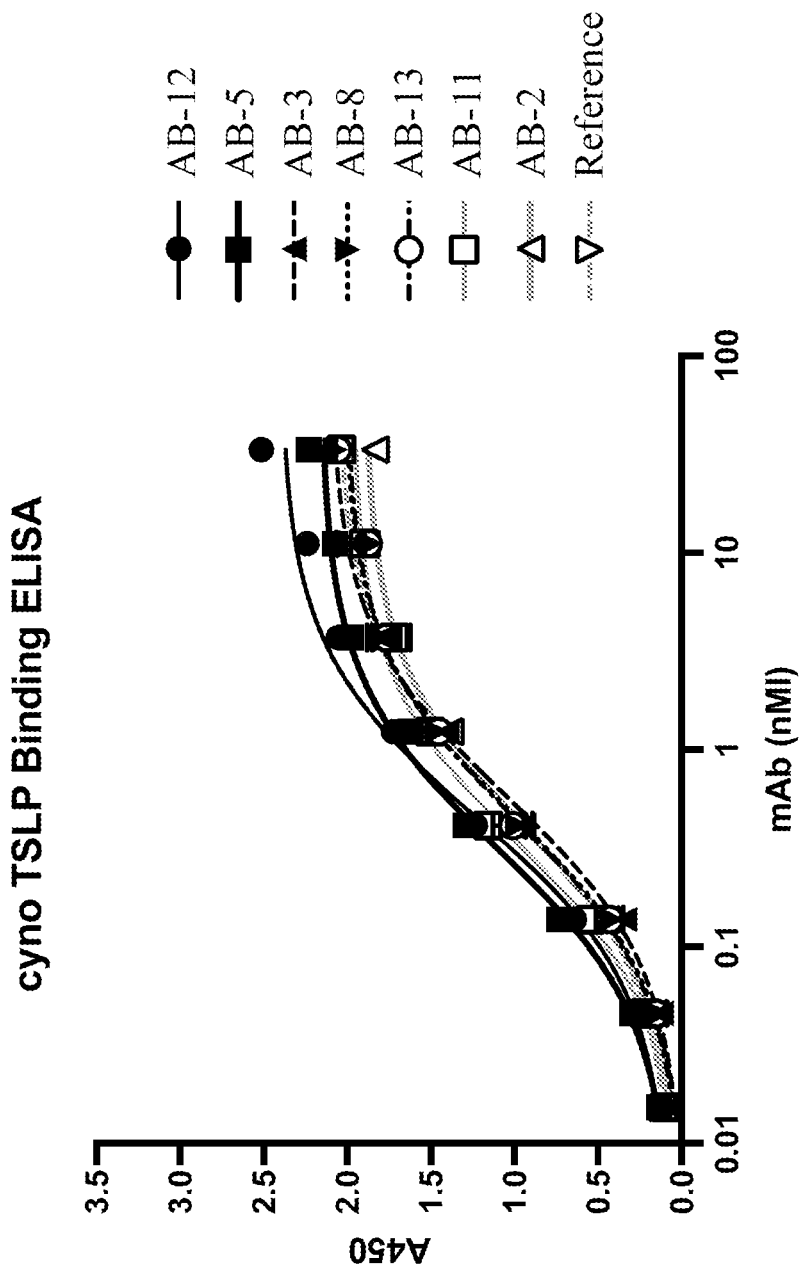

To determine the binding profile of anti-TSLP antibodies, a binding ELISA against recombinant cynomolgus TSLP was completed. ELISA assay plates were coated with cynomolgus TSLP cytokine and subsequently serial dilutions of anti-TSLP antibodies were plated. After one hour of incubation, the plates were washed and the binding of anti-TSLP antibodies to cynoTSLP was detected with anti-human IgG Fc conjugated to HRP and developed with TMB substrate. FIGS. 5A-5B demonstrate the binding profile of anti-TSLP mAbs to cynoTSLP The $EC_{50}$ values were determined by curve fitting (non-linear regression) (Table 7).

Example 5. TSLP Blocking ELISA

Human TSLP Blocking ELISA

A 96 well half area flat bottom plate was coated with 50 µL of recombinant heterodimeric human TSLPR and human IL-7Rα Fc tagged fusion protein (2 pg/mL) in ELISA coating buffer. The plate was incubated overnight at 4° C. and was washed thrice with 150 µL ELISA Wash Buffer (1×PBS-Tween 0.5%) the next day. The plate was blocked with 50 µL of ELISA assay diluent for one hour at 37° C. and was washed three times with 150 µL of ELISA wash buffer. Serial dilutions of primary antibodies were pre-incubated with hTSLP-biotin cytokine in 50 µl of ELISA assay diluent for 30 minutes at 37° C., followed by addition to the ELISA plate. The ELISA plate was incubated for 1 hour at 37° C. followed by washing three times with ELISA wash buffer. HRP-Streptavidin (Thermo Fisher Scientific) was diluted 1:2000 in ELISA assay diluent 50 µl was added to each well and incubated for 30 minutes at 37° C. followed by washing three times with ELISA wash buffer. The ELISA was developed by addition of 50 µL of TMB substrate (Thermo Fisher Scientific) and incubation for 2-3 minutes at room temperature (protected from light). The reaction was stopped with acidic stop solution (Thermo Fisher Scientific), and the absorbance was read at 450 nm wavelength using a standard plate reader. Percent inhibition of signal and $IC_{50}$ values were determined.

Figure 6A:
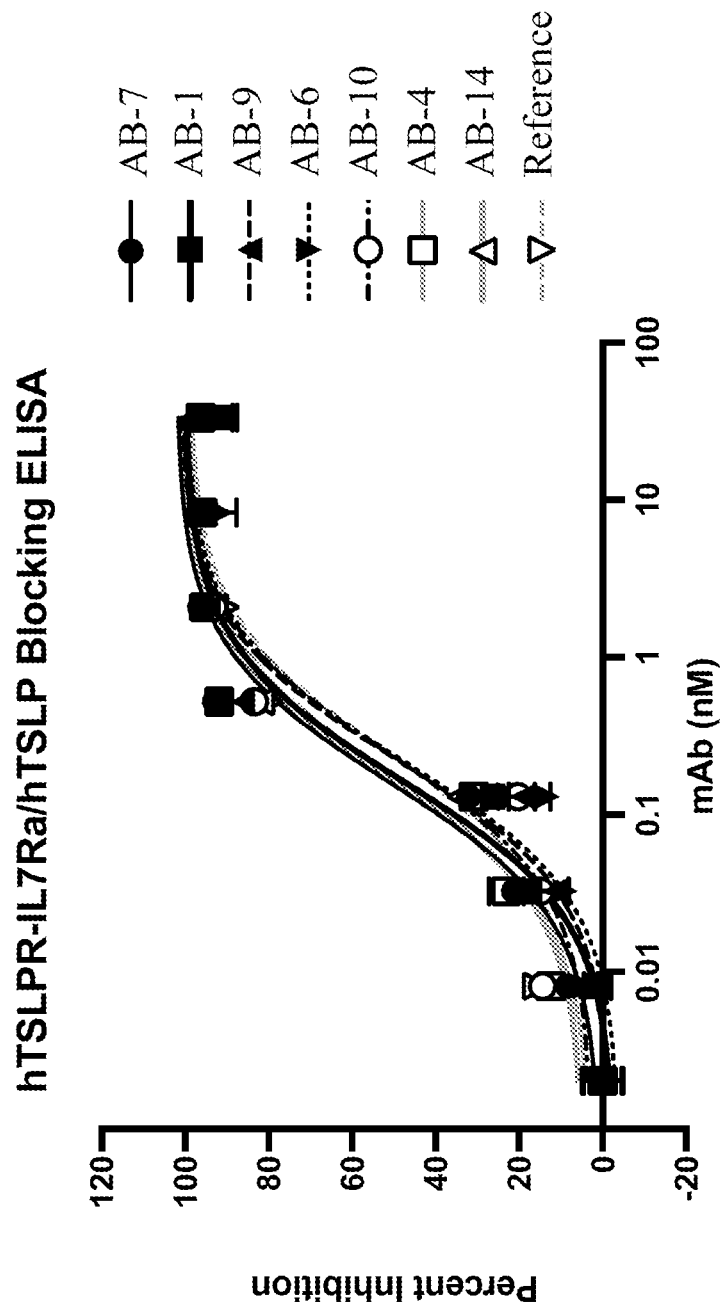
Figure 6B:
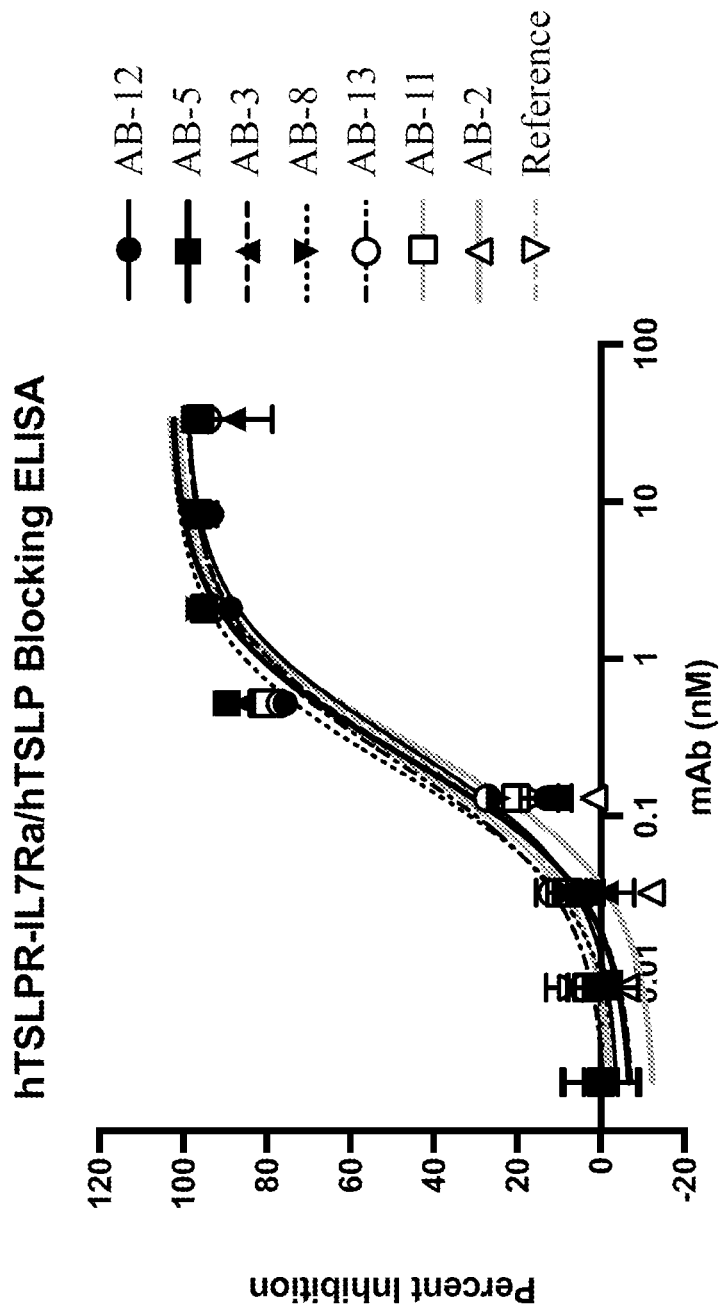

FIGS. 6A-6B demonstrate the ability of anti-TSLP antibodies to block hTSLP from binding its receptor (TSLPR). A blocking ELISA was performed by coating an ELISA plate with hTSLPR overnight. The next day, serial dilutions of primary antibodies were pre-incubated with hTSLP-biotin cytokine for 30 minutes at 37° C., followed by addition to the ELISA plate. The ELISA plate was incubated for 1 hour at 37° C., followed by washing of the plate. To detect blocking of hTSLP cytokines from binding to the receptors, a detection HRP-Streptavidin was added to the plate and incubated for 30 minutes at 37° C., followed by washing of the plate. The ELISA was developed with TMB substrate, and the HRP enzymatic reaction was stopped with sulfuric acid solution. Percent inhibition of signal and $IC_{50}$ values were determined (Table 8).

Cynomolgus Monkey TSLP Blocking ELISA

The human TSLP blocking ELISA assay protocol as described previously was used to determine the ability of primary antibodies to block cynomolgus TSLP cytokine from binding cynomolgus TSLPR. $IC_{50}$ values for primary antibodies ability to block cynomolgus monkey TSLP and human TSLP from binding the TSLPR were compared.

Figure 7A:
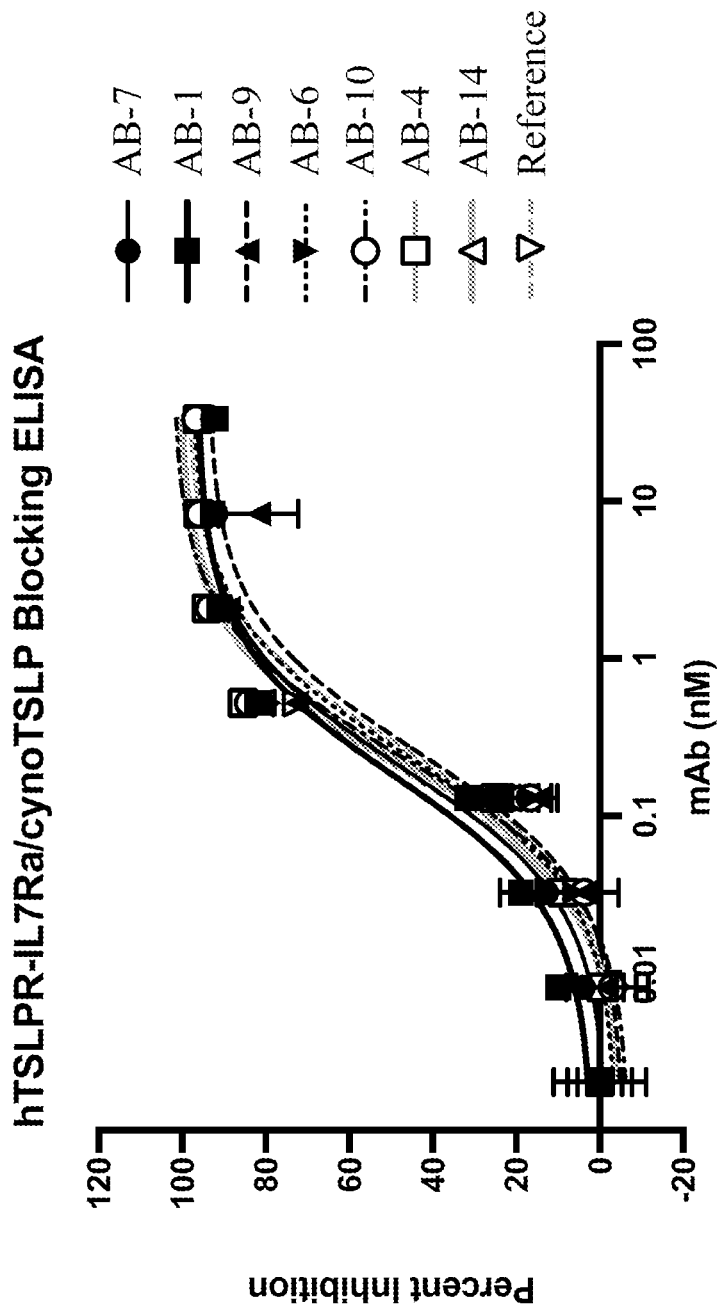
Figure 7B:
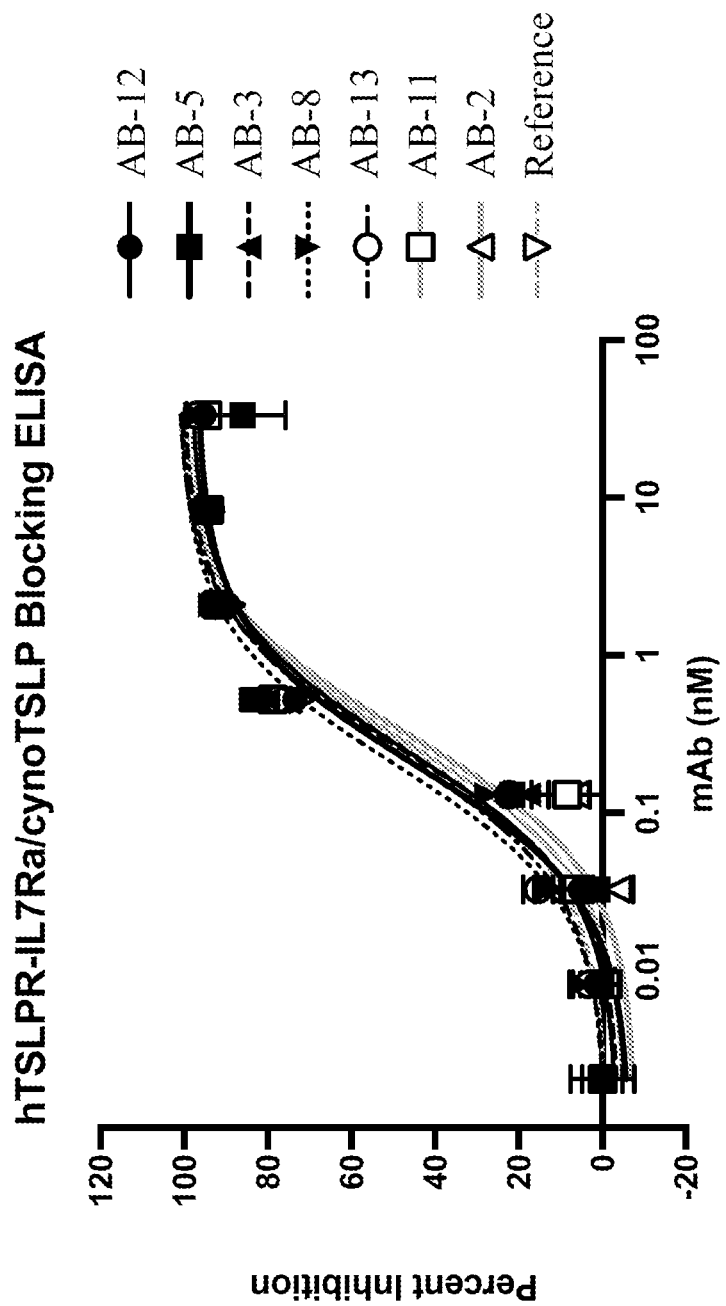

FIGS. 7A-7B demonstrate the ability of anti-TSLP antibodies to block cynoTSLP from binding its receptor (TSLPR). A blocking ELISA was performed by coating an ELISA plate with hTSLPR overnight. The next day, serial dilutions of primary antibodies were pre-incubated with cynoTSLP-biotin cytokine for 30 minutes at 37° C., followed by addition to the ELISA plate. The ELISA plate was incubated for 1 hour at 37° C., followed by washing of the plate. To detect blocking of cynoTSLP cytokines from binding to the receptors, a detection HRP-Streptavidin was added to the plate and incubated for 30 minutes at 37° C., followed by washing of the plate. The ELISA was developed with TMB substrate, and the HRP enzymatic reaction was stopped with sulfuric acid solution. Percent inhibition of signal and $IC_{50}$ values were determined (Table 8).

Example 6. Kinetic Exclusion Assay (KinExA)

The solution equilibrium binding experiments were performed using KinExA 3200 instrument equipped with an autosampler (Sapidyne Instruments, Boise, ID, USA). All analyses were performed at 25° C., and all samples were prepared in 1× phosphate-buffered saline (PBS) filtered buffer supplemented with 1 mg/mL bovine serum albumin (BSA) and 0.02% sodium azide. Human TSLP and cyno TSLP were covalently immobilized onto azlactone beads. To a 50 mg aliquot of azlactone beads, 20 pg of human TSLP or 20 pg of cyno TSLP diluted in 1 mL of coating solution (50 mM sodium carbonate, 0.5 M sodium citrate, pH 9.0) was added to the azlactone beads and rocked for 2 hours. The beads were washed with blocking buffer (1 M Tris supplemented with 10 mg/mL BSA, pH 8.0) and rocked for 1 hour.

The sample injection volumes and flow rates were varied depending upon the antibody tested. Fixed concentrations of antibody (referred to as the constant binding partner or CBP) were incubated with two-fold serial dilutions of human TSLP or cyno TSLP (referred to as the titrant) to generate two equilibrium titration curves. The samples containing human TSLP or cyno TSLP were equilibrated for at least 36 hours under constant rocking before measuring the unbound antibody on KinExA 3200. The antibody bound to human TSLP or cyno TSLP coated azlactone beads was detected using Alexa Fluor647 AffiniPure goat anti-human IgG (H+L) secondary antibody. The concentration, volume and flow rate of the secondary antibody were varied to achieve a signal at less than 1.0 V.

For each antibody-TSLP interaction, multiple curves from independent experiments were analyzed using the N-curve analysis tool to obtain $K_D$ values and CBP activities with 95% confidence intervals from $K_D$-controlled and concentration-controlled curves, respectively. A 1:1 binding equilibrium model was used with the titrant selected as the reference concentration. The drift correction option was used where appropriate.

The $k_a$ of each antibody-TSLP interaction was measured using the direct method. Fixed concentrations of antibody were mixed with the human TSLP or cyno TSLP concentration that bound approximately 80% of the CBP in the solution equilibrium binding experiments, and the concentration of free CBP present in the sample was repeatedly measured over time using the human TSLP or cyno TSLP coated azlactone beads. The resulting exponential curve of unbound antibody as a function of time was fitted to calculate the $k_a$ of the antibody-TSLP interaction. The $k_d$ was determined by multiplying the ka value measured from the direct method by the $K_D$ value obtained from the solution equilibrium binding experiment (Table 9).

Example 7. Inhibition of STAT5-Luciferase Signal

Generation of the Ba/F3-STAT5-Luciferase-hTSLPR/hIL-7R Cell Line

Figure 8A:
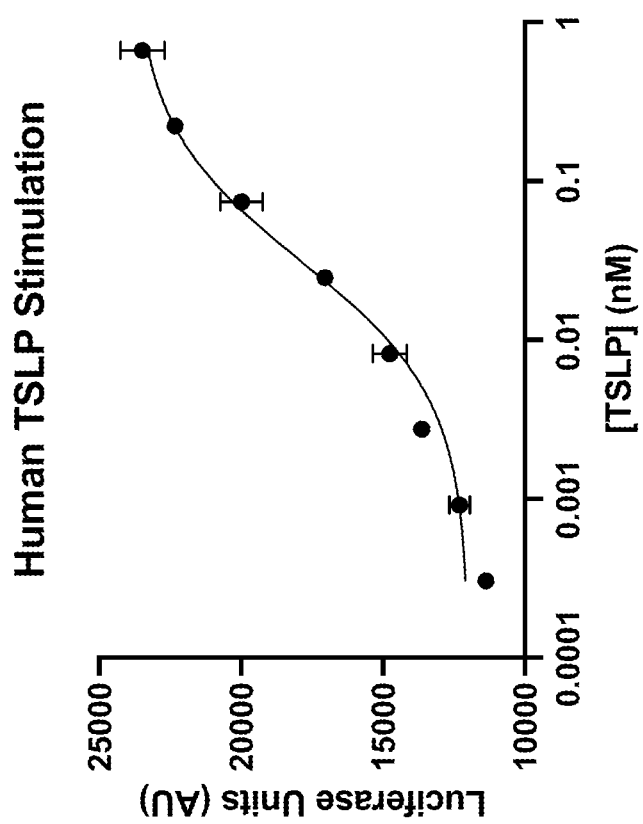

Human TSLP Receptor (CRLF2) forms a heterodimeric complex with the IL-7Rα (CD127) after binding of TSLP. A hIL-7Rα-P2A-hTSLPR construct was synthesized and cloned into a pcDNA3.1(+)/Hygro plasmid. The plasmid was transfected into the Ba/F3-STAT5-Luc cell line, which contains a STS5-inducible Luciferase reporter, to create a stable cell line expressing hTSLPR and hIL-7Rα. Ba/F3-STAT5-Luc cells expressing hTSLPR/hIL-7R were maintained in RPMI-1640 with Glutamax medium containing 10% fetal bovine serum (FBS), 1% penicillin-streptomycin, 10 ng/mL hTSLP, and 400 pg/mL hygromycin selection antibiotic. The hTSLPR/hIL-7R-expressing Ba/F3-STAT5-Luc cells had a dose dependent response to hTSLP with an $EC_{50}$ of 0.03 nM (FIG. 8A).

Ba/F3-STAT5-Luc Assay

In a 96-well maxi-sorp (Thermo Fisher Scientific) plate, serial dilutions of anti-TSLP antibodies in 25 μl of Assay Media (RPMI-1640+10% FBS) were pre-incubated with 25 μl of 4 ng/mL hTSLP cytokine (BioLegend) at 37° C. for 30 minutes. After incubation, 20,000 Ba/F3-STAT5-hTSLPR/hIL-7R-Luc cells in 50 μl of cell media were plated and incubated with antibodies and TSLP cytokine for four hours. After four hours, 100 μl of luciferase reagent (BPS Bioscience Inc., San Diego, CA) was added to each well of the plate and rocked gently for 15 minutes at room temperature, protected from light. Luminescence was measured with a luminometer within one hour of luciferase reagent addition.

Figure 8B:
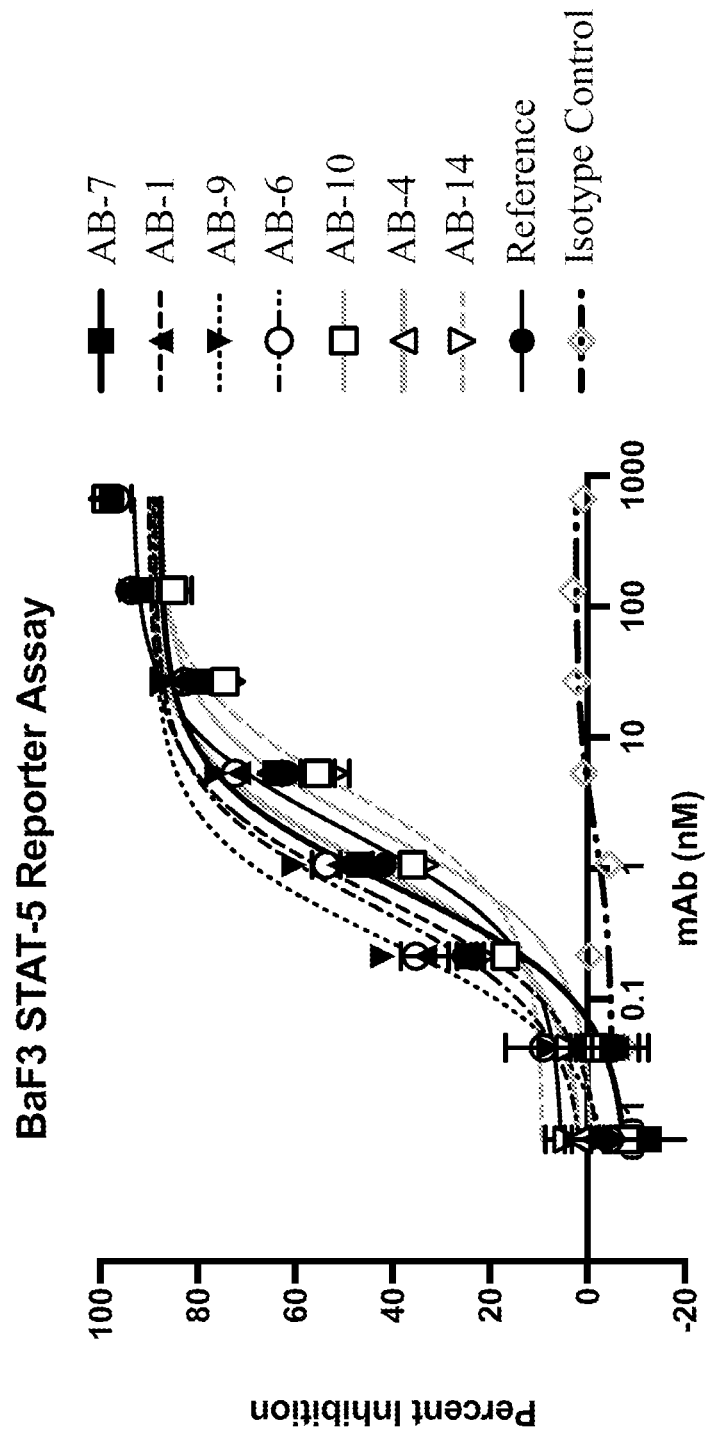
Figure 8C:
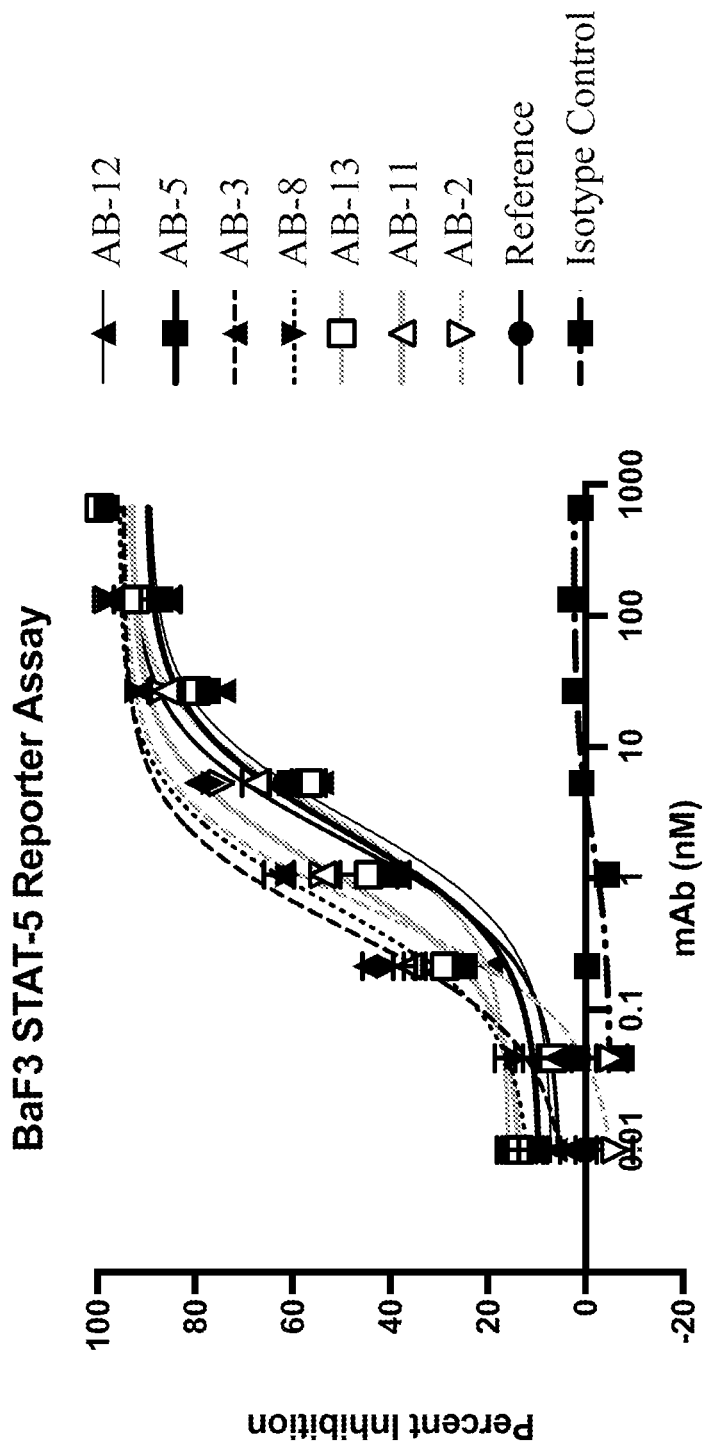

FIGS. 8B-8C show effects of the anti-TSLP antibodies on STAT5-dependent luciferase expression. The results demonstrate that the anti-TSLP antibodies block binding of hTSLP to TSLPR and in turn, inhibit STAT5 signaling. The luminescence signal values were baseline corrected and transformed to percent inhibition using the STAT5-luciferase signal of unstimulated cells. The $IC_{50}$ values were obtained by a non-linear curve fit (Table 10). The tested anti-TSLP antibodies can block TSLP from binding the TSLPR on cells.

Example 8. Inhibition of STAT5-Luciferase Signal

Myeloid Dendritic Cell (mDC) TSLP Stimulation Assay

Peripheral Blood Mononuclear Cells (PBMCs) were isolated from fresh whole blood by Ficoll-Paque density centrifugation from 5 independent donors and cryopreserved in medium containing 90% fetal bovine serum and 10% DMSO. PBMCs were thawed into PBS containing 5 mM EDTA and 2% FBS, counted and myeloid dendritic cells (mDCs) were isolated using StemCell Technologies EasySep Human Myeloid DC Enrichment Kit. In a 96-well maxi-sorp (Thermo Fisher Scientific) plate serial dilutions of anti-TSLP antibodies in 25 μl of Assay Media (RPMI-1640+10% FBS) are pre-incubated with 25 μl of 1 ng/ml hTSLP cytokine (BioLegend) at 37° C. for 30 minutes. After incubation 1E5 mDCs were plated and incubated with the antibodies and TSLP cytokine for forty-eight hours at 37° C. Media were collected, and the concentrations of CCL17 (TARC) were measured on an MSD instrument.

Figure 9A:
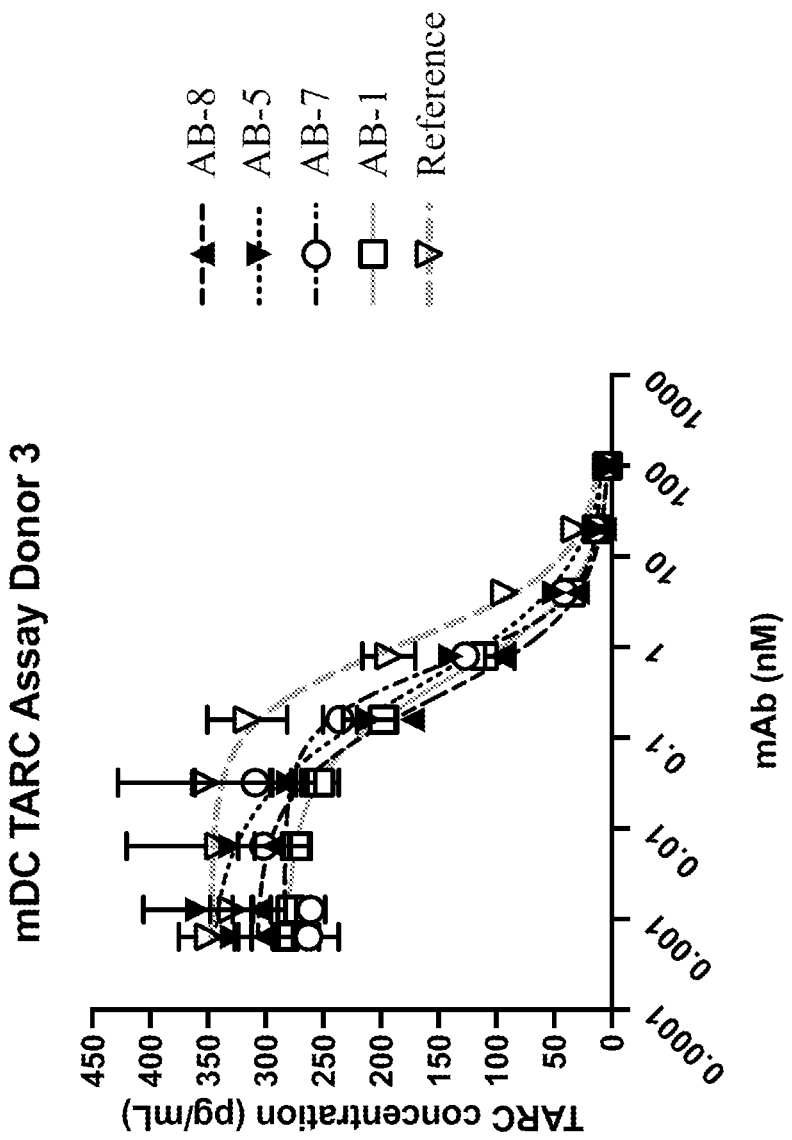
Figure 9B:
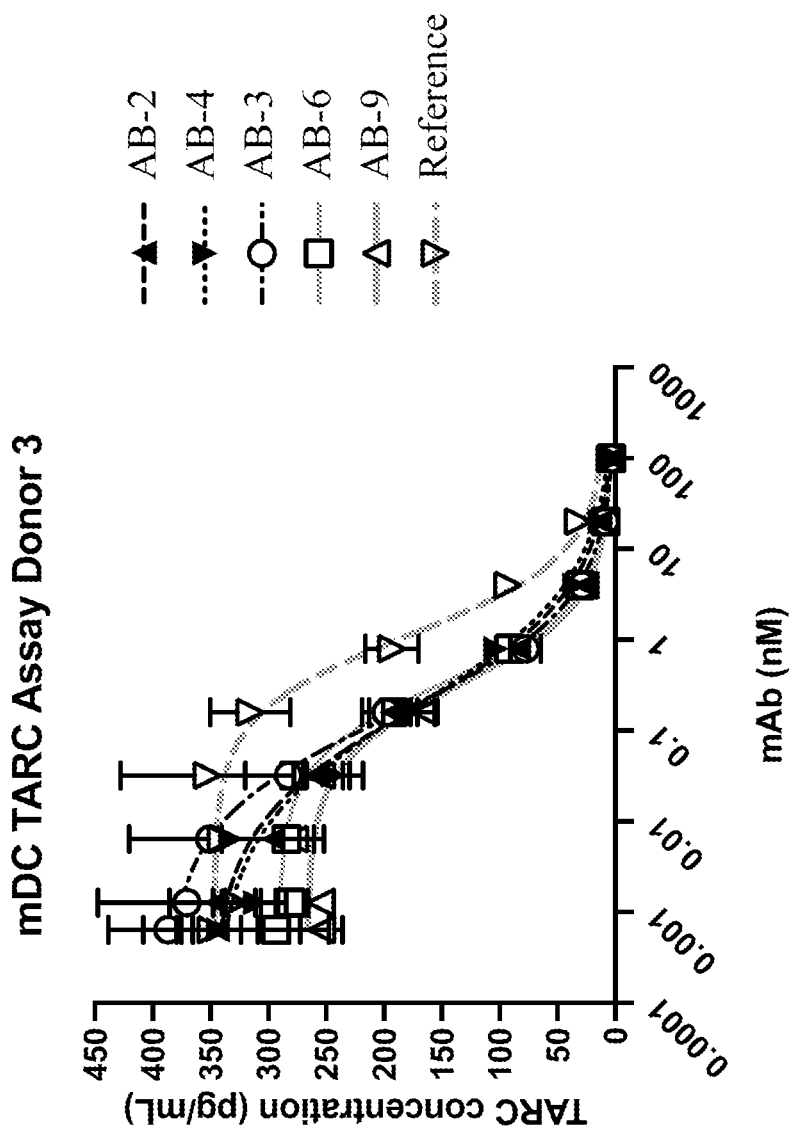

FIGS. 9B-9C show effects of the anti-TSLP antibodies on TSLP-induced CCL17 expression by mDCs from one representative donor. The results demonstrate that the anti-TSLP antibodies block binding of hTSLP to TSLPR and in turn, inhibit CCL17 secretion by mDCs. The $IC_{50}$ values were obtained by a non-linear curve fit (Table 11). The tested anti-TSLP antibodies can block TSLP from binding the human mDCs from peripheral blood.

Example 9. Human TSLP Binding Enzyme-Linked Immunosorbent Assay (ELISA)

The binding affinity of anti-TSLP monoclonal antibodies (mAbs) to human TSLP, cyno TSLP, mouse TSLP, and human IL-7 was assessed using an indirect ELISA assay. A 96 well half area plate was coated with 2 μg/mL of recombinant protein (human TSLP, cyno TSLP, mouse TSLP, human IL-7) overnight at 4° C. The next day, the plates were washed three times with ELISA wash buffer and blocked with ELISA assay diluent B (BioLegend) for one hour at room temperature (RT). Plates were then washed three times with ELISA wash buffer, afterwards anti-TSLP antibodies (AB-2a, AB-2b, the Reference Antibody, IgG1 and IgG2 isotype controls) were added at the indicated concentrations and incubated at RT for one hour. Antibody binding was assessed using an 8-point titration curve in triplicates (1:3 serial dilution starting at 10 pg/mL). The plate was washed three times with ELISA wash buffer, and HRP-conjugated anti-human IgG-HRP secondary antibody (Jackson ImmunoResearch Laboratories, Inc.) was added to wells at a 1:5000 dilution in 1× ELISA assay diluent. Secondary antibody was added to detect binding of the primary antibody to the antigen. The plate was incubated for 30 minutes at room temperature with the secondary detection antibody, then the plates were washed three times with ELISA wash buffer and developed with TMB substrate solution (Invitrogen, Waltham, MA). The HRP enzymatic reaction was stopped after about 1 minute with acidic stop solution (Invitrogen), and the absorbance at 450 nm on a Biotek plate reader.

Figure 10A:
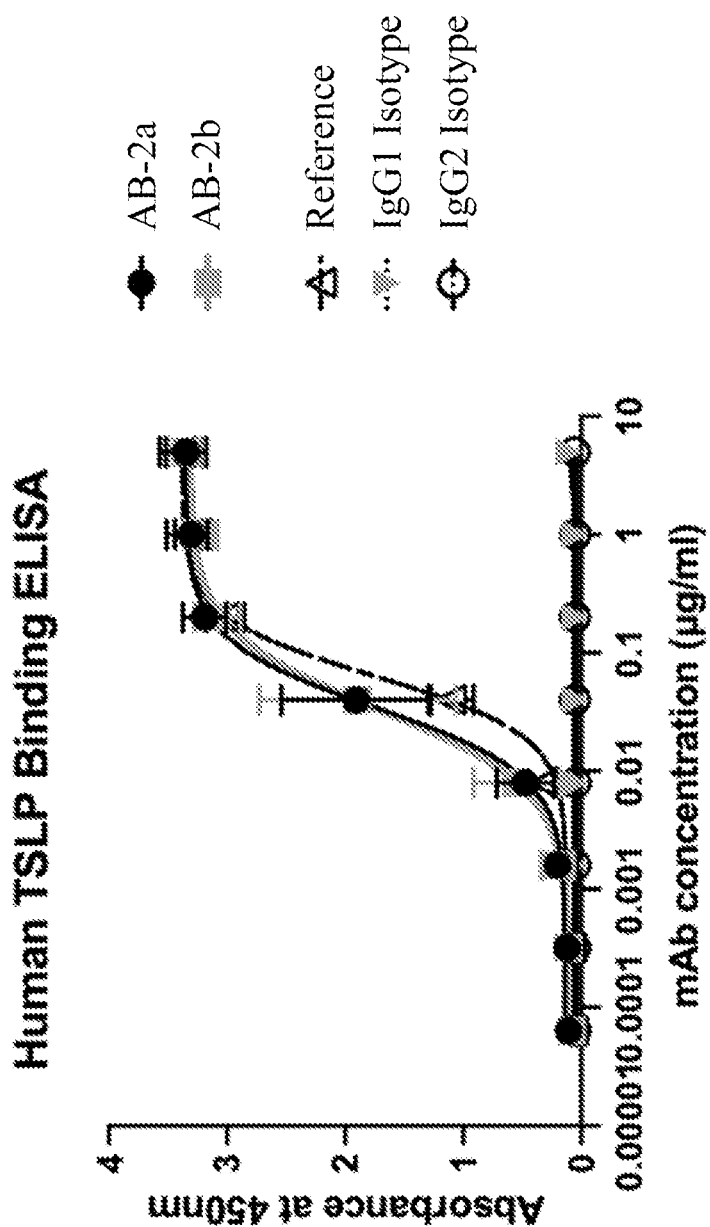
Figure 10B:
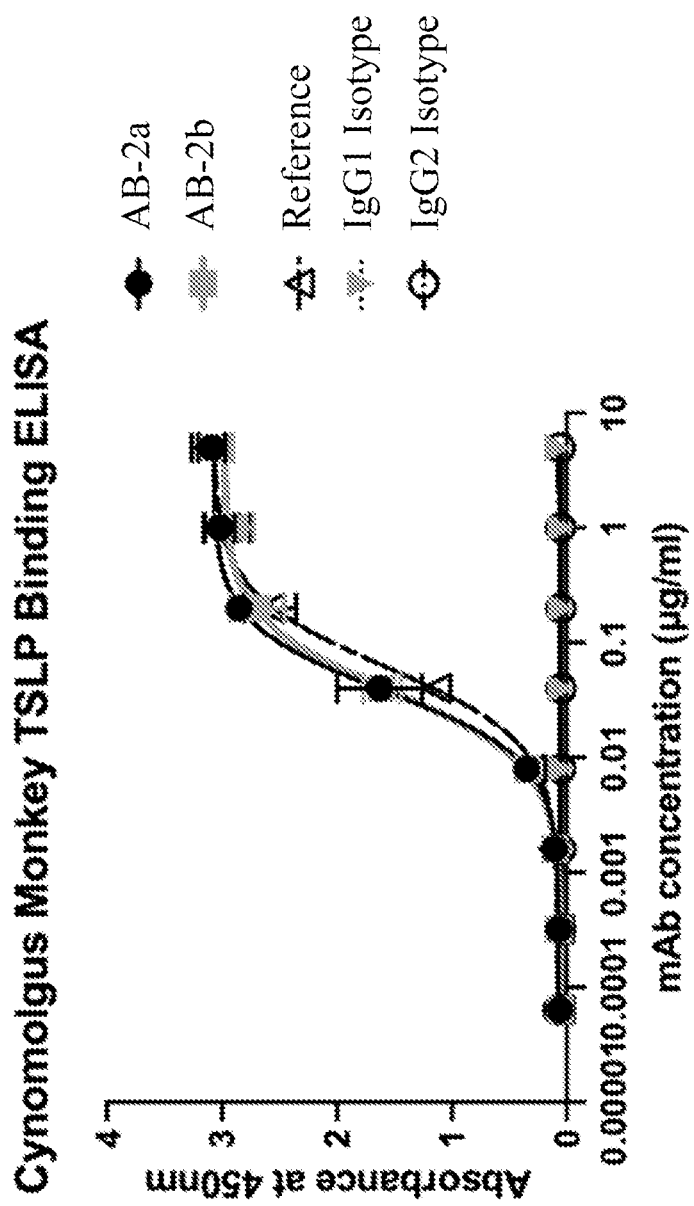

The $EC_{50}$ values were calculated using Graphpad Prism 9.2.0 by fitting a four-parameter non-linear regression curve to the average absorbance values of three technical replicates per concentration with three independent experiments. Curve fitting was set up as reported in Graphpad Prism 9.2.0 software documentation. Results for human TSLP are displayed as $EC_{50}$, $EC_{80}$, $EC_{90}$ (µg/mL) with 95% confidence intervals (Table 12, FIG. 10A). N=4 independent experiments with 3 technical replicates. Results for cyno TSLP are displayed as $EC_{50}$, $EC_{80}$, $EC_{90}$ (µg/mL) with 95% confidence intervals (Table 12, FIG. 10B). N=3 independent experiments with 3 technical replicates.

Figure 10C:
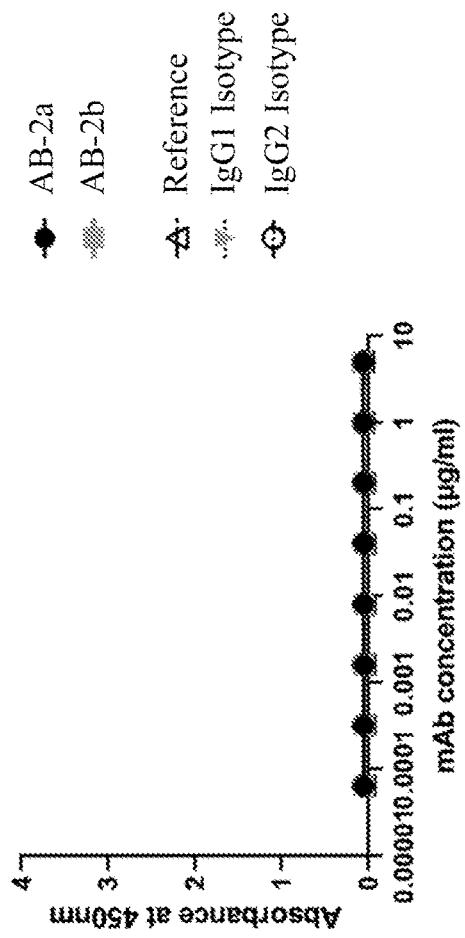
Figure 10D:
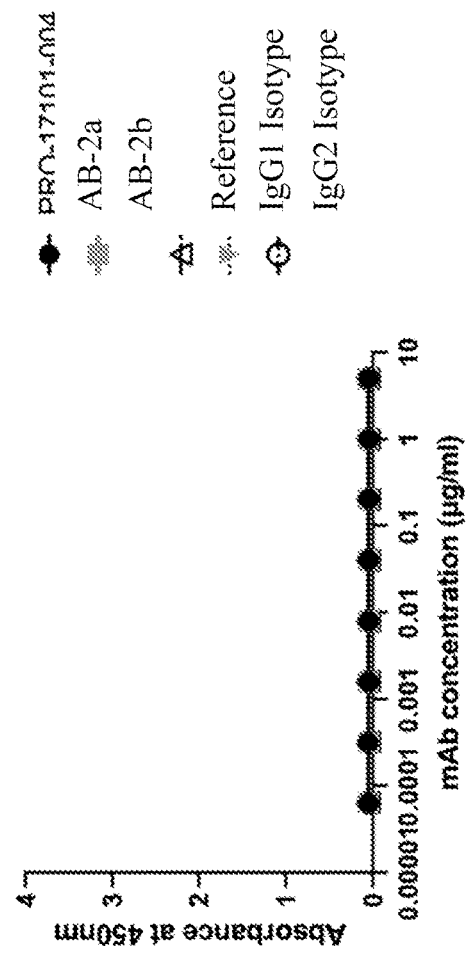

Results for mouse TSLP and human IL-7 are displayed in FIG. 10C and FIG. OD, respectively. N=3 independent experiments with 3 technical replicates. Results are displayed as mean with SEM. N=3 independent experiments with 3 technical replicates. The ELISA results of AB-2a, AB-2b and the Reference Antibody demonstrate a lack of binding to mouse TSLP cytokine and human IL-7.

Example 10. Human (TSLPR IL-7Rα) Ba F3 Assay

Materials

Antibodies: (1) AB-2a (Lot #REQ0000500); (2) AB-2b (lot #1098-260922-02, production #GFA-002); (3) the Reference Antibody (lot #1143666, SN:100000005714, GTIN: 00355513112017); (4) IgG1 isotype (BioLegend, Cat #403502, Lot #B372653); (5) IgG2 isotype (BioLegend, Cat #400264, Lot #B341585).

Antigens: (1) Human TSLP (AGN-000143, ACRO Biosystems, Newark, DE); (2) Human TSLP, His Tag (Cat #TSP-H52Hb, Lot #2671b-2158F1-12T).

Cell line: BA/F3 cell line with STAT5 Reporter (Luc) (BPS Bioscience Inc., Cat No: 79772 Lot No: 200504 #18), transfected with hTSLPR/hIL-7Rα expression vector from GenScript Biotech (Piscataway, New Jersey).

Assay plates: Cell culture microplate, 96-well, PS, F-bottom, white, CELLSTAR© with lid (Greiner bio-one, Kremsmünster, Austria, Cat no: 655083, Lot no: E211036T).

Assay Medium: RPMI+ GlutaMAX (lx) (RPMI Medium 1640, Gibco, Billings, Montana, Cat no: 61870-036, Lot No: 2472360)+10% FBS (R&D Systems, Minneapolis, MN, Cat no: 512495H Lot no: A21012)+1% Penicillin-Streptomycin (Gibco, Cat no: 15140-122, Lot no: 2441835).

Luciferase reagent: One-step Luciferase Assay system (BPS Bioscience Inc., Cat No: 78262, Lot No:230201).

To assess functional potency of anti-TSLP mAbs in vitro, a Ba/F3 reporter cell line expressing human TSLP receptor and IL-7Rα with a luciferase readout was created. Human TSLP receptor (TSLPR) forms a heterodimeric complex with the IL-7Rα (CD127) and signals through STAT5 after binding of TSLP. A hIL-7Rα-P2A-hTSLPR construct was synthesized and cloned into a pcDNA3.1(+)/Hygro plasmid. The plasmid was transfected into the Ba/F3-STAT5-Luc cell line, which contains a STAT5-inducible luciferase reporter, to create a stable cell line expressing hTSLPR and hIL-7Rα. Ba/F3-STAT5-Luciferase cells stably expressing hTSLPR/hIL-7R were maintained in RPMI-1640 with Glutamax medium containing 10% fetal bovine serum (FBS), 1% penicillin-streptomycin, 10 ng/mL hTSLP, and 400 µg/mL hygromycin selection antibiotic, cells were deprived of hTSLP for 24 hours prior to use in the assay. The Ba/F3-STAT5-hTSLPR/hIL-7R-Luc cells had a dose dependent response to hTSLP, 1 ng/mL hTSLP was used as a final concentration for this assay.

In a 96-well cell culture microplate, serial dilutions of 4× anti-TSLP antibodies in 25 µl of assay media (RPMI-1640+ 10% FBS+1% P/S) were pre-incubated with 25 µl of 4 ng/mL (4×) hTSLP cytokine at 37° C. for 30 minutes. The cytokines used in this assay were purchased from a single source commercial vendor and reconstituted based on vendor instructions. Afterwards 20,000 Ba/F3-STAT5-hTSLPR/ hIL-7R-Luc cells in 50 µl of cell media were plated and incubated with 4× antibodies (each of AB-2a, AB-2b, the Reference Antibody, IgG1 isotype control, and IgG2 isotype control was added at 4× concentration) and TSLP cytokine for four hours. After four hours, 100 µl of luciferase reagent was added to each well of the plate and rocked gently for 15 minutes at room temperature (RT), protected from light. Luminescence was measured with a luminometer (Envision) within one hour of luciferase reagent addition.

Figure 11A:
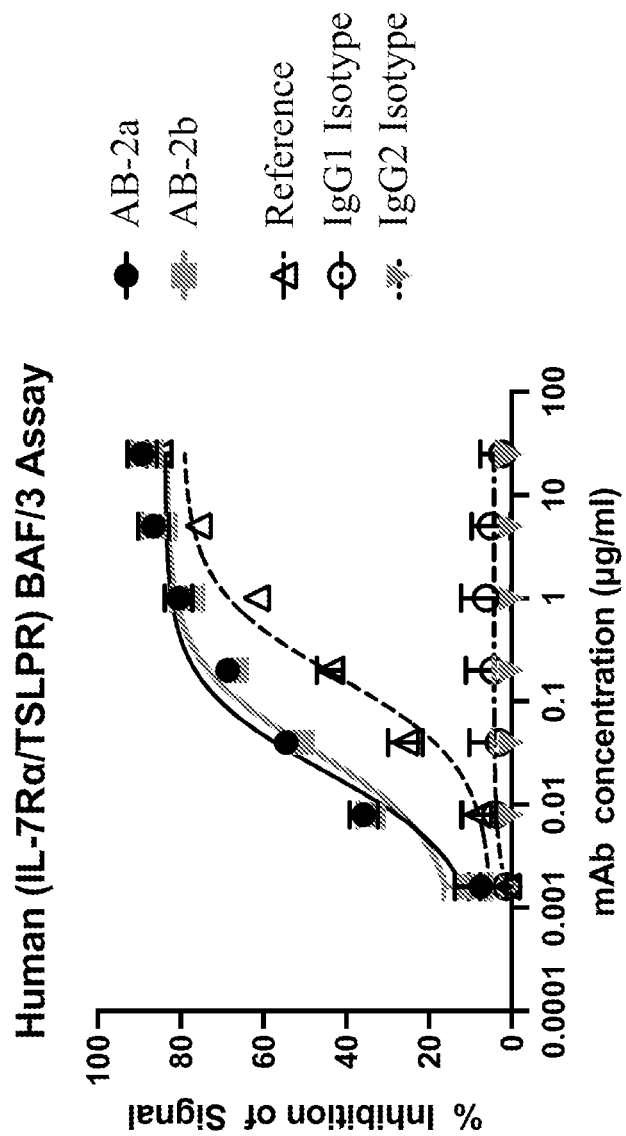

Graphpad Prism 9.2.0 was used to analyze data. Average luminescence values of three technical replicates per concentration from three independent experiments were baseline corrected and transformed to percent inhibition of signal. $IC_{50}$ values were obtained by non-linear regression curve fitting, set up as reported in Graphpad Prism 9.2.0 software documentation. N=3 independent experiments with 3 technical replicates. Functional potency in blocking receptor binding to hTSLP cytokine are displayed as $IC_{50}$ (pg/mL) with 95% confidence intervals. As shown in FIG. 11A and Table 13, AB-2b has improved functional potency compared to the Reference Antibody.

Example 11. Cyno (TSLPR IL-7Rα) Ba F3 Assay

Materials

Antibodies: (1) AB-2a (Lot #REQ0000500); (2) AB-2b (lot #1098-260922-02, production #GFA-002); (3) the Reference Antibody (lot #1143666, SN:100000005714, GTIN: 00355513112017); (4) IgG1 isotype (BioLegend, Cat #403502, Lot #B372653); (5) IgG2 isotype (BioLegend, Cat #400264, Lot #B341585).

Antigens: (1) Cyno TSLP (AGN-000144, ACRO Biosystems); (2) Cyno TSLP His Tag (Cat #TSP-C52H8, Lot #3509-2182F1-12T).

Cell line: Ba/F3 cell line with STAT5 Reporter (Luc) (BPS Bioscience Inc., Cat No: 79772 Lot No: 200504 #18), transfected with cyno TSLPR/cyno IL-7Rα expression vector from GenScript Biotech.

Assay plates: Cell culture microplate, 96-well, PS, F-bottom, white, CELLSTAR© with lid (Greiner bio-one, Kremsmünster, Austria, Cat no: 655083, Lot no: E211036T).

Assay Medium: RPMI+ GlutaMAX (1×) (RPMI Medium 1640, Gibco, Billings, Montana, Cat no: 61870-036, Lot No: 2472360)+10% FBS (R&D Systems, Minneapolis, MN, Cat no: 512495H Lot no: A21012)+1% Penicillin-Streptomycin (Gibco, Cat no: 15140-122, Lot no: 2441835).

Luciferase reagent: One-step Luciferase Assay system (BPS Bioscience Inc., Cat No: 78262, Lot No:230201).

To assess functional potency of anti-TSLP mAbs in vitro a Ba/F3 reporter cell line expressing cynomolgus monkey TSLP receptor and IL-7Rα with a luciferase readout was created. TSLP receptor (TSLPR) forms a heterodimeric complex with the IL-7Rα (CD127) and signals through STAT5 after binding of TSLP. A cynoIL-7Rα-P2A-cynoTSLPR construct was synthesized and cloned into a pcDNA3.1(+)/Hygro plasmid. The plasmid was transfected into the Ba/F3-STAT5-Luc cell line, which contains a STS5-inducible luciferase reporter, to create a stable cell line expressing cynomolgus TSLPR and cynoIL-7Rα. Ba/F3-STAT5-Luciferase cells expressing cynoTSLPR/cynoIL-7R were maintained in RPMI-1640 with Glutamax medium containing 10% fetal bovine serum (FBS), 1% penicillin-streptomycin, 10 ng/mL cynoTSLP, 10 ng/mL hIL-7, and 200 µg/mL hygromycin selection antibiotic, cells were deprived of cynoTSLP for 24 hours prior to use in the assay. The Ba/F3-STAT5-cynoTSLPR/cynoIL-7R-Luc cells had a dose dependent response to cynoTSLP, 1 ng/mL cynoTSLP was used as a final concentration for this assay.

In a 96-well cell culture microplate, serial dilutions of 4× anti-TSLP antibodies in 25 µl of assay media (RPMI-1640+ 10% FBS+1% penicillin-streptomycin) were pre-incubated with 25 µl of 4 ng/mL (4×) cynoTSLP cytokine at 37° C. for 30 minutes. Afterwards 20,000 Ba/F3-STAT5-cynoTSLPR/cynoIL-7R-Luc cells in 50 µl of cell media were plated and incubated with antibodies and cynoTSLP cytokine for four hours. After four hours, 100 µl of luciferase reagent was added to each well of the plate and rocked gently for 15 minutes at room temperature (RT), protected from light. Luminescence was measured with a luminometer (Envision) within one hour of luciferase reagent addition.

Figure 11B:
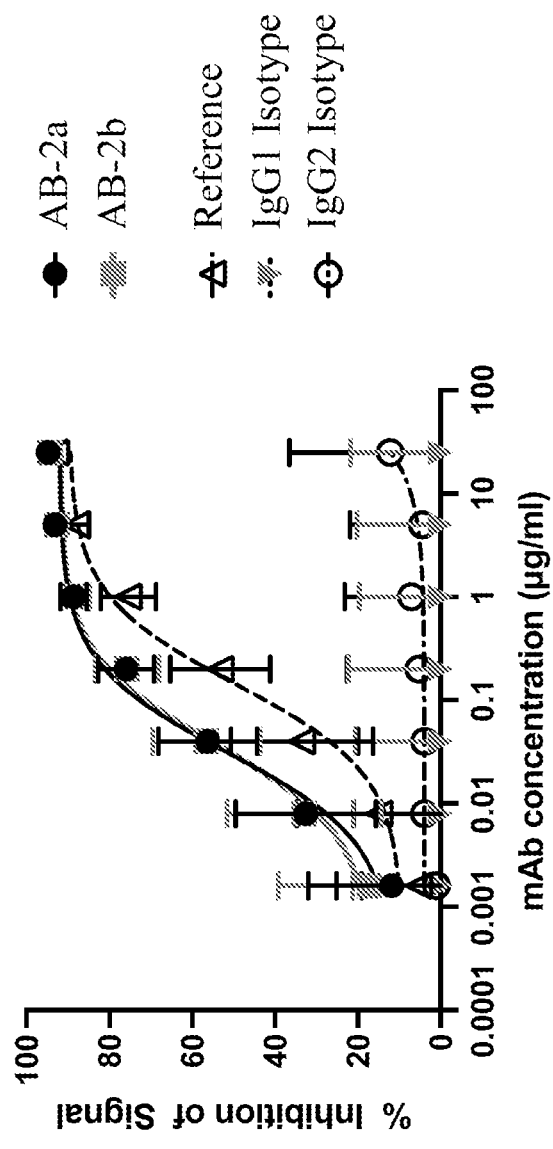

Graphpad Prism 9.2.0 was used to analyze data. Average luminescence values of three technical replicates per concentration with three independent experiments were baseline corrected and transformed to percent inhibition of signal. $IC_{50}$ values were obtained by non-linear regression curve fitting, set up as reported in Graphpad Prism 9.2.0 software documentation. Functional potency in blocking receptor binding to cynoTSLP cytokine are displayed as $IC_{50}$ (µg/mL) with 95% confidence intervals. As shown in FIG. 11B and Table 13, AB-2b can block cynoTSLP and prevent signaling through the TSLPR/IL-7Rα complex. AB-2b has improved functional potency compared to the Reference Antibody.

TABLE 1

$V_H$ Amino Acid Sequences

| Name | SEQ ID | Amino Acid Sequence |
|---|---|---|
| Consensus | NO: 2 | QMQLVESGGGVVQPGRSLRLSCAASGFTFRTYGMHWVRQAPGKGLEWVAVX$_1$X$_2$YX$_3$GX$_4$X$_5$X$_6$HYADSVKGRFTITRDNSKNTLNLQMNSLRAEDTAVYYCX$_7$RX$_8$PQWEX$_9$X$_{10}$X$_{11}$EX$_{12}$X$_{13}$DX$_{14}$WGQGTMVTVSS |
| Reference | NO: 3 | QMQLVESGGGVVQPGRSLRLSCAASGFTFRTYGMHWVRQAPGKGLEWVAVIWYDGSNKHYADSVKGRFTITRDNSKNTLNLQMNSLRAEDTAVYYCARAPQWELVHEAFDIWGQGTMVTVSS |
| AB-1 | NO: 4 | QMQLVESGGGVVQPGRSLRLSCAASGFTFRTYGMHWVRQAPGKGLEWVAVVWYSGSYTHYADSVKGRFTITRDNSKNTLNLQMNSLRAEDTAVYYCSRSPQWEDIFEAMDIWGQGTMVTVSS |
| AB-2 | NO: 5 | QMQLVESGGGVVQPGRSLRLSCAASGFTFRTYGMHWVRQAPGKGLEWVAVVWYDGSYTHYADSVKGRFTITRDNSKNTLNLQMNSLRAEDTAVYYCARSPQWEEIFEAMDIWGQGTMVTVSS |
| AB-3 | NO: 6 | QMQLVESGGGVVQPGRSLRLSCAASGFTFRTYGMHWVRQAPGKGLEWVAVIWYDGTYTHYADSVKGRFTITRDNSKNTLNLQMNSLRAEDTAVYYCARSPQWESIFEAFDIWGQGTMVTVSS |
| AB-4 | NO: 7 | QMQLVESGGGVVQPGRSLRLSCAASGFTFRTYGMHWVRQAPGKGLEWVAVIWYSGSDTHYADSVKGRFTITRDNSKNTLNLQMNSLRAEDTAVYYCARSPQWEDIFESMDVWGQGTMVTVSS |
| AB-5 | NO: 8 | QMQLVESGGGVVQPGRSLRLSCAASGFTFRTYGMHWVRQAPGKGLEWVAVVWYDGYDTHYADSVKGRFTITRDNSKNTLNLQMNSLRAEDTAVYYCSRSPQWEDIFESMDIWGQGTMVTVSS |
| AB-6 | NO: 9 | QMQLVESGGGVVQPGRSLRLSCAASGFTFRTYGMHWVRQAPGKGLEWVAVVWYDGSDIHYADSVKGRFTITRDNSKNTLNLQMNSLRAEDTAVYYCSRSPQWEDIFESMDIWGQGTMVTVSS |
| AB-7 | NO: 10 | QMQLVESGGGVVQPGRSLRLSCAASGFTFRTYGMHWVRQAPGKGLEWVAVIWYSGAYIHYADSVKGRFTITRDNSKNTLNLQMNSLRAEDTAVYYCSRSPQWEDIFEAMDIWGQGTMVTVSS |

TABLE 1-continued

V_H Amino Acid Sequences

| Name | SEQ ID | Amino Acid Sequence |
|---|---|---|
| AB-8 | NO: 11 | QMQLVESGGGVVQPGRSLRLSCAASGFTFRTYGMHWVRQAPGKGLEWVAVIWYDGSYTHYADSVKGRFTITRDNSKNTLNLQMNSLRAEDTAVYYCARSPQWEDIFEAFDIWGQGTMVTVSS |
| AB-9 | NO: 12 | QMQLVESGGGVVQPGRSLRLSCAASGFTFRTYGMHWVRQAPGKGLEWVAVIWYDGSYTHYADSVKGRFTITRDNSKNTLNLQMNSLRAEDTAVYYCARSPQWESIFEAFDIWGQGTMVTVSS |
| AB-10 | NO: 13 | QMQLVESGGGVVQPGRSLRLSCAASGFTFRTYGMHWVRQAPGKGLEWVAVIWYSGTTTHYADSVKGRFTITRDNSKNTLNLQMNSLRAEDTAVYYCSRSPQWEDIFESMDIWGQGTMVTVSS |
| AB-11 | NO: 14 | QMQLVESGGGVVQPGRSLRLSCAASGFTFRTYGMHWVRQAPGKGLEWVAVISYSGSYIHYADSVKGRFTITRDNSKNTLNLQMNSLRAEDTAVYYCTRSPQWEEVYEALDIWGQGTMVTVSS |
| AB-12 | NO: 15 | QMQLVESGGGVVQPGRSLRLSCAASGFTFRTYGMHWVRQAPGKGLEWVAVVWYDGSNTHYADSVKGRFTITRDNSKNTLNLQMNSLRAEDTAVYYCARAPQWESVHEAFDIWGQGTMVTVSS |
| AB-13 | NO: 16 | QMQLVESGGGVVQPGRSLRLSCAASGFTFRTYGMHWVRQAPGKGLEWVAVISYDGSTKHYADSVKGRFTITRDNSKNTLNLQMNSLRAEDTAVYYCARAPQWESVYEAFDIWGQGTMVTVSS |
| AB-14 | NO: 17 | QMQLVESGGGVVQPGRSLRLSCAASGFTFRTYGMHWVRQAPGKGLEWVAVIWYDGSTKHYADSVKGRFTITRDNSKNTLNLQMNSLRAEDTAVYYCARAPQWELVHEAFDIWGQGTMVTVSS |

TABLE 2

V_L Amino Acid Sequences

| Name | SEQ ID | Amino Acid Sequence |
|---|---|---|
| Consensus | NO: 18 | SYVLTQPPSVSVAPGQTARITCGGN$X_{15}$$X_{16}$G$X_{17}$$X_{18}$$X_{19}$VHWYQQKPGQAPVLVVYDDSDRPSWIPERFSGSNSGNTATLTISRGEAGDEADYYCQ$X_{20}$$X_{21}$$X_{22}$$X_{23}$$X_{24}$$X_{25}$$X_{26}$$X_{27}$VVFGGGTKLTVL |
| Reference | NO: 19 | SYVLTQPPSVSVAPGQTARITCGGNNLGSKSVHWYQQKPGQAPVLVVYDDSDRPSWIPERFSGSNSGNTATLTISRGEAGDEADYYCQVWDSSSDHVVFGGGTKLTVL |
| AB-1, 3, 8, 9 | NO: 20 | SYVLTQPPSVSVAPGQTARITCGGNNIGSKSVHWYQQKPGQAPVLVVYDDSDRPSWIPERFSGSNSGNTATLTISRGEAGDEADYYCQVWDSSSSLVVFGGGTKLTVL |
| AB-2 | NO: 21 | SYVLTQPPSVSVAPGQTARITCGGNNIGSKSVHWYQQKPGQAPVLVVYDDSDRPSWIPERFSGSNSGNTATLTISRGEAGDEADYYCQIWDSSSSLVVFGGGTKLTVL |
| AB-4 | NO: 22 | SYVLTQPPSVSVAPGQTARITCGGNYIGSFSVHWYQQKPGQAPVLVVYDDSDRPSWIPERFSGSNSGNTATLTISRGEAGDEADYYCQIYVSASRLVVFGGGTKLTVL |
| AB-5 | NO: 23 | SYVLTQPPSVSVAPGQTARITCGGNNLGSKSVHWYQQKPGQAPVLVVYDDSDRPSWIPERFSGSNSGNTATLTISRGEAGDEADYYCQVWDMSSDLVVFGGGTKLTVL |
| AB-6 | NO: 24 | SYVLTQPPSVSVAPGQTARITCGGNNIGSKSVHWYQQKPGQAPVLVVYDDSDRPSWIPERFSGSNSGNTATLTISRGEAGDEADYYCQIWDSSSDHVVFGGGTKLTVL |
| AB-7 | NO: 25 | SYVLTQPPSVSVAPGQTARITCGGNNLGSYSVHWYQQKPGQAPVLVVYDDSDRPSWIPERFSGSNSGNTATLTISRGEAGDEADYYCQVWDMSSSLVVFGGGTKLTVL |
| AB-10 | NO: 26 | SYVLTQPPSVSVAPGQTARITCGGNNIGSKNVHWYQQKPGQAPVLVVYDDSDRPSWIPERFSGSNSGNTATLTISRGEAGDEADYYCQVWDSSDFLVVFGGGTKLTVL |
| AB-11 | NO: 27 | SYVLTQPPSVSVAPGQTARITCGGNNIGSFSVHWYQQKPGQAPVLVVYDDSDRPSWIPERFSGSNSGNTATLTISRGEAGDEADYYCQVWSSTSRHVVFGGGTKLTVL |
| AB-12 | NO: 28 | SYVLTQPPSVSVAPGQTARITCGGNNIGRFSVHWYQQKPGQAPVLVVYDDSDRPSWIPERFSGSNSGNTATLTISRGEAGDEADYYCQVWVSTSDKVVFGGGTKLTVL |
| AB-13 | NO: 29 | SYVLTQPPSVSVAPGQTARITCGGNNLGSFSVHWYQQKPGQAPVLVVYDDSDRPSWIPERFSGSNSGNTATLTISRGEAGDEADYYCQVWDSSEDLVVFGGGTKLTVL |
| AB-14 | NO: 30 | SYVLTQPPSVSVAPGQTARITCGGNNIGSKNVHWYQQKPGQAPVLVVYDDSDRPSWIPERFSGSNSGNTATLTISRGEAGDEADYYCQVWDESSDEVVFGGGTKLTVL |

TABLE 3

CDR Amino Acid Sequences as Determined by ImMunoGeneTics (IMGT) Numbering

| Name | SEQ ID | Amino Acid Sequence |
|---|---|---|
| HCDR1 | | |
| Consensus, Reference, AB-1-14 | NO: 31 | GFTFRTYG |
| HCDR2 | | |
| Consensus | NO: 32 | $X_1X_2YX_3GX_4X_5X_6$ |
| Reference | NO: 33 | IWYDGSNK |
| AB-1 | NO: 34 | VWYSGSYT |
| AB-2 | NO: 35 | VWYDGSYT |
| AB-3 | NO: 36 | IWYDGTYT |
| AB-4 | NO: 37 | IWYSGSDT |
| AB-5 | NO: 38 | VWYDGYDT |
| AB-6 | NO: 39 | VWYDGSDI |
| AB-7 | NO: 40 | IWYSGAYI |
| AB-8, 9 | NO: 41 | IWYDGSYT |
| AB-10 | NO: 42 | IWYSGTTT |
| AB-11 | NO: 43 | ISYSGSYI |
| AB-12 | NO: 44 | VWYDGSNT |
| AB-13 | NO: 45 | ISYDGSTK |
| AB-14 | NO: 46 | IWYDGSTK |
| HCDR3 | | |
| Consensus | NO: 47 | $X_7RX_8PQWEX_9X_{10}X_{11}EX_{12}X_{13}DX_{14}$ |
| Reference, AB-14 | NO: 48 | ARAPQWELVHEAFDI |
| AB-1, 7 | NO: 49 | SRSPQWEDIFEAMDI |
| AB-2 | NO: 50 | ARSPQWEEIFEAMDI |
| AB-3, 9 | NO: 51 | ARSPQWESIFEAFDI |
| AB-4 | NO: 52 | ARSPQWEDIFESMDV |
| AB-5, 6, 10 | NO: 53 | SRSPQWEDIFESMDI |
| AB-8 | NO: 54 | ARSPQWEDIFEAFDI |
| AB-11 | NO: 55 | TRSPQWEEVYEALDI |
| AB-12 | NO: 56 | ARAPQWESVHEAFDI |
| AB-13 | NO: 57 | ARAPQWESVYEAFDI |
| LCDR1 | | |
| Consensus | NO: 58 | $X_{15}X_{16}GX_{17}X_{18}X_{19}$ |
| Reference, AB-5 | NO: 59 | NLGSKS |
| AB-1-3, 6, 8, 9 | NO: 60 | NIGSKS |
| AB-4 | NO: 61 | YIGSFS |
| AB-7 | NO: 62 | NLGSYS |
| AB-10, 14 | NO: 63 | NIGSKN |
| AB-11 | NO: 64 | NIGSFS |
| AB-12 | NO: 65 | NIGRFS |
| AB-13 | NO: 66 | NLGSFS |
| LCDR2 | | |
| Consensus, Reference, AB-1-14 | | DDS |
| LCDR3 | | |
| Consensus | NO: 68 | $QX_{20}X_{21}X_{22}X_{23}X_{24}X_{25}X_{26}X_{27}VV$ |
| Reference | NO: 69 | QVWDSSSDHVV |
| AB-1, 3, 8, 9 | NO: 70 | QVWDSSSSLVV |
| AB-2 | NO: 71 | QIWDSSSSLVV |
| AB-4 | NO: 72 | QIYVSASRLVV |
| AB-5 | NO: 73 | QVWDMSSDLVV |
| AB-6 | NO: 74 | QIWDSSSDHVV |
| AB-7 | NO: 75 | QVWDMSSSLVV |
| AB-10 | NO: 76 | QVWDSSDFLVV |
| AB-11 | NO: 77 | QVWSSTSRHVV |
| AB-12 | NO: 78 | QVWVSTSDKVV |
| AB-13 | NO: 79 | QVWDSSEDLVV |
| AB-14 | NO: 80 | QVWDESSDEVV |

TABLE 4

Heavy Chain Amino Acid Sequences

| Name | SEQ ID | Amino Acid Sequence |
|---|---|---|
| Reference | NO: 81 | QMQLVESGGGVVQPGRSLRLSCAASGFTFRTYGMHWVRQAPGKGLEWVAVIWYD GSNKHYADSVKGRFTITRDNSKNTLNLQMNSLRAEDTAVYYCARAPQWELVHEA FDIWGQGTMVTVSSASTKGPSVFPLAPCSRSTSESTAALGCLVKDYFPEPVTVS WNSGALTSGVHTFPAVLQSSGLYSLSSVVTVPSSNFGTQTYTCNVDHKPSNTKV DKTVERKCCVECPPCPAPPVAGPSVFLFPPKPKDTLMISRTPEVTCVVVDVSHE DPEVQFNWYVDGVEVHNAKTKPREEQFNSTFRVVSVLTVVHQDWLNGKEYKCKV |

TABLE 4-continued

Heavy Chain Amino Acid Sequences

| Name | SEQ ID | Amino Acid Sequence |
|---|---|---|
| | | SNKGLPAPIEKTISKTKGQPREPQVYTLPPSREEMTKNQVSLTCLVKGFYPSDI<br>AVEWESNGQPENNYKTTPPMLDSDGSFFLYSKLTVDKSRWQQGNVFSCSVMHEA<br>LHNHYTQKSLSLSPGK |
| AB-1a | NO: 91 | QMQLVESGGGVVQPGRSLRLSCAASGFTFRTYGMHWVRQAPGKGLEWVAVVWYS<br>GSYTHYADSVKGRFTITRDNSKNTLNLQMNSLRAEDTAVYYCSRSPQWEDIFEA<br>MDIWGQGTMVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKV<br>DKRVEPKSCDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |
| AB-2a | NO: 92 | QMQLVESGGGVVQPGRSLRLSCAASGFTFRTYGMHWVRQAPGKGLEWVAVVWYD<br>GSYTHYADSVKGRFTITRDNSKNTLNLQMNSLRAEDTAVYYCARSPQWEEIFEA<br>MDIWGQGTMVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKV<br>DKRVEPKSCDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |
| AB-3a | NO: 93 | QMQLVESGGGVVQPGRSLRLSCAASGFTFRTYGMHWVRQAPGKGLEWVAVIWYD<br>GTYTHYADSVKGRFTITRDNSKNTLNLQMNSLRAEDTAVYYCARSPQWESIFEA<br>FDIWGQGTMVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKV<br>DKRVEPKSCDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |
| AB-4a | NO: 94 | QMQLVESGGGVVQPGRSLRLSCAASGFTFRTYGMHWVRQAPGKGLEWVAVIWYS<br>GSDTHYADSVKGRFTITRDNSKNTLNLQMNSLRAEDTAVYYCARSPQWEDIFEA<br>MDVWGQGTMVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKV<br>DKRVEPKSCDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |
| AB-5a | NO: 95 | QMQLVESGGGVVQPGRSLRLSCAASGFTFRTYGMHWVRQAPGKGLEWVAVVWYD<br>GYDTHYADSVKGRFTITRDNSKNTLNLQMNSLRAEDTAVYYCSRSPQWEDIFES<br>MDIWGQGTMVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKV<br>DKRVEPKSCDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |
| AB-6a | NO: 96 | QMQLVESGGGVVQPGRSLRLSCAASGFTFRTYGMHWVRQAPGKGLEWVAVVWYD<br>GSDIHYADSVKGRFTITRDNSKNTLNLQMNSLRAEDTAVYYCSRSPQWEDIFES<br>MDIWGQGTMVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKV<br>DKRVEPKSCDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |
| AB-7a | NO: 97 | QMQLVESGGGVVQPGRSLRLSCAASGFTFRTYGMHWVRQAPGKGLEWVAVIWYS<br>GAYIHYADSVKGRFTITRDNSKNTLNLQMNSLRAEDTAVYYCSRSPQWEDIFEA<br>MDIWGQGTMVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKV<br>DKRVEPKSCDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |

TABLE 4-continued

Heavy Chain Amino Acid Sequences

| Name | SEQ ID | Amino Acid Sequence |
|---|---|---|
| AB-8a | NO: 98 | QMQLVESGGGVVQPGRSLRLSCAASGFTFRTYGMHWVRQAPGKGLEWVAVIWYD
GSYTHYADSVKGRFTITRDNSKNTLNLQMNSLRAEDTAVYYCARSPQWEDIFEA
FDIWGQGTMVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSV
MHEALHNHYTQKSLSLSPGK |
| AB-9a | NO: 99 | QMQLVESGGGVVQPGRSLRLSCAASGFTFRTYGMHWVRQAPGKGLEWVAVIWYD
GSYTHYADSVKGRFTITRDNSKNTLNLQMNSLRAEDTAVYYCARSPQWESIFEA
FDIWGQGTMVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSV
MHEALHNHYTQKSLSLSPGK |
| AB-10a | NO: 100 | QMQLVESGGGVVQPGRSLRLSCAASGFTFRTYGMHWVRQAPGKGLEWVAVIWYS
GTTTHYADSVKGRFTITRDNSKNTLNLQMNSLRAEDTAVYYCSRSPQWEDIFES
MDIWGQGTMVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSV
MHEALHNHYTQKSLSLSPGK |
| AB-11a | NO: 101 | QMQLVESGGGVVQPGRSLRLSCAASGFTFRTYGMHWVRQAPGKGLEWVAVISYS
GSYIHYADSVKGRFTITRDNSKNTLNLQMNSLRAEDTAVYYCTRSPQWEEVYEA
LDIWGQGTMVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSV
MHEALHNHYTQKSLSLSPGK |
| AB-12a | NO: 102 | QMQLVESGGGVVQPGRSLRLSCAASGFTFRTYGMHWVRQAPGKGLEWVAVVWYD
GSNTHYADSVKGRFTITRDNSKNTLNLQMNSLRAEDTAVYYCARAPQWESVHEA
FDIWGQGTMVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSV
MHEALHNHYTQKSLSLSPGK |
| AB-13a | NO: 103 | QMQLVESGGGVVQPGRSLRLSCAASGFTFRTYGMHWVRQAPGKGLEWVAVISYD
GSTKHYADSVKGRFTITRDNSKNTLNLQMNSLRAEDTAVYYCARAPQWESVYEA
FDIWGQGTMVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSV
MHEALHNHYTQKSLSLSPGK |
| AB-14a | NO: 104 | QMQLVESGGGVVQPGRSLRLSCAASGFTFRTYGMHWVRQAPGKGLEWVAVIWYD
GSTKHYADSVKGRFTITRDNSKNTLNLQMNSLRAEDTAVYYCARAPQWELVHEA
FDIWGQGTMVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSV
MHEALHNHYTQKSLSLSPGK |
| AB-1b | NO: 105 | QMQLVESGGGVVQPGRSLRLSCAASGFTFRTYGMHWVRQAPGKGLEWVAVVWYS
GSYTHYADSVKGRFTITRDNSKNTLNLQMNSLRAEDTAVYYCSRSPQWEDIFEA
MDIWGQGTMVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLYITREPEVTCVVVD |

TABLE 4-continued

Heavy Chain Amino Acid Sequences

| Name | SEQ ID | Amino Acid Sequence |
|---|---|---|
| | | VSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSV
MHEALHNHYTQKSLSLSPGK |
| AB-2b | NO: 106 | QMQLVESGGGVVQPGRSLRLSCAASGFTFRTYGMHWVRQAPGKGLEWVAVVWYD
GSYTHYADSVKGRFTITRDNSKNTLNLQMNSLRAEDTAVYYCARSPQWEEIFEA
MDIWGQGTMVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLYITREPEVTCVVVD
VSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSV
MHEALHNHYTQKSLSLSPGK |
| AB-3b | NO: 107 | QMQLVESGGGVVQPGRSLRLSCAASGFTFRTYGMHWVRQAPGKGLEWVAVIWYD
GTYTHYADSVKGRFTITRDNSKNTLNLQMNSLRAEDTAVYYCARSPQWESIFEA
FDIWGQGTMVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLYITREPEVTCVVVD
VSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSV
MHEALHNHYTQKSLSLSPGK |
| AB-4b | NO: 108 | QMQLVESGGGVVQPGRSLRLSCAASGFTFRTYGMHWVRQAPGKGLEWVAVIWYS
GSDTHYADSVKGRFTITRDNSKNTLNLQMNSLRAEDTAVYYCARSPQWEDIFES
MDVWGQGTMVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLYITREPEVTCVVVD
VSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSV
MHEALHNHYTQKSLSLSPGK |
| AB-5b | NO: 109 | QMQLVESGGGVVQPGRSLRLSCAASGFTFRTYGMHWVRQAPGKGLEWVAVVWYD
GYDTHYADSVKGRFTITRDNSKNTLNLQMNSLRAEDTAVYYCSRSPQWEDIFES
MDIWGQGTMVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLYITREPEVTCVVVD
VSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSV
MHEALHNHYTQKSLSLSPGK |
| AB-6b | NO: 110 | QMQLVESGGGVVQPGRSLRLSCAASGFTFRTYGMHWVRQAPGKGLEWVAVVWYD
GSDIHYADSVKGRFTITRDNSKNTLNLQMNSLRAEDTAVYYCSRSPQWEDIFES
MDIWGQGTMVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLYITREPEVTCVVVD
VSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSV
MHEALHNHYTQKSLSLSPGK |
| AB-7b | NO: 111 | QMQLVESGGGVVQPGRSLRLSCAASGFTFRTYGMHWVRQAPGKGLEWVAVIWYS
GAYIHYADSVKGRFTITRDNSKNTLNLQMNSLRAEDTAVYYCSRSPQWEDIFEA
MDIWGQGTMVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLYITREPEVTCVVVD
VSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSV
MHEALHNHYTQKSLSLSPGK |
| AB-8b | NO: 112 | QMQLVESGGGVVQPGRSLRLSCAASGFTFRTYGMHWVRQAPGKGLEWVAVIWYD
GSYTHYADSVKGRFTITRDNSKNTLNLQMNSLRAEDTAVYYCARSPQWEDIFEA
FDIWGQGTMVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLYITREPEVTCVVVD
VSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSV
MHEALHNHYTQKSLSLSPGK |

TABLE 4-continued

Heavy Chain Amino Acid Sequences

| Name | SEQ ID | Amino Acid Sequence |
|---|---|---|
| AB-9b | NO: 113 | QMQLVESGGGVVQPGRSLRLSCAASGFTFRTYGMHWVRQAPGKGLEWVAVIWYD<br>GSYTHYADSVKGRFTITRDNSKNTLNLQMNSLRAEDTAVYYCARSPQWESIFEA<br>FDIWGQGTMVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKV<br>DKRVEPKSCDKTHTCPPCPAPELLGGPSVFLFPPKPKDTLYITREPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |
| AB-10b | NO: 114 | QMQLVESGGGVVQPGRSLRLSCAASGFTFRTYGMHWVRQAPGKGLEWVAVIWYS<br>GTTTHYADSVKGRFTITRDNSKNTLNLQMNSLRAEDTAVYYCSRSPQWEDIFES<br>MDIWGQGTMVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKV<br>DKRVEPKSCDKTHTCPPCPAPELLGGPSVFLFPPKPKDTLYITREPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |
| AB-11b | NO: 115 | QMQLVESGGGVVQPGRSLRLSCAASGFTFRTYGMHWVRQAPGKGLEWVAVISYS<br>GSYIHYADSVKGRFTITRDNSKNTLNLQMNSLRAEDTAVYYCTRSPQWEEVYEA<br>LDIWGQGTMVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKV<br>DKRVEPKSCDKTHTCPPCPAPELLGGPSVFLFPPKPKDTLYITREPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |
| AB-12b | NO: 116 | QMQLVESGGGVVQPGRSLRLSCAASGFTFRTYGMHWVRQAPGKGLEWVAVVWYD<br>GSNTHYADSVKGRFTITRDNSKNTLNLQMNSLRAEDTAVYYCARAPQWESVHEA<br>FDIWGQGTMVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKV<br>DKRVEPKSCDKTHTCPPCPAPELLGGPSVFLFPPKPKDTLYITREPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |
| AB-13b | NO: 117 | QMQLVESGGGVVQPGRSLRLSCAASGFTFRTYGMHWVRQAPGKGLEWVAVISYD<br>GSTKHYADSVKGRFTITRDNSKNTLNLQMNSLRAEDTAVYYCARAPQWESVHEA<br>FDIWGQGTMVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKV<br>DKRVEPKSCDKTHTCPPCPAPELLGGPSVFLFPPKPKDTLYITREPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |
| AB-14b | NO: 118 | QMQLVESGGGVVQPGRSLRLSCAASGFTFRTYGMHWVRQAPGKGLEWVAVIWYD<br>GSTKHYADSVKGRFTITRDNSKNTLNLQMNSLRAEDTAVYYCARAPQWELVHEA<br>FDIWGQGTMVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKV<br>DKRVEPKSCDKTHTCPPCPAPELLGGPSVFLFPPKPKDTLYITREPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |

TABLE 5

Light Chain Amino Acid Sequences

| Name | SEQ ID | Amino Acid Sequence |
|---|---|---|
| Reference | NO: 82 | SYVLTQPPSVSVAPGQTARITCGGNNLGSKSVHWYQQKPGQAPVLVVYDDSDRPS<br>WIPERFSGSNSGNTATLTISRGEAGDEADYYCQVWDSSSDHVVFGGGTKLTVLGQ<br>PKAAPSVTLFPPSSEELQANKATLVCLISDFYPGAVTVAWKADSSPVKAGVETTT<br>PSKQSNNKYAASSYLSLTPEQWKSHRSYSCQVTHEGSTVEKTVAPTECS |

TABLE 5-continued

Light Chain Amino Acid Sequences

| Name | SEQ ID | Amino Acid Sequence |
|---|---|---|
| AB-1, 3, 8, 9 | NO: 119 | SYVLTQPPSVSVAPGQTARITCGGNNIGSKSVHWYQQKPGQAPVLVVYDDSDRPS<br>WIPERFSGSNSGNTATLTISRGEAGDEADYYCQVWDSSSSLVVFGGGTKLTVLGQ<br>PKAAPSVTLFPPSSEELQANKATLVCLISDFYPGAVTVAWKADSSPVKAGVETTT<br>PSKQSNNKYAASSYLSLTPEQWKSHRSYSCQVTHEGSTVEKTVAPTECS |
| AB-2 | NO: 120 | SYVLTQPPSVSVAPGQTARITCGGNNIGSKSVHWYQQKPGQAPVLVVYDDSDRPS<br>WIPERFSGSNSGNTATLTISRGEAGDEADYYCQIWDSSSSLVVFGGGTKLTVLGQ<br>PKAAPSVTLFPPSSEELQANKATLVCLISDFYPGAVTVAWKADSSPVKAGVETTT<br>PSKQSNNKYAASSYLSLTPEQWKSHRSYSCQVTHEGSTVEKTVAPTECS |
| AB-4 | NO: 121 | SYVLTQPPSVSVAPGQTARITCGGNYIGSFSVHWYQQKPGQAPVLVVYDDSDRPS<br>WIPERFSGSNSGNTATLTISRGEAGDEADYYCQIYVSASRLVVFGGGTKLTVLGQ<br>PKAAPSVTLFPPSSEELQANKATLVCLISDFYPGAVTVAWKADSSPVKAGVETTT<br>PSKQSNNKYAASSYLSLTPEQWKSHRSYSCQVTHEGSTVEKTVAPTECS |
| AB-5 | NO: 122 | SYVLTQPPSVSVAPGQTARITCGGNNLGSKSVHWYQQKPGQAPVLVVYDDSDRPS<br>WIPERFSGSNSGNTATLTISRGEAGDEADYYCQVWDMSSDLVVFGGGTKLTVLGQ<br>PKAAPSVTLFPPSSEELQANKATLVCLISDFYPGAVTVAWKADSSPVKAGVETTT<br>PSKQSNNKYAASSYLSLTPEQWKSHRSYSCQVTHEGSTVEKTVAPTECS |
| AB-6 | NO: 123 | SYVLTQPPSVSVAPGQTARITCGGNNIGSKSVHWYQQKPGQAPVLVVYDDSDRPS<br>WIPERFSGSNSGNTATLTISRGEAGDEADYYCQIWDSSSDHVVFGGGTKLTVLGQ<br>PKAAPSVTLFPPSSEELQANKATLVCLISDFYPGAVTVAWKADSSPVKAGVETTT<br>PSKQSNNKYAASSYLSLTPEQWKSHRSYSCQVTHEGSTVEKTVAPTECS |
| AB-7 | NO: 124 | SYVLTQPPSVSVAPGQTARITCGGNNLGSYSVHWYQQKPGQAPVLVVYDDSDRPS<br>WIPERFSGSNSGNTATLTISRGEAGDEADYYCQVWDMSSSLVVFGGGTKLTVLGQ<br>PKAAPSVTLFPPSSEELQANKATLVCLISDFYPGAVTVAWKADSSPVKAGVETTT<br>PSKQSNNKYAASSYLSLTPEQWKSHRSYSCQVTHEGSTVEKTVAPTECS |
| AB-10 | NO: 125 | SYVLTQPPSVSVAPGQTARITCGGNNIGSKNVHWYQQKPGQAPVLVVYDDSDRPS<br>WIPERFSGSNSGNTATLTISRGEAGDEADYYCQVWDSSDFLVVFGGGTKLTVLGQ<br>PKAAPSVTLFPPSSEELQANKATLVCLISDFYPGAVTVAWKADSSPVKAGVETTT<br>PSKQSNNKYAASSYLSLTPEQWKSHRSYSCQVTHEGSTVEKTVAPTECS |
| AB-11 | NO: 126 | SYVLTQPPSVSVAPGQTARITCGGNNIGSFSVHWYQQKPGQAPVLVVYDDSDRPS<br>WIPERFSGSNSGNTATLTISRGEAGDEADYYCQVWSSTSRHVVFGGGTKLTVLGQ<br>PKAAPSVTLFPPSSEELQANKATLVCLISDFYPGAVTVAWKADSSPVKAGVETTT<br>PSKQSNNKYAASSYLSLTPEQWKSHRSYSCQVTHEGSTVEKTVAPTECS |
| AB-12 | NO: 127 | SYVLTQPPSVSVAPGQTARITCGGNNIGRFSVHWYQQKPGQAPVLVVYDDSDRPS<br>WIPERFSGSNSGNTATLTISRGEAGDEADYYCQVWVSTSDKVVFGGGTKLTVLGQ<br>PKAAPSVTLFPPSSEELQANKATLVCLISDFYPGAVTVAWKADSSPVKAGVETTT<br>PSKQSNNKYAASSYLSLTPEQWKSHRSYSCQVTHEGSTVEKTVAPTECS |
| AB-13 | NO: 128 | SYVLTQPPSVSVAPGQTARITCGGNNLGSFSVHWYQQKPGQAPVLVVYDDSDRPS<br>WIPERFSGSNSGNTATLTISRGEAGDEADYYCQVWDSSEDLVVFGGGTKLTVLGQ<br>PKAAPSVTLFPPSSEELQANKATLVCLISDFYPGAVTVAWKADSSPVKAGVETTT<br>PSKQSNNKYAASSYLSLTPEQWKSHRSYSCQVTHEGSTVEKTVAPTECS |
| AB-14 | NO: 129 | SYVLTQPPSVSVAPGQTARITCGGNNIGSKNVHWYQQKPGQAPVLVVYDDSDRPS<br>WIPERFSGSNSGNTATLTISRGEAGDEADYYCQVWDESSDEVVFGGGTKLTVLGQ<br>PKAAPSVTLFPPSSEELQANKATLVCLISDFYPGAVTVAWKADSSPVKAGVETTT<br>PSKQSNNKYAASSYLSLTPEQWKSHRSYSCQVTHEGSTVEKTVAPTECS |

TABLE 6

Self-association Properties

| clone | AC-SINS Score | PSR Score |
|---|---|---|
| AB-1 | 7 | 4 |
| AB-2 | 4 | 4 |
| AB-3 | 6 | 4 |
| AB-4 | 6 | 4 |
| AB-5 | 7 | 3 |
| AB-6 | 7 | 3 |
| AB-7 | 4 | 4 |
| AB-8 | 5 | 4 |
| AB-9 | 6 | 4 |
| AB-10 | 6 | 2 |
| AB-11 | 4 | 4 |
| AB-12 | 6 | 4 |
| AB-13 | 5 | 3 |
| AB-14 | 5 | 4 |
| Reference | 5 | 2 |

TABLE 7

TSLP Binding ELISA

| clone | hTSLP $EC_{50}$ (nM) | cynoTSLP $EC_{50}$ (nM) |
|---|---|---|
| AB-1 | 0.2651 | 0.4464 |
| AB-2 | 0.2037 | 0.4019 |
| AB-3 | 0.2369 | 0.5755 |
| AB-4 | 0.2595 | 0.3314 |
| AB-5 | 0.2635 | 0.3152 |
| AB-6 | 0.3967 | 0.4243 |
| AB-7 | 0.2898 | 0.6176 |
| AB-8 | 0.2484 | 0.4624 |
| AB-9 | 0.3881 | 0.4803 |
| AB-10 | 0.2856 | 0.4352 |
| AB-11 | 0.1734 | 0.336 |
| AB-12 | 0.2912 | 0.4571 |
| AB-13 | 0.2303 | 0.448 |
| AB-14 | 0.264 | 0.3674 |
| Reference | 0.2387 | 0.5242 |

TABLE 8

TSLP Blocking ELISA

| clone | hTSLP $IC_{50}$ (nM) | cynoTSLP $IC_{50}$ (nM) |
|---|---|---|
| AB-1 | 0.1693 | 0.1782 |
| AB-2 | 0.29 | 0.3181 |
| AB-3 | 0.2318 | 0.2574 |
| AB-4 | 0.1704 | 0.2017 |
| AB-5 | 0.2457 | 0.2045 |
| AB-6 | 0.2224 | 0.2492 |
| AB-7 | 0.1624 | 0.2051 |
| AB-8 | 0.1995 | 0.2041 |
| AB-9 | 0.2265 | 0.2597 |
| AB-10 | 0.2505 | 0.2379 |
| AB-11 | 0.2427 | 0.287 |
| AB-12 | 0.29 | 0.2538 |
| AB-13 | 0.2232 | 0.2449 |
| AB-14 | 0.1865 | 0.2293 |
| Reference | 0.2939 | 0.2796 |

TABLE 9

KinExA Binding Affinities

| | hTSLP Binding | | | cynoTSLP Binding | | |
|---|---|---|---|---|---|---|
| clone | $K_D$ (pM) | $k_a$ (1/Ms) | $k_d$ (1/s) | $K_D$ (pM) | $k_a$ (1/Ms) | $k_d$ (1/s) |
| AB-1 | 0.208 | 2.66E+07 | 5.53E−06 | 3.28 | 1.34E+07 | 4.41E−05 |
| AB-2 | 0.123 | 2.38E+07 | 2.93E−06 | 1.25 | 5.25E+07 | 6.56E−05 |
| AB-3 | 0.302 | 1.65E+07 | 4.99E−06 | 1.72 | 1.98E+07 | 3.40E−06 |
| AB-4 | 0.208 | 2.72E+07 | 5.66E−06 | 0.929 | 3.06E+07 | 2.84E−05 |
| AB-5 | 0.14 | 5.83E+07 | 8.17E−06 | 2.01 | 2.58E+07 | 6.37E−05 |
| AB-6 | 0.133 | 2.01E+08 | 2.65E−05 | 1.97 | 1.97E+07 | 3.83E−05 |
| AB-7 | 0.184 | 2.21E+07 | 4.06E−06 | 0.754 | 2.71E+07 | 2.05E−05 |
| AB-8 | 0.335 | 2.45E+07 | 5.62E−06 | 1.56 | 1.91E+07 | 2.97E−05 |
| AB-9 | 0.496 | 1.73E+07 | 8.57E−06 | 2.17 | 3.47E+07 | 7.52E−05 |
| AB-10 | 0.395 | 2.40E+07 | 9.48E−06 | | | |
| AB-11 | 0.754 | 2.23E+07 | 1.68E−06 | | | |
| AB-12 | 1.020 | 2.29E+07 | 2.33E−05 | | | |
| AB-13 | | | | | | |
| AB-14 | 0.877 | 2.63E+07 | 2.31E−05 | | | |
| Reference | 2.15 | 1.54E+07 | 3.30E−05 | 9.05 | 9.80E+06 | 8.87E−05 |

TABLE 10

Inhibition of TSLP binding

| clone | $IC_{50}$ (nM) |
|---|---|
| AB-1 | 0.6233 |
| AB-2 | 0.5868 |
| AB-3 | 0.4106 |
| AB-4 | 1.106 |
| AB-5 | 2.329 |
| AB-6 | 0.5309 |
| AB-7 | 0.7316 |
| AB-8 | 0.667 |
| AB-9 | 0.2872 |
| AB-10 | 1.993 |
| AB-11 | 1.164 |
| AB-12 | 2.784 |
| AB-13 | 3.333 |
| AB-14 | 3.942 |
| Reference | 1.931 |

TABLE 11

Inhibition of TSLP-Mediated STAT5 Signaling

| | $IC_{50}$ (nM) | | | | |
|---|---|---|---|---|---|
| clone | Donor 1 | Donor 2 | Donor 3 | Donor 4 | Donor 5 |
| AB-1 | 0.1675 | 0.6433 | 0.4553 | 0.1368 | 0.4494 |
| AB-2 | 0.2402 | 0.349 | 0.1774 | 0.1427 | 0.3544 |
| AB-3 | 0.1051 | 0.3053 | 0.1471 | 0.1326 | 0.1888 |
| AB-4 | 0.1909 | 0.6764 | 0.1842 | 0.1994 | 0.4266 |
| AB-5 | 0.1891 | 1.152 | 0.3254 | 0.4966 | 0.6762 |
| AB-6 | 0.2321 | 0.7187 | 0.3392 | 0.2735 | 0.4777 |
| AB-7 | 0.3685 | 1.31 | 0.6447 | 0.4997 | 0.7363 |
| AB-8 | 0.1487 | 0.579 | 0.2684 | 0.2153 | 0.3164 |
| AB-9 | 0.1958 | 0.7094 | 0.3161 | 0.1567 | 0.4098 |
| Reference | 1.158 | 1.402 | 1.132 | 1.044 | 1.774 |

TABLE 12

TSLP Binding ELISA

| EC (95% confidence intervals) (μg/mL) | AB-2a | AB-2b | Reference Antibody | Human Isotype IgG1 | Human Isotype IgG2 |
|---|---|---|---|---|---|
| Human TSLP | | | | | |
| $EC_{50}$ | 0.03 (0.03 to 0.04) | 0.03 (0.02 to 0.05) | 0.06 (0.06 to 0.07) | N/A | N/A |
| $EC_{80}$ | 0.09 (0.06 to 0.13) | 0.10 (0.06 to 0.19) | 0.14 (0.11 to 0.18) | N/A | N/A |
| $EC_{90}$ | 0.15 (0.08 to 0.27) | 0.18 (0.09 to 0.45) | 0.23 (0.16 to 0.31) | N/A | N/A |

TABLE 12-continued

TSLP Binding ELISA

| EC (95% confidence intervals) (μg/mL) | AB-2a | AB-2b | Reference Antibody | Human Isotype | |
|---|---|---|---|---|---|
| | | | | IgG1 | IgG2 |
| Cyno TSLP | | | | | |
| $EC_{50}$ | 0.04 (0.03 to 0.04) | 0.04 (0.03 to 0.04) | 0.06 (0.05 to 0.07) | N/A | N/A |
| $EC_{80}$ | 0.10 (0.07 to 0.13) | 0.10 (0.08 to 0.14) | 0.18 (0.13 to 0.24) | N/A | N/A |
| $EC_{90}$ | 0.17 (0.11 to 0.26) | 0.19 (0.13 to 0.29) | 0.33 (0.22 to 0.50) | N/A | N/A |

TABLE 13

TSLPR/IL-7Rα BAF/3 Assay

| IC (95% confidence intervals) (μg/mL) | AB-2a | AB-2b | Reference Antibody | Human Isotype | |
|---|---|---|---|---|---|
| | | | | IgG1 | IgG2 |
| Human TSLPR/IL-7Rα | | | | | |
| $IC_{50}$ | 0.02 (0.004 to 0.12) | 0.03 (0.006 to 0.18) | 0.17 (0.05 to 0.65) | N/A | N/A |
| Cyno TSLPR/IL-7Rα | | | | | |
| $IC_{50}$ | 0.03 (0.01 to 0.07) | 0.04 (0.02 to 0.07) | 0.14 (0.05 to 0.40) | N/A | N/A |

TABLE 14

Example Sequences and Potts Model Scores

| protein | vht | vlt | vhvlt | potts_model_score |
|---|---|---|---|---|
| AB-2 | GTRYVWDSYTASQWEEIFEAMI (SEQ ID NO: 137) | NIGSKSDSQIWDSSSSLVV (SEQ ID NO: 138) | GTRYVWDSYTASQWEEIFEAMINIGSKSDSQIWDSSSSLVV (SEQ ID NO: 139) | -4.8525944 |
| AB-1 | GTRYVWSSYTSSQWEDIFEAMI (SEQ ID NO: 140) | NIGSKSDSQVWDSSSSLVV (SEQ ID NO: 141) | GTRYVWSSYTSSQWEDIFEAMINIGSKSDSQVWDSSSSLVV (SEQ ID NO: 142) | -2.9628694 |
| AB-8 | GTRYIWDSYTASQWEDIFEAFI (SEQ ID NO: 143) | NIGSKSDSQVWDSSSSLVV (SEQ ID NO: 141) | GTRYIWDSYTASQWEDIFEAFINIGSKSDSQVWDSSSSLVV (SEQ ID NO: 144) | -2.9442153 |
| AB-6 | GTRYVWDSDISSQWEDIFESMI (SEQ ID NO: 145) | NIGSKSDSQIWDSSDHVV (SEQ ID NO: 146) | GTRYVWDSDISSQWEDIFESMINIGSKSDSQIWDSSSDHVV (SEQ ID NO: 147) | -2.3772101 |
| AB-3 | GTRYIWDTYTASQWESIFEAFI (SEQ ID NO: 148) | NIGSKSDSQVWDSSSSLVV (SEQ ID NO: 141) | GTRYIWDTYTASQWESIFEAFINIGSKSDSQVWDSSSSLVV (SEQ ID NO: 149) | -2.1100748 |
| AB-5 | GTRYVWDYDTSSQWEDIFESMI (SEQ ID NO: 150) | NLGSKSDSQVWDMSSDLVV (SEQ ID NO: 151) | GTRYVWDYDTSSQWEDIFESMINLGSKSDSQVWDMSSDLVV (SEQ ID NO: 152) | -1.8960481 |
| AB-7 | GTRYIWSAYISSQWEDIFEAMI (SEQ ID NO: 153) | NLGSYSDSQVWDMSSSLVV (SEQ ID NO: 154) | GTRYIWSAYISSQWEDIFEAMINLGSYSDSQVWDMSSSLVV (SEQ ID NO: 155) | -1.6204025 |
| AB-10 | GTRYIWSTTTSSQWEDIFESMI (SEQ ID NO: 156) | NIGSKNDSQVWDSSDFLVV (SEQ ID NO: 157) | GTRYIWSTTTSSQWEDIFESMINIGSKNDSQVWDSSDFLVV (SEQ ID NO: 158) | -1.4744515 |
| AB-13 | GTRYISDSTKAAQWESVYEAFI (SEQ ID NO: 159) | NLGSFSDSQVWDSSEDLVV (SEQ ID NO: 160) | GTRYISDSTKAAQWESVYEAFINLGSFSDSQVWDSSEDLVV (SEQ ID NO: 161) | -1.3488145 |
| AB-14 | GTRYIWDSTKAAQWELVHEAFI (SEQ ID NO: 162) | NIGSKNDSQVWDESSDEVV (SEQ ID NO: 163) | GTRYIWDSTKAAQWELVHEAFINIGSKNDSQVWDESSDEVV (SEQ ID NO: 164) | -1.1853998 |

TABLE 14-continued

Example Sequences and Potts Model Scores

| protein | vht | vlt | vhvlt | potts_model_score |
|---|---|---|---|---|
| AB-12 | GTRYVWDSNTAAQWESVHEAFI (SEQ ID NO: 165) | NIGRFSDSQVWVSTSDKVV (SEQ ID NO: 166) | GTRYVWDSNTAAQWESVHEAFINIGRFSDSQVWVSTSDKVV (SEQ ID NO: 167) | -0.6803217 |
| AB-11 | GTRYISSSYITSQWEEVYEALI (SEQ ID NO: 168) | NIGSFSDSQVWSSTSRHVV (SEQ ID NO: 169) | GTRYISSSYITSQWEEVYEALINIGSFSDSQVWSSTSRHVV (SEQ ID NO: 170) | -0.6461612 |
| AB-4 | GTRYIWSSDTASQWEDIFESMV (SEQ ID NO: 171) | YIGSFSDSQIYVSASRLVV (SEQ ID NO: 172) | GTRYIWSSDTASQWEDIFESMVYIGSFSDSQIYVSASRLVV (SEQ ID NO: 173) | -0.62289006 |

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

---

What is claimed is:

1. An anti-thymic stromal lymphopoietin (TSLP) antibody or antigen-binding fragment thereof comprising:
   a) a heavy chain variable domain ($V_H$) that comprises a heavy chain complementarity-determining region (HCDR) 1 comprising the amino acid sequence of SEQ ID NO:31, a HCDR2 comprising the amino acid sequence of SEQ ID NO:35, and a HCDR3 comprising the amino acid sequence of SEQ ID NO:50; and
   b) a light chain variable domain ($V_L$) that comprises a light chain complementarity-determining region (LCDR) 1 comprising the amino acid sequence of SEQ ID NO:60, a LCDR2 comprising the amino acid sequence DDS, and a LCDR3 comprising the amino acid sequence of SEQ ID NO:71.

2. An anti-TSLP antibody or antigen-binding fragment thereof comprising:
   a) a heavy chain variable domain ($V_H$) that comprises a heavy chain complementarity-determining region (HCDR) 1 consisting of the amino acid sequence of SEQ ID NO:31, a HCDR2 consisting of the amino acid sequence of SEQ ID NO:35, and a HCDR3 consisting of the amino acid sequence of SEQ ID NO:50; and
   b) a light chain variable domain ($V_L$) that comprises a light chain complementarity-determining region (LCDR) 1 consisting of the amino acid sequence of SEQ ID NO:60, a LCDR2 consisting of the amino acid sequence DDS, and a LCDR3 consisting of the amino acid sequence of SEQ ID NO:71.

3. The anti-TSLP antibody or antigen-binding fragment thereof of claim 1, comprising a heavy chain variable domain ($V_H$) that is humanized, contains human framework regions, or a combination thereof.

4. The anti-TSLP antibody or antigen-binding fragment thereof of claim 1, comprising a $V_H$ comprising the amino acid sequence of SEQ ID NO:5.

5. The anti-TSLP antibody or antigen-binding fragment thereof of claim 1, comprising a light chain variable domain ($V_L$) that is humanized, contains human framework regions, or a combination thereof.

6. The anti-TSLP antibody or antigen-binding fragment thereof of claim 1, comprising a $V_L$ comprising the amino acid sequence of SEQ ID NO:21.

7. The anti-TSLP antibody or antigen-binding fragment thereof of claim 1, comprising a $V_H$ comprising the amino acid sequence of SEQ ID NO:5, and a $V_L$ comprising the amino acid sequence of SEQ ID NO:21.

8. The anti-TSLP antibody or antigen-binding fragment thereof of claim 1, wherein the antigen-binding fragment comprises a single-chain fragment variable (scFv), a fragment antigen-binding (Fab), a Fab' or a F(ab')$_2$.

9. The anti-TSLP antibody or antigen-binding fragment thereof of claim 1, comprising an antibody heavy chain constant domain, an antibody light chain constant domain, or both an antibody heavy chain constant domain and an antibody light chain constant domain.

10. The anti-TSLP antibody or antigen-binding fragment thereof of claim 9, wherein the antibody heavy chain constant domain is an IgG1, IgG2, IgG3 or IgG4 constant domain.

11. The anti-TSLP antibody or antigen-binding fragment thereof of claim 9, wherein the antibody heavy chain constant domain is an IgG1 or IgG2 constant domain.

12. The anti-TSLP antibody or antigen-binding fragment thereof of claim 10, wherein the antibody heavy chain constant domain comprises one or more mutations which increase serum half-life of the antibody or antigen-binding fragment thereof in humans.

13. The anti-TSLP antibody or antigen-binding fragment thereof of claim 10, wherein the antibody heavy chain constant domain comprises, relative to a wild-type human IgG constant domain, amino acid substitutions with tyrosine, threonine and glutamic acid at amino acid residues 252, 254 and 256, respectively, wherein the amino acid residues are numbered according to the EU index as in Kabat.

14. The anti-TSLP antibody or antigen-binding fragment thereof of claim 2, comprising an antibody heavy chain (HC) comprising the amino acid sequence of SEQ ID NO:106.

15. The anti-TSLP antibody or antigen-binding fragment thereof of claim 1, comprising an antibody heavy chain (HC) comprising the amino acid sequence of SEQ ID NO: 106.

16. The anti-TSLP antibody or antigen-binding fragment thereof of claim 1, comprising an antibody light chain (LC) comprising the amino acid sequence of SEQ ID NO:120.

17. The anti-TSLP antibody or antigen-binding fragment thereof of claim 14, comprising an antibody light chain (LC) comprising the amino acid sequence of SEQ ID NO:120.

18. The anti-TSLP antibody or antigen-binding fragment thereof of claim 15, comprising an antibody light chain (LC) consisting of the amino acid sequence of SEQ ID NO:120.

19. A composition comprising the anti-TSLP antibody or antigen-binding fragment thereof of claim 1, and one or more pharmaceutical excipients, diluents, or carriers.

20. The composition of claim 19, further comprising one or more additional therapeutic agents.

21. A polynucleotide comprising a nucleotide sequence encoding the anti-TSLP antibody or antigen-binding fragment thereof of claim 1.

22. A host cell comprising the polynucleotide of claim 21.

23. A method of making the anti-TSLP antibody or antigen-binding fragment thereof of claim 1, comprising culturing a host cell comprising a nucleotide sequence encoding the anti-TSLP antibody or antigen-binding fragment thereof under conditions where the anti-TSLP antibody or antigen-binding fragment thereof is expressed in the host cell.

* * * * *

SEQUENCE LISTING

```
Sequence total quantity: 173
SEQ ID NO: 1              moltype = AA   length = 159
FEATURE                   Location/Qualifiers
source                    1..159
                          mol_type = protein
                          organism = Homo sapiens
SEQUENCE: 1
MFPFALLYVL SVSFRKIFIL QLVGLVLTYD FTNCDFEKIK AAYLSTISKD LITYMSGTKS  60
TEFNNTVSCS NRPHCLTEIQ SLTFNPTAGC ASLAKEMFAM KTKAALAIWC PGYSETQINA 120
TQAMKKRRKR KVTTNKCLEQ VSQLQGLWRR FNRPLLKQQ                        159

SEQ ID NO: 2              moltype = AA   length = 122
FEATURE                   Location/Qualifiers
REGION                    1..122
                          note = Consensus
VARIANT                   51
                          note = MISC_FEATURE - X1 is I or V
VARIANT                   52
                          note = MISC_FEATURE - X2 is W or S
VARIANT                   54
                          note = MISC_FEATURE - X3 is D or S
VARIANT                   56
                          note = MISC_FEATURE - X4 is S, T, Y or A
VARIANT                   57
                          note = MISC_FEATURE - X5 is N, Y, D or T
VARIANT                   58
                          note = MISC_FEATURE - X6 is K, T or I
VARIANT                   97
                          note = MISC_FEATURE - X7 is A, S or T
VARIANT                   99
                          note = MISC_FEATURE - X8 is A or S
VARIANT                   104
                          note = MISC_FEATURE - X9 is L, D, E or S
VARIANT                   105
                          note = MISC_FEATURE - X10 is V or I
VARIANT                   106
                          note = MISC_FEATURE - X11 is H, F or Y
VARIANT                   108
                          note = MISC_FEATURE - X12 is A or S
VARIANT                   109
                          note = MISC_FEATURE - X13 is F, M or L
VARIANT                   111
                          note = MISC_FEATURE - X14 is I or V
source                    1..122
                          mol_type = protein
```

US 12,110,324 B2

151

152

-continued

```
                        organism = synthetic construct
SEQUENCE: 2
QMQLVESGGG VVQPGRSLRL SCAASGFTFR TYGMHWVRQA PGKGLEWVAV XXYXGXXXHY    60
ADSVKGRFTI TRDNSKNTLN LQMNSLRAED TAVYYCXRXP QWEXXXEXXD XWGQGTMVTV   120
SS                                                                  122

SEQ ID NO: 3            moltype = AA  length = 122
FEATURE                 Location/Qualifiers
REGION                  1..122
                        note = Reference
source                  1..122
                        mol_type = protein
                        organism = synthetic construct
SEQUENCE: 3
QMQLVESGGG VVQPGRSLRL SCAASGFTFR TYGMHWVRQA PGKGLEWVAV IWYDGSNKHY    60
ADSVKGRFTI TRDNSKNTLN LQMNSLRAED TAVYYCARAP QWELVHEAFD IWGQGTMVTV   120
SS                                                                  122

SEQ ID NO: 4            moltype = AA  length = 122
FEATURE                 Location/Qualifiers
REGION                  1..122
                        note = AB-1
source                  1..122
                        mol_type = protein
                        organism = synthetic construct
SEQUENCE: 4
QMQLVESGGG VVQPGRSLRL SCAASGFTFR TYGMHWVRQA PGKGLEWVAV VWYSGSYTHY    60
ADSVKGRFTI TRDNSKNTLN LQMNSLRAED TAVYYCSRSP QWEDIFEAMD IWGQGTMVTV   120
SS                                                                  122

SEQ ID NO: 5            moltype = AA  length = 122
FEATURE                 Location/Qualifiers
REGION                  1..122
                        note = AB-2
source                  1..122
                        mol_type = protein
                        organism = synthetic construct
SEQUENCE: 5
QMQLVESGGG VVQPGRSLRL SCAASGFTFR TYGMHWVRQA PGKGLEWVAV VWYDGSYTHY    60
ADSVKGRFTI TRDNSKNTLN LQMNSLRAED TAVYYCARSP QWEEIFEAMD IWGQGTMVTV   120
SS                                                                  122

SEQ ID NO: 6            moltype = AA  length = 122
FEATURE                 Location/Qualifiers
REGION                  1..122
                        note = AB-3
source                  1..122
                        mol_type = protein
                        organism = synthetic construct
SEQUENCE: 6
QMQLVESGGG VVQPGRSLRL SCAASGFTFR TYGMHWVRQA PGKGLEWVAV IWYDGTYTHY    60
ADSVKGRFTI TRDNSKNTLN LQMNSLRAED TAVYYCARSP QWESIFEAFD IWGQGTMVTV   120
SS                                                                  122

SEQ ID NO: 7            moltype = AA  length = 122
FEATURE                 Location/Qualifiers
REGION                  1..122
                        note = AB-4
source                  1..122
                        mol_type = protein
                        organism = synthetic construct
SEQUENCE: 7
QMQLVESGGG VVQPGRSLRL SCAASGFTFR TYGMHWVRQA PGKGLEWVAV IWYSGSDTHY    60
ADSVKGRFTI TRDNSKNTLN LQMNSLRAED TAVYYCARSP QWEDIFESMD VWGQGTMVTV   120
SS                                                                  122

SEQ ID NO: 8            moltype = AA  length = 122
FEATURE                 Location/Qualifiers
REGION                  1..122
                        note = AB-5
source                  1..122
                        mol_type = protein
                        organism = synthetic construct
SEQUENCE: 8
QMQLVESGGG VVQPGRSLRL SCAASGFTFR TYGMHWVRQA PGKGLEWVAV VWYDGYDTHY    60
ADSVKGRFTI TRDNSKNTLN LQMNSLRAED TAVYYCSRSP QWEDIFESMD IWGQGTMVTV   120
SS                                                                  122

SEQ ID NO: 9            moltype = AA  length = 122
```

```
FEATURE                 Location/Qualifiers
REGION                  1..122
                        note = AB-6
source                  1..122
                        mol_type = protein
                        organism = synthetic construct
SEQUENCE: 9
QMQLVESGGG VVQPGRSLRL SCAASGFTFR TYGMHWVRQA PGKGLEWVAV VWYDGSDIHY    60
ADSVKGRFTI TRDNSKNTLN LQMNSLRAED TAVYYCSRSP QWEDIFESMD IWGQGTMVTV   120
SS                                                                  122

SEQ ID NO: 10           moltype = AA  length = 122
FEATURE                 Location/Qualifiers
REGION                  1..122
                        note = AB-7
source                  1..122
                        mol_type = protein
                        organism = synthetic construct
SEQUENCE: 10
QMQLVESGGG VVQPGRSLRL SCAASGFTFR TYGMHWVRQA PGKGLEWVAV IWYSGAYIHY    60
ADSVKGRFTI TRDNSKNTLN LQMNSLRAED TAVYYCSRSP QWEDIFEAMD IWGQGTMVTV   120
SS                                                                  122

SEQ ID NO: 11           moltype = AA  length = 122
FEATURE                 Location/Qualifiers
REGION                  1..122
                        note = AB-8
source                  1..122
                        mol_type = protein
                        organism = synthetic construct
SEQUENCE: 11
QMQLVESGGG VVQPGRSLRL SCAASGFTFR TYGMHWVRQA PGKGLEWVAV IWYDGSYTHY    60
ADSVKGRFTI TRDNSKNTLN LQMNSLRAED TAVYYCARSP QWEDIFEAFD IWGQGTMVTV   120
SS                                                                  122

SEQ ID NO: 12           moltype = AA  length = 122
FEATURE                 Location/Qualifiers
REGION                  1..122
                        note = AB-9
source                  1..122
                        mol_type = protein
                        organism = synthetic construct
SEQUENCE: 12
QMQLVESGGG VVQPGRSLRL SCAASGFTFR TYGMHWVRQA PGKGLEWVAV IWYDGSYTHY    60
ADSVKGRFTI TRDNSKNTLN LQMNSLRAED TAVYYCARSP QWESIFEAFD IWGQGTMVTV   120
SS                                                                  122

SEQ ID NO: 13           moltype = AA  length = 122
FEATURE                 Location/Qualifiers
REGION                  1..122
                        note = AB-10
source                  1..122
                        mol_type = protein
                        organism = synthetic construct
SEQUENCE: 13
QMQLVESGGG VVQPGRSLRL SCAASGFTFR TYGMHWVRQA PGKGLEWVAV IWYSGTTTHY    60
ADSVKGRFTI TRDNSKNTLN LQMNSLRAED TAVYYCSRSP QWEDIFESMD IWGQGTMVTV   120
SS                                                                  122

SEQ ID NO: 14           moltype = AA  length = 122
FEATURE                 Location/Qualifiers
REGION                  1..122
                        note = AB-11
source                  1..122
                        mol_type = protein
                        organism = synthetic construct
SEQUENCE: 14
QMQLVESGGG VVQPGRSLRL SCAASGFTFR TYGMHWVRQA PGKGLEWVAV ISYSGSYIHY    60
ADSVKGRFTI TRDNSKNTLN LQMNSLRAED TAVYYCTRSP QWEEVYEALD IWGQGTMVTV   120
SS                                                                  122

SEQ ID NO: 15           moltype = AA  length = 122
FEATURE                 Location/Qualifiers
REGION                  1..122
                        note = AB-12
source                  1..122
                        mol_type = protein
                        organism = synthetic construct
SEQUENCE: 15
```

```
QMQLVESGGG VVQPGRSLRL SCAASGFTFR TYGMHWVRQA PGKGLEWVAV VWYDGSNTHY    60
ADSVKGRFTI TRDNSKNTLN LQMNSLRAED TAVYYCARAP QWESVHEAFD IWGQGTMVTV   120
SS                                                                 122

SEQ ID NO: 16           moltype = AA  length = 122
FEATURE                 Location/Qualifiers
REGION                  1..122
                        note = AB-13
source                  1..122
                        mol_type = protein
                        organism = synthetic construct
SEQUENCE: 16
QMQLVESGGG VVQPGRSLRL SCAASGFTFR TYGMHWVRQA PGKGLEWVAV ISYDGSTKHY    60
ADSVKGRFTI TRDNSKNTLN LQMNSLRAED TAVYYCARAP QWESVYEAFD IWGQGTMVTV   120
SS                                                                 122

SEQ ID NO: 17           moltype = AA  length = 122
FEATURE                 Location/Qualifiers
REGION                  1..122
                        note = AB-14
source                  1..122
                        mol_type = protein
                        organism = synthetic construct
SEQUENCE: 17
QMQLVESGGG VVQPGRSLRL SCAASGFTFR TYGMHWVRQA PGKGLEWVAV IWYDGSTKHY    60
ADSVKGRFTI TRDNSKNTLN LQMNSLRAED TAVYYCARAP QWELVHEAFD IWGQGTMVTV   120
SS                                                                 122

SEQ ID NO: 18           moltype = AA  length = 108
FEATURE                 Location/Qualifiers
REGION                  1..108
                        note = Consensus
VARIANT                 26
                        note = MISC_FEATURE - X15 is N or Y
VARIANT                 27
                        note = MISC_FEATURE - X16 is L or I
VARIANT                 29
                        note = MISC_FEATURE - X17 is S or R
VARIANT                 30
                        note = MISC_FEATURE - X18 is K, F or Y
VARIANT                 31
                        note = MISC_FEATURE - X19 is S or N
VARIANT                 89
                        note = MISC_FEATURE - X20 is V or I
VARIANT                 90
                        note = MISC_FEATURE - X21 is W or Y
VARIANT                 91
                        note = MISC_FEATURE - X22 is D, V or S
VARIANT                 92
                        note = MISC_FEATURE - X23 is S, M or E
VARIANT                 93
                        note = MISC_FEATURE - X24 is S, A or T
VARIANT                 94
                        note = MISC_FEATURE - X25 is S, D or E
VARIANT                 95
                        note = MISC_FEATURE - X26 is D, S, R or F
VARIANT                 96
                        note = MISC_FEATURE - X27 is H, L, K or E
source                  1..108
                        mol_type = protein
                        organism = synthetic construct
SEQUENCE: 18
SYVLTQPPSV SVAPGQTARI TCGGNXXGXX XVHWYQQKPG QAPVLVVYDD SDRPSWIPER    60
FSGSNSGNTA TLTISRGEAG DEADYYCQXX XXXXXXVVFG GGTKLTVL               108

SEQ ID NO: 19           moltype = AA  length = 108
FEATURE                 Location/Qualifiers
REGION                  1..108
                        note = Reference
source                  1..108
                        mol_type = protein
                        organism = synthetic construct
SEQUENCE: 19
SYVLTQPPSV SVAPGQTARI TCGGNNLGSK SVHWYQQKPG QAPVLVVYDD SDRPSWIPER    60
FSGSNSGNTA TLTISRGEAG DEADYYCQVW DSSSDHVVFG GGTKLTVL               108

SEQ ID NO: 20           moltype = AA  length = 108
FEATURE                 Location/Qualifiers
REGION                  1..108
```

```
                        note = AB-1, 3, 8, 9
source                  1..108
                        mol_type = protein
                        organism = synthetic construct
SEQUENCE: 20
SYVLTQPPSV SVAPGQTARI TCGGNNIGSK SVHWYQQKPG QAPVLVVYDD SDRPSWIPER  60
FSGSNSGNTA TLTISRGEAG DEADYYCQVW DSSSSLVVFG GGTKLTVL              108

SEQ ID NO: 21           moltype = AA   length = 108
FEATURE                 Location/Qualifiers
REGION                  1..108
                        note = AB-2
source                  1..108
                        mol_type = protein
                        organism = synthetic construct
SEQUENCE: 21
SYVLTQPPSV SVAPGQTARI TCGGNNIGSK SVHWYQQKPG QAPVLVVYDD SDRPSWIPER  60
FSGSNSGNTA TLTISRGEAG DEADYYCQIW DSSSSLVVFG GGTKLTVL              108

SEQ ID NO: 22           moltype = AA   length = 108
FEATURE                 Location/Qualifiers
REGION                  1..108
                        note = AB-4
source                  1..108
                        mol_type = protein
                        organism = synthetic construct
SEQUENCE: 22
SYVLTQPPSV SVAPGQTARI TCGGNYIGSF SVHWYQQKPG QAPVLVVYDD SDRPSWIPER  60
FSGSNSGNTA TLTISRGEAG DEADYYCQIY VSASRLVVFG GGTKLTVL              108

SEQ ID NO: 23           moltype = AA   length = 108
FEATURE                 Location/Qualifiers
REGION                  1..108
                        note = AB-5
source                  1..108
                        mol_type = protein
                        organism = synthetic construct
SEQUENCE: 23
SYVLTQPPSV SVAPGQTARI TCGGNNLGSK SVHWYQQKPG QAPVLVVYDD SDRPSWIPER  60
FSGSNSGNTA TLTISRGEAG DEADYYCQVW DMSSDLVVFG GGTKLTVL              108

SEQ ID NO: 24           moltype = AA   length = 108
FEATURE                 Location/Qualifiers
REGION                  1..108
                        note = AB-6
source                  1..108
                        mol_type = protein
                        organism = synthetic construct
SEQUENCE: 24
SYVLTQPPSV SVAPGQTARI TCGGNNIGSK SVHWYQQKPG QAPVLVVYDD SDRPSWIPER  60
FSGSNSGNTA TLTISRGEAG DEADYYCQIW DSSSDHVVFG GGTKLTVL              108

SEQ ID NO: 25           moltype = AA   length = 108
FEATURE                 Location/Qualifiers
REGION                  1..108
                        note = AB-7
source                  1..108
                        mol_type = protein
                        organism = synthetic construct
SEQUENCE: 25
SYVLTQPPSV SVAPGQTARI TCGGNLGSY SVHWYQQKPG QAPVLVVYDD SDRPSWIPER   60
FSGSNSGNTA TLTISRGEAG DEADYYCQVW DMSSSLVVFG GGTKLTVL              108

SEQ ID NO: 26           moltype = AA   length = 108
FEATURE                 Location/Qualifiers
REGION                  1..108
                        note = AB-10
source                  1..108
                        mol_type = protein
                        organism = synthetic construct
SEQUENCE: 26
SYVLTQPPSV SVAPGQTARI TCGGNNIGSK NVHWYQQKPG QAPVLVVYDD SDRPSWIPER  60
FSGSNSGNTA TLTISRGEAG DEADYYCQVW DSSDFLVVFG GGTKLTVL              108

SEQ ID NO: 27           moltype = AA   length = 108
FEATURE                 Location/Qualifiers
REGION                  1..108
                        note = AB-11
source                  1..108
```

```
                        mol_type = protein
                        organism = synthetic construct
SEQUENCE: 27
SYVLTQPPSV SVAPGQTARI TCGGNNIGSF SVHWYQQKPG QAPVLVVYDD SDRPSWIPER    60
FSGSNSGNTA TLTISRGEAG DEADYYCQVW SSTSRHVVFG GGTKLTVL                108

SEQ ID NO: 28           moltype = AA  length = 108
FEATURE                 Location/Qualifiers
REGION                  1..108
                        note = AB-12
source                  1..108
                        mol_type = protein
                        organism = synthetic construct
SEQUENCE: 28
SYVLTQPPSV SVAPGQTARI TCGGNNIGRF SVHWYQQKPG QAPVLVVYDD SDRPSWIPER    60
FSGSNSGNTA TLTISRGEAG DEADYYCQVW VSTSDKVVFG GGTKLTVL                108

SEQ ID NO: 29           moltype = AA  length = 108
FEATURE                 Location/Qualifiers
REGION                  1..108
                        note = AB-13
source                  1..108
                        mol_type = protein
                        organism = synthetic construct
SEQUENCE: 29
SYVLTQPPSV SVAPGQTARI TCGGNNLGSF SVHWYQQKPG QAPVLVVYDD SDRPSWIPER    60
FSGSNSGNTA TLTISRGEAG DEADYYCQVW DSSEDLVVFG GGTKLTVL                108

SEQ ID NO: 30           moltype = AA  length = 108
FEATURE                 Location/Qualifiers
REGION                  1..108
                        note = AB-14
source                  1..108
                        mol_type = protein
                        organism = synthetic construct
SEQUENCE: 30
SYVLTQPPSV SVAPGQTARI TCGGNNIGSK NVHWYQQKPG QAPVLVVYDD SDRPSWIPER    60
FSGSNSGNTA TLTISRGEAG DEADYYCQVW DESSDEVVFG GGTKLTVL                108

SEQ ID NO: 31           moltype = AA  length = 8
FEATURE                 Location/Qualifiers
REGION                  1..8
                        note = Consensus, Reference, AB-1-14
source                  1..8
                        mol_type = protein
                        organism = synthetic construct
SEQUENCE: 31
GFTFRTYG                                                              8

SEQ ID NO: 32           moltype =    length =
SEQUENCE: 32
000

SEQ ID NO: 33           moltype = AA  length = 8
FEATURE                 Location/Qualifiers
REGION                  1..8
                        note = Reference
source                  1..8
                        mol_type = protein
                        organism = synthetic construct
SEQUENCE: 33
IWYDGSNK                                                              8

SEQ ID NO: 34           moltype = AA  length = 8
FEATURE                 Location/Qualifiers
REGION                  1..8
                        note = AB-1
source                  1..8
                        mol_type = protein
                        organism = synthetic construct
SEQUENCE: 34
VWYSGSYT                                                              8

SEQ ID NO: 35           moltype = AA  length = 8
FEATURE                 Location/Qualifiers
REGION                  1..8
                        note = AB-2
source                  1..8
                        mol_type = protein
```

```
                          organism = synthetic construct
SEQUENCE: 35
VWYDGSYT                                                                        8

SEQ ID NO: 36             moltype = AA  length = 8
FEATURE                   Location/Qualifiers
REGION                    1..8
                          note = AB-3
source                    1..8
                          mol_type = protein
                          organism = synthetic construct
SEQUENCE: 36
IWYDGTYT                                                                        8

SEQ ID NO: 37             moltype = AA  length = 8
FEATURE                   Location/Qualifiers
REGION                    1..8
                          note = AB-4
source                    1..8
                          mol_type = protein
                          organism = synthetic construct
SEQUENCE: 37
IWYSGSDT                                                                        8

SEQ ID NO: 38             moltype = AA  length = 8
FEATURE                   Location/Qualifiers
REGION                    1..8
                          note = AB-5
source                    1..8
                          mol_type = protein
                          organism = synthetic construct
SEQUENCE: 38
VWYDGYDT                                                                        8

SEQ ID NO: 39             moltype = AA  length = 8
FEATURE                   Location/Qualifiers
REGION                    1..8
                          note = AB-6
source                    1..8
                          mol_type = protein
                          organism = synthetic construct
SEQUENCE: 39
VWYDGSDI                                                                        8

SEQ ID NO: 40             moltype = AA  length = 8
FEATURE                   Location/Qualifiers
REGION                    1..8
                          note = AB-7
source                    1..8
                          mol_type = protein
                          organism = synthetic construct
SEQUENCE: 40
IWYSGAYI                                                                        8

SEQ ID NO: 41             moltype = AA  length = 8
FEATURE                   Location/Qualifiers
REGION                    1..8
                          note = AB-8, 9
source                    1..8
                          mol_type = protein
                          organism = synthetic construct
SEQUENCE: 41
IWYDGSYT                                                                        8

SEQ ID NO: 42             moltype = AA  length = 8
FEATURE                   Location/Qualifiers
REGION                    1..8
                          note = AB-10
source                    1..8
                          mol_type = protein
                          organism = synthetic construct
SEQUENCE: 42
IWYSGTTT                                                                        8

SEQ ID NO: 43             moltype = AA  length = 8
FEATURE                   Location/Qualifiers
REGION                    1..8
                          note = AB-11
source                    1..8
```

```
                        mol_type = protein
                        organism = synthetic construct
SEQUENCE: 43
ISYSGSYI                                                                  8

SEQ ID NO: 44           moltype = AA   length = 8
FEATURE                 Location/Qualifiers
REGION                  1..8
                        note = AB-12
source                  1..8
                        mol_type = protein
                        organism = synthetic construct
SEQUENCE: 44
VWYDGSNT                                                                  8

SEQ ID NO: 45           moltype = AA   length = 8
FEATURE                 Location/Qualifiers
REGION                  1..8
                        note = AB-13
source                  1..8
                        mol_type = protein
                        organism = synthetic construct
SEQUENCE: 45
ISYDGSTK                                                                  8

SEQ ID NO: 46           moltype = AA   length = 8
FEATURE                 Location/Qualifiers
REGION                  1..8
                        note = AB-14
source                  1..8
                        mol_type = protein
                        organism = synthetic construct
SEQUENCE: 46
IWYDGSTK                                                                  8

SEQ ID NO: 47           moltype = AA   length = 15
FEATURE                 Location/Qualifiers
REGION                  1..15
                        note = Consensus
VARIANT                 1
                        note = MISC_FEATURE - X7 is A, S or T
VARIANT                 3
                        note = MISC_FEATURE - X8 is A or S
VARIANT                 8
                        note = MISC_FEATURE - X9 is L, D, E or S
VARIANT                 9
                        note = MISC_FEATURE - X10 is V or I
VARIANT                 10
                        note = MISC_FEATURE - X11 is H, F or Y
VARIANT                 12
                        note = MISC_FEATURE - X12 is A or S
VARIANT                 13
                        note = MISC_FEATURE - X13 is F, M or L
VARIANT                 15
                        note = MISC_FEATURE - X14 is I or V
source                  1..15
                        mol_type = protein
                        organism = synthetic construct
SEQUENCE: 47
XRXPQWEXXX EXXDX                                                         15

SEQ ID NO: 48           moltype = AA   length = 15
FEATURE                 Location/Qualifiers
REGION                  1..15
                        note = Reference, AB-14
source                  1..15
                        mol_type = protein
                        organism = synthetic construct
SEQUENCE: 48
ARAPQWELVH EAFDI                                                         15

SEQ ID NO: 49           moltype = AA   length = 15
FEATURE                 Location/Qualifiers
REGION                  1..15
                        note = AB-1, 7
source                  1..15
                        mol_type = protein
                        organism = synthetic construct
SEQUENCE: 49
```

```
SRSPQWEDIF EAMDI                                                                 15

SEQ ID NO: 50           moltype = AA  length = 15
FEATURE                 Location/Qualifiers
REGION                  1..15
                        note = AB-2
source                  1..15
                        mol_type = protein
                        organism = synthetic construct
SEQUENCE: 50
ARSPQWEEIF EAMDI                                                                 15

SEQ ID NO: 51           moltype = AA  length = 15
FEATURE                 Location/Qualifiers
REGION                  1..15
                        note = AB-3, 9
source                  1..15
                        mol_type = protein
                        organism = synthetic construct
SEQUENCE: 51
ARSPQWESIF EAFDI                                                                 15

SEQ ID NO: 52           moltype = AA  length = 15
FEATURE                 Location/Qualifiers
REGION                  1..15
                        note = AB-4
source                  1..15
                        mol_type = protein
                        organism = synthetic construct
SEQUENCE: 52
ARSPQWEDIF ESMDV                                                                 15

SEQ ID NO: 53           moltype = AA  length = 15
FEATURE                 Location/Qualifiers
REGION                  1..15
                        note = AB-5, 6, 10
source                  1..15
                        mol_type = protein
                        organism = synthetic construct
SEQUENCE: 53
SRSPQWEDIF ESMDI                                                                 15

SEQ ID NO: 54           moltype = AA  length = 15
FEATURE                 Location/Qualifiers
REGION                  1..15
                        note = AB-8
source                  1..15
                        mol_type = protein
                        organism = synthetic construct
SEQUENCE: 54
ARSPQWEDIF EAFDI                                                                 15

SEQ ID NO: 55           moltype = AA  length = 15
FEATURE                 Location/Qualifiers
REGION                  1..15
                        note = AB-11
source                  1..15
                        mol_type = protein
                        organism = synthetic construct
SEQUENCE: 55
TRSPQWEEVY EALDI                                                                 15

SEQ ID NO: 56           moltype = AA  length = 15
FEATURE                 Location/Qualifiers
REGION                  1..15
                        note = AB-12
source                  1..15
                        mol_type = protein
                        organism = synthetic construct
SEQUENCE: 56
ARAPQWESVH EAFDI                                                                 15

SEQ ID NO: 57           moltype = AA  length = 15
FEATURE                 Location/Qualifiers
REGION                  1..15
                        note = AB-13
source                  1..15
                        mol_type = protein
                        organism = synthetic construct
```

```
SEQUENCE: 57
ARAPQWESVY EAFDI                                                          15

SEQ ID NO: 58            moltype =   length =
SEQUENCE: 58
000

SEQ ID NO: 59            moltype = AA   length = 6
FEATURE                  Location/Qualifiers
REGION                   1..6
                         note = Reference, AB-5
source                   1..6
                         mol_type = protein
                         organism = synthetic construct
SEQUENCE: 59
NLGSKS                                                                     6

SEQ ID NO: 60            moltype = AA   length = 6
FEATURE                  Location/Qualifiers
REGION                   1..6
                         note = AB-1-3, 6, 8, 9
source                   1..6
                         mol_type = protein
                         organism = synthetic construct
SEQUENCE: 60
NIGSKS                                                                     6

SEQ ID NO: 61            moltype = AA   length = 6
FEATURE                  Location/Qualifiers
REGION                   1..6
                         note = AB-4
source                   1..6
                         mol_type = protein
                         organism = synthetic construct
SEQUENCE: 61
YIGSFS                                                                     6

SEQ ID NO: 62            moltype = AA   length = 6
FEATURE                  Location/Qualifiers
REGION                   1..6
                         note = AB-7
source                   1..6
                         mol_type = protein
                         organism = synthetic construct
SEQUENCE: 62
NLGSYS                                                                     6

SEQ ID NO: 63            moltype = AA   length = 6
FEATURE                  Location/Qualifiers
REGION                   1..6
                         note = AB-10, 14
source                   1..6
                         mol_type = protein
                         organism = synthetic construct
SEQUENCE: 63
NIGSKN                                                                     6

SEQ ID NO: 64            moltype = AA   length = 6
FEATURE                  Location/Qualifiers
REGION                   1..6
                         note = AB-11
source                   1..6
                         mol_type = protein
                         organism = synthetic construct
SEQUENCE: 64
NIGSFS                                                                     6

SEQ ID NO: 65            moltype = AA   length = 6
FEATURE                  Location/Qualifiers
REGION                   1..6
                         note = AB-12
source                   1..6
                         mol_type = protein
                         organism = synthetic construct
SEQUENCE: 65
NIGRFS                                                                     6

SEQ ID NO: 66            moltype = AA   length = 6
FEATURE                  Location/Qualifiers
```

```
REGION                  1..6
                        note = AB-13
source                  1..6
                        mol_type = protein
                        organism = synthetic construct
SEQUENCE: 66
NLGSFS                                                                    6

SEQ ID NO: 67           moltype =    length =
SEQUENCE: 67
000

SEQ ID NO: 68           moltype =    length =
SEQUENCE: 68
000

SEQ ID NO: 69           moltype = AA   length = 11
FEATURE                 Location/Qualifiers
REGION                  1..11
                        note = Reference
source                  1..11
                        mol_type = protein
                        organism = synthetic construct
SEQUENCE: 69
QVWDSSSDHV V                                                             11

SEQ ID NO: 70           moltype = AA   length = 11
FEATURE                 Location/Qualifiers
REGION                  1..11
                        note = AB-1, 3, 8, 9
source                  1..11
                        mol_type = protein
                        organism = synthetic construct
SEQUENCE: 70
QVWDSSSSLV V                                                             11

SEQ ID NO: 71           moltype = AA   length = 11
FEATURE                 Location/Qualifiers
REGION                  1..11
                        note = AB-2
source                  1..11
                        mol_type = protein
                        organism = synthetic construct
SEQUENCE: 71
QIWDSSSSLV V                                                             11

SEQ ID NO: 72           moltype = AA   length = 11
FEATURE                 Location/Qualifiers
REGION                  1..11
                        note = AB-4
source                  1..11
                        mol_type = protein
                        organism = synthetic construct
SEQUENCE: 72
QIYVSASRLV V                                                             11

SEQ ID NO: 73           moltype = AA   length = 11
FEATURE                 Location/Qualifiers
REGION                  1..11
                        note = AB-5
source                  1..11
                        mol_type = protein
                        organism = synthetic construct
SEQUENCE: 73
QVWDMSSDLV V                                                             11

SEQ ID NO: 74           moltype = AA   length = 11
FEATURE                 Location/Qualifiers
REGION                  1..11
                        note = AB-6
source                  1..11
                        mol_type = protein
                        organism = synthetic construct
SEQUENCE: 74
QIWDSSSDHV V                                                             11

SEQ ID NO: 75           moltype = AA   length = 11
FEATURE                 Location/Qualifiers
REGION                  1..11
```

```
                          note = AB-7
source                    1..11
                          mol_type = protein
                          organism = synthetic construct
SEQUENCE: 75
QVWDMSSSLV V                                                              11

SEQ ID NO: 76             moltype = AA   length = 11
FEATURE                   Location/Qualifiers
REGION                    1..11
                          note = AB-10
source                    1..11
                          mol_type = protein
                          organism = synthetic construct
SEQUENCE: 76
QVWDSSDFLV V                                                              11

SEQ ID NO: 77             moltype = AA   length = 11
FEATURE                   Location/Qualifiers
REGION                    1..11
                          note = AB-11
source                    1..11
                          mol_type = protein
                          organism = synthetic construct
SEQUENCE: 77
QVWSSTSRHV V                                                              11

SEQ ID NO: 78             moltype = AA   length = 11
FEATURE                   Location/Qualifiers
REGION                    1..11
                          note = AB-12
source                    1..11
                          mol_type = protein
                          organism = synthetic construct
SEQUENCE: 78
QVWVSTSDKV V                                                              11

SEQ ID NO: 79             moltype = AA   length = 11
FEATURE                   Location/Qualifiers
REGION                    1..11
                          note = AB-13
source                    1..11
                          mol_type = protein
                          organism = synthetic construct
SEQUENCE: 79
QVWDSSEDLV V                                                              11

SEQ ID NO: 80             moltype = AA   length = 11
FEATURE                   Location/Qualifiers
REGION                    1..11
                          note = AB-14
source                    1..11
                          mol_type = protein
                          organism = synthetic construct
SEQUENCE: 80
QVWDESSDEV V                                                              11

SEQ ID NO: 81             moltype = AA   length = 448
FEATURE                   Location/Qualifiers
REGION                    1..263
                          note = Reference Antibody
source                    1..448
                          mol_type = protein
                          organism = synthetic construct
SEQUENCE: 81
QMQLVESGGG VVQPGRSLRL SCAASGFTFR TYGMHWVRQA PGKGLEWVAV IWYDGSNKHY          60
ADSVKGRFTI TRDNSKNTLN LQMNSLRAED TAVYYCARAP QWELVHEAFD IWGQGTMVTV         120
SSASTKGPSV FPLAPCSRST SESTAALGCL VKDYFPEPVT VSWNSGALTS GVHTFPAVLQ         180
SSGLYSLSSV VTVPSSNFGT QTYTCNVDHK PSNTKVDKTV ERKCCVECPP CPAPPVAGPS         240
VFLFPPKPKD TLMISRTPEV TCVVVDVSHE DPEVQFNWYV DGVEVHNAKT KPREEQFNST         300
FRVVSVLTVV HQDWLNGKEY KCKVSNKGLP APIEKTISKT KGQPREPQVY TLPPSREEMT         360
KNQVSLTCLV KGFYPSDIAV EWESNGQPEN NYKTTPPMLD SDGSFFLYSK LTVDKSRWQQ         420
GNVFSCSVMH EALHNHYTQK SLSLSPGK                                           448

SEQ ID NO: 82             moltype = AA   length = 214
FEATURE                   Location/Qualifiers
REGION                    1..214
                          note = Reference Antibody
source                    1..214
```

-continued

```
                            mol_type = protein
                            organism = synthetic construct
SEQUENCE: 82
SYVLTQPPSV SVAPGQTARI TCGGNNLGSK SVHWYQQKPG QAPVLVVYDD SDRPSWIPER    60
FSGSNSGNTA TLTISRGEAG DEADYYCQVW DSSSDHVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                              214

SEQ ID NO: 83               moltype = AA   length = 159
FEATURE                     Location/Qualifiers
REGION                      1..159
                            note = antibody heavy chain
source                      1..159
                            mol_type = protein
                            organism = synthetic construct
SEQUENCE: 83
MKSLGQSKKE EVSFRKFFIF QLVGLVLTYD FTNCDFQKIE ADYLRTISKD LITYMSGTKS    60
TDFNNTVSCS NRPHCLTEIQ SLTFNPTPRC ASLAKEMFAR KTKATLALWC PGYSETQINA   120
TQAMKKRRKR KVTTNKCLEQ VSQLLGLWRR FIRTLLKKQ                          159

SEQ ID NO: 84               moltype = AA   length = 330
FEATURE                     Location/Qualifiers
REGION                      1..107
                            note = antibody light chain
source                      1..330
                            mol_type = protein
                            organism = synthetic construct
SEQUENCE: 84
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 85               moltype = AA   length = 330
FEATURE                     Location/Qualifiers
REGION                      1..106
                            note = antibody light chain
source                      1..330
                            mol_type = protein
                            organism = synthetic construct
SEQUENCE: 85
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 86               moltype = AA   length = 330
FEATURE                     Location/Qualifiers
source                      1..330
                            mol_type = protein
                            organism = Macaca fascicularis
SEQUENCE: 86
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 87               moltype = AA   length = 326
FEATURE                     Location/Qualifiers
source                      1..326
                            mol_type = protein
                            organism = synthetic construct
SEQUENCE: 87
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF   120
LFPPKPKDTL MISRTPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDIAVEW ESNGQPENNY KTTPPMLDSD GSFFLYSKLT VDKSRWQQGN   300
VFSCSVMHEA LHNHYTQKSL SLSPGK                                       326

SEQ ID NO: 88               moltype = AA   length = 326
FEATURE                     Location/Qualifiers
source                      1..326
```

-continued

```
                      mol_type = protein
                      organism = synthetic construct
SEQUENCE: 88
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF   120
LFPPKPKDTL MISRTPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDIAVEW ESNGQPENNY KTFPPMLDSD GSFFLYSKLT VDKSRWQQGN   300
VFSCSVMHEA LHNHYTQKSL SLSPGK                                       326

SEQ ID NO: 89         moltype = AA  length = 107
FEATURE               Location/Qualifiers
source                1..107
                      mol_type = protein
                      organism = synthetic construct
SEQUENCE: 89
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 90         moltype = AA  length = 106
FEATURE               Location/Qualifiers
source                1..106
                      mol_type = protein
                      organism = synthetic construct
SEQUENCE: 90
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTECS                  106

SEQ ID NO: 91         moltype = AA  length = 452
FEATURE               Location/Qualifiers
source                1..452
                      mol_type = protein
                      organism = synthetic construct
SEQUENCE: 91
QMQLVESGGG VVQPGRSLRL SCAASGFTFR TYGMHWVRQA PGKGLEWVAV VWYSGSYTHY    60
ADSVKGRFTI TRDNSKNTLN LQMNSLRAED TAVYYCSRSP QWEDIFEAMD IWGQGTMVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 92         moltype = AA  length = 452
FEATURE               Location/Qualifiers
source                1..452
                      mol_type = protein
                      organism = synthetic construct
SEQUENCE: 92
QMQLVESGGG VVQPGRSLRL SCAASGFTFR TYGMHWVRQA PGKGLEWVAV VWYDGSYTHY    60
ADSVKGRFTI TRDNSKNTLN LQMNSLRAED TAVYYCARSP QWEEIFEAMD IWGQGTMVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 93         moltype = AA  length = 452
FEATURE               Location/Qualifiers
source                1..452
                      mol_type = protein
                      organism = synthetic construct
SEQUENCE: 93
QMQLVESGGG VVQPGRSLRL SCAASGFTFR TYGMHWVRQA PGKGLEWVAV IWYDGTYTHY    60
ADSVKGRFTI TRDNSKNTLN LQMNSLRAED TAVYYCARSP QWESIFEAFD IWGQGTMVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 94         moltype = AA  length = 452
FEATURE               Location/Qualifiers
source                1..452
                      mol_type = protein
                      organism = synthetic construct
SEQUENCE: 94
```

```
QMQLVESGGG VVQPGRSLRL SCAASGFTFR TYGMHWVRQA PGKGLEWVAV IWYSGSDTHY      60
ADSVKGRFTI TRDNSKNTLN LQMNSLRAED TAVYYCARSP QWEDIFESMD VWGQGTMVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSNTKVDKRV EPKSCDKTHT CPPCPAPELL     240
GGPSVFLFPP KPKDTLMISR TPEVTCVVVD VSHEDPEVKF NWYVDGVEVH NAKTKPREEQ     300
YNSTYRVVSV LTVLHQDWLN GKEYKCKVSN KALPAPIEKT ISKAKGQPRE PQVYTLPPSR     360
EEMTKNQVSL TCLVKGFYPS DIAVEWESNG QPENNYKTTP PVLDSDGSFF LYSKLTVDKS     420
RWQQGNVFSC SVMHEALHNH YTQKSLSLSP GK                                   452

SEQ ID NO: 95          moltype = AA   length = 452
FEATURE                Location/Qualifiers
source                 1..452
                       mol_type = protein
                       organism = synthetic construct
SEQUENCE: 95
QMQLVESGGG VVQPGRSLRL SCAASGFTFR TYGMHWVRQA PGKGLEWVAV VWYDGYDTHY      60
ADSVKGRFTI TRDNSKNTLN LQMNSLRAED TAVYYCSRSP QWEDIFESMD IWGQGTMVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSNTKVDKRV EPKSCDKTHT CPPCPAPELL     240
GGPSVFLFPP KPKDTLMISR TPEVTCVVVD VSHEDPEVKF NWYVDGVEVH NAKTKPREEQ     300
YNSTYRVVSV LTVLHQDWLN GKEYKCKVSN KALPAPIEKT ISKAKGQPRE PQVYTLPPSR     360
EEMTKNQVSL TCLVKGFYPS DIAVEWESNG QPENNYKTTP PVLDSDGSFF LYSKLTVDKS     420
RWQQGNVFSC SVMHEALHNH YTQKSLSLSP GK                                   452

SEQ ID NO: 96          moltype = AA   length = 452
FEATURE                Location/Qualifiers
source                 1..452
                       mol_type = protein
                       organism = synthetic construct
SEQUENCE: 96
QMQLVESGGG VVQPGRSLRL SCAASGFTFR TYGMHWVRQA PGKGLEWVAV VWYDGSDIHY      60
ADSVKGRFTI TRDNSKNTLN LQMNSLRAED TAVYYCSRSP QWEDIFESMD IWGQGTMVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSNTKVDKRV EPKSCDKTHT CPPCPAPELL     240
GGPSVFLFPP KPKDTLMISR TPEVTCVVVD VSHEDPEVKF NWYVDGVEVH NAKTKPREEQ     300
YNSTYRVVSV LTVLHQDWLN GKEYKCKVSN KALPAPIEKT ISKAKGQPRE PQVYTLPPSR     360
EEMTKNQVSL TCLVKGFYPS DIAVEWESNG QPENNYKTTP PVLDSDGSFF LYSKLTVDKS     420
RWQQGNVFSC SVMHEALHNH YTQKSLSLSP GK                                   452

SEQ ID NO: 97          moltype = AA   length = 452
FEATURE                Location/Qualifiers
source                 1..452
                       mol_type = protein
                       organism = synthetic construct
SEQUENCE: 97
QMQLVESGGG VVQPGRSLRL SCAASGFTFR TYGMHWVRQA PGKGLEWVAV IWYSGAYIHY      60
ADSVKGRFTI TRDNSKNTLN LQMNSLRAED TAVYYCSRSP QWEDIFEAMD IWGQGTMVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSNTKVDKRV EPKSCDKTHT CPPCPAPELL     240
GGPSVFLFPP KPKDTLMISR TPEVTCVVVD VSHEDPEVKF NWYVDGVEVH NAKTKPREEQ     300
YNSTYRVVSV LTVLHQDWLN GKEYKCKVSN KALPAPIEKT ISKAKGQPRE PQVYTLPPSR     360
EEMTKNQVSL TCLVKGFYPS DIAVEWESNG QPENNYKTTP PVLDSDGSFF LYSKLTVDKS     420
RWQQGNVFSC SVMHEALHNH YTQKSLSLSP GK                                   452

SEQ ID NO: 98          moltype = AA   length = 452
FEATURE                Location/Qualifiers
source                 1..452
                       mol_type = protein
                       organism = synthetic construct
SEQUENCE: 98
QMQLVESGGG VVQPGRSLRL SCAASGFTFR TYGMHWVRQA PGKGLEWVAV IWYDGSYTHY      60
ADSVKGRFTI TRDNSKNTLN LQMNSLRAED TAVYYCARSP QWEDIFEAFD IWGQGTMVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSNTKVDKRV EPKSCDKTHT CPPCPAPELL     240
GGPSVFLFPP KPKDTLMISR TPEVTCVVVD VSHEDPEVKF NWYVDGVEVH NAKTKPREEQ     300
YNSTYRVVSV LTVLHQDWLN GKEYKCKVSN KALPAPIEKT ISKAKGQPRE PQVYTLPPSR     360
EEMTKNQVSL TCLVKGFYPS DIAVEWESNG QPENNYKTTP PVLDSDGSFF LYSKLTVDKS     420
RWQQGNVFSC SVMHEALHNH YTQKSLSLSP GK                                   452

SEQ ID NO: 99          moltype = AA   length = 452
FEATURE                Location/Qualifiers
source                 1..452
                       mol_type = protein
                       organism = synthetic construct
SEQUENCE: 99
QMQLVESGGG VVQPGRSLRL SCAASGFTFR TYGMHWVRQA PGKGLEWVAV IWYDGSYTHY      60
ADSVKGRFTI TRDNSKNTLN LQMNSLRAED TAVYYCARSP QWESIFEAFD IWGQGTMVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSNTKVDKRV EPKSCDKTHT CPPCPAPELL     240
```

```
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                452

SEQ ID NO: 100         moltype = AA   length = 452
FEATURE                Location/Qualifiers
source                 1..452
                       mol_type = protein
                       organism = synthetic construct
SEQUENCE: 100
QMQLVESGGG VVQPGRSLRL SCAASGFTFR TYGMHWVRQA PGKGLEWVAV IWYSGTTTHY    60
ADSVKGRFTI TRDNSKNTLN LQMNSLRAED TAVYYCSRSP QWEDIFESMD IWGQGTMVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                452

SEQ ID NO: 101         moltype = AA   length = 452
FEATURE                Location/Qualifiers
source                 1..452
                       mol_type = protein
                       organism = synthetic construct
SEQUENCE: 101
QMQLVESGGG VVQPGRSLRL SCAASGFTFR TYGMHWVRQA PGKGLEWVAV ISYSGSYIHY    60
ADSVKGRFTI TRDNSKNTLN LQMNSLRAED TAVYYCTRSP QWEEVYEALD IWGQGTMVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                452

SEQ ID NO: 102         moltype = AA   length = 452
FEATURE                Location/Qualifiers
source                 1..452
                       mol_type = protein
                       organism = synthetic construct
SEQUENCE: 102
QMQLVESGGG VVQPGRSLRL SCAASGFTFR TYGMHWVRQA PGKGLEWVAV VWYDGSNTHY    60
ADSVKGRFTI TRDNSKNTLN LQMNSLRAED TAVYYCARAP QWESVHEAFD IWGQGTMVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                452

SEQ ID NO: 103         moltype = AA   length = 452
FEATURE                Location/Qualifiers
source                 1..452
                       mol_type = protein
                       organism = synthetic construct
SEQUENCE: 103
QMQLVESGGG VVQPGRSLRL SCAASGFTFR TYGMHWVRQA PGKGLEWVAV ISYDGSTKHY    60
ADSVKGRFTI TRDNSKNTLN LQMNSLRAED TAVYYCARAP QWESVYEAFD IWGQGTMVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                452

SEQ ID NO: 104         moltype = AA   length = 452
FEATURE                Location/Qualifiers
source                 1..452
                       mol_type = protein
                       organism = synthetic construct
SEQUENCE: 104
QMQLVESGGG VVQPGRSLRL SCAASGFTFR TYGMHWVRQA PGKGLEWVAV IWYDGSTKHY    60
ADSVKGRFTI TRDNSKNTLN LQMNSLRAED TAVYYCARAP QWELVHEAFD IWGQGTMVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                452
```

```
SEQ ID NO: 105          moltype = AA   length = 452
FEATURE                 Location/Qualifiers
source                  1..452
                        mol_type = protein
                        organism = synthetic construct
SEQUENCE: 105
QMQLVESGGG VVQPGRSLRL SCAASGFTFR TYGMHWVRQA PGKGLEWVAV VWYSGSYTHY     60
ADSVKGRFTI TRDNSKNTLN LQMNSLRAED TAVYYCSRSP QWEDIFEAMD IWGQGTMVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKRV EPKSCDKTHT CPPCPAPELL    240
GGPSVFLFPP KPKDTLYITR EPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 106          moltype = AA   length = 452
FEATURE                 Location/Qualifiers
source                  1..452
                        mol_type = protein
                        organism = synthetic construct
SEQUENCE: 106
QMQLVESGGG VVQPGRSLRL SCAASGFTFR TYGMHWVRQA PGKGLEWVAV VWYDGSYTHY     60
ADSVKGRFTI TRDNSKNTLN LQMNSLRAED TAVYYCARSP QWEEIFEAMD IWGQGTMVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKRV EPKSCDKTHT CPPCPAPELL    240
GGPSVFLFPP KPKDTLYITR EPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 107          moltype = AA   length = 452
FEATURE                 Location/Qualifiers
source                  1..452
                        mol_type = protein
                        organism = synthetic construct
SEQUENCE: 107
QMQLVESGGG VVQPGRSLRL SCAASGFTFR TYGMHWVRQA PGKGLEWVAV IWYDGTYTHY     60
ADSVKGRFTI TRDNSKNTLN LQMNSLRAED TAVYYCARSP QWESIFEAFD IWGQGTMVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKRV EPKSCDKTHT CPPCPAPELL    240
GGPSVFLFPP KPKDTLYITR EPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 108          moltype = AA   length = 452
FEATURE                 Location/Qualifiers
source                  1..452
                        mol_type = protein
                        organism = synthetic construct
SEQUENCE: 108
QMQLVESGGG VVQPGRSLRL SCAASGFTFR TYGMHWVRQA PGKGLEWVAV IWYSGSDTHY     60
ADSVKGRFTI TRDNSKNTLN LQMNSLRAED TAVYYCARSP QWEDIFESMD VWGQGTMVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKRV EPKSCDKTHT CPPCPAPELL    240
GGPSVFLFPP KPKDTLYITR EPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 109          moltype = AA   length = 452
FEATURE                 Location/Qualifiers
source                  1..452
                        mol_type = protein
                        organism = synthetic construct
SEQUENCE: 109
QMQLVESGGG VVQPGRSLRL SCAASGFTFR TYGMHWVRQA PGKGLEWVAV VWYDGYDTHY     60
ADSVKGRFTI TRDNSKNTLN LQMNSLRAED TAVYYCSRSP QWEDIFESMD IWGQGTMVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKRV EPKSCDKTHT CPPCPAPELL    240
GGPSVFLFPP KPKDTLYITR EPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 110          moltype = AA   length = 452
FEATURE                 Location/Qualifiers
source                  1..452
```

```
                         mol_type = protein
                         organism = synthetic construct
SEQUENCE: 110
QMQLVESGGG VVQPGRSLRL SCAASGFTFR TYGMHWVRQA PGKGLEWVAV VWYDGSDIHY   60
ADSVKGRFTI TRDNSKNTLN LQMNSLRAED TAVYYCSRSP QWEDIFESMD IWGQGTMVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLYITR EPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 111           moltype = AA length = 452
FEATURE                  Location/Qualifiers
source                   1..452
                         mol_type = protein
                         organism = synthetic construct
SEQUENCE: 111
QMQLVESGGG VVQPGRSLRL SCAASGFTFR TYGMHWVRQA PGKGLEWVAV IWYSGAYIHY   60
ADSVKGRFTI TRDNSKNTLN LQMNSLRAED TAVYYCSRSP QWEDIFEAMD IWGQGTMVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLYITR EPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 112           moltype = AA length = 452
FEATURE                  Location/Qualifiers
source                   1..452
                         mol_type = protein
                         organism = synthetic construct
SEQUENCE: 112
QMQLVESGGG VVQPGRSLRL SCAASGFTFR TYGMHWVRQA PGKGLEWVAV IWYDGSYTHY   60
ADSVKGRFTI TRDNSKNTLN LQMNSLRAED TAVYYCARSP QWEDIFEAFD IWGQGTMVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLYITR EPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 113           moltype = AA length = 452
FEATURE                  Location/Qualifiers
source                   1..452
                         mol_type = protein
                         organism = synthetic construct
SEQUENCE: 113
QMQLVESGGG VVQPGRSLRL SCAASGFTFR TYGMHWVRQA PGKGLEWVAV IWYDGSYTHY   60
ADSVKGRFTI TRDNSKNTLN LQMNSLRAED TAVYYCARSP QWESIFEAFD IWGQGTMVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLYITR EPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 114           moltype = AA length = 452
FEATURE                  Location/Qualifiers
source                   1..452
                         mol_type = protein
                         organism = synthetic construct
SEQUENCE: 114
QMQLVESGGG VVQPGRSLRL SCAASGFTFR TYGMHWVRQA PGKGLEWVAV IWYSGTTTHY   60
ADSVKGRFTI TRDNSKNTLN LQMNSLRAED TAVYYCSRSP QWEDIFESMD IWGQGTMVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLYITR EPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 115           moltype = AA length = 452
FEATURE                  Location/Qualifiers
source                   1..452
                         mol_type = protein
                         organism = synthetic construct
SEQUENCE: 115
QMQLVESGGG VVQPGRSLRL SCAASGFTFR TYGMHWVRQA PGKGLEWVAV ISYSGSYIHY   60
```

```
ADSVKGRFTI TRDNSKNTLN LQMNSLRAED TAVYYCTRSP QWEEVYEALD IWGQGTMVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLYITR EPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 116           moltype = AA  length = 452
FEATURE                  Location/Qualifiers
source                   1..452
                         mol_type = protein
                         organism = synthetic construct
SEQUENCE: 116
QMQLVESGGG VVQPGRSLRL SCAASGFTFR TYGMHWVRQA PGKGLEWVAV VWYDGSNTHY   60
ADSVKGRFTI TRDNSKNTLN LQMNSLRAED TAVYYCARAP QWESVHEAFD IWGQGTMVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLYITR EPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 117           moltype = AA  length = 452
FEATURE                  Location/Qualifiers
source                   1..452
                         mol_type = protein
                         organism = synthetic construct
SEQUENCE: 117
QMQLVESGGG VVQPGRSLRL SCAASGFTFR TYGMHWVRQA PGKGLEWVAV ISYDGSTKHY   60
ADSVKGRFTI TRDNSKNTLN LQMNSLRAED TAVYYCARAP QWESVYEAFD IWGQGTMVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLYITR EPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 118           moltype = AA  length = 452
FEATURE                  Location/Qualifiers
source                   1..452
                         mol_type = protein
                         organism = synthetic construct
SEQUENCE: 118
QMQLVESGGG VVQPGRSLRL SCAASGFTFR TYGMHWVRQA PGKGLEWVAV IWYDGSTKHY   60
ADSVKGRFTI TRDNSKNTLN LQMNSLRAED TAVYYCARAP QWELVHEAFD IWGQGTMVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLYITR EPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 119           moltype = AA  length = 214
FEATURE                  Location/Qualifiers
source                   1..214
                         mol_type = protein
                         organism = synthetic construct
SEQUENCE: 119
SYVLTQPPSV SVAPGQTARI TCGGNNIGSK SVHWYQQKPG QAPVLVVYDD SDRPSWIPER   60
FSGSNSGNTA TLTISRGEAG DEADYYCQVW DSSSSLVVFG GGTKLTVLGQ PKAAPSVTLF  120
PPSSEELQAN KATLVCLISD FYPGAVTVAW KADSSPVKAG VETTTPSKQS NNKYAASSYL  180
SLTPEQWKSH RSYSCQVTHE GSTVEKTVAP TECS                              214

SEQ ID NO: 120           moltype = AA  length = 214
FEATURE                  Location/Qualifiers
source                   1..214
                         mol_type = protein
                         organism = synthetic construct
SEQUENCE: 120
SYVLTQPPSV SVAPGQTARI TCGGNNIGSK SVHWYQQKPG QAPVLVVYDD SDRPSWIPER   60
FSGSNSGNTA TLTISRGEAG DEADYYCQIW DSSSSLVVFG GGTKLTVLGQ PKAAPSVTLF  120
PPSSEELQAN KATLVCLISD FYPGAVTVAW KADSSPVKAG VETTTPSKQS NNKYAASSYL  180
SLTPEQWKSH RSYSCQVTHE GSTVEKTVAP TECS                              214

SEQ ID NO: 121           moltype = AA  length = 214
FEATURE                  Location/Qualifiers
source                   1..214
                         mol_type = protein
```

```
                         organism = synthetic construct
SEQUENCE: 121
SYVLTQPPSV SVAPGQTARI TCGGNYIGSF SVHWYQQKPG QAPVLVVYDD SDRPSWIPER    60
FSGSNSGNTA TLTISRGEAG DEADYYCQIY VSASRLVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 122            moltype = AA  length = 214
FEATURE                   Location/Qualifiers
source                    1..214
                          mol_type = protein
                          organism = synthetic construct
SEQUENCE: 122
SYVLTQPPSV SVAPGQTARI TCGGNNLGSK SVHWYQQKPG QAPVLVVYDD SDRPSWIPER    60
FSGSNSGNTA TLTISRGEAG DEADYYCQVW DMSSDLVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 123            moltype = AA  length = 214
FEATURE                   Location/Qualifiers
source                    1..214
                          mol_type = protein
                          organism = synthetic construct
SEQUENCE: 123
SYVLTQPPSV SVAPGQTARI TCGGNNIGSK SVHWYQQKPG QAPVLVVYDD SDRPSWIPER    60
FSGSNSGNTA TLTISRGEAG DEADYYCQIW DSSSDHVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 124            moltype = AA  length = 214
FEATURE                   Location/Qualifiers
source                    1..214
                          mol_type = protein
                          organism = synthetic construct
SEQUENCE: 124
SYVLTQPPSV SVAPGQTARI TCGGNNLGSY SVHWYQQKPG QAPVLVVYDD SDRPSWIPER    60
FSGSNSGNTA TLTISRGEAG DEADYYCQVW DMSSSLVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 125            moltype = AA  length = 214
FEATURE                   Location/Qualifiers
source                    1..214
                          mol_type = protein
                          organism = synthetic construct
SEQUENCE: 125
SYVLTQPPSV SVAPGQTARI TCGGNNIGSK NVHWYQQKPG QAPVLVVYDD SDRPSWIPER    60
FSGSNSGNTA TLTISRGEAG DEADYYCQVW DSSDFLVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 126            moltype = AA  length = 214
FEATURE                   Location/Qualifiers
source                    1..214
                          mol_type = protein
                          organism = synthetic construct
SEQUENCE: 126
SYVLTQPPSV SVAPGQTARI TCGGNNIGSF SVHWYQQKPG QAPVLVVYDD SDRPSWIPER    60
FSGSNSGNTA TLTISRGEAG DEADYYCQVW SSTSRHVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 127            moltype = AA  length = 214
FEATURE                   Location/Qualifiers
source                    1..214
                          mol_type = protein
                          organism = synthetic construct
SEQUENCE: 127
SYVLTQPPSV SVAPGQTARI TCGGNNIGRF SVHWYQQKPG QAPVLVVYDD SDRPSWIPER    60
FSGSNSGNTA TLTISRGEAG DEADYYCQVW VSTSDKVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 128            moltype = AA  length = 214
FEATURE                   Location/Qualifiers
source                    1..214
                          mol_type = protein
                          organism = synthetic construct
SEQUENCE: 128
```

```
SYVLTQPPSV SVAPGQTARI TCGGNNLGSF SVHWYQQKPG QAPVLVVYDD SDRPSWIPER    60
FSGSNSGNTA TLTISRGEAG DEADYYCQVW DSSEDLVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 129          moltype = AA   length = 214
FEATURE                 Location/Qualifiers
source                  1..214
                        mol_type = protein
                        organism = synthetic construct
SEQUENCE: 129
SYVLTQPPSV SVAPGQTARI TCGGNNIGSK NVHWYQQKPG QAPVLVVYDD SDRPSWIPER    60
FSGSNSGNTA TLTISRGEAG DEADYYCQVW DESSDEVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 130          moltype = AA   length = 5
FEATURE                 Location/Qualifiers
source                  1..5
                        mol_type = protein
                        organism = synthetic construct
SEQUENCE: 130
TYGMH                                                                 5

SEQ ID NO: 131          moltype = AA   length = 17
FEATURE                 Location/Qualifiers
source                  1..17
                        mol_type = protein
                        organism = synthetic construct
SEQUENCE: 131
VVWYDGSYTH YADSVKG                                                   17

SEQ ID NO: 132          moltype = AA   length = 13
FEATURE                 Location/Qualifiers
source                  1..13
                        mol_type = protein
                        organism = synthetic construct
SEQUENCE: 132
SPQWEEIFEA MDI                                                       13

SEQ ID NO: 133          moltype = AA   length = 11
FEATURE                 Location/Qualifiers
source                  1..11
                        mol_type = protein
                        organism = synthetic construct
SEQUENCE: 133
GGNNIGSKSV H                                                         11

SEQ ID NO: 134          moltype = AA   length = 7
FEATURE                 Location/Qualifiers
source                  1..7
                        mol_type = protein
                        organism = synthetic construct
SEQUENCE: 134
DDSDRPS                                                               7

SEQ ID NO: 135          moltype = AA   length = 7
FEATURE                 Location/Qualifiers
source                  1..7
                        mol_type = protein
                        organism = synthetic construct
SEQUENCE: 135
GFTFRTY                                                               7

SEQ ID NO: 136          moltype = AA   length = 6
FEATURE                 Location/Qualifiers
source                  1..6
                        mol_type = protein
                        organism = synthetic construct
SEQUENCE: 136
WYDGSY                                                                6

SEQ ID NO: 137          moltype = AA   length = 22
FEATURE                 Location/Qualifiers
source                  1..22
                        mol_type = protein
                        organism = synthetic construct
SEQUENCE: 137
GTRYVWDSYT ASQWEEIFEA MI                                             22
```

```
SEQ ID NO: 138          moltype = AA  length = 19
FEATURE                 Location/Qualifiers
source                  1..19
                        mol_type = protein
                        organism = synthetic construct
SEQUENCE: 138
NIGSKSDSQI WDSSSSLVV                                                          19

SEQ ID NO: 139          moltype = AA  length = 41
FEATURE                 Location/Qualifiers
source                  1..41
                        mol_type = protein
                        organism = synthetic construct
SEQUENCE: 139
GTRYVWDSYT ASQWEEIFEA MINIGSKSDS QIWDSSSSLV V                                  41

SEQ ID NO: 140          moltype = AA  length = 22
FEATURE                 Location/Qualifiers
source                  1..22
                        mol_type = protein
                        organism = synthetic construct
SEQUENCE: 140
GTRYVWSSYT SSQWEDIFEA MI                                                      22

SEQ ID NO: 141          moltype = AA  length = 19
FEATURE                 Location/Qualifiers
source                  1..19
                        mol_type = protein
                        organism = synthetic construct
SEQUENCE: 141
NIGSKSDSQV WDSSSSLVV                                                          19

SEQ ID NO: 142          moltype = AA  length = 41
FEATURE                 Location/Qualifiers
source                  1..41
                        mol_type = protein
                        organism = synthetic construct
SEQUENCE: 142
GTRYVWSSYT SSQWEDIFEA MINIGSKSDS QVWDSSSSLV V                                  41

SEQ ID NO: 143          moltype = AA  length = 22
FEATURE                 Location/Qualifiers
source                  1..22
                        mol_type = protein
                        organism = synthetic construct
SEQUENCE: 143
GTRYIWDSYT ASQWEDIFEA FI                                                      22

SEQ ID NO: 144          moltype = AA  length = 41
FEATURE                 Location/Qualifiers
source                  1..41
                        mol_type = protein
                        organism = synthetic construct
SEQUENCE: 144
GTRYIWDSYT ASQWEDIFEA FINIGSKSDS QVWDSSSSLV V                                  41

SEQ ID NO: 145          moltype = AA  length = 22
FEATURE                 Location/Qualifiers
source                  1..22
                        mol_type = protein
                        organism = synthetic construct
SEQUENCE: 145
GTRYVWDSDI SSQWEDIFES MI                                                      22

SEQ ID NO: 146          moltype = AA  length = 19
FEATURE                 Location/Qualifiers
source                  1..19
                        mol_type = protein
                        organism = synthetic construct
SEQUENCE: 146
NIGSKSDSQI WDSSSDHVV                                                          19

SEQ ID NO: 147          moltype = AA  length = 41
FEATURE                 Location/Qualifiers
source                  1..41
                        mol_type = protein
                        organism = synthetic construct
SEQUENCE: 147
```

```
GTRYVWDSDI SSQWEDIFES MINIGSKSDS QIWDSSSDHV V                          41

SEQ ID NO: 148          moltype = AA   length = 22
FEATURE                 Location/Qualifiers
source                  1..22
                        mol_type = protein
                        organism = synthetic construct
SEQUENCE: 148
GTRYIWDTYT ASQWESIFEA FI                                              22

SEQ ID NO: 149          moltype = AA   length = 41
FEATURE                 Location/Qualifiers
source                  1..41
                        mol_type = protein
                        organism = synthetic construct
SEQUENCE: 149
GTRYIWDTYT ASQWESIFEA FINIGSKSDS QVWDSSSSLV V                          41

SEQ ID NO: 150          moltype = AA   length = 22
FEATURE                 Location/Qualifiers
source                  1..22
                        mol_type = protein
                        organism = synthetic construct
SEQUENCE: 150
GTRYVWDYDT SSQWEDIFES MI                                              22

SEQ ID NO: 151          moltype = AA   length = 19
FEATURE                 Location/Qualifiers
source                  1..19
                        mol_type = protein
                        organism = synthetic construct
SEQUENCE: 151
NLGSKSDSQV WDMSSDLVV                                                  19

SEQ ID NO: 152          moltype = AA   length = 41
FEATURE                 Location/Qualifiers
source                  1..41
                        mol_type = protein
                        organism = synthetic construct
SEQUENCE: 152
GTRYVWDYDT SSQWEDIFES MINLGSKSDS QVWDMSSDLV V                          41

SEQ ID NO: 153          moltype = AA   length = 22
FEATURE                 Location/Qualifiers
source                  1..22
                        mol_type = protein
                        organism = synthetic construct
SEQUENCE: 153
GTRYIWSAYI SSQWEDIFEA MI                                              22

SEQ ID NO: 154          moltype = AA   length = 19
FEATURE                 Location/Qualifiers
source                  1..19
                        mol_type = protein
                        organism = synthetic construct
SEQUENCE: 154
NLGSYSDSQV WDMSSSLVV                                                  19

SEQ ID NO: 155          moltype = AA   length = 41
FEATURE                 Location/Qualifiers
source                  1..41
                        mol_type = protein
                        organism = synthetic construct
SEQUENCE: 155
GTRYIWSAYI SSQWEDIFEA MINLGSYSDS QVWDMSSSLV V                          41

SEQ ID NO: 156          moltype = AA   length = 22
FEATURE                 Location/Qualifiers
source                  1..22
                        mol_type = protein
                        organism = synthetic construct
SEQUENCE: 156
GTRYIWSTTT SSQWEDIFES MI                                              22

SEQ ID NO: 157          moltype = AA   length = 19
FEATURE                 Location/Qualifiers
source                  1..19
                        mol_type = protein
                        organism = synthetic construct
```

```
SEQUENCE: 157
NIGSKNDSQV WDSSDFLVV                                                        19

SEQ ID NO: 158          moltype = AA  length = 41
FEATURE                 Location/Qualifiers
source                  1..41
                        mol_type = protein
                        organism = synthetic construct
SEQUENCE: 158
GTRYIWSTTT SSQWEDIFES MINIGSKNDS QVWDSSDFLV V                                41

SEQ ID NO: 159          moltype = AA  length = 22
FEATURE                 Location/Qualifiers
source                  1..22
                        mol_type = protein
                        organism = synthetic construct
SEQUENCE: 159
GTRYISDSTK AAQWESVYEA FI                                                    22

SEQ ID NO: 160          moltype = AA  length = 19
FEATURE                 Location/Qualifiers
source                  1..19
                        mol_type = protein
                        organism = synthetic construct
SEQUENCE: 160
NLGSFSDSQV WDSSEDLVV                                                        19

SEQ ID NO: 161          moltype = AA  length = 41
FEATURE                 Location/Qualifiers
source                  1..41
                        mol_type = protein
                        organism = synthetic construct
SEQUENCE: 161
GTRYISDSTK AAQWESVYEA FINLGSFSDS QVWDSSEDLV V                                41

SEQ ID NO: 162          moltype = AA  length = 22
FEATURE                 Location/Qualifiers
source                  1..22
                        mol_type = protein
                        organism = synthetic construct
SEQUENCE: 162
GTRYIWDSTK AAQWELVHEA FI                                                    22

SEQ ID NO: 163          moltype = AA  length = 19
FEATURE                 Location/Qualifiers
source                  1..19
                        mol_type = protein
                        organism = synthetic construct
SEQUENCE: 163
NIGSKNDSQV WDESSDEVV                                                        19

SEQ ID NO: 164          moltype = AA  length = 41
FEATURE                 Location/Qualifiers
source                  1..41
                        mol_type = protein
                        organism = synthetic construct
SEQUENCE: 164
GTRYIWDSTK AAQWELVHEA FINIGSKNDS QVWDESSDEV V                                41

SEQ ID NO: 165          moltype = AA  length = 22
FEATURE                 Location/Qualifiers
source                  1..22
                        mol_type = protein
                        organism = synthetic construct
SEQUENCE: 165
GTRYVWDSNT AAQWESVHEA FI                                                    22

SEQ ID NO: 166          moltype = AA  length = 19
FEATURE                 Location/Qualifiers
source                  1..19
                        mol_type = protein
                        organism = synthetic construct
SEQUENCE: 166
NIGRFSDSQV WVSTSDKVV                                                        19

SEQ ID NO: 167          moltype = AA  length = 41
FEATURE                 Location/Qualifiers
source                  1..41
                        mol_type = protein
```

```
                        organism = synthetic construct
SEQUENCE: 167
GTRYVWDSNT AAQWESVHEA FINIGRFSDS QVWVSTSDKV V                              41

SEQ ID NO: 168          moltype = AA  length = 22
FEATURE                 Location/Qualifiers
source                  1..22
                        mol_type = protein
                        organism = synthetic construct
SEQUENCE: 168
GTRYISSSYI TSQWEEVYEA LI                                                  22

SEQ ID NO: 169          moltype = AA  length = 19
FEATURE                 Location/Qualifiers
source                  1..19
                        mol_type = protein
                        organism = synthetic construct
SEQUENCE: 169
NIGSFSDSQV WSSTSRHVV                                                      19

SEQ ID NO: 170          moltype = AA  length = 41
FEATURE                 Location/Qualifiers
source                  1..41
                        mol_type = protein
                        organism = synthetic construct
SEQUENCE: 170
GTRYISSSYI TSQWEEVYEA LINIGSFSDS QVWSSTSRHV V                              41

SEQ ID NO: 171          moltype = AA  length = 22
FEATURE                 Location/Qualifiers
source                  1..22
                        mol_type = protein
                        organism = synthetic construct
SEQUENCE: 171
GTRYIWSSDT ASQWEDIFES MV                                                  22

SEQ ID NO: 172          moltype = AA  length = 19
FEATURE                 Location/Qualifiers
source                  1..19
                        mol_type = protein
                        organism = synthetic construct
SEQUENCE: 172
YIGSFSDSQI YVSASRLVV                                                      19

SEQ ID NO: 173          moltype = AA  length = 41
FEATURE                 Location/Qualifiers
source                  1..41
                        mol_type = protein
                        organism = synthetic construct
SEQUENCE: 173
GTRYIWSSDT ASQWEDIFES MVYIGSFSDS QIYVSASRLV V                              41
```